(12) United States Patent
Bebbington et al.

(10) Patent No.: US 10,604,577 B2
(45) Date of Patent: Mar. 31, 2020

(54) METHODS AND COMPOSITIONS FOR TREATING SYSTEMIC MASTOCYTOSIS

(71) Applicant: Allakos Inc., San Carlos, CA (US)

(72) Inventors: Christopher Robert Bebbington, San Mateo, CA (US); Nenad Tomasevic, Foster City, CA (US); Rustom Falahati, Lafayette, CA (US)

(73) Assignee: Allakos Inc., Redwood City, CA (US)

( * ) Notice: Subject to any disclaimer, the term of this patent is extended or adjusted under 35 U.S.C. 154(b) by 0 days.

(21) Appl. No.: 15/299,349

(22) Filed: Oct. 20, 2016

(65) Prior Publication Data

US 2017/0114138 A1 Apr. 27, 2017

Related U.S. Application Data

(60) Provisional application No. 62/245,218, filed on Oct. 22, 2015.

(51) Int. Cl.
| | | |
|---|---|---|
| *C07K 16/28* | (2006.01) | |
| *A61P 37/00* | (2006.01) | |
| *A61P 35/00* | (2006.01) | |
| *A61K 39/395* | (2006.01) | |
| *A61K 45/06* | (2006.01) | |
| *A61K 39/00* | (2006.01) | |

(52) U.S. Cl.
CPC ...... *C07K 16/2851* (2013.01); *A61K 39/3955* (2013.01); *A61K 45/06* (2013.01); *A61P 35/00* (2018.01); *A61P 37/00* (2018.01); *C07K 16/2803* (2013.01); *A61K 2039/505* (2013.01); *A61K 2039/507* (2013.01); *C07K 2317/24* (2013.01); *C07K 2317/41* (2013.01); *C07K 2317/73* (2013.01); *C07K 2317/732* (2013.01)

(58) Field of Classification Search
None
See application file for complete search history.

(56) References Cited

U.S. PATENT DOCUMENTS

| | | |
|---|---|---|
| 30,985 A | 12/1860 | Pye |
| RE30,985 E | 6/1982 | Cartaya |
| 4,419,446 A | 12/1983 | Howley et al. |
| 4,560,655 A | 12/1985 | Baker |
| 4,601,978 A | 7/1986 | Karin |
| 4,657,866 A | 4/1987 | Kumar |
| 4,676,980 A | 6/1987 | Segal et al. |
| 4,767,704 A | 8/1988 | Cleveland et al. |
| 4,816,567 A | 3/1989 | Cabilly et al. |
| 4,927,762 A | 5/1990 | Darfler |
| 4,965,199 A | 10/1990 | Capon et al. |
| 5,122,464 A | 6/1992 | Wilson et al. |
| 5,122,469 A | 6/1992 | Mather et al. |
| 5,264,365 A | 11/1993 | Georgiou et al. |
| 5,500,362 A | 3/1996 | Robinson et al. |
| 5,508,192 A | 4/1996 | Georgiou et al. |
| 5,571,894 A | 11/1996 | Wels et al. |
| 5,587,458 A | 12/1996 | King et al. |
| 5,624,821 A | 4/1997 | Winter et al. |
| 5,639,635 A | 6/1997 | Joly et al. |
| 5,641,870 A | 6/1997 | Rinderknecht et al. |
| 5,648,237 A | 7/1997 | Carter |
| 5,648,260 A | 7/1997 | Winter et al. |
| 5,677,425 A | 10/1997 | Bodmer et al. |
| 5,739,277 A | 4/1998 | Presta et al. |
| 5,821,337 A | 10/1998 | Carter et al. |
| 5,834,597 A | 11/1998 | Tso et al. |
| 5,840,523 A | 11/1998 | Simmons et al. |
| 5,869,046 A | 2/1999 | Presta et al. |
| 5,885,573 A | 3/1999 | Bluestone et al. |
| 5,891,693 A | 4/1999 | Bebbington et al. |
| 6,027,888 A | 2/2000 | Georgiou et al. |
| 6,083,715 A | 7/2000 | Georgiou et al. |
| 6,121,022 A | 9/2000 | Presta et al. |
| 6,165,745 A | 12/2000 | Ward et al. |
| 6,194,551 B1 | 2/2001 | Idusogie et al. |
| 6,227,375 B1 | 5/2001 | Powollik et al. |
| 6,248,516 B1 | 6/2001 | Winter et al. |
| 6,277,375 B1 | 8/2001 | Ward |

(Continued)

FOREIGN PATENT DOCUMENTS

| | | |
|---|---|---|
| EP | 2465873 A1 | 6/2012 |
| JP | 2003525615 A | 9/2003 |

(Continued)

OTHER PUBLICATIONS

Kiwamoto et al. (Pharmacology & Therapeutics, 135: 327-336, 2012).*
Hoermann et al. (FASEB J., 28: 3540-3551, 2014).*
Florian et al. (Leukemia Research, 30: 1201-1205, 2006).*
Casassus et al. (British Journal of Haematology, 119: 1090-1097, 2002).*
Alegre et al., "A Non-Activating "Humanized" Anti-CD3 Monoclonal Antibody Retains Immunosuppressive Properties in Vivo", Transplantation, vol. 57, No. 11, Jun. 1994, pp. 1537-1543.
Angal et al., "A Single Amino Acid Substitution Abolishes the Heterogeneity of Chimeric Mouse/human (igG4) Antibody", Molecular Immunology, vol. 30, No. 1, Jan. 1993, pp. 105-108.

(Continued)

*Primary Examiner* — Nelson B Moseley, II
(74) *Attorney, Agent, or Firm* — Morrison & Foerster LLP

(57) ABSTRACT

The invention provides methods and compositions for the prevention and treatment of advanced systemic mastocytosis such as systemic mastocytosis with an associated hematologic non-mast-cell lineage disease (SM-AHNMD). In particular, the invention provides methods for the prevention and treatment of advanced systemic mastocytosis through administration of antibodies or agonists that bind to human Siglec-8 or compositions comprising said antibodies or agonists. The invention also provides articles of manufacture or kits comprising antibodies or agonists that bind to human Siglec-8 for the prevention and treatment of advanced systemic mastocytosis such as SM-AHNMD.

10 Claims, 6 Drawing Sheets

Specification includes a Sequence Listing.

(56) References Cited

U.S. PATENT DOCUMENTS

| | | | |
|---|---|---|---|
| 6,602,684 | B1 | 8/2003 | Umana et al. |
| 6,737,056 | B1 | 5/2004 | Presta |
| 6,821,505 | B2 | 11/2004 | Ward |
| 6,982,321 | B2 | 1/2006 | Winter |
| 7,087,409 | B2 | 8/2006 | Barbas, III et al. |
| 7,317,091 | B2 | 1/2008 | Lazar et al. |
| 7,335,742 | B2 | 2/2008 | Presta |
| 7,557,191 | B2 | 7/2009 | Abrahamson et al. |
| 7,745,421 | B2 | 6/2010 | Bochner et al. |
| 7,871,612 | B2 | 1/2011 | Abrahamson et al. |
| 7,981,843 | B2 | 7/2011 | Flynn et al. |
| 8,178,512 | B2 | 5/2012 | Bochner et al. |
| 8,197,811 | B2 | 6/2012 | Abrahamson et al. |
| 8,207,305 | B2 | 6/2012 | Abrahamson et al. |
| 8,357,671 | B2 | 1/2013 | Paulson et al. |
| 8,574,907 | B2 | 11/2013 | Alley et al. |
| 9,546,215 | B2 | 1/2017 | Bebbington et al. |
| 10,183,996 | B2 | 1/2019 | Bebbington |
| 2002/0106738 | A1 | 8/2002 | Foussias et al. |
| 2002/0164328 | A1 | 11/2002 | Shinkawa et al. |
| 2003/0092091 | A1 | 5/2003 | Abrahamson et al. |
| 2003/0115614 | A1 | 6/2003 | Kanda et al. |
| 2003/0157108 | A1 | 8/2003 | Presta |
| 2003/0190311 | A1 | 10/2003 | Dall'Acqua et al. |
| 2004/0093621 | A1 | 5/2004 | Shitara et al. |
| 2004/0109865 | A1 | 6/2004 | Niwa et al. |
| 2004/0110282 | A1 | 6/2004 | Kanda et al. |
| 2004/0110704 | A1 | 6/2004 | Yamane et al. |
| 2004/0132140 | A1 | 7/2004 | Satoh et al. |
| 2005/0014934 | A1 | 1/2005 | Hinton et al. |
| 2005/0123546 | A1 | 6/2005 | Umana et al. |
| 2006/0134098 | A1 | 6/2006 | Bebbington et al. |
| 2007/0134259 | A1 | 6/2007 | Bundle et al. |
| 2007/0264258 | A1 | 11/2007 | Abrahamson et al. |
| 2008/0050310 | A1* | 2/2008 | Ebens, Jr. ......... C07K 16/2803 424/1.49 |
| 2008/0139485 | A1 | 6/2008 | Bochner et al. |
| 2008/0213212 | A1 | 9/2008 | Abrahamson et al. |
| 2009/0238837 | A1 | 9/2009 | Paulson et al. |
| 2010/0056760 | A1 | 3/2010 | Abrahamson et al. |
| 2011/0046078 | A1 | 2/2011 | Bochner et al. |
| 2011/0059107 | A1 | 3/2011 | Allison et al. |
| 2011/0217319 | A1 | 9/2011 | Abrahamson et al. |
| 2011/0293631 | A1 | 12/2011 | Thumbikat et al. |
| 2012/0214975 | A1 | 8/2012 | Sandig et al. |
| 2015/0203578 | A1* | 7/2015 | Bebbington ....... C07K 16/2803 424/133.1 |
| 2017/0073413 | A1 | 3/2017 | Bebbington et al. |
| 2017/0209556 | A1 | 7/2017 | Bebbington et al. |
| 2018/0179279 | A1 | 6/2018 | Bebbington et al. |

FOREIGN PATENT DOCUMENTS

| | | | |
|---|---|---|---|
| KR | 10-20150044680 A | | 4/2015 |
| KR | 10-20150044687 A | | 4/2015 |
| WO | 1987/000195 A1 | | 1/1987 |
| WO | 1990/003430 A1 | | 4/1990 |
| WO | 1993/006213 A1 | | 4/1993 |
| WO | 1993/008829 A1 | | 5/1993 |
| WO | 1993/016185 A2 | | 8/1993 |
| WO | 1994/011026 A2 | | 5/1994 |
| WO | 1994/029351 A2 | | 12/1994 |
| WO | 1997/030087 A1 | | 8/1997 |
| WO | 1998/058964 A1 | | 12/1998 |
| WO | 1999/022764 A1 | | 5/1999 |
| WO | 1999/051642 A1 | | 10/1999 |
| WO | 2000/042072 A2 | | 7/2000 |
| WO | 2000/061739 A1 | | 10/2000 |
| WO | 2001/029246 A1 | | 4/2001 |
| WO | 2001/66126 A1 | | 9/2001 |
| WO | WO 01/66126 | * 9/2001 | ............ A61K 38/00 |
| WO | 2003/011878 A2 | | 2/2003 |
| WO | 2003/084570 A1 | | 10/2003 |
| WO | 2003/085119 A1 | | 10/2003 |
| WO | 2004/056312 A2 | | 7/2004 |
| WO | 2005/035586 A1 | | 4/2005 |
| WO | 2005/035778 A1 | | 4/2005 |
| WO | 2005/053742 A1 | | 6/2005 |
| WO | 2005/116088 A2 | | 12/2005 |
| WO | 2007/056525 A2 | | 5/2007 |
| WO | 2008/077546 A1 | | 7/2008 |
| WO | WO-2008/145142 A1 | | 12/2008 |
| WO | WO-2010/063785 A2 | | 6/2010 |
| WO | WO-2010/063785 A3 | | 6/2010 |
| WO | WO-2011/147982 A2 | | 12/2011 |
| WO | WO-2011/147982 A3 | | 12/2011 |
| WO | WO-2013/126834 A1 | | 8/2013 |
| WO | 2015/089117 A1 | | 6/2015 |
| WO | 2015/131155 A1 | | 9/2015 |
| WO | WO-2016/205567 A1 | | 12/2016 |
| WO | WO-2018/129400 A1 | | 7/2018 |

OTHER PUBLICATIONS

Arié et al., "Chaperone Function of FkpA, a Heat Shock Prolyl Isomerase, in the Periplasm of *Escherichia coli*", Molecular Microbiology, vol. 39, No. 1, 2001, pp. 199-210.

Armour et al., "Recombinant Human IgG Molecules Lacking Fcγ Receptor I Binding and Monocyte Triggering Activities", Eur. J. Immunol., vol. 29, 1999, pp. 2613-2624.

Bachmann, Barbara J., "Derivations and Genotypes of Some Mutant Derivatives of *Escherichia coli* K-12", Cellular and Molecular Biology, vol. 2, 1987, 37 pages.

Barnes et al., "Methods for Growth of Cultured Cells in Serum-Free Medium", Analytical Biochemistry, vol. 102, 1980, pp. 255-270.

Bass et al., "Hormone Phage: An Enrichment Method for Variant Proteins With Altered Binding Properties", Proteins: Structure, Function, and Genetics, vol. 8, 1990, pp. 309-314.

Boerner et al., "Production of Antigen-Specific Human Monoclonal Antibodies from in Vitro-Primed Human Splenocytes", The Journal of Immunology, vol. 147, No. 1, Jul. 1, 1991, pp. 86-95.

Bothmann et al., "The Periplasmic *Escherichia coli* Peptidylprolyl cis, Trans-Isomerase FkpA", The Journal of Biological Chemistry, vol. 275, No. 22, Jun. 2, 2000, pp. 17100-17105.

Brennan et al., "Preparation of Bispecific Antibodies by Chemical Recombination of Monoclonal Immunoglobulin G1 Fragments", Science, vol. 229, Jul. 5, 1985, pp. 81-83.

Brodeur et al., "Mouse-Human Myeloma Partners for the Production of Heterohybridomas", Monoclonal Antibody Production Techniques and Applications, Chapter 4, 1987, pp. 51-63.

Brüggermann et al., "Designer Mice: The Production of Human Antibody Repertoires in Transgenic Animals", The Year in Immunology, vol. 7, 1993, pp. 33-40.

Brunner et al., "Quantitative Assay of the Lytic Action of Immune Lymphoid Cells on $^{51}$Cr-Labelled Allogeneic Target Cells In Vitro; Inhibition by Isoantibody and by Drugs", Immunology, vol. 14, 1968, pp. 181-196.

Carter et al., "High Level *Escherichia coli* Expression and Production of a Bivalent Humanized Antibody Fragment", Biotechnology, vol. 10, Feb. 1992, pp. 163-167.

Carter et al., "Humanization of an Anti-p185$^{HER2}$ Antibody for Human Cancer Therapy", Proceedings of the National Academy of Sciences of the United States of America, vol. 89, May 1992, pp. 4285-4289.

Chen et al., "Chaperone Activity of DsbC*", The Journal of Biological Chemistry, vol. 274, No. 28, Jul. 9, 1999, pp. 19601-19605.

Chen et al., "Selection and Analysis of an Optimized Anti-VEGF Antibody: Crystal Structure of an Affinity-matured Fab in Complex with Antigen", J. Mol. Biol., vol. 293, 1999, pp. 865-881.

Cheng et al., "NK cell-based Immunotherapy for Malignant Diseases", Cellular & Molecular Immunology, vol. 10, 2013, pp. 230-252.

Chothia et al., "Canonical Structures for the Hypervariable Regions of Immunoglobulins", Journal of Molecular Biology, vol. 196, 1987, pp. 901-917.

(56) References Cited

OTHER PUBLICATIONS

Clynes et al., "Fc Receptors are Required in Passive and Active Immunity to Melanoma", Proceedings of the National Academy of Sciences of the United States of America, vol. 95, Jan. 1998, pp. 652-656.

Cunningham et al., "High-Resolution Epitope Mapping of hGH-Receptor Interactions by Alanine-Scanning Mutagenesis", Science, vol. 244, Jun. 2, 1989, pp. 1081-1085.

Duncan et al., "Localization of the Binding Site for the Human High-affinity Fc Receptor on IgG", Nature, vol. 332, Apr. 1988, pp. 563-564.

Duncan et al., "The Binding Site for Clq on IgG", Nature, vol. 332, Apr. 21, 1988, pp. 738-740.

Ghetie et al., "Increasing the Serum Persistence of an IgG Fragment by Random Mutagenesis", Nature Biotechnology, vol. 15, Jul. 1997, pp. 637-640.

Gotlib et al., "International Working Group-Myeloproliferative Neoplasms Research and Treatment (IWG-MRT) & European Competence Network on Mastocytosis (ECNM) Consensus Response Criteria in Advanced Systemic Mastocytosis", Blood, vol. 121, No. 13, Mar. 28, 2013, pp. 2393-2401.

Graham et al., "Characteristics of a Human Cell Line Transformed by DNA from Human Adenovirus Type 5", Journal of General Virology, vol. 36, 1977, pp. 59-72.

Guhl et al., "Long-Term Cultured Human Skin Mast Cells are Suitable for Pharmacological Studies of Anti-Allergic Drugs Due to High Responsiveness to FceRI Cross-Linking", Biosci. Biotechnol. Biochem., vol. 75, No. 2, 2011, pp. 382-384.

Guss et al., "Structure of the IgG-binding Regions of Streptococcal Protein G", The Embo Journal vol. 5, No. 7, 1986, pp. 1567-1575.

Guyer et al., "Immunoglobulin Binding by Mouse Intestinal Epithelial Cell Receptors", The Journal of Immunology, vol. 117, No. 2, Aug. 1976, pp. 587-593.

Ham et al., "Media and Growth Requirements", Methods in Enzymology, vol. 58, 1979, pp. 44-93.

Hamers-Casterman et al., "Naturally Occurring Antibodies Devoid of Light Chains", Nature, vol. 363, Jun. 3, 1993, pp. 446-448.

Hara et al., "Overproduction of Penicillin-binding Protein 7 Suppresses Thermosensitive Growth Defect at Low Osmolarity due to an spr Mutation of *Escherichia coli*.", Microbial Drug Resistance. vol. 2, No. 1, 1996, 63-72.

Harris, W. J., "Production of Humanized Monoclonal Antibodies for in Vivo Imaging and Therapy", Therapeutic Monoclonals, vol. 23, 1995, pp. 1035-1038.

Hermine et al., "Case-Control Cohort Study of Patients' Perceptions of Disability in Mastocytosis", PLoS One, vol. 3, No. 5, May 2008, pp. 1-14.

Hudson et al., "Engineered Antibodies", Nature Medicine, vol. 9, No. 1, Jan. 2003, pp. 129-134.

Hudson et al., "Eosinophil-Selective Binding and Proapoptotic Effect in Vitro of a Synthetic Siglec-8 Ligand, Polymeric 6'-Sulfated Sialyl Lewis X", The Journal of Pharmacology and Experimental Therapeutics, vol. 330, No. 2, 2009, pp. 608-612.

Hurle et al., "Protein Engineering Techniques for Antibody Humanization", Current Opinion in Biotechnology, vol. 5, 1994, pp. 428-433.

Hutchins et al., "Improved Biodistribution, Tumor Targeting, and Reduced Immunogenicity in Mice with a γ4 Variant of Campath-1H", Proc. Natl. Acad. Sci., vol. 92, Dec. 1995, pp. 11980-11984.

Idusogie et al., "Engineered Antibodies with Increased Activity to Recruit Complement", The Journal of Immunology, vol. 166, 2001, pp. 2571-2575.

Idusogie et al., "Mapping of the Clq Binding Site on Rituxan, A Chimeric Antibody with a Human IgG1 Fc", The Journal of Immunology, vol. 164, 2000, pp. 4178-4184.

Jakobovits et al., "Analysis of Homozygous Mutant Chimeric Mice: Deletion of the Immunoglobulin Heavy-chain Joining Region Blocks B-cell Development and Antibody Production", PNAS, Proceedings of the National Academy of Sciences, vol. 90, Mar. 1993, pp. 2551-2555.

Jakobovits et al., "Germ-line Transmission and Expression of a Human-Derived Yeast Artificial Chromosome", Nature, vol. 362, Mar. 18, 1993, pp. 255-258.

Jefferis et al., "Human Immunoglobulin Allotypes", mAbs, vol. 1, No. 4, Jul./Aug. 2009, pp. 1-7.

Jefferis et al., "Interaction Sites on Human IgG-fc for FcγR: Current Models", Immunology Letters, vol. 82, 2002, pp. 57-65.

Jefferis et al., "Modulation of FcγR and Human Complement Activation by IgG3-Core Oligosaccharide Interactions", Immunology Letters, vol. 54, 1996, pp. 101-104.

Jefferis et al., "Recognition Sites on Human IgG for Fcγ Receptors: The Role of Glycosylation", Immunology Letters, vol. 44, 1995, pp. 111-117.

Johnson et al., "The Kabat Database and a Bioinformatics Example", Methods in Molecular Biology, vol. 248, 2004, pp. 11-25.

Jones et al., "Replacing the Complementarity-Determining Regions in a Human Antibody with those from a Mouse", Nature, vol. 321, May 29, 1986, pp. 522-525.

Kiladjian et al., "Cytolytic Function and Survival of Natural Killer Cells are Severely Altered in Myelodysplastic Syndromes", Leukemia, vol. 20, 2006, pp. 463-470.

Kim et al., "Localization of the Site of the Murine IgG1 Molecule that is Involved in Binding to the Murine Intestinal Fc Receptor" Eur. J. Immunol, vol. 24, 1994, 2429-2434.

Kozbor et al., "A Human Hybrid Myeloma for Production of Human Monoclonal Antibodies", The Journal of Immunology, vol. 133, No. 6, Dec. 1984, pp. 3001-3005.

Lazar et al., "Engineered Antibody Fc Variants with Enhanced Effector Function", PNAS, vol. 103, No. 11, Mar. 14, 2006, pp. 4005-4010.

Lichtenfels et al., "CARE-LASS (calcein-release-assay), An Improved Fluorescence-based Test System to Measure Cytotoxic T Lymphocyte Activity", Journal of Immunological Methods, vol. 172, 1994, pp. 227-239.

Lindmark et al., "Binding of Immunoglobulins to Protein A and Immunoglobulin Levels in Mammalian Sera", Journal of Immunological Methods, vol. 62, 1983, pp. 1-13.

Lund et al., "Human FcγRI and FcγRII Interact with Distinct but Overlapping Sites on Human IgG", The Journal of Immunology, vol. 147, No. 8, Oct. 15, 1991, pp. 2657-2662.

Lund et al., "Multiple Binding Sites on the $C_H2$ Domain of IgG for Mouse FcγRII", Molecular Immunology, vol. 29, No. 1, Jan. 1992, pp. 53-59.

Lund et al., "Multiple Interactions of IgG with Its Core Oligosaccharide Can Modulate Recognition by Complement and Human Fcγ Receptor I and Influence the Synthesis of Its Oligosaccharide Chains", The Journal of Immunology, vol. 157, 1996, pp. 4963-4969.

Lund et al., "Oligosaccharide-Protein Interactions in IgG can Modulate Recognition by Fcγ Receptors", The FASEB Journal, vol. 9, Jan. 1995, pp. 115-119.

Marcondes et al., "Dysregulation of IL-32 in Myelodysplastic Syndrome and Chronic Myelomonocytic Leukemia Modulates Apoptosis and Impairs NK Function", PNAS, vol. 105, No. 8, Feb. 26, 2008, pp. 2865-2870.

Mather et al., "Culture of Testicular Cells in Hormone-Supplemented Serum-Free Medium", Annals New York Academy of Sciences, 1982, pp. 44-68.

Mather, Jennie P., "Establishment and Characterization of Two Distinct Mouse Testicular Epithelial Cell Lines", Biology of Reproduction, vol. 23, 1980, pp. 243-252.

Milstein et al., "Hybrid Hybridomas and their Use in Immunohistochemisty", Nature, vol. 305, Oct. 6, 1983, pp. 537-540.

Morimoto et al., "Single-step Purification of F(ab')₂ Fragments of Mouse Monoclonal Antibodies (immunoglobulins G1) by Hydrophobic Interaction High Performance Liquid Chromatography Using TSKgel Phenyl-5pw", Journal of Biochemical and Biophysical Methods, vol. 24, 1992, pp. 107-117.

Morrison et al., "Chimeric Human Antibody Molecules: Mouse Antigen-Binding Domains With Human Constant Region Domains", PNAS, vol. 81, Nov. 1984, pp. 6851-6855.

(56) References Cited

OTHER PUBLICATIONS

Munson et al., "Ligand: A Versatile Computerized Approach for Characterization of Ligand-binding Systems", Analytical Biochemistry, vol. 107, 1980, pp. 220-239.
Nutku et al., "Mechanism of Siglec-8-Induced Human Eosinophil Apoptosis: Role of Caspases and Mitochondrial Injury", Biochemical and Biophysical Research Communications, vol. 336, 2005, pp. 918-924.
Okazaki et al., "Fucose Depletion from Human IgG1 Oligosaccharide Enhances Binding Enthalpy and Association Rate Between IgG1 and FcγRIIIa", Journal of Molecular Biology, vol. 336, 2004, pp. 1239-1249.
Pahl et al., "Tricking the Balance: NK Cells in Anti-Cancer Immunity", Immunobiology, 2015, pp. 1-10.
Patel et al., "An Improved Assay for Antibody Dependent Cellular Cytotoxicity Based on Time Resolved Fluorometry", Journal of Immunological Methods, vol. 184, 1995, pp. 29-38.
Patnaik et al., "Systemic Mastocytosis: A Concise Clinical and Laboratory Review", Arch Pathol Lab Med, vol. 131, May 2007, pp. 784-791.
Pillai et al., "Siglecs and Immune Regulation", Annu. Rev. Immunol, vol. 30, 2012, pp. 357-392.
Presta et al., "Engineering Therapeutic Antibodies for Improved Function", Biochemical Society Transactions, vol. 30, No. 4, 2002, pp. 487-490.
Presta et al., "Humanization of an Antibody Directed Against IgE", The Journal of Immunology, vol. 151, No. 5, Sep. 1, 1993, pp. 2623-2632.
Presta, Leonard G., "Antibody Engineering", Current Opinion in Structural Biology, vol. 2, 1992, pp. 593-596.
Proba et al., "Functional Antibody Single-chain Fragments from the Cytoplasm of *Escherichia coli*: Influence of Thioredoxin Reductase (TrxB)", Gene, vol. 159, 1995, pp. 203-207.
Ramm et al., "The Periplasmic *Escherichia coli* Peptidylprolyl Cis, Trans-Isomerase FkpA", The Journal of Biological Chemistry, vol. 275, No. 22, Jun. 2, 2000, pp. 17106-17113.
Ravetch et al., "Fc Receptors", Annu. Rev. Immunol., vol. 9, 1991, pp. 457-492.
Reddy et al., "Elimination of Fc Receptor-Dependent Effector Functions of a Modified IgG4 Monoclonal Antibody to Human CD4", The Journal of Immunology, vol. 164, 2000, pp. 1925-1933.
Reyes et al., "Expression of Human β-Interferon cDNA Under the Control of a Thymidine Kinase Promoter from Herpes Simplex Virus", Nature, vol. 297, Jun. 17, 1982, pp. 598-601.
Riechmann et al., "Reshaping Human Antibodies for Therapy", Nature, vol. 332, Mar. 24, 1988, pp. 323-327.
Ripka et al., "Two Chinese Hamster Ovary Glycosylation Mutants Affected in the Conversion of GDP-Mannose to GDP-Fucose", Archives of Biochemistry and Biophysics, vol. 249, No. 2, Sep. 1986, pp. 533-545.
Scatchard, George, "The Attractions of Proteins for Small Molecules and Ions", Annals New York Academy of Sciences, vol. 51, 1947, pp. 660-672.
Sheriff et al., "Redefining the Minimal Antigen-binding Fragment", Nature Structural Molecular Biology, vol. 3, No. 9, Sep. 1996, pp. 733-736.
Shields et al., "High Resolution Mapping of the Binding Site on Human IgG1 for FcγRI, FcγRII, FcγRIII, and FcRn and Design of IgG1 Variants with Improved Binding to the FcγR", The Journal of Biological Chemistry, vol. 276, No. 9, Mar. 2, 2001, pp. 6591-6604.
Siebenlist et al., "*E. coli* RNA Polymerase Interacts Homologously With Two Different Promoters", Cell, vol. 20, Jun. 1980, pp. 269-281.
Simmons et al., "Expression of Full-Length Immunoglobulins in *Escherichia coli*: Rapid and Efficient Production of Aglycosylated Antibodies", Journal of Immunological Methods, vol. 263, 2000, pp. 133-147.
Sims et al., "A Humanized CD18 Antibody Can Block Function Without Cell Destruction", The Journal of Immunology, vol. 151, No. 4, Aug. 15, 1993, pp. 2296-2308.

Suresh et al., "Bispecific Monoclonal Antibodies from Hybrid Hybridomas", Methods in Enzymology, vol. 121, 1986, pp. 210-228.
Tashiro et al., "Zearalenone Reductase from Rat Liver", Journal of Biochemistry, vol. 93, 1983, pp. 1557-1566.
Traunecker et al., "Bispecific Single Chain Molecules (Janusins) Target Cytotoxic Lymphocytes on HIV Infected Cells", The EMBO Journal, vol. 10, No. 12, 1991, pp. 3655-3659.
Urlaub et al., "Isolation of Chinese Hamster Cell Mutants Deficient in Dihydrofolate Reductase Activity", Proc. Natl. Acad. Sci., vol. 77, No. 7, Jul. 1980, pp. 4216-4220.
Unpublished U.S. Appl. No. 15/121,756, titled "Methods and Compositions for Treating Siglec-8 Associated Diseases", filed Aug. 25, 2016.
Valent et al., "Proposed Diagnostic Algorithm for Patients With Suspected Mastocytosis: A Proposal of the European Competence Network on Mastocytosis", European Journal of Allergy and Clinical Immunology, vol. 69, 2014, pp. 1267-1274.
Valent et al., "Standards and Standardization in Mastocytosis: Consensus Statements on Diagnostics, Treatment Recommendations and Response Criteria", European Journal of Clinical Investigation, vol. 37, 2007, pp. 435-453.
Valent, Peter, "Diagnostic Evaluation and Classification of Mastocytosis", Immunol Allergy Clin North Am, vol. 26, 2006, pp. 515-534.
Vaswani et al., "Humanized Antibodies as Potential Therapeutic Drugs", Annals of Allergy, Asthma & Immunology, vol. 81, Aug. 1998, pp. 105-116 & 119.
Verhoeyen et al., "Reshaping Human Antibodies: Grafting an Antilysozyme Activity", Science, vol. 239, 1988, pp. 1534-1536.
Verstovsek, Srdan, "Advanced Systemic Mastocytosis: The Impact of KIT Mutations in Diagnosis, Treatment and Progression", European Journal of Haematology, vol. 90, 2012, pp. 89-98.
Xu et al., "Diversity in the CDR3 Region of $V_H$ is Sufficient for Most Antibody Specificities", Immunity, vol. 13, Jul. 2000, pp. 37-45.
Xu et al., "In Vitro Characterization of Five Humanized OKT3 Effector Function Variant Antibodies", Cellular Immunology, vol. 200, 2000, pp. 16-26.
Yamane-Ohnuki et al., "Establishment of FUT8 Knockout Chinese Hamster Ovary Cells: An Ideal Host Cell Line for Producing Completely Defucosylated Antibodies with Enhanced Antibody-Dependent Cellular Cytotoxicity", Biotechnology and Bioengineering, vol. 87, No. 5, Sep. 5, 2004, pp. 614-622.
Yaniv, Moshe, "Enhancing Elements for Activation of Eukaryotic Promoters", Nature, vol. 297, May 6, 1982, pp. 17-18.
Yansura et al., "Nucleotide Sequence Selection for Increased Expression of Heterologous Genes in *Escherichia coli*", Methods: A Companion to Methods in Enzymology, vol. 4, 1992, pp. 151-158.
Yokoi et al., "Inhibition of FcεRI-Dependent Mediator Release and Calcium Flux from Human Mast Cells by Sialic Acid-Binding Immunoglobulin-Like Lectin 8 Engagement", J. Allergy Clin. Immunol, vol. 121, No. 2, Feb. 2008, pp. 499-505.e1.
Zapata et al., "Engineering Linear F(ab')₂ Fragments for Efficient Production in *Escherichia coli* and Enhanced Antiproliferative Activity", Protein Engineering, vol. 8, No. 10,1995, pp. 1057-1062.
International Search Report and Written Opinion for PCT Application No. PCT/US2016/058199, dated Jan. 9, 2017, 11 pages.
Hudson et al., "Developmental, Malignancy-Related, and Cross-Species Analysis of Eosinophil, Mast Cell, and Basophil Siglec-8 Expression", Journal of Clinical Immunology, vol. 31, No. 6, Dec. 2011, pp. 1045-1053.
Kiwamoto et al., "Siglec-8 as a Drugable Target to Treat Eosinophil and Mast Cell Associated Conditions", Pharmacology Therapeutics, vol. 135, No. 3, Sep. 2012, pp. 327-336.
Berges-Gimeno et al., "The Natural History and Clinical Characteristics of Asprin-Exacerbaated Respiratory Disease," Annals of Allergy, Asthma & Immunology, vol. 89, Nov. 2002, pp. 474-478.
Bryson et al., "Local and Systemic Eosinophilia in Patients Undergoing Endoscopic Sinus Surgery for Chronic Rhinosinusitis with and Without Polyposis," Clin. Otolaryngol, vol. 28, 2003, pp. 55-58.

(56) References Cited

OTHER PUBLICATIONS

Casset et al., "A Peptide Mimetic of an Anti-CD4 Monoclonal Antibody by Rational Design," Biochem. Biophys. Res. Comm. 2003, 307:198-205.
Eswar et al., "Comparative Protein Structure Modeling Using Modeller", Current Protocols in Bioinformatics, Unit—5.6, Oct. 2006, pp. 1-47.
Fairclough et al., "Killer Cells in Chronic Obstructive Pulmonary Disease", Clinical Science, vol. 114, 2008, pp. 533-541.
Ferrara et al., "Modulation of Therapeutic Antibody Effector Functions by Glycosylation Engineering: Influence of Golgi Enzyme Localization Domain and Co-Expression of Heterologous β1, 4-N-acetylglucosaminyltransferase III and Golgi α-Mannosidase II", Biotechnology and Bioengineering, vol. 93, Issue No. 5, Apr. 5, 2006, pp. 851-861.
Floyd et al., "Siglec-8: A novel Eosinophil-Specific Member of the Immunoglobulin Superfamily", Journal of Biological Chemistry, vol. 275, No. 2, 2000, 861-866.
Fokkens et al., "European Position Paper on Rhinosinusitis and Nasal Polyps", EPOS, vol. 50, Supp.ementa 23, Mar. 2012, pp. 1-299.
Gevaert et al., "Omalizumab is Effective in Allergic and Nonallergic Patients with Nasal Polyps and Asthma", The Journal of Allergy and Clinical of Immunology, vol. 131, No. 1, Jan. 2013, pp. 110-116.
Goodman et al., "Immunoglobulin Proteins", Chapter 6, Basic and Clinical Immunology, 1994, pp. 66-79.
Gunten et al., "Intravenous Immunoglobulin Preparations Contain Anti-Siglec-8 Autoantibodies", Journal of Allergy and Clinical Immunology, vol. 119, No. 4, 2007, pp. 1005-1011.
Hermine et al, "Case-Control Cohort study of Patients' Perceptions of Disability in Mastocytosis", Plos ONE, vol. 3, No. 5, 2008, pp. 1-14.
Holm et al., "Functional Mapping and Single Chain Construction of the Anti-Cytokeratin 8 Monoclonal Antibody TS1," Mol. Immunol. 2007; 44(6):1075-1084.
Hori et al., "Eosinopenia as a predictive Factor of the Short-Term Risk of Mortality and Infection After Acute Cerebral Infarction", J. Stroke Cerebrovasc. Dis. 25(6):1307-1312, (Jun. 2016).
Hu et al., "Diagnostic Significance of Blood Eosinophil Count in Eosinophilic Chronic Rhinosinusitis With Nasal Polys in Chinese Adults", Laryngoscope, vol. 122, Mar. 2012, pp. 498-503.
Jenkins et al., "Systematic Review of Prevalence of Asprin Induced Astham and its Implications for Clinical Practice" BMJ, Papers, 2004, pp. 1-7.
Joly et al., "Overexpression of *Escherichia coli* Oxidoreductases Increases Recombinant Insulin Like Growth Factor-I Accumulation", Proc. Natl. Acad. Sci., vol. 95, Mar. 1998, pp. 2773-2777.
Kikly et al., "Identification of Saf-2, a Novel Siglec Expressed on Eosinophils, Mast Cells, and Basophils", The Journal of Allergy and Clinical Immunology, vol. 105, Issue 6, Part 1, 2000, pp. 1093-1100.
Kim et al., "Natural Killer Cells from Patients with Chronic Rhinosinusitis have Impaired Effector Functions", Plos One, vol. 8, No. 10, e-77177, Oct. 2013, pp. 1-9.
Kowalski, Marek L., Aspirin Exacerbated Respiratory Disease (AERD)*, World Allergy Organization, Available at [http://www.worldallergy.org/professional/allergic_diseases_center/aspirin/], 2006, 6 pages.
Lange et al., "The Sino-Nasal Outcome Test 22 Validated for Danish Patients", Dan. Med. Bull, vol. 58, No. 2, Feb. 2011, pp. 1-6.
Lefranc, Marie-Paule, "IMGT, The International ImMunoGeneTics Database®", Nucleic Acids Research, vol. 31, No. 1, 2003, pp. 307-310.
MacCallum et al. "Antibody-Antigen Interactions: Contact Analysis and Binding Site Topography," J. Mol. Biol. 262:732-745, (1996).
Mroz et al., "Siglec-8 in Induced Sputum of COPD Patients", Advances in Experimental Medicine and Biology, vol. 788, 2013, pp. 19-23.

Muroi et al., "The Composite Effect of Transgenic Plant Volatiles for Acquired Immunity to Herbivory Caused by Inter-Plant Communications", Plus One, vol. 6 No. 10, e24594, Oct. 2011, pp. 1-8.
Nutku et al. "Mechanism of Siglec-8-induced Human Eosinophil Apoptosis: Role of Caspases and Mitochondrial Injury". Biochemical and Biophysical Research Communications vol. 336. No. 3, Oct. 28, 2005, pp. 918-924.
O'Reilly et al., "Siglecs as Targets for Therapy in Immune Cell Mediated Diseases", Trends Parmacol. Sci., vol. 30, No. 5, May 2009, pp. 240-248.
Paul, ed., Fundamental Immunology, 1993, Raven Press, New York, pp. 292-295.
Plückthun, A., "Antibodies from *Escherichia coli*", Chapter 11, The Pharmacology of Monoclonal Antibodies, 1994, pp. 269-315.
Prieto et al. "Defective Natural Killer and Phagocytic Activities in Chronic Obstructive Pulmonary Disease are Restored by Glycophosphopeptical (Inmunoferón)", American Journal of Respiratory and Critical Care Medicne, vol. 163, 2001, pp. 1578-1583.
Rahimi-Rad et al., (2015), "Eosinopenia as a Marker of Outcome in Acute Exacerbations of Chronic Obstructive Pulmonary Disease," J. Clin. Med., 10(1):10-13.
Ruhno et al., "The Increased Number of Epithelial Mast Cells in Nasal Polyps and Adjacent Turbinates is not Allergy-Dependent", Allergy, vol. 45, 1990, pp. 370-374.
Settipane, Guy A., "Epidemiology of Nasal Polyps", Allergy and Asthma Proceedings, vol. 17, No. 5, Sep.-Oct. 1996, pp. 231-236.
Shi et al., "Characterizing T-Cell Phenotypes in Nasal Polyposis in Chinese Patients", Journal of Investigational Allergology and Clinical Immunology, vol. 19, No. 4, 2009, pp. 276-282.
Spronsen et al., "Evidence-Based Recommendations Regarding the Differential Diagnosis and Assessment of Nasal Congestion: Using the New GRADE System", Allergy, vol. 63, 2008, pp. 820-833.
Song et al. "Anti-Siglec-F Antibody Reduces Allergen-Induced Eosinophilic Inflammation and Airway Remodeling" The Journal of Immunology 2009 183(8):5333-5341.
Steinke et al., "Interleukin-4 in the Generation of the AERD Phenotype: Implications for Molecular Mechanisms Driving Therapeutic Benefit of Aspirin Desensitization", Journal of Allergy, vol. 2012, Issue 182090, 2012, pp. 1-9.
Steinke et al., "Prominent Role of IFN-γ in Patients with Aspirin-Exacerbated Respiratory Disease", Journal of Allergy and Clinical Immunology, vol. 132, Issue 4, Oct. 2013, pp. 856-865.
Stevenson et al. "Clinical and Pathologic Perspective on Aspirin Sensitivity and Asthma", The Journal of Allergy and Clinical Immunology, vol. 118, No. 4, Oct. 2006, pp. 773-786.
Stevenson et al., "Pathogenesis of Aspirin-Exacerbated Respiratory Disease", Clinical Reviews in Allergy and Immunology, vol. 24, 2003, pp. 169-187.
Szczeklik, Andrzej, "Aspirin-Induced Asthma: A Tribute to John Vane as a Source of Inspiration", Pharmacological Reports, vol. 62, 2010, pp. 526-529.
Szczeklik et al., "Hypersensitivity to Aspirin and Non-steroidal Anti-Inflammatory Drugs", In: Middleton's Allergy, 7$^{th}$ Edition, 2009, pp. 1227-1243.
Tanaka et al., "Development of Mature and Functional Human Myeloid subsets in HSC Engrafted NOD/SCID/IL2rγKO Mice", The Journal of Immunology, vol. 188, No. 12, Jun. 2012, pp. 6145-6155.
Territo, http://www.merckmanuals.com/home/blood-disorders/white-blood-cell-disorders/eosinophilic-disorders, accessed Aug. 2, 2016.
Unpublished U.S. Appl. No. 15/737,270, titled "Methods and Compositions for Treating Fibrotic Diseases", filed Dec. 15, 2017, for Bebbington et al.
Vajdos et al. "Comprehensive Functional Maps of the Antigen-Binding Site of an Anti-ErbB2 Antibody Obtained With Shotgun Scanning Mutagenesis," J. Mol. Biol. 2002, 320(2):415-428.
Van Veen et al., "Consistency of Sputum Eosinophilia in Difficult-to-Treat Asthma: A 5-year Follow-Up Study", The Journal of Allergy and Clinical Immunology, vol. 124, No. 3, Sep. 2009, pp. 615-617.
Wechsler et al., "Novel Targeted Therapies for Eosinophilic Disorders", Journal of Allergy and Clinical Immunology, vol. 130, No. 3, Sep. 2012, pp. 563-571.

(56) References Cited

OTHER PUBLICATIONS

International Preliminary Report on Patentability for PCT Patent Application No. PCT/US2014/069409, dated Jun. 23, 2016, 12 pages.
International Preliminary Report on Patentability for PCT Patent Application No. PCT/US2015/018188, dated Sep. 15, 2016, 8 Pages.
International Preliminary Report on Patentability for PCT Application No. PCT/US2016/037935, dated Dec. 28, 2017, 11 pages.
International Search Report and Written Opinion for PCT Application No. PCT/US2014/069409, dated Mar. 6, 2015, 19 pages.
International Search Report and Written Opinion for PCT Application No. PCT/US2015/018188, dated Apr. 28, 2015, 13 pages.
International Search Report and Written Opinion for PCT Application No. PCT/US2016/037935, dated Aug. 10, 2016, 15 pages.
Extended European Search Report dated Jun. 29, 2017, for European Patent Application No. 14869424.3, filed on Jun. 24, 2016, 11 pages.
European Partial Search Report dated Aug. 30, 2017, for European Patent Application No. 15755175.5, filed on Aug. 25, 2016, 8 pages.
European Search Report dated Dec. 8, 2017, for European Patent Application No. 15755175.5, filed on Aug. 25, 2016, 15 pages.
Fulkerson et al. "Targeting Eosinophils in Allergy, Inflammation and Beyond," *Nat. Rev. Drug Discov.* vol. 12, No. 2, Feb. 2013, Article NRD3838, pp. 1-23.
O'Donnell, R. et al. (May 2006). "Inflammatory cells in the airways in COPD." *Thorax.* 61(5):448-454.
Rubinstein et al. "Siglec-F Inhibition Reduces Esophageal Eosinophilia and Angiogenesis in a Mouse Model of Eosinophilic Esophagitis," *J. Pediatr. Gastroenterol. Nutr.* vol. 53, No. 4, Oct. 2011, pp. 409-416.
Saha, S. et al. (2006). "Eosinophilic airway inflammation in COPD." *Int. J. Chron. Obstruct. Pulmon Dis.* 1(1):39-47.
Song et al. "Anti-Siglec-F antibody inhibits oral egg allergen induced intestinal eosinophilic inflammation in a mouse model," *Clin. Immunol.* vol. 131, No. 1, Apr. 2009, pp. 157-169.
Spiess, C. et al. (Jul. 23, 2013). "Development of a Human IgG4 Bispecific Antibody for Dual Targeting of Interleukin-4 (IL-4) and Interleukin-13 (IL-13) Cytokines," *J Biol. Chem.* 288(37):26583-26593.
Zimmerman et al. "Siglec-F antibody administration to mice selectively reduces blood and tissue eosinophils," Allergy vol. 63, No. 9, Sep. 2008, pp. 1156-1163.
International Preliminary Report on Patentability for PCT Application No. PCT/US2016/058199, dated Apr. 24, 2018, 6 pages.
International Search Report and Written Opinion for PCT Application No. PCT/US2018/012694, dated Mar. 20, 2018, 12 pages.
International Search Report and Written Opinion for PCT Application No. PCT/US2018/031231, dated Aug. 1, 2018, 19 pages.
International Search Report and Written Opinion for PCT Application No. PCT/US2018/031226, dated Aug. 6, 2018, 16 pages.
Non-Final Office Action dated Dec. 26, 2017, for U.S. Appl. No. 15/121,756, filed Aug. 25, 2016, 22 pages.
Almagro, J. et al. (Jan. 2008). "Humanization of Antibodies," Frontiers in Bioscience 13:1619-1633.
Andersson, C.K. et al. (2011). "Activated MCTC Mast Cells Infiltrate Diseased Lung Areas in Cystic Fibrosis and Idiopathic Pulmonary Fibrosis," Respiratory Research 12:139-151, 13 pages.
Beckett, E.L. et al. (Mar. 2013). "A Short-Term Model of COPD Identifies a Role for mast cell Tryptase," J. Allergy Clin. Immunol. 131(1):752-762.
clinicaltrials.gov. (Apr. 5, 2018). "A Study to Assess the Efficacy and Safety of AK002 in Subjects With Antihistamine-Resistant Chronic Urticaria, NCT03436797," downloaded from https://clinicaltrials.gov/ct2/history/NCT03436797?V_6=View#StudyPageTop, on Jun. 5, 2019, 8 pages.
European Examination Report dated Apr. 1, 2019, for European Patent Application No. 15755175.5, filed on Aug. 25, 2016, 6 pages.
European Extended Search Report dated May 15, 2019 for European Patent No. 16858333.4, filed on Apr. 17, 2019, 7 pages.
European Extended Search Report dated Nov. 15, 2018, for European Patent No. 16812473.3, filed on Jan. 10, 2018, 10 pages.
International Search Report and Written Opinion for PCT Application No. PCT/SU2019/030523, dated Jul. 2, 2019, 8 pages.
Ishitoya, J. (Sep. 29, 2007). "Eosinophilic Sinusitis/Eosinophilic Otitis Media—Chronic Eosinophilic Inflammation of the Upper Respiratory Tract Which has Been Recently Focused," Japan Medical Journal 4353:.53-57, with English Translation, 17 pages total.
O'Brien-Ladner, A.R. et al. (1993). "Bleomycin Injury of the Lung in a Mast-Cell-Deficient Model," Agents Actions 39:20-24.
Rasmussen, H. et al. (Feb. 2018). "A Randomized, Double-Blind, Placebo-Controlled, Ascending Dose Phase 1 Study of AK002, a Novel Siglec-8 Selective Monoclonal Antibody, in Healthy Subjects," J. Allergy Clin. Immunol. 141(2):AB403, Abstract No. L15, 1 page.
Rüger, B. et al. (1994). "Human Mast Cells Produce Type VIII Collagen in vivo," Int. J. Exp. Path. 75:397-404.
Scordamaglia, F. et al. (Feb. 2008). "Perturbations of Natural Killer Cell Regulatory Functions in Respiratory Allergic Diseases," Journal of Allergy and Clinical Immunology 121(2):479-485.
Seibold, J.R. et al. (Nov. 1990). "Dermal Mast Cell Degranulation in Systemic Sclerosis," Arthritis and Rheumatism 33(11):1702-1709.
Takeno, S. et al. (2012). "What is the Difference Between Paranasal Sinus Bronchial Syndrome and Asthma?," Pathology and Treatment of Chronic Sinusitis Associated With Asthma 143:45-53, with English Translation 33 pages total.
Villar, J. et al. (Apr. 2015). "Tryptase is Involved in the Development of Early Ventilator-Induced Pulmonary Fibrosis in Sepsis-Induced Lung Injury," Critical Care 19(138)1-9.

\* cited by examiner

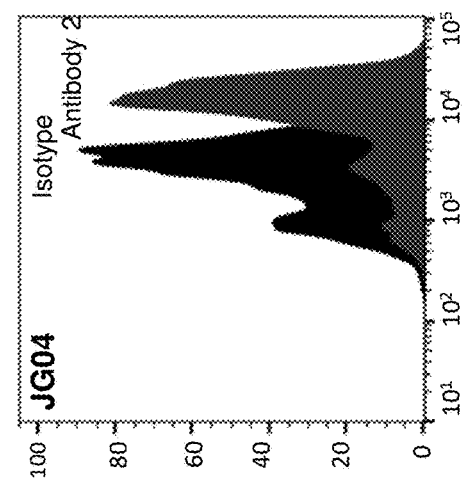
FIG. 3A JG01
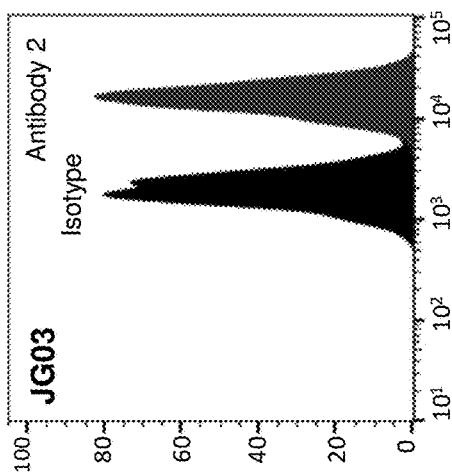
FIG. 3B JG03
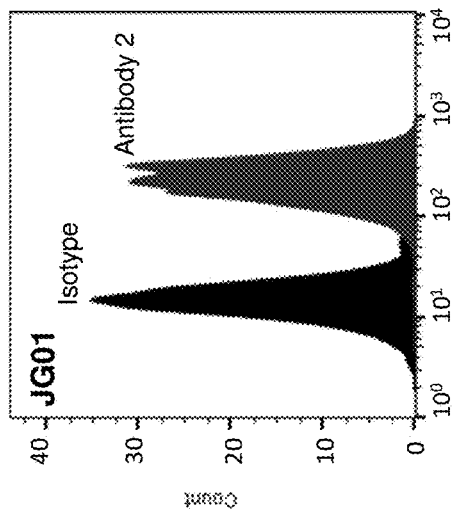
FIG. 3C JG04
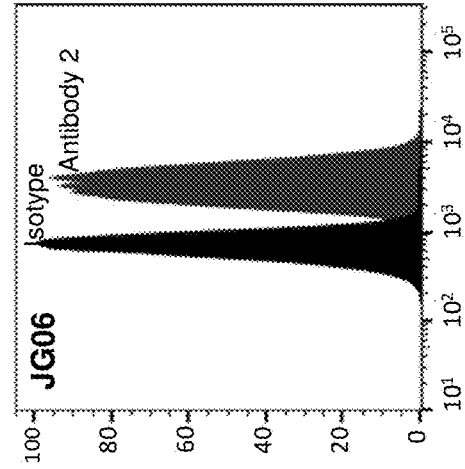
FIG. 3D JG05
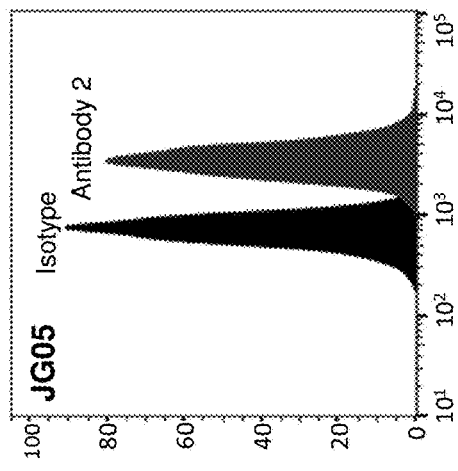
FIG. 3E JG06

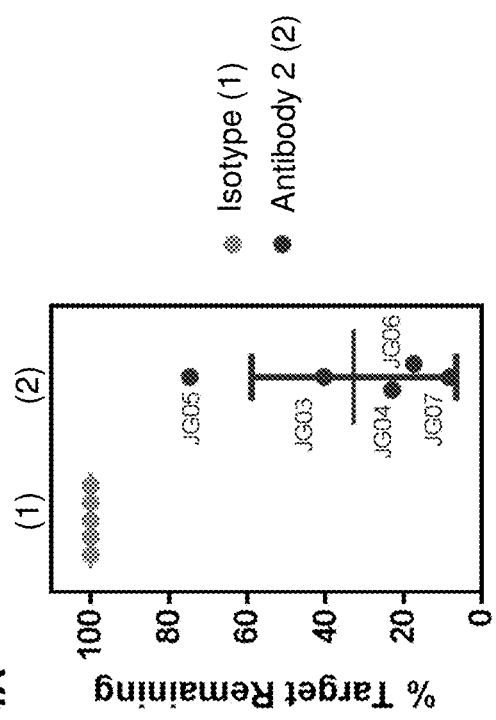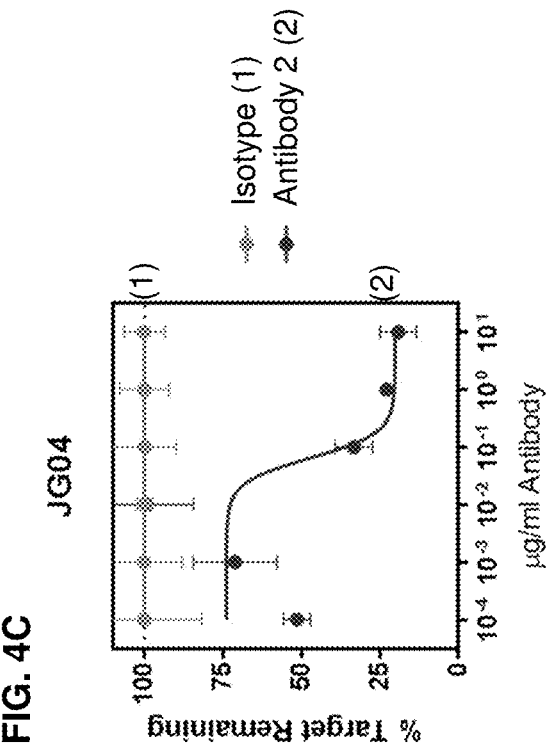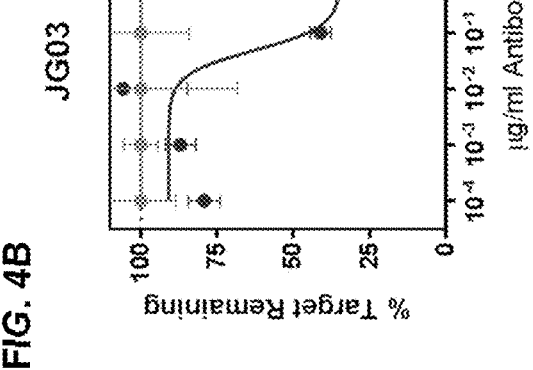
FIG. 4A
FIG. 4B
FIG. 4C

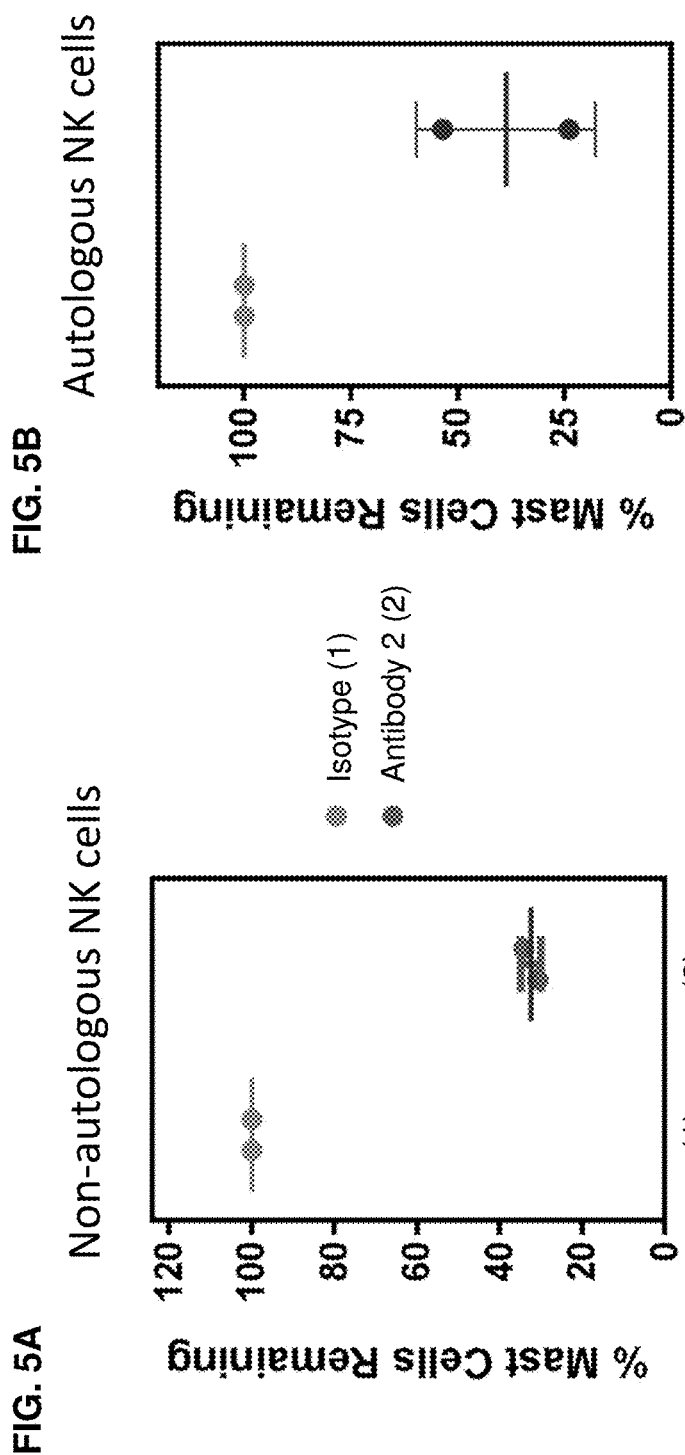

METHODS AND COMPOSITIONS FOR TREATING SYSTEMIC MASTOCYTOSIS

CROSS-REFERENCE TO RELATED APPLICATIONS

This application claims priority to U.S. Provisional Application Ser. No. 62/245,218, filed Oct. 22, 2015, the disclosure of which is incorporated herein by reference in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 701712000400SEQLIST.txt, date recorded: Oct. 7, 2016, size: 91 KB).

FIELD OF THE INVENTION

This invention relates to methods for preventing or treating advanced systemic mastocytosis by administration of antibodies or agonists that bind to human Siglec-8 or compositions comprising said antibodies or agonists.

BACKGROUND OF THE INVENTION

Systemic mastocytosis (SM) is a rare myeloproliferative neoplasm characterized by the accumulation of neoplastic mast cells in one or more extracutaneous organs. The 2008 World Health Organization (WHO) classification recognizes 7 variants and 1 subvariant of systemic mastocytosis patients. These include cutaneous mastocytosis (CM), indolent systemic mastocytosis (ISM), aggressive systemic mastocytosis (ASM), systemic mastocytosis with an associated clonal hematologic non-mast cell lineage disease (SM-AHNMD), mast cell leukemia (MCL), mast cell sarcoma, and extracutaneous mastocytoma, plus a subvariant of ISM termed smoldering systemic mastocytosis (SSM). The major diagnostic criterion in systemic mastocytosis is the presence of multifocal clusters of morphologically abnormal mast cells in the bone marrow in association. Minor diagnostic criteria include elevated serum tryptase level, abnormal mast cell expression of CD25 and/or CD2, and presence of $KIT^{D816V}$ mutation. Advanced systemic mastocytosis is characterized by organ damage due to infiltration of mast cells. See Valent et al., Eur. J. Clin Invest., 2007, 37:435-453 and Valent et al., Allergy, 2014, 69:1267-1274.

In all forms of systemic mastocytosis, anti-mediator drugs are used to control symptoms of mast cell degranulation. In advanced forms of systemic mastocytosis, organ damage is common and patients exhibit reduced life expectancy. In these individuals, cytoreductive agents such as cladribine and interferon-alpha have been used off-label, and inhibitors of KIT D816V are under investigation. A significant unmet need exists for these patients.

Siglecs (sialic acid-binding immunoglobulin-like lectins) are single-pass transmembrane cell surface proteins found predominantly on leukocytes and are characterized by their specificity for sialic acids attached to cell-surface glycoconjugates. The Siglec family contains at least 15 members that are found in mammals (Pillai et al., *Annu Rev Immunol.*, 30:357-392, 2012). These members include sialoadhesion (Siglec-1), CD22 (Siglec-2), CD33 (Siglec-3), myelin associated glycoprotein (Siglec-4), Siglec-5, OBBP1 (Siglec-6), AIRM1 (Siglec-7), SAF-2 (Siglec-8), and CD329 (Siglec-9). Siglec-8 was first discovered as part of efforts to identify novel human eosinophil proteins. In addition to expression by eosinophils, it is also expressed by mast cells and basophils. Siglec-8 recognizes a sulfated glycan, i.e., 6'-sulfo-sialyl Lewis X or 6'-sulfo-sialyl-N-acetyl-S-lactosamine, and contains an intracellular immunoreceptor tyrosine-based inhibitory motif (ITIM) domain shown to inhibit mast cell function. Anti-Siglec-8 antibodies do not directly affect mast cell viability but antibodies with effector function can induce antibody cell-mediated cytotoxicity (ADCC). However, Natural Killer (NK) cells, an important mediator of ADCC activity, have been reported to be defective in some patients with SM-AHNMD, such as patients with chronic myelomonocytic leukemia (CMML) and patients with myelodysplastic syndrome (MDS). See Marcondes et al. PNAS, 2008, 105:2865-2870 and Kiladjian et al., Leukemia, 2006, 20:463-470. In addition, defective cytotoxicity and reduced receptor expression has been observed in tumor-associated and peripheral blood NK cells of cancer patients. See Pahl et al., Immunobiology, 2015, doi: 10.1016/j.imbio.2015.07.012. Therefore, it is unclear if systemic mastocytosis patients have an intact ADCC function that can be induced to kill mast cells.

All references cited herein, including patent applications, patent publications, and scientific literature, are herein incorporated by reference in their entirety, as if each individual reference were specifically and individually indicated to be incorporated by reference.

SUMMARY OF THE INVENTION

Provided herein are methods of using antibodies or agonists that bind to human Siglec-8, or compositions comprising thereof, for the prevention or treatment of advanced systemic mastocytosis. Advanced systemic mastocytosis include, but are not limited to, aggressive systemic mastocytosis (ASM), mast cell leukemia (MCL), and systemic mastocytosis with an associated hematologic non-mast-cell lineage disease (SM-AHNMD). In some embodiments, the SM-AHNMD is selected from the group consisting of: SM-myelodysplastic syndrome (SM-MDS), SM-myeloproliferative neoplasm (SM-MPN), SM-chronic myelomonocytic leukemia (SM-CMML), SM-chronic eosinophilic leukemia (SM-CEL), and SM-acute myeloid leukemia (SM-AML).

In one aspect, provided herein is a method for treating or preventing advanced systemic mastocytosis in an individual comprising administering to the individual an effective amount of an antibody or an agonist that binds to human Siglec-8. In some embodiments herein, the advanced systemic mastocytosis is selected from the group consisting of: aggressive systemic mastocytosis (ASM), mast cell leukemia (MCL), and systemic mastocytosis with an associated hematologic non-mast-cell lineage disease (SM-AHNMD). In a further embodiment, the SM-AHNMD is selected from the group consisting of: SM-myelodysplastic syndrome (SM-MDS), SM-myeloproliferative neoplasm (SM-MPN), SM-chronic myelomonocytic leukemia (SM-CMML), SM-chronic eosinophilic leukemia (SM-CEL), and SM-acute myeloid leukemia (SM-AML). In some embodiments herein, the advanced systemic mastocytosis is associated with eosinophilia. In some embodiments herein, the advanced systemic mastocytosis is not adequately controlled by cladribine, interferon-α, a corticosteroid, a tyrosine kinase inhibitor or a combination thereof. In some embodiments herein, the individual has a KIT D816V mutation. In some embodiments herein, the antibody or agonist depletes or reduces at least about 20% of the mast cells expressing Siglec-8 in a sample obtained from the individual as compared to a baseline level before administration of the antibody or agonist. In some embodiments herein, the antibody or agonist depletes or reduces at least about 30%, about 40% or about 50% of the mast cells expressing Siglec-8 in a sample obtained from the individual as compared to a baseline level before administration of the antibody or agonist. In some further embodiments, the sample is a tissue sample or a biological sample. In a further embodiment, the biological fluid sample is a blood sample. In a further embodiment, the tissue sample is a bone marrow sample, a skin sample, a spleen sample, a lymph node sample, a liver sample or a gastrointestinal tract sample. In some of the embodiments herein, one or more symptom in the individual with advanced systemic mastocytosis is reduced as compared to a baseline level before administration of the antibody or the agonist that binds to human Siglec-8. In some embodiments, one or more pathologic parameter in the individual with advanced systemic mastocytosis is reduced or improved as compared to a baseline level before administration of the antibody or the agonist that binds to human Siglec-8. In some of the embodiments herein, the individual is diagnosed with advanced systemic mastocytosis before administration of the antibody. In any of the embodiments herein, the individual can be a human. In any of the embodiments herein, the antibody can be in a pharmaceutical composition comprising the antibody and a pharmaceutically acceptable carrier. In any of the embodiments herein, the agonist can be in a pharmaceutical composition comprising the agonist and a pharmaceutically acceptable carrier.

In another aspect, provided herein is a method for depleting mast cells expressing Siglec-8 in an individual with advanced systemic mastocytosis comprising administering to the individual an effective amount of an antibody or an agonist that binds to human Siglec-8, wherein the antibody or agonist kills mast cells expressing Siglec-8 by ADCC activity. In some embodiments herein, the advanced systemic mastocytosis is selected from the group consisting of: aggressive systemic mastocytosis (ASM), mast cell leukemia (MCL), and systemic mastocytosis with an associated hematologic non-mast-cell lineage disease (SM-AHNMD). In a further embodiment, the SM-AHNMD is selected from the group consisting of: SM-myelodysplastic syndrome (SM-MDS), SM-myeloproliferative neoplasm (SM-MPN), SM-chronic myelomonocytic leukemia (SM-CMML), SM-chronic eosinophilic leukemia (SM-CEL), and SM-acute myeloid leukemia (SM-AML). In some embodiments herein, the advanced systemic mastocytosis is associated with eosinophilia. In some embodiments herein, the advanced systemic mastocytosis is not adequately controlled by cladribine, interferon-α, a corticosteroid, a tyrosine kinase inhibitor or a combination thereof. In some embodiments herein, the individual has a KIT D816V mutation. In some embodiments herein, the antibody or agonist depletes at least about 20% of the mast cells expressing Siglec-8 in a sample obtained from the individual as compared to a baseline level before administration of the antibody or agonist. In some embodiments herein, the antibody or agonist depletes at least about 30%, about 40% or about 50% of the mast cells expressing Siglec-8 in a sample obtained from the individual as compared to a baseline level before administration of the antibody or agonist. In some further embodiments, the sample is a tissue sample or a biological sample. In a further embodiment, the biological fluid sample is a blood sample. In a further embodiment, the tissue sample is a bone marrow sample, a skin sample, a spleen sample, a lymph node sample, a liver sample or a gastrointestinal tract sample. In some of the embodiments herein, one or more symptom in the individual with advanced systemic mastocytosis is reduced as compared to a baseline level before administration of the antibody or the agonist that binds to human Siglec-8. In some embodiments, one or more pathologic parameter in the individual with advanced systemic mastocytosis is reduced or improved as compared to a baseline level before administration of the antibody or the agonist that binds to human Siglec-8. In some of the embodiments herein, the individual is diagnosed with advanced systemic mastocytosis before administration of the antibody. In any of the embodiments herein, the individual can be a human. In any of the embodiments herein, the antibody can be in a pharmaceutical composition comprising the antibody and a pharmaceutically acceptable carrier. In any of the embodiments herein, the agonist can be in a pharmaceutical composition comprising the agonist and a pharmaceutically acceptable carrier.

In another aspect, provided herein is a composition comprising an antibody or an agonist that binds to human Siglec-8 for use in treating or preventing advanced systemic mastocytosis in an individual. In some embodiments, the antibody comprises a Fc region and N-glycoside-linked carbohydrate chains linked to the Fc region, wherein less than 50% of the N-glycoside-linked carbohydrate chains contain a fucose residue. In a further embodiment, substantially none of the N-glycoside-linked carbohydrate chains contain a fucose residue. In some embodiments herein, the advanced systemic mastocytosis is selected from the group consisting of: aggressive systemic mastocytosis (ASM), mast cell leukemia (MCL), and systemic mastocytosis with an associated hematologic non-mast-cell lineage disease (SM-AHNMD). In a further embodiment, the SM-AHNMD is selected from the group consisting of: SM-myelodysplastic syndrome (SM-MDS), SM-myeloproliferative neoplasm (SM-MPN), SM-chronic myelomonocytic leukemia (SM-CMML), SM-chronic eosinophilic leukemia (SM-CEL), and SM-acute myeloid leukemia (SM-AML). In some embodiments herein, the advanced systemic mastocytosis is associated with eosinophilia. In some embodiments herein, the advanced systemic mastocytosis is not adequately controlled by cladribine, interferon-α, a corticosteroid, a tyrosine kinase inhibitor or a combination thereof. In some embodiments herein, the individual has a KIT D816V mutation. In some embodiments herein, the antibody or agonist depletes or reduces at least about 20% of the mast cells expressing Siglec-8 in a sample obtained from the individual as compared to a baseline level before administration of the antibody or agonist. In some embodiments herein, the antibody or agonist depletes or reduces at least about 30%, about 40% or about 50% of the mast cells expressing Siglec-8 in a sample obtained from the individual as compared to a baseline level before administration of the antibody or agonist. In some further embodiments, the sample is a tissue sample or a biological sample. In a further embodiment, the biological fluid sample is a blood sample. In a further embodiment, the tissue sample is a bone marrow sample, a skin sample, a spleen sample, a lymph node sample, a liver sample or a gastrointestinal tract sample. In some of the embodiments herein, one or more symptom in the individual with advanced systemic mastocytosis is reduced as compared to a baseline level before administration of the antibody or the agonist that binds to human Siglec-8. In some embodiments, one or more pathologic parameter in the individual with advanced systemic mastocytosis is reduced or improved as compared to a baseline level before administration of the antibody or the agonist that binds to human Siglec-8. In some of the embodiments herein, the individual is diagnosed with advanced systemic mastocytosis before administration of the antibody. In any of the embodiments herein, the individual can be a human. In any of the embodiments herein, the composition can further comprise a pharmaceutically acceptable carrier.

In another aspect, provided herein is a composition comprising an antibody or an agonist that binds to human Siglec-8 for use in depleting mast cells expressing Siglec-8 in an individual with advanced systemic mastocytosis, wherein the antibody or agonist kills mast cells expressing Siglec-8 by ADCC activity. In some embodiments, the antibody comprises a Fc region and N-glycoside-linked carbohydrate chains linked to the Fc region, wherein less than 50% of the N-glycoside-linked carbohydrate chains contain a fucose residue. In a further embodiment, substantially none of the N-glycoside-linked carbohydrate chains contain a fucose residue. In some embodiments herein, the advanced systemic mastocytosis is selected from the group consisting of: aggressive systemic mastocytosis (ASM), mast cell leukemia (MCL), and systemic mastocytosis with an associated hematologic non-mast-cell lineage disease (SM-AHNMD). In a further embodiment, the SM-AHNMD is selected from the group consisting of: SM-myelodysplastic syndrome (SM-MDS), SM-myeloproliferative neoplasm (SM-MPN), SM-chronic myelomonocytic leukemia (SM-CMML), SM-chronic eosinophilic leukemia (SM-CEL), and SM-acute myeloid leukemia (SM-AML). In some embodiments herein, the advanced systemic mastocytosis is associated with eosinophilia. In some embodiments herein, the advanced systemic mastocytosis is not adequately controlled by cladribine, interferon-α, a corticosteroid, a tyrosine kinase inhibitor or a combination thereof. In some embodiments herein, the individual has a KIT D816V mutation. In some embodiments herein, the antibody or agonist depletes at least about 20% of the mast cells expressing Siglec-8 in a sample obtained from the individual as compared to a baseline level before administration of the antibody or agonist. In some embodiments herein, the antibody or agonist depletes or reduces at least about 30%, about 40% or about 50% of the mast cells expressing Siglec-8 in a sample obtained from the individual as compared to a baseline level before administration of the antibody or agonist. In some further embodiments, the sample is a tissue sample or a biological sample. In a further embodiment, the biological fluid sample is a blood sample. In a further embodiment, the tissue sample is a bone marrow sample, a skin sample, a spleen sample, a lymph node sample, a liver sample or a gastrointestinal tract sample. In some of the embodiments herein, one or more symptom in the individual with advanced systemic mastocytosis is reduced as compared to a baseline level before administration of the antibody or the agonist that binds to human Siglec-8. In some embodiments, one or more pathologic parameter in the individual with advanced systemic mastocytosis is reduced or improved as compared to a baseline level before administration of the antibody or the agonist that binds to human Siglec-8. In some of the embodiments herein, the individual is diagnosed with advanced systemic mastocytosis before administration of the antibody. In any of the embodiments herein, the individual can be a human. In any of the embodiments herein, the composition can further comprise a pharmaceutically acceptable carrier.

In some aspects, also provided herein is an article of manufacture or kit comprising a medicament comprising an antibody or an agonist that binds to human Siglec-8 and a package insert comprising instructions for administration of the medicament in an individual in need thereof to treat or prevent advanced systemic mastocytosis. In some embodiments herein, the advanced systemic mastocytosis is selected from the group consisting of: aggressive systemic mastocytosis (ASM), mast cell leukemia (MCL), and systemic mastocytosis with an associated hematologic non-mast-cell lineage disease (SM-AHNMD). In a further embodiment, the SM-AHNMD is selected from the group consisting of: SM-myelodysplastic syndrome (SM-MDS), SM-myeloproliferative neoplasm (SM-MPN), SM-chronic myelomonocytic leukemia (SM-CMML), SM-chronic eosinophilic leukemia (SM-CEL), and SM-acute myeloid leukemia (SM-AML). In some embodiments herein, the advanced systemic mastocytosis is associated with eosinophilia. In some embodiments herein, the advanced systemic mastocytosis is not adequately controlled by cladribine, interferon-α, a corticosteroid, a tyrosine kinase inhibitor or a combination thereof. In some embodiments herein, the individual has a KIT D816V mutation. In some embodiments herein, the package insert further indicates that the treatment is effective in depleting or reduces at least about 20% of the mast cells expressing Siglec-8 in a sample obtained from the individual as compared to a baseline level before administration of the medicament comprising the antibody or agonist. In some embodiments herein, the package insert further indicates that the treatment is effective in depleting or reduces at least about 30%, about 40% or about 50% of the mast cells expressing Siglec-8 in a sample obtained from the individual as compared to a baseline level before administration of the antibody or agonist. In some further embodiments, the sample is a tissue sample or a biological sample. In a further embodiment, the biological fluid sample is a blood sample. In a further embodiment, the tissue sample is a bone marrow sample, a skin sample, a spleen sample, a lymph node sample, a liver sample or a gastrointestinal tract sample. In some of the embodiments herein, the package insert further indicates that the treatment is effective in reducing or improving one or more symptom in the individual with advanced systemic mastocytosis as compared to a baseline level before administration of the medicament comprising the antibody or the agonist. In some embodiments, the package insert further indicates that the treatment is effective in reducing or improving one or more pathologic parameter in the individual with advanced systemic mastocytosis as compared to a baseline level before administration of the medicament comprising the antibody or the agonist. In some embodiments herein, the article of manufacture or kit further comprises one or more additional medicament, and wherein the package insert further comprises instructions for simultaneous or sequential administration of the one or more additional medicament in combination with the medicament comprising the antibody or agonist that binds to Siglec-8. In some embodiments, the one or more additional medicament comprises a therapeutic agent selected from the group consisting of: a cytotoxic agent, a cytokine, a growth inhibitory agent, a protein kinase inhibitor, a corticosteroid, an antibody, or an anti-cancer agent. In some of the embodiments herein, the individual is diagnosed with advanced systemic mastocytosis before administration of the antibody. In any of the embodiments herein, the individual can be a human. In any of the embodiments herein, the antibody can be in a pharmaceutical composition comprising the antibody and a pharmaceutically acceptable carrier. In any of the embodiments herein, the agonist can be in a pharmaceutical composition comprising the agonist and a pharmaceutically acceptable carrier.

In some aspects, also provided herein is an article of manufacture or kit comprising a medicament comprising an antibody or an agonist that binds to human Siglec-8 and a package insert comprising instructions for administration of the medicament in an individual with advanced systemic mastocytosis to deplete mast cells, wherein the antibody or agonist kills mast cells expressing Siglec-8 by ADCC activity. In some embodiments herein, the advanced systemic mastocytosis is selected from the group consisting of: aggressive systemic mastocytosis (ASM), mast cell leukemia (MCL), and systemic mastocytosis with an associated hematologic non-mast-cell lineage disease (SM-AHNMD). In a further embodiment, the SM-AHNMD is selected from the group consisting of: SM-myelodysplastic syndrome (SM-MDS), SM-myeloproliferative neoplasm (SM-MPN), SM-chronic myelomonocytic leukemia (SM-CMML), SM-chronic eosinophilic leukemia (SM-CEL), and SM-acute myeloid leukemia (SM-AML). In some embodiments herein, the advanced systemic mastocytosis is associated with eosinophilia. In some embodiments herein, the advanced systemic mastocytosis is not adequately controlled by cladribine, interferon-α, a corticosteroid, a tyrosine kinase inhibitor or a combination thereof. In some embodiments herein, the individual has a KIT D816V mutation. In some embodiments herein, the package insert further indicates that the treatment is effective in depleting at least about 20% of the mast cells expressing Siglec-8 in a sample obtained from the individual as compared to a baseline level before administration of the medicament comprising the antibody or agonist. In some embodiments herein, the package insert further indicates that the treatment is effective in depleting at least about 30%, about 40% or about 50% of the mast cells expressing Siglec-8 in a sample obtained from the individual as compared to a baseline level before administration of the medicament comprising the antibody or agonist. In some further embodiments, the sample is a tissue sample or a biological sample. In a further embodiment, the biological fluid sample is a blood sample. In a further embodiment, the tissue sample is a bone marrow sample, a skin sample, a spleen sample, a lymph node sample, a liver sample or a gastrointestinal tract sample. In some of the embodiments herein, the package insert further indicates that the treatment is effective in reducing or improving one or more symptom in the individual with advanced systemic mastocytosis as compared to a baseline level before administration of the medicament comprising the antibody or the agonist. In some embodiments, the package insert further indicates that the treatment is effective in reducing or improving one or more pathologic parameter in the individual with advanced systemic mastocytosis as compared to a baseline level before administration of the medicament comprising the antibody or the agonist. In some embodiments herein, the article of manufacture or kit further comprises one or more additional medicament, and wherein the package insert further comprises instructions for simultaneous or sequential administration of the one or more additional medicament in combination with the medicament comprising the antibody or agonist that binds to Siglec-8. In some embodiments, the one or more additional medicament comprises a therapeutic agent selected from the group consisting of: a cytotoxic agent, a cytokine, a growth inhibitory agent, a protein kinase inhibitor, a corticosteroid, an antibody, or an anti-cancer agent. In some of the embodiments herein, the individual is diagnosed with advanced systemic mastocytosis before administration of the antibody. In any of the embodiments herein, the individual can be a human. In any of the embodiments herein, the antibody can be in a pharmaceutical composition comprising the antibody and a pharmaceutically acceptable carrier. In any of the embodiments herein, the agonist can be in a pharmaceutical composition comprising the agonist and a pharmaceutically acceptable carrier.

In other aspects, provided herein is a method for treating or preventing advanced systemic mastocytosis in an individual comprising administering to the individual an effective amount of an agonist that binds to human Siglec-8. In some embodiments herein, the agonist is a 6'-sulfo-sLe$^X$-containing agonist selected from the group consisting of: a 6'-sulfo-sLe$^X$-containing ligand, a 6'-sulfo-sLe$^X$-containing oligosaccharide, a 6'-sulfo-sLe$^X$-containing polypeptide, and a 6'-sulfo-sLe$^X$-containing glycoprotein. In some embodiments, the agonist is an agonist antibody that binds to human Siglec-8.

In yet another aspect, provided herein is a method for depleting or reducing mast cells in an individual with advanced mastocytosis comprising administering to the individual an effective amount of an agonist that binds to human Siglec-8. In some embodiments herein, the agonist is a 6'-sulfo-sLe$^X$-containing agonist selected from the group consisting of: a 6'-sulfo-sLe$^X$-containing ligand, a 6'-sulfo-sLe$^X$-containing oligosaccharide, a 6'-sulfo-sLe$^X$-containing polypeptide, and a 6'-sulfo-sLe$^X$-containing glycoprotein. In some embodiments, the agonist is an agonist antibody that binds to human Siglec-8.

In any of the embodiments of the methods and compositions for use therein, the antibody can be a monoclonal antibody. In any of the embodiments of the methods and compositions for use therein, the antibody can be an IgG1 antibody. In any of the embodiments of the methods and compositions for use therein, the antibody can be engineered to improve antibody-dependent cell-mediated cytotoxicity (ADCC) activity. In a further embodiment, the antibody comprises at least one amino acid substitution in the Fc region that improves ADCC activity. In any of the embodiments of the methods and compositions for use therein, one or two of the heavy chains of the antibody can be non-fucosylated. In any of the embodiments of the methods and compositions for use therein, the antibody can be a human antibody, a humanized antibody or a chimeric antibody. In some of the embodiments of the methods and compositions for use herein, the antibody is an antibody fragment selected from the group consisting of Fab, Fab'-SH, Fv, scFv, and (Fab')$_2$ fragments. In some of the embodiments of the methods and compositions for use herein, the antibody comprises an antibody fragment selected from the group consisting of Fab, Fab'-SH, Fv, scFv, and (Fab')$_2$ fragments. In any of the embodiments of the methods and compositions for use herein, the antibody can be administered in combination with one or more additional therapeutic agent selected from the group consisting of: a cytotoxic agent, a cytokine, a growth inhibitory agent, a protein kinase inhibitor, a corticosteroid, an antibody, or an anti-cancer agent. In some embodiments, the antibody comprises a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence of SEQ ID NO:63; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:66. In some embodiments, the antibody comprises a heavy chain variable region comprising the amino acid sequence of SEQ ID NO:6; and/or a light chain variable region comprising the amino acid sequence selected from SEQ ID NOs:16 or 21. In some embodiments, the antibody comprises a heavy chain Fc region comprising a human IgG Fc region. In a further embodiment, the human IgG Fc region comprises a human IgG1 or a human IgG4. In a further embodiment, the human IgG4 comprises the amino acid substitution S228P, and wherein the amino acid residues are numbered according to the EU index as in Kabat. In some embodiments, the human IgG1 comprises the amino acid sequence of SEQ ID NO:78. In some embodiments, the human IgG4 comprises the amino acid sequence of SEQ ID NO:79. In some embodiments, the antibody comprises a heavy chain comprising the amino acid sequence of SEQ ID NO:75; and/or a light chain comprising the amino acid sequence SEQ ID NOs:76 or 77. In some embodiments, the antibody comprises a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence selected from SEQ ID NOs:67-70; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:71. In some embodiments, the antibody comprises a heavy chain variable region comprising the amino acid sequence selected from SEQ ID NOs:11-14; and/or a light chain variable region comprising the amino acid sequence selected from SEQ ID NOs:23-24. In some embodiments, the antibody comprises a heavy chain variable region comprising the amino acid sequence selected from SEQ ID NOs:2-14; and/or a light chain variable region comprising the amino acid sequence selected from SEQ ID NOs:16-24. In some embodiments, the antibody comprises a heavy chain variable region comprising the amino acid sequence selected from SEQ ID NOs:2-10; and/or a light chain variable region comprising the amino acid sequence selected from SEQ ID NOs:16-22. In some embodiments, the antibody comprises: (a) heavy chain variable region comprising: (1) an HC-FR1 comprising the amino acid sequence selected from SEQ ID NOs:26-29; (2) an HVR-H1 comprising the amino acid sequence of SEQ ID NO:61; (3) an HC-FR2 comprising the amino acid sequence selected from SEQ ID NOs:31-36; (4) an HVR-H2 comprising the amino acid sequence of SEQ ID NO:62; (5) an HC-FR3 comprising the amino acid sequence selected from SEQ ID NOs:38-43; (6) an HVR-H3 comprising the amino acid sequence of SEQ ID NO:63; and (7) an HC-FR4 comprising the amino acid sequence selected from SEQ ID NOs:45-46, and/or (b) a light chain variable region comprising: (1) an LC-FR1 comprising the amino acid sequence selected from SEQ ID NOs:48-49; (2) an HVR-L1 comprising the amino acid sequence of SEQ ID NO:64; (3) an LC-FR2 comprising the amino acid sequence selected from SEQ ID NOs:51-53; (4) an HVR-L2 comprising the amino acid sequence of SEQ ID NO:65; (5) an LC-FR3 comprising the amino acid sequence selected from SEQ ID NOs:55-58; (6) an HVR-L3 comprising the amino acid sequence of SEQ ID NO:66; and (7) an LC-FR4 comprising the amino acid sequence of SEQ ID NO:60. In some embodiments, the antibody comprises: (a) heavy chain variable region comprising: (1) an HC-FR1 comprising the amino acid sequence of SEQ ID NO:26; (2) an HVR-H1 comprising the amino acid sequence of SEQ ID NO:61; (3) an HC-FR2 comprising the amino acid sequence of SEQ ID NO:34; (4) an HVR-H2 comprising the amino acid sequence of SEQ ID NO:62; (5) an HC-FR3 comprising the amino acid sequence of SEQ ID NO:38; (6) an HVR-H3 comprising the amino acid sequence of SEQ ID NO:63; and (7) an HC-FR4 comprising the amino acid sequence of SEQ ID NOs:45; and/or (b) a light chain variable region comprising: (1) an LC-FR1 comprising the amino acid sequence of SEQ ID NO:48; (2) an HVR-L1 comprising the amino acid sequence of SEQ ID NO:64; (3) an LC-FR2 comprising the amino acid sequence of SEQ ID NO:51; (4) an HVR-L2 comprising the amino acid sequence of SEQ ID NO:65; (5) an LC-FR3 comprising the amino acid sequence of SEQ ID NO:55; (6) an HVR-L3 comprising the amino acid sequence of SEQ ID NO:66; and (7) an LC-FR4 comprising the amino acid sequence of SEQ ID NO:60. In some embodiments, the antibody comprises: (a) heavy chain variable region comprising: (1) an HC-FR1 comprising the amino acid sequence of SEQ ID NO:26; (2) an HVR-H1 comprising the amino acid sequence of SEQ ID NO:61; (3) an HC-FR2 comprising the amino acid sequence of SEQ ID NO:34; (4) an HVR-H2 comprising the amino acid sequence of SEQ ID NO:62; (5) an HC-FR3 comprising the amino acid sequence of SEQ ID NO:38; (6) an HVR-H3 comprising the amino acid sequence of SEQ ID NO:63; and (7) an HC-FR4 comprising the amino acid sequence of SEQ ID NOs:45; and/or (b) a light chain variable region comprising: (1) an LC-FR1 comprising the amino acid sequence of SEQ ID NO:48; (2) an HVR-L1 comprising the amino acid sequence of SEQ ID NO:64; (3) an LC-FR2 comprising the amino acid sequence of SEQ ID NO:51; (4) an HVR-L2 comprising the amino acid sequence of SEQ ID NO:65; (5) an LC-FR3 comprising the amino acid sequence of SEQ ID NO:58; (6) an HVR-L3 comprising the amino acid sequence of SEQ ID NO:66; and (7) an LC-FR4 comprising the amino acid sequence of SEQ ID NO:60. In some embodiments, the antibody comprises a heavy chain variable region comprising (i) HVR-H1 comprising the amino acid sequence of SEQ ID NO:88, (ii) HVR-H2 comprising the amino acid sequence of SEQ ID NO:91, and (iii) HVR-H3 comprising the amino acid sequence of SEQ ID NO:94; and/or a light chain variable region comprising (i) HVR-L1 comprising the amino acid sequence of SEQ ID NO:97, (ii) HVR-L2 comprising the amino acid sequence of SEQ ID NO:100, and (iii) HVR-L3 comprising the amino acid sequence of SEQ ID NO:103. In some embodiments, the antibody comprises a heavy chain variable region comprising (i) HVR-H1 comprising the amino acid sequence of SEQ ID NO:89, (ii) HVR-H2 comprising the amino acid sequence of SEQ ID NO:92, and (iii) HVR-H3 comprising the amino acid sequence of SEQ ID NO:95; and/or a light chain variable region comprising (i) HVR-L1 comprising the amino acid sequence of SEQ ID NO:98, (ii) HVR-L2 comprising the amino acid sequence of SEQ ID NO:101, and (iii) HVR-L3 comprising the amino acid sequence of SEQ ID NO:104. In some embodiments, the antibody comprises a heavy chain variable region comprising (i) HVR-H1 comprising the amino acid sequence of SEQ ID NO:90, (ii) HVR-H2 comprising the amino acid sequence of SEQ ID NO:93, and (iii) HVR-H3 comprising the amino acid sequence of SEQ ID NO:96; and/or a light chain variable region comprising (i) HVR-L1 comprising the amino acid sequence of SEQ ID NO:99, (ii) HVR-L2 comprising the amino acid sequence of SEQ ID NO:102, and (iii) HVR-L3 comprising the amino acid sequence of SEQ ID NO:105. In some embodiments, the antibody comprises a heavy chain variable region comprising the amino acid sequence of SEQ ID NO:106; and/or a light chain variable region comprising the amino acid sequence of SEQ ID NO:109. In some embodiments, the antibody comprises a heavy chain variable region comprising the amino acid sequence of SEQ ID NO:107; and/or a light chain variable region comprising the amino acid sequence of SEQ ID NO:110. In some embodiments, the antibody comprises a heavy chain variable region comprising the amino acid sequence of SEQ ID NO:108; and/or a light chain variable region comprising the amino acid sequence of SEQ ID NO:111.

It is to be understood that one, some, or all of the properties of the various embodiments described herein may be combined to form other embodiments of the present invention. These and other aspects of the invention will become apparent to one of skill in the art. These and other embodiments of the invention are further described by the detailed description that follows.

BRIEF DESCRIPTION OF THE DRAWINGS

FIG. 1A-E) Siglec-8 expression (middle panel for each patient) or FIG. 1A-E) CD25 expression (right panel for each patient) on the defined mast cell population are shown compared to isotype-matched control antibodies.

FIG. 3A-B is a series of histograms showing binding of non-fucosylated humanized anti-Siglec-8 antibody to NK Cells from bone marrow or PBL of systemic mastocytosis patients. PBL or bone marrow aspirates from mastocytosis patients were incubated with fluorochrome-labeled non-fucosylated humanized anti-Siglec-8 antibody (Antibody 2) or isotype-matched antibody (Isotype) at 1 mg/mL and fluorochrome-labeled antibodies against CD16 and CD56. Binding of non-fucosylated humanized anti-Siglec-8 antibody to $CD16^+CD56^+SSC^{low}$ NK cells in samples from FIG. 3A) patient JG01, FIG. 3B) patient JG03, FIG. 3C) patient JG04, FIG. 3D) patient JG05, and FIG. 3E) patient JG06 is shown as compared to isotype-matched control antibodies.

FIG. 4A-C is a series of graphs showing peripheral blood leukocytes (PBL) from systemic mastocytosis patients can mediate non-fucosylated humanized anti-Siglec-8 antibody-induced ADCC activity against Siglec-8 positive target cells. FIG. 4A) PBLs from five systemic mastocytosis patients (JG03, JG04, JG05, JG06, and JG07) were incubated for 48 hours with 1 µg/mL non-fucosylated humanized anti-Siglec-8 antibody (Antibody 2), or isotype control antibody (isotype) at the indicated concentrations in the presence of the Ramos 2C10 target cell line at an Effector:Target cell ratio of 10:1. After incubation, residual $CD20^+FSC^{hi}/SSC^{mid}$ Ramos 2C10 target cells were quantified by flow cytometry and the percentage remaining were compared to samples incubated with isotype control antibodies. Mean±SD of two biological replicates are shown. Comparisons with p<0.05 are indicated with an asterisk (*). PBLs from FIG. 4B) patient JG03 and FIG. 4C) patient JG04 were incubated with increasing amounts of non-fucosylated humanized anti-Siglec-8 antibody (Antibody 2), or isotype control antibody (isotype) in the presence of the Ramos 2C10 target cell line at an Effector:Target cell ratio of 10:1. After incubation, residual $CD20^+FSC^{hi}/SSC^{mid}$ Ramos 2C10 target cells were quantified by flow cytometry and the percentage remaining were compared to samples incubated with isotype control antibodies. Mean±SD of two biological replicates are shown. Comparisons with p<0.05 are indicated with an asterisk (*).

FIG. 5A-B is a series of graphs showing non-fucosylated humanized anti-Siglec-8 antibody induced ADCC activity against systemic mastocytosis bone marrow mast cells with non-autologous and autologous NK cells. Enriched mast cells were treated with either isotype-matched (isotype) or non-fucosylated humanized anti-Siglec-8 antibody (Antibody 2) at a concentration of 1 mg/mL. FIG. 5A) Purified CD16+ NK cells from a healthy donor (non-autologous NK cells) were added to enriched mast cells from patient JG01 at an Effector:Target cell ratio of 10:1. FIG. 5B) Purified CD16+ NK cells from patient JG07 (autologous NK cells) were added to enriched mast cells from patient JG07 at an Effector:Target cell ratio of 10:1. Percentage of $CD117^+ IgER^+$ mast cells remaining after 48 hours of incubation was compared to isotype control treated groups.

DETAILED DESCRIPTION

I. Definitions

Figures 1A, 1B, 1C:
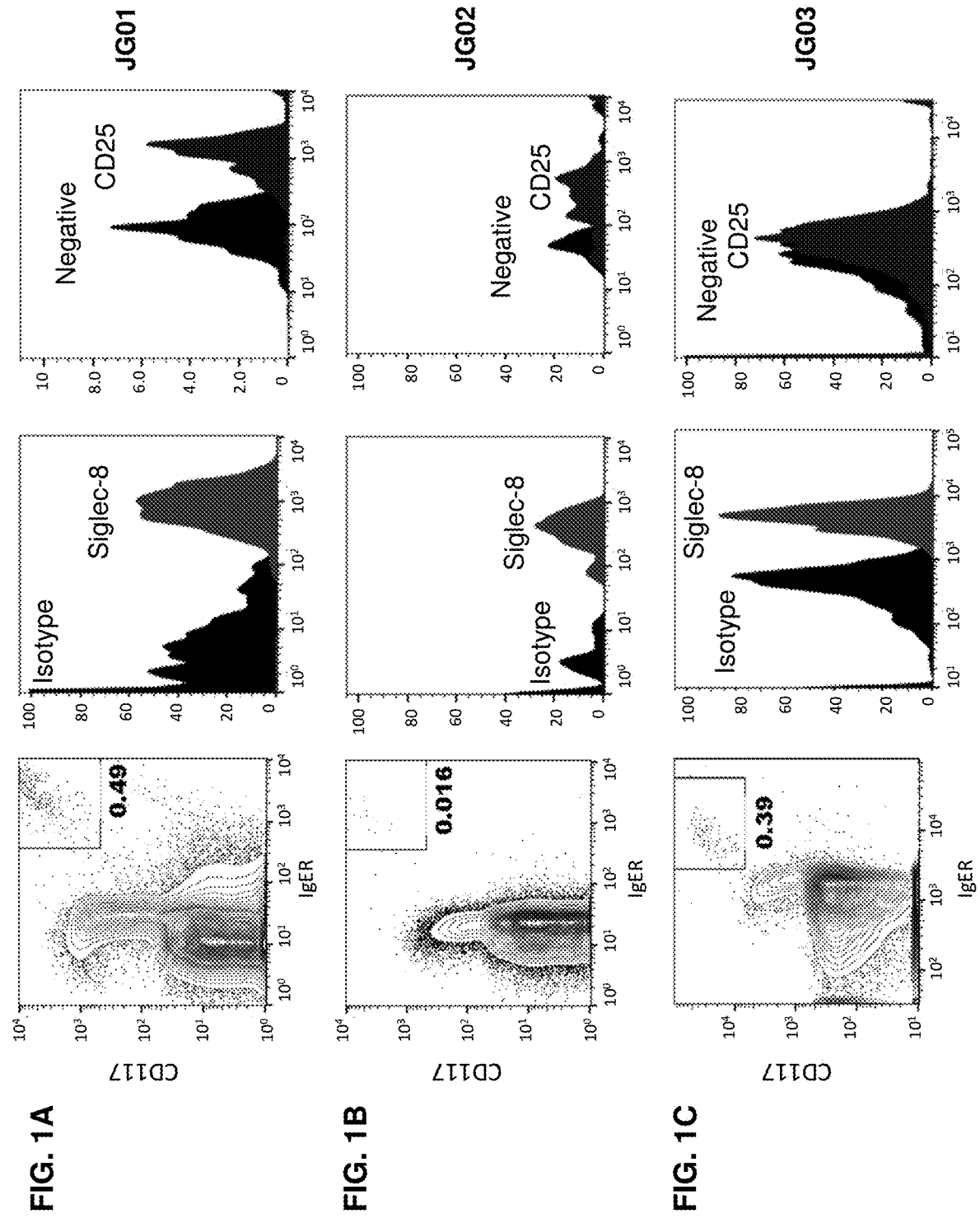
FIG. 1A-E is a series of histograms showing Siglec-8 expression on the surface of mast cells in bone marrow of systemic mastocytosis patients including aberrant mast cells expressing CD25. Bone marrow aspirates from mastocytosis patients were incubated with fluorochrome labeled antibodies targeting CD117, IgE receptor (IgER), Siglec-8, or CD25. Percentage of CD117+IgER+ mast cells are shown for each patient, FIG. 1A) JG01 (left panel), FIG. 1B) JG02 (left panel), FIG. 1C) JG03 (left panel), FIG. 1D) JG04 (left panel), and FIG. 1E) JG05 (left panel).
Figures 1D, 1E:
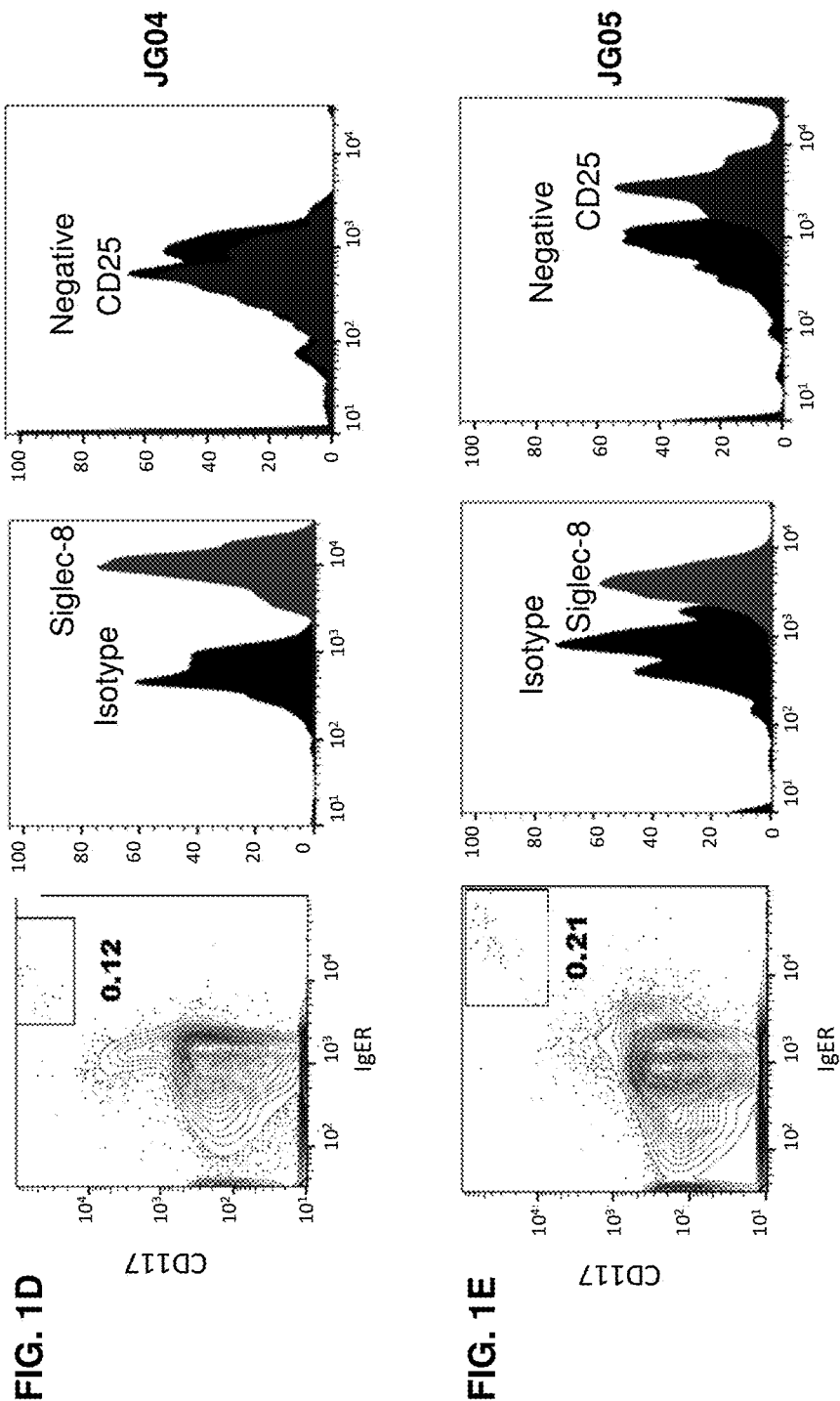

Before describing the invention in detail, it is to be understood that this invention is not limited to particular compositions or biological systems, which can, of course, vary. It is also to be understood that the terminology used herein is for the purpose of describing particular embodiments only, and is not intended to be limiting. As used in this specification and the appended claims, the singular forms "a", "an" and "the" include plural referents unless the content clearly dictates otherwise. Thus, for example, reference to "a molecule" optionally includes a combination of two or more such molecules, and the like.

The term "about" as used herein refers to the usual error range for the respective value readily known to the skilled person in this technical field. Reference to "about" a value or parameter herein includes (and describes) embodiments that are directed to that value or parameter per se.

It is understood that aspects and embodiments of the invention described herein include "comprising," "consisting," and "consisting essentially of" aspects and embodiments.

The term "antibody" includes polyclonal antibodies, monoclonal antibodies (including full length antibodies which have an immunoglobulin Fc region), antibody compositions with polyepitopic specificity, multispecific antibodies (e.g., bispecific antibodies, diabodies, and single-chain molecules, as well as antibody fragments (e.g., Fab, F(ab')$_2$, and Fv). The term "immunoglobulin" (Ig) is used interchangeably with "antibody" herein.

The basic 4-chain antibody unit is a heterotetrameric glycoprotein composed of two identical light (L) chains and two identical heavy (H) chains. An IgM antibody consists of 5 of the basic heterotetramer units along with an additional polypeptide called a J chain, and contains 10 antigen binding sites, while IgA antibodies comprise from 2-5 of the basic 4-chain units which can polymerize to form polyvalent assemblages in combination with the J chain. In the case of IgGs, the 4-chain unit is generally about 150,000 daltons. Each L chain is linked to an H chain by one covalent disulfide bond, while the two H chains are linked to each other by one or more disulfide bonds depending on the H chain isotype. Each H and L chain also has regularly spaced intrachain disulfide bridges. Each H chain has at the N-terminus, a variable domain ($V_H$) followed by three constant domains ($C_H$) for each of the α and γ chains and four $C_H$ domains for μ, and ε isotypes. Each L chain has at the N-terminus, a variable domain ($V_L$) followed by a constant domain at its other end. The $V_L$ is aligned with the $V_H$ and the $C_L$ is aligned with the first constant domain of the heavy chain ($C_H1$). Particular amino acid residues are believed to form an interface between the light chain and heavy chain variable domains. The pairing of a $V_H$ and $V_L$ together forms a single antigen-binding site. For the structure and properties of the different classes of antibodies, see e.g., *Basic and Clinical Immunology*, 8th Edition, Daniel P. Sties, Abba I. Terr and Tristram G. Parsolw (eds), Appleton & Lange, Norwalk, Conn., 1994, page 71 and Chapter 6.

The L chain from any vertebrate species can be assigned to one of two clearly distinct types, called kappa and lambda, based on the amino acid sequences of their constant domains. Depending on the amino acid sequence of the constant domain of their heavy chains (CH), immunoglobulins can be assigned to different classes or isotypes. There are five classes of immunoglobulins: IgA, IgD, IgE, IgG and IgM, having heavy chains designated α, δ, ε, γ and μ, respectively. The γ and α classes are further divided into subclasses on the basis of relatively minor differences in the CH sequence and function, e.g., humans express the following subclasses: IgG1, IgG2, IgG3, IgG4, IgA1 and IgA2. IgG1 antibodies can exist in multiple polymorphic variants termed allotypes (reviewed in Jefferis and Lefranc 2009. mAbs Vol 1 Issue 4 1-7) any of which are suitable for use in the invention. Common allotypic variants in human populations are those designated by the letters a, f, n, z.

An "isolated" antibody is one that has been identified, separated and/or recovered from a component of its production environment (e.g., naturally or recombinantly). In some embodiments, the isolated polypeptide is free of association with all other components from its production environment. Contaminant components of its production environment, such as that resulting from recombinant transfected cells, are materials that would typically interfere with research, diagnostic or therapeutic uses for the antibody, and may include enzymes, hormones, and other proteinaceous or non-proteinaceous solutes. In some embodiments, the polypeptide is purified: (1) to greater than 95% by weight of antibody as determined by, for example, the Lowry method, and in some embodiments, to greater than 99% by weight; (1) to a degree sufficient to obtain at least 15 residues of N-terminal or internal amino acid sequence by use of a spinning cup sequenator, or (3) to homogeneity by SDS-PAGE under non-reducing or reducing conditions using Coomassie blue or silver stain. Isolated antibody includes the antibody in situ within recombinant cells since at least one component of the antibody's natural environment will not be present. Ordinarily, however, an isolated polypeptide or antibody is prepared by at least one purification step.

The term "monoclonal antibody" as used herein refers to an antibody obtained from a population of substantially homogeneous antibodies, i.e., the individual antibodies comprising the population are identical except for possible naturally occurring mutations and/or post-translation modifications (e.g., isomerizations, amidations) that may be present in minor amounts. In some embodiments, monoclonal antibodies have a C-terminal cleavage at the heavy chain and/or light chain. For example, 1, 2, 3, 4, or 5 amino acid residues are cleaved at the C-terminus of heavy chain and/or light chain. In some embodiments, the C-terminal cleavage removes a C-terminal lysine from the heavy chain. In some embodiments, monoclonal antibodies have an N-terminal cleavage at the heavy chain and/or light chain. For example, 1, 2, 3, 4, or 5 amino acid residues are cleaved at the N-terminus of heavy chain and/or light chain. In some embodiments, monoclonal antibodies are highly specific, being directed against a single antigenic site. In some embodiments, monoclonal antibodies are highly specific, being directed against multiple antigenic sites (such as a bispecific antibody or a multispecific antibody). The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method, recombinant DNA methods, phage-display technologies, and technologies for producing human or human-like antibodies in animals that have parts or all of the human immunoglobulin loci or genes encoding human immunoglobulin sequences.

The term "naked antibody" refers to an antibody that is not conjugated to a cytotoxic moiety or radiolabel.

The terms "full-length antibody," "intact antibody" or "whole antibody" are used interchangeably to refer to an antibody in its substantially intact form, as opposed to an antibody fragment. Specifically whole antibodies include those with heavy and light chains including an Fc region. The constant domains may be native sequence constant domains (e.g., human native sequence constant domains) or amino acid sequence variants thereof. In some cases, the intact antibody may have one or more effector functions.

An "antibody fragment" comprises a portion of an intact antibody, the antigen binding and/or the variable region of the intact antibody. Examples of antibody fragments include Fab, Fab', F(ab')$_2$ and Fv fragments; diabodies; linear antibodies (see U.S. Pat. No. 5,641,870, Example 2; Zapata et al., *Protein Eng.* 8(10): 1057-1062 [1995]); single-chain antibody molecules and multispecific antibodies formed from antibody fragments.

Papain digestion of antibodies produced two identical antigen-binding fragments, called "Fab" fragments, and a residual "Fc" fragment, a designation reflecting the ability to crystallize readily. The Fab fragment consists of an entire L chain along with the variable region domain of the H chain ($V_H$), and the first constant domain of one heavy chain ($C_H1$). Each Fab fragment is monovalent with respect to antigen binding, i.e., it has a single antigen-binding site. Pepsin treatment of an antibody yields a single large F(ab')$_2$ fragment which roughly corresponds to two disulfide linked Fab fragments having different antigen-binding activity and is still capable of cross-linking antigen. Fab' fragments differ from Fab fragments by having a few additional residues at the carboxy terminus of the $C_H1$ domain including one or more cysteines from the antibody hinge region. Fab'-SH is the designation herein for Fab' in which the cysteine residue(s) of the constant domains bear a free thiol group. $F(ab')_2$ antibody fragments originally were produced as pairs of Fab' fragments which have hinge cysteines between them. Other chemical couplings of antibody fragments are also known.

The Fc fragment comprises the carboxy-terminal portions of both H chains held together by disulfides. The effector functions of antibodies are determined by sequences in the Fc region, the region which is also recognized by Fc receptors (FcR) found on certain types of cells.

"Fv" is the minimum antibody fragment which contains a complete antigen-recognition and -binding site. This fragment consists of a dimer of one heavy- and one light-chain variable region domain in tight, non-covalent association. From the folding of these two domains emanate six hypervariable loops (3 loops each from the H and L chain) that contribute the amino acid residues for antigen binding and confer antigen binding specificity to the antibody. However, even a single variable domain (or half of an Fv comprising only three HVRs specific for an antigen) has the ability to recognize and bind antigen, although at a lower affinity than the entire binding site.

"Single-chain Fv" also abbreviated as "sFv" or "scFv" are antibody fragments that comprise the VH and VL antibody domains connected into a single polypeptide chain. In some embodiments, the sFv polypeptide further comprises a polypeptide linker between the $V_H$ and $V_L$ domains which enables the sFv to form the desired structure for antigen binding. For a review of the sFv, see Pluckthun in *The Pharmacology of Monoclonal Antibodies*, vol. 113, Rosenburg and Moore eds., Springer-Verlag, New York, pp. 269-315 (1994).

"Functional fragments" of the antibodies of the invention comprise a portion of an intact antibody, generally including the antigen binding or variable region of the intact antibody or the Fv region of an antibody which retains or has modified FcR binding capability. Examples of antibody fragments include linear antibody, single-chain antibody molecules and multispecific antibodies formed from antibody fragments.

The monoclonal antibodies herein specifically include "chimeric" antibodies (immunoglobulins) in which a portion of the heavy and/or light chain is identical with or homologous to corresponding sequences in antibodies derived from a particular species or belonging to a particular antibody class or subclass, while the remainder of the chain(s) is (are) identical with or homologous to corresponding sequences in antibodies derived from another species or belonging to another antibody class or subclass, as well as fragments of such antibodies, so long as they exhibit the desired biological activity (U.S. Pat. No. 4,816,567; Morrison et al., *Proc. Natl. Acad. Sci. USA,* 81:6851-6855 (1984)). Chimeric antibodies of interest herein include PRIMATIZED® antibodies wherein the antigen-binding region of the antibody is derived from an antibody produced by, e.g., immunizing macaque monkeys with an antigen of interest. As used herein, "humanized antibody" is used as a subset of "chimeric antibodies."

"Humanized" forms of non-human (e.g., murine) antibodies are chimeric antibodies that contain minimal sequence derived from non-human immunoglobulin. In one embodiment, a humanized antibody is a human immunoglobulin (recipient antibody) in which residues from an HVR of the recipient are replaced by residues from an HVR of a non-human species (donor antibody) such as mouse, rat, rabbit or non-human primate having the desired specificity, affinity, and/or capacity. In some instances, FR residues of the human immunoglobulin are replaced by corresponding non-human residues. Furthermore, humanized antibodies may comprise residues that are not found in the recipient antibody or in the donor antibody. These modifications may be made to further refine antibody performance, such as binding affinity. In general, a humanized antibody will comprise substantially all of at least one, and typically two, variable domains, in which all or substantially all of the hypervariable loops correspond to those of a non-human immunoglobulin sequence, and all or substantially all of the FR regions are those of a human immunoglobulin sequence, although the FR regions may include one or more individual FR residue substitutions that improve antibody performance, such as binding affinity, isomerization, immunogenicity, etc. In some embodiments, the number of these amino acid substitutions in the FR are no more than 6 in the H chain, and in the L chain, no more than 3. The humanized antibody optionally will also comprise at least a portion of an immunoglobulin constant region (Fc), typically that of a human immunoglobulin. For further details, see, e.g., Jones et al., *Nature* 321:522-525 (1986); Riechmann et al., *Nature* 332: 323-329 (1988); and Presta, *Curr. Op. Struct. Biol.* 2:593-596 (1992). See also, for example, Vaswani and Hamilton, *Ann. Allergy, Asthma & Immunol.* 1:105-115 (1998); Harris, *Biochem. Soc. Transactions* 23:1035-1038 (1995); Hurle and Gross, *Curr. Op. Biotech.* 5:428-433 (1994); and U.S. Pat. Nos. 6,982,321 and 7,087,409. In some embodiments, humanized antibodies are directed against a single antigenic site. In some embodiments, humanized antibodies are directed against multiple antigenic sites. An alternative humanization method is described in U.S. Pat. No. 7,981, 843 and U.S. Patent Application Publication No. 2006/0134098.

The "variable region" or "variable domain" of an antibody refers to the amino-terminal domains of the heavy or light chain of the antibody. The variable domains of the heavy chain and light chain may be referred to as "VH" and "VL", respectively. These domains are generally the most variable parts of the antibody (relative to other antibodies of the same class) and contain the antigen binding sites.

The term "hypervariable region," "HVR," or "HV," when used herein refers to the regions of an antibody-variable domain that are hypervariable in sequence and/or form structurally defined loops. Generally, antibodies comprise six HVRs; three in the VH (H1, H2, H3), and three in the VL (L1, L2, L3). In native antibodies, H3 and L3 display the most diversity of the six HVRs, and H3 in particular is believed to play a unique role in conferring fine specificity to antibodies. See, e.g., Xu et al. *Immunity* 13:37-45 (2000); Johnson and Wu in *Methods in Molecular Biology* 248:1-25 (Lo, ed., Human Press, Totowa, N.J., 2003)). Indeed, naturally occurring camelid antibodies consisting of a heavy chain only are functional and stable in the absence of light chain. See, e.g., Hamers-Casterman et al., *Nature* 363:446-448 (1993) and Sheriff et al., *Nature Struct. Biol.* 3:733-736 (1996).

A number of HVR delineations are in use and are encompassed herein. The HVRs that are Kabat complementarity-determining regions (CDRs) are based on sequence variability and are the most commonly used (Kabat et al., *Sequences of Proteins of Immunological Interest, 5th* Ed.

Public Health Service, National Institute of Health, Bethesda, Md. (1991)). Chothia HVRs refer instead to the location of the structural loops (Chothia and Lesk *J. Mol. Biol.* 196:901-917 (1987)). The "contact" HVRs are based on an analysis of the available complex crystal structures. The residues from each of these HVRs are noted below.

| Loop | Kabat | Chothia | Contact | |
|------|---------|----------|----------|----------------------|
| L1 | L24-L34 | L26-L34 | L30-L36 | |
| L2 | L50-L56 | L50-L56 | L46-L55 | |
| L3 | L89-L97 | L91-L96 | L89-L96 | |
| H1 | H31-H35B | H26-H32 | H30-H35B | (Kabat Numbering) |
| H1 | H31-H35 | H26-H32 | H30-H35 | (Chothia Numbering) |
| H2 | H50-H65 | H53-H56 | H47-H58 | |
| H3 | H95-H102 | H95-H102 | H93-H101 | |

Unless otherwise indicated, the variable-domain residues (HVR residues and framework region residues) are numbered according to Kabat et al., supra.

"Framework" or "FR" residues are those variable-domain residues other than the HVR residues as herein defined.

The expression "variable-domain residue-numbering as in Kabat" or "amino-acid-position numbering as in Kabat," and variations thereof, refers to the numbering system used for heavy-chain variable domains or light-chain variable domains of the compilation of antibodies in Kabat et al., supra. Using this numbering system, the actual linear amino acid sequence may contain fewer or additional amino acids corresponding to a shortening of, or insertion into, a FR or HVR of the variable domain. For example, a heavy-chain variable domain may include a single amino acid insert (residue 52a according to Kabat) after residue 52 of H2 and inserted residues (e.g. residues 82a, 82b, and 82c, etc. according to Kabat) after heavy-chain FR residue 82. The Kabat numbering of residues may be determined for a given antibody by alignment at regions of homology of the sequence of the antibody with a "standard" Kabat numbered sequence.

An "acceptor human framework" for the purposes herein is a framework comprising the amino acid sequence of a VL or VH framework derived from a human immunoglobulin framework or a human consensus framework. An acceptor human framework "derived from" a human immunoglobulin framework or a human consensus framework may comprise the same amino acid sequence thereof, or it may contain pre-existing amino acid sequence changes. In some embodiments, the number of pre-existing amino acid changes are 10 or less, 9 or less, 8 or less, 7 or less, 6 or less, 5 or less, 4 or less, 3 or less, or 2 or less.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For example, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A.

An antibody that "binds to", "specifically binds to" or is "specific for" a particular a polypeptide or an epitope on a particular polypeptide is one that binds to that particular polypeptide or epitope on a particular polypeptide without substantially binding to any other polypeptide or polypeptide epitope. In some embodiments, binding of an anti-Siglec-8 antibody described herein (e.g., an antibody that binds to human Siglec-8) to an unrelated non-Siglec-8 polypeptide is less than about 10% of the antibody binding to Siglec-8 as measured by methods known in the art (e.g., enzyme-linked immunosorbent assay (ELISA)). In some embodiments, an antibody that binds to a Siglec-8 (e.g., an antibody that binds to human Siglec-8) has a dissociation constant (Kd) of ≤1 µM, ≤100 nM, ≤10 nM, ≤2 nM, ≤1 nM, ≤0.7 nM, ≤0.6 nM, ≤0.5 nM, ≤0.1 nM, ≤0.01 nM, or ≤0.001 nM (e.g. $10^{-8}$M or less, e.g. from $10^{-8}$M to $10^{-13}$M, e.g., from $10^{-9}$M to $10^{-13}$ M).

The term "anti-Siglec-8 antibody" or "an antibody that binds to human Siglec-8" refers to an antibody that binds to a polypeptide or an epitope of human Siglec-8 without substantially binding to any other polypeptide or epitope of an unrelated non-Siglec-8 polypeptide. The term "Siglec-8" as used herein refers to a human Siglec-8 protein. The term also includes naturally occurring variants of Siglec-8, including splice variants or allelic variants. The amino acid sequence of an exemplary human Siglec-8 is shown in SEQ ID NO:72. The amino acid sequence of another exemplary human Siglec-8 is shown in SEQ ID NO:73. In some embodiments, a human Siglec-8 protein comprises the human Siglec-8 extracellular domain fused to an immunoglobulin Fc region. The amino acid sequence of an exemplary human Siglec-8 extracellular domain fused to an immunoglobulin Fc region is shown in SEQ ID NO:74. The amino acid sequence underlined in SEQ ID NO:74 indicates the Fc region of the Siglec-8 Fc fusion protein amino acid sequence.

Human Siglec-8 Amino Acid Sequence (SEQ ID NO: 72)

QYLLQVQELVTVQEGLCVHVPCSFSYPQDGWTDSDPVHGYWFRAGDRPY

QDAPVATNNPDREVQAETQGRFQLLGDIWSNDCSLSIRDARKRDKGSYF

FRLERGSMKWSYKSQLNYKTKQLSVFVTALTHRPDILILGTLESGHSRN

LTCSVPWACKQGTPPMISWIGASVSSPGPTTARSSVLTLTPKPQDHGTS

LTCQVTLPGTGVTTTSTVRLDVSYPPWNLTMTVFQGDATASTALGNGSS

LSVLEGQSLRLVCAVNSNPPARLSWTRGSLTLCPSRSSNPGLLELPRVH

VRDEGEFTCRAQNAQGSQHISLSLSLQNEGTGTSRPVSQVTLAAVGGAG

```
ATALAFLSFCIIFIIVRSCRKKSARPAAGVGDTGMEDAKAIRGSASQGP

LTESWKDGNPLKKPPPAVAPSSGEEGELHYATLSFHKVKPQDPQGQEAT

DSEYSEIKIHKRETAETQACLRNHNPSSKEVRG

Human Siglec-8 Amino Acid Sequence
                                          (SEQ ID NO: 73)
GYLLQVQELVTVQEGLCVHVPCSFSYPQDGWTDSDPVHGYWFRAGDRPY

QDAPVATNNPDREVQAETQGRFQLLGDIWSNDCLSIRDARKRDKGSYFF

RLERGSMKWSYKSQLNYKTKQLSVFVTALTHRPDILILGTLESGHPRNL

TCSVPWACKQGTPPMISWIGASVSSPGPTTARSSVLTLTPKPQDHGTSL

TCQVTLPGTGVTTTSTVRLDVSYPPWNLTMTVFQGDATASTALGNSLLS

LVLEGQSLRLVCAVNSNPPARLSWTRGSLTLCPSRSSNPGLLELPRVHV

RDEGEFTCRAQNAQGSQHISLSLSLQNEGTGTSRPVSQVTLAAVGGAGA

TALAFLSFCIIFIIVRSCRKKSARPAAGVGDTGMEDAKAIRGSASQGPL

TESWKDGNPLKKPPPAVAPSSGEEGELHYATLSFHKVKPQDPQGQEATD

SEYSEIKIHKRETAETQACLRNHNPSSKEVRG

Siglec-8 Fc Fusion Protein Amino Acid Sequence
                                          (SEQ ID NO: 74)
GYLLQVQELVTVQEGLCVHNPCSFSYPQDGWTDSDPVHGYWFRAGDRPY

QDAPVATNNPDREVQAETQGRFQLLGDIWSNDCSLSIRDARKRDKGSYF

FRLERGSMKWSYKSQLNYKTKQLSVFVTALTHRPDILILGTLESGHSRN

LTCSVPWACKQGTPPMISWIGASVSSPGPTTARSSVLTLTPKPQDHGTS

LTCQVTLPGTGVTTTSTVRLDVSYPPWNLTMTVFQGDATASTALGNGSS

LSVLEGQSLRLVCAVNSNPPARLSWTRGSLTLCPSRSSNPGLLELPRVH

VRDEGEFTCRAQNAQGSQHISLSLSLQNEGTGTSRPVSQVTLAAVGGIE

GRSDKTHTCPPCPAPELLGGPSVFLFPPKPKDTLMISRTPEVTCVVVDV

SHEDPEVKFNWYVDGVEVHANKTKPREEQYNSTYRVVSVLTVLHQDWLN

GKEYKCKVSNKALPAPIEKTISKAKGQPREPQVYTLPPSREEMTKNQVS

LTCLVKGFYPSDIAVEWESNGQPENNYKTTPPVLDSDGSFFLYSKLTVD

KSRWQQGNVFSCSVMHEALHNHYTQKSLSLSPGK
```

Antibodies that "induce apoptosis" or are "apoptotic" are those that induce programmed cell death as determined by standard apoptosis assays, such as binding of annexin V, fragmentation of DNA, cell shrinkage, dilation of endoplasmic reticulum, cell fragmentation, and/or formation of membrane vesicles (called apoptotic bodies). For example, the apoptotic activity of the anti-Siglec-8 antibodies (e.g., an antibody that binds to human Siglec-8) of the present invention can be showed by staining cells with annexin V.

Antibody "effector functions" refer to those biological activities attributable to the Fc region (a native sequence Fc region or amino acid sequence variant Fc region) of an antibody, and vary with the antibody isotype. Examples of antibody effector functions include: C1q binding and complement dependent cytotoxicity; Fc receptor binding; antibody-dependent cell-mediated cytotoxicity (ADCC); phagocytosis; down regulation of cell surface receptors (e.g., B cell receptors); and B cell activation.

"Antibody-dependent cell-mediated cytotoxicity" or "ADCC" refers to a form of cytotoxicity in which secreted Ig bound onto Fc receptors (FcRs) present on certain cytotoxic cells (e.g., natural killer (NK) cells, neutrophils and macrophages) enable these cytotoxic effector cells to bind specifically to an antigen-bearing target cell and subsequently kill the target cell with cytotoxins. The antibodies "arm" the cytotoxic cells and are required for killing of the target cell by this mechanism. The primary cells for mediating ADCC, NK cells, express FcγRIII only, whereas monocytes express FcγRI, FcγRII and FcγRIII Fc expression on hematopoietic cells is summarized in Table 3 on page 464 of Ravetch and Kinet, Annu. Rev. Immunol. 9: 457-92 (1991). In some embodiments, an anti-Siglec-8 antibody (e.g., an antibody that binds to human Siglec-8) described herein enhances ADCC. To assess ADCC activity of a molecule of interest, an in vitro ADCC assay, such as that described in U.S. Pat. No. 5,500,362 or 5,821,337 may be performed. Useful effector cells for such assays include peripheral blood mononuclear cells (PBMC) and natural killer (NK) cells. Alternatively, or additionally, ADCC activity of the molecule of interest may be assessed in vivo, e.g., in an animal model such as that disclosed in Clynes et al., PNAS USA 95:652-656 (1998). Other Fc variants that alter ADCC activity and other antibody properties include those disclosed by Ghetie et al., Nat Biotech. 15:637-40, 1997; Duncan et al, Nature 332:563-564, 1988; Lund et al., J. Immunol 147:2657-2662, 1991; Lund et al, Mol Immunol 29:53-59, 1992; Alegre et al, Transplantation 57:1537-1543, 1994; Hutchins et al., Proc Natl. Acad Sci USA 92:11980-11984, 1995; Jefferis et al, Immunol Lett. 44:111-117, 1995; Lund et al., FASEB J9:115-119, 1995; Jefferis et al, Immunol Lett 54:101-104, 1996; Lund et al, J Immunol 157:4963-4969, 1996; Armour et al., Eur J Immunol 29:2613-2624, 1999; Idusogie et al, J Immunol 164:4178-4184, 200; Reddy et al, J Immunol 164:1925-1933, 2000; Xu et al., Cell Immunol 200:16-26, 2000; Idusogie et al, J Immunol 166: 2571-2575, 2001; Shields et al., J Biol Chem 276:6591-6604, 2001; Jefferis et al, Immunol Lett 82:57-65. 2002; Presta et al., Biochem Soc Trans 30:487-490, 2002; Lazar et al., Proc. Natl. Acad. Sci. USA 103:4005-4010, 2006; U.S. Pat. Nos. 5,624,821; 5,885,573; 5,677,425; 6,165,745; 6,277,375; 5,869,046; 6,121,022; 5,624,821; 5,648,260; 6,194,551; 6,737,056; 6,821,505; 6,277,375; 7,335,742; and 7,317,091.

The term "Fc region" herein is used to define a C-terminal region of an immunoglobulin heavy chain, including native-sequence Fc regions and variant Fc regions. Although the boundaries of the Fc region of an immunoglobulin heavy chain might vary, the human IgG heavy-chain Fc region is usually defined to stretch from an amino acid residue at position Cys226, or from Pro230, to the carboxyl-terminus thereof. Suitable native-sequence Fc regions for use in the antibodies of the invention include human IgG1, IgG2, IgG3 and IgG4. A single amino acid substitution (S228P according to Kabat numbering; designated IgG4Pro) may be introduced to abolish the heterogeneity observed in recombinant IgG4 antibody. See Angal, S. et al. (1993) Mol Immunol 30, 105-108.

"Non-fucosylated" or "fucose-deficient" antibody refers to a glycosylation antibody variant comprising an Fc region wherein a carbohydrate structure attached to the Fc region has reduced fucose or lacks fucose. In some embodiments, an antibody with reduced fucose or lacking fucose has improved ADCC function. Non-fucosylated or fucose-deficient antibodies have reduced fucose relative to the amount of fucose on the same antibody produced in a cell line. In some embodiments, a non-fucosylated or fucose-deficient antibody composition contemplated herein is a composition wherein less than about 50% of the N-linked glycans attached to the Fc region of the antibodies in the composition comprise fucose.

The terms "fucosylation" or "fucosylated" refers to the presence of fucose residues within the oligosaccharides attached to the peptide backbone of an antibody. Specifically, a fucosylated antibody comprises α (1,6)-linked fucose at the innermost N-acetylglucosamine (GlcNAc) residue in one or both of the N-linked oligosaccharides attached to the antibody Fc region, e.g. at position Asn 297 of the human IgG1 Fc domain (EU numbering of Fc region residues). Asn297 may also be located about +3 amino acids upstream or downstream of position 297, i.e. between positions 294 and 300, due to minor sequence variations in immunoglobulins.

The "degree of fucosylation" is the percentage of fucosylated oligosaccharides relative to all oligosaccharides identified by methods known in the art e.g., in an N-glycosidase F treated antibody composition assessed by matrix-assisted laser desorption-ionization time-of-flight mass spectrometry (MALDI TOF MS). In a composition of a "fully fucosylated antibody" essentially all oligosaccharides comprise fucose residues, i.e. are fucosylated. In some embodiments, a composition of a fully fucosylated antibody has a degree of fucosylation of at least about 90%. Accordingly, an individual antibody in such a composition typically comprises fucose residues in each of the two N-linked oligosaccharides in the Fc region. Conversely, in a composition of a "fully non-fucosylated" antibody essentially none of the oligosaccharides are fucosylated, and an individual antibody in such a composition does not contain fucose residues in either of the two N-linked oligosaccharides in the Fc region. In some embodiments, a composition of a fully non-fucosylated antibody has a degree of fucosylation of less than about 10%. In a composition of a "partially fucosylated antibody" only part of the oligosaccharides comprise fucose. An individual antibody in such a composition can comprise fucose residues in none, one or both of the N-linked oligosaccharides in the Fc region, provided that the composition does not comprise essentially all individual antibodies that lack fucose residues in the N-linked oligosaccharides in the Fc region, nor essentially all individual antibodies that contain fucose residues in both of the N-linked oligosaccharides in the Fc region. In one embodiment, a composition of a partially fucosylated antibody has a degree of fucosylation of about 10% to about 80% (e.g., about 50% to about 80%, about 60% to about 80%, or about 70% to about 80%).

"Binding affinity" as used herein refers to the strength of the non-covalent interactions between a single binding site of a molecule (e.g., an antibody) and its binding partner (e.g., an antigen). In some embodiments, the binding affinity of an antibody for a Siglec-8 (which may be a dimer, such as the Siglec-8-Fc fusion protein described herein) can generally be represented by a dissociation constant (Kd). Affinity can be measured by common methods known in the art, including those described herein.

"Binding avidity" as used herein refers to the binding strength of multiple binding sites of a molecule (e.g., an antibody) and its binding partner (e.g., an antigen).

An "isolated" nucleic acid molecule encoding the antibodies herein is a nucleic acid molecule that is identified and separated from at least one contaminant nucleic acid molecule with which it is ordinarily associated in the environment in which it was produced. In some embodiments, the isolated nucleic acid is free of association with all components associated with the production environment. The isolated nucleic acid molecules encoding the polypeptides and antibodies herein is in a form other than in the form or setting in which it is found in nature. Isolated nucleic acid molecules therefore are distinguished from nucleic acid encoding the polypeptides and antibodies herein existing naturally in cells.

The term "pharmaceutical formulation" refers to a preparation that is in such form as to permit the biological activity of the active ingredient to be effective, and that contains no additional components that are unacceptably toxic to an individual to which the formulation would be administered. Such formulations are sterile.

"Carriers" as used herein include pharmaceutically acceptable carriers, excipients, or stabilizers that are non-toxic to the cell or mammal being exposed thereto at the dosages and concentrations employed. Often the physiologically acceptable carrier is an aqueous pH buffered solution. Examples of physiologically acceptable carriers include buffers such as phosphate, citrate, and other organic acids; antioxidants including ascorbic acid; low molecular weight (less than about 10 residues) polypeptide; proteins, such as serum albumin, gelatin, or immunoglobulins; hydrophilic polymers such as polyvinylpyrrolidone; amino acids such as glycine, glutamine, asparagine, arginine or lysine; monosaccharides, disaccharides, and other carbohydrates including glucose, mannose, or dextrins; chelating agents such as EDTA; sugar alcohols such as mannitol or sorbitol; salt-forming counterions such as sodium; and/or nonionic surfactants such as TWEEN™, polyethylene glycol (PEG), and PLURONICS™.

As used herein, the term "treatment" or "treating" refers to clinical intervention designed to alter the natural course of the individual or cell being treated during the course of clinical pathology. Desirable effects of treatment include decreasing the rate of disease progression, ameliorating or palliating the disease state, and remission or improved prognosis. An individual is successfully "treated", for example, if one or more symptoms associated with a disease (e.g., advanced systemic mastocytosis) are mitigated or eliminated. For example, an individual is successfully "treated" if treatment results in increasing the quality of life of those suffering from a disease, decreasing the dose of other medications required for treating the disease, reducing the frequency of recurrence of the disease, lessening severity of the disease, delaying the development or progression of the disease, and/or prolonging survival of individuals.

As used herein, "in conjunction with" or "in combination with" refers to administration of one treatment modality in addition to another treatment modality. As such, "in conjunction with" or "in combination with" refers to administration of one treatment modality before, during or after administration of the other treatment modality to the individual.

As used herein, the term "prevention" or "preventing" includes providing prophylaxis with respect to occurrence or recurrence of a disease in an individual. An individual may be predisposed to, susceptible to a disease, or at risk of developing a disease, but has not yet been diagnosed with the disease. In some embodiments, anti-Siglec-8 antibodies (e.g., an antibody that binds to human Siglec-8) described herein are used to delay development of a disease (e.g., advanced systemic mastocytosis).

As used herein, an individual "at risk" of developing a disease (e.g., advanced systemic mastocytosis) may or may not have detectable disease or symptoms of disease, and may or may not have displayed detectable disease or symptoms of disease prior to the treatment methods described herein.

"At risk" denotes that an individual has one or more risk factors, which are measurable parameters that correlate with development of the disease (e.g., advanced systemic mastocytosis), as known in the art. An individual having one or more of these risk factors has a higher probability of developing the disease than an individual without one or more of these risk factors.

An "effective amount" refers to at least an amount effective, at dosages and for periods of time necessary, to achieve the desired or indicated effect, including a therapeutic or prophylactic result. An effective amount can be provided in one or more administrations. A "therapeutically effective amount" is at least the minimum concentration required to effect a measurable improvement of a particular disease. A therapeutically effective amount herein may vary according to factors such as the disease state, age, sex, and weight of the patient, and the ability of the antibody to elicit a desired response in the individual. A therapeutically effective amount may also be one in which any toxic or detrimental effects of the antibody are outweighed by the therapeutically beneficial effects. A "prophylactically effective amount" refers to an amount effective, at the dosages and for periods of time necessary, to achieve the desired prophylactic result. Typically but not necessarily, since a prophylactic dose is used in individuals prior to or at the earlier stage of disease, the prophylactically effective amount can be less than the therapeutically effective amount.

"Chronic" administration refers to administration of the medicament(s) in a continuous as opposed to acute mode, so as to maintain the initial therapeutic effect (activity) for an extended period of time. "Intermittent" administration is treatment that is not consecutively done without interruption, but rather is cyclic in nature.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, an "individual" or a "subject" is a mammal. A "mammal" for purposes of treatment includes humans, domestic and farm animals, and zoo, sports, or pet animals, such as dogs, horses, rabbits, cattle, pigs, hamsters, gerbils, mice, ferrets, rats, cats, etc. In some embodiments, the individual or subject is a human.

II. Compositions and Methods

A. Methods of the Invention

Provided herein are methods for treating or preventing advanced systemic mastocytosis (e.g., SM-AHNMD) in an individual comprising administering to the individual an effective amount of an antibody described herein that binds to human Siglec-8 (e.g., an anti-Siglec-8 antibody), or compositions thereof. Also provided herein are methods for treating or preventing advanced systemic mastocytosis (e.g., SM-AHNMD) in an individual comprising administering to the individual an effective amount of an agonist described herein that binds to human Siglec-8 (e.g., a 6'-sulfo-sLe$^x$-containing agonist or agonist antibodies), or compositions thereof. In some embodiments, the individual (e.g., a human) has been diagnosed with advanced systemic mastocytosis (e.g., SM-AHNMD) or is at risk of developing advanced systemic mastocytosis. As used herein the term "advanced systemic mastocytosis" can refer to a disease, disorder or condition associated with increased proliferation (e.g., increased numbers) or activation of Siglec-8 expressing mast cells. In some embodiments, advanced systemic mastocytosis is associated with increased proliferation (e.g., increased numbers) or activation of eosinophils (e.g., Siglec-8 expression eosinophils). Non-limiting examples of advanced systemic mastocytosis that are treatable with the antibodies and agonists, and compositions thereof, of the present invention include advanced systemic mastocytosis associated with eosinophilia, advanced systemic mastocytosis without eosinophilia, aggressive systemic mastocytosis (ASM), mast cell leukemia (MCL), and systemic mastocytosis with an associated hematologic non-mast-cell lineage disease (SM-AHNMD) such as SM-myelodysplastic syndrome (SM-MDS), SM-myeloproliferative neoplasm (SM-MPN), SM-chronic myelomonocytic leukemia (SM-CMML), SM-chronic eosinophilic leukemia (SM-CEL), and SM-acute myeloid leukemia (SM-AML).

Systemic mastocytosis (SM) is a rare myeloproliferative neoplasm characterized by the proliferation and accumulation of neoplastic mast cells in one or more organs. Symptoms from systemic mastocytosis arise from the release of chemical mediators (e.g., histamine) by mast cells and mast cell infiltration of tissues such as bone marrow, skin, spleen, lymph nodes, liver and the gastrointestinal tract. Accumulation of mast cells in organs can inhibit organ function which may lead to organ failure. The World Health Organization (WHO) 2008 classification for systemic mastocytosis identified seven variants of the disease plus a provisional subvariant. The variants include, cutaneous mastocytosis (CM), indolent systemic mastocytosis (ISM), aggressive systemic mastocytosis (ASM), systemic mastocytosis with an associated clonal hematologic non-mast cell lineage disease (SM-AHNMD), mast cell leukemia (MCL), mast cell sarcoma, and extracutaneous mastocytoma as well as a provisional subvariant of ISM termed smoldering systemic mastocytosis (SSM). See Gotlib et al., Blood, 2013, 121(13):2393-2401; Valent et al., Immunol Allergy Clin North Am., 2006, 26(3):515-534; Patnaik et al., Arch Pathol Lab Med., 2007, 131(5):784-791; Valent et al., Eur. J. Clin Invest., 2007, 37:435-453; and Valent et al., Allergy, 2014, 69:1267-1274. The WHO diagnostic criteria for systemic mastocytosis includes one major diagnostic criterion and four minor diagnostic criteria. The major diagnostic criterion is the presence of mast cell aggregates (>15 mast cells in aggregates) in the bone marrow and/or other extracutaneous organ of an individual. The four minor diagnostic criteria are: 1) the presence of morphologically atypical bone marrow mast cells in biopsy section of bone marrow or other extracutaneous organs (>25% of the mast cells in the infiltrate are spindle shaped, have atypical morphologic features or of all mast cells in bone marrow aspirate smear, >25% are immature or atypical); 2) mast cells in bone marrow, blood, or other extracutaneous organs express CD2 and/or CD25 in additional to normal mast cell marker; 3) detection of an activating point mutation at codon 816 in KIT in bone marrow, blood or another extracutaneous organ; 4) and serum total tryptase persistently exceeds 20 ng/mL level, except in cases where there an associated clonal myeloid disorder. The major diagnostic criterion in association with one minor diagnostic criterion of the four minor diagnostic criteria above, or three diagnostic minor criteria of the four minor diagnostic criteria above are required to establish a diagnosis of systemic mastocytosis. Systemic variants are distinguished by the presence of diagnostic criteria referred to as B finding(s) and C finding(s). B findings include >30% bone marrow mast cells on biopsy and/or serum tryptase levels >200 ng/mL; increased marrow cellularity/dysplasia without meeting diagnostic criteria for a hematopoietic neoplasm (AHNMD); and enlargement of the liver without impairment of liver function and/or enlarged of spleen without hypersplenism and/or enlarged lymph nodes (>2 cm). C findings include bone marrow dysfunction manifested by 1 or more cytopenia (absolute neutrophil count <1×10$^9$/L, Hb<10 g/dL, or platelets <100× 10$^9$ L); enlarged liver with impairment of liver function, ascites, and/or portal hypertension; enlarged spleen with hypersplenism; large osteolytic lesions and/or pathologic fractures; and malabsorption with weight loss caused by mast cell infiltration in the gastrointestinal tract. See Gotlib et al., Blood, 2013, 121(13):2393-2401.

Advanced systemic mastocytosis is typically characterized by organ damage and shortened survival. There are different types of advanced systemic mastocytosis and they include mast cell leukemia (MCL), aggressive systemic mastocytosis (ASM), and systemic mastocytosis with an associated clonal hematologic non-mast cell lineage disease (SM-AHNMD). An individual is diagnosed with ASM if they meet the diagnostic criteria for systemic mastocytosis, exhibit one or more of the C finding(s) diagnostic criteria, and show no evidence of mast cell leukemia. ASM is characterized by multifocal bone marrow infiltration by atypical, often immature mast cells with marked fibrosis. A positive status for the KIT D816V mutation is often found in an individual with ASM. See Gotlib et al., Blood, 2013, 121(13):2393-2401. An individual is diagnosed with MCL if they meet the diagnostic criteria for systemic mastocytosis as well as other criteria. In MCL, mast cells account for more than 20% of nucleated cells on bone marrow aspirate smears and atypical immature mast cells form a diffuse yet compact infiltrate on the core biopsy with low levels of fibrosis. An individual with MCL may not exhibit a positive status for the KIT D816V mutation. MCL can present without overt organ damage but organ damage usually develops within a short period. MCL includes typical MCL and aleukemic MCL. In typical MCL, mast cells comprise 10% or more of peripheral white blood cells. In aleukemic MCL, <10% of peripheral white blood cells are mast cells. See Gotlib et al., Blood, 2013, 121(13):2393-2401. An individual is diagnosed with AM-AHNMD if they meet the diagnostic criteria for systemic mastocytosis and criteria for an associated clonal hematologic non-mast cell lineage disease such myelodysplastic syndrome, myeloproliferative neoplasm, chronic myelomonocytic leukemia, eosinophilic disorders (e.g., chronic eosinophilic leukemia), and acute myeloid leukemia. SM-AHNMD includes SM-myelodysplastic syndrome (SM-MDS), SM-myeloproliferative neoplasm (SM-MPN), SM-chronic myelomonocytic leukemia (SM-CMML), SM-chronic eosinophilic leukemia (SM-CEL), and SM-acute myeloid leukemia (SM-AML). As used herein an individual with "advanced systemic mastocytosis" may or may not have eosinophilia. Symptoms of advanced systemic mastocytosis include, but are not limited to, weight loss, skin lesions, enlarged spleen, enlarged liver, enlarged lymph nodes, abdominal discomfort or pain, early satiety, anemia, thrombocytopenia, ascites, bone fractures, vomiting, nausea, diarrhea, flushing, pruritus, uticaria pigmentosa, angioedema, episodic anaphylactoid attacks, and organ dysfunction.

Response to treatment in individuals with advanced systemic mastocytosis can be assessed by methods well known in the art. See Gotlib et al., Blood, 2013, 121(13):2393-2401 and Verstovsek, Eur J Haematol., 2013, 90(2):89-98. For example, response to treatment in an individual with advanced systemic mastocytosis can be the reduction or improvement of any symptom of advanced systemic mastocytosis described herein (e.g., skin lesions). In another example, response to treatment in an individual with advanced systemic mastocytosis can be the reduction or improvement of a pathologic parameter described herein such as ascites or pleural effusions, liver function abnormalities, hypoalbuminemia, symptomatic marked splenomegaly, absolute neutrophil count, anemia (transfusion-independent and transfusion-dependent), thrombocytopenia (transfusion-independent and transfusion-dependent), serum tryptase levels, mast cell infiltration, mast cell number, mast cell degranulation, and any other pathologic parameter described herein as a diagnostic criteria of systemic mastocytosis. Response to treatment may result in complete remission (CR), partial remission (PR), or a clinical improvement (Cl) of advanced systemic mastocytosis in an individual.

Methodologies and assays known in the art and described herein can be used for assessment of any type of advanced systemic mastocytosis described herein (e.g., SM-myelodysplastic syndrome (SM-MDS), SM-chronic myelomonocytic leukemia (SM-CMML), SM-chronic eosinophilic leukemia (SM-CEL), ASM, etc.), a symptom of advanced systemic mastocytosis described herein, or diagnostic criteria of advanced systemic mastocytosis described herein. For example, mast cell burden can be quantified by morphologic analysis and immunohistochemical stains for tryptase, CD117, and CD25 on a core biopsy. Alternatively, or in addition, flow cytometric analysis of bone marrow aspirates can be used to quantify the percentage of mast cells. See Gotlib et al., Blood, 2013, 121(13):2393-2401; Hermine et al., 2008, PLos One, 3:e2266; and Verstovsek, Eur J Haematol., 2013, 90(2):89-98.

In some embodiments of the methods provided herein, the method further comprises a step of diagnosing an individual (e.g., a patient) with advanced systemic mastocytosis (e.g., SM-AHNMD), selecting an individual (e.g., a patient) advanced systemic mastocytosis (e.g., SM-AHNMD) for treatment, and/or determining if an individual (e.g., a patient) has advanced systemic mastocytosis (e.g., SM-AHNMD). In some embodiments, the method further comprises a step of diagnosing an individual with advanced systemic mastocytosis (e.g., SM-AHNMD), selecting an individual with advanced systemic mastocytosis (e.g., SM-AHNMD) for treatment, and/or determining if an individual has advanced systemic mastocytosis (e.g., SM-AHNMD) before treating or preventing advanced systemic mastocytosis (e.g., SM-AHNMD) in the individual, wherein the method comprises administering an effective amount of an antibody (e.g., an anti-Siglec-8 antibody) or an agonist (e.g., a 6'-sulfo-sLe$^x$-containing agonist) that binds to human Siglec-8. In some embodiments, the method further comprises a step of diagnosing an individual with advanced systemic mastocytosis (e.g., SM-AHNMD), selecting an individual with advanced systemic mastocytosis (e.g., SM-AHNMD) for treatment, and/or determining if an individual has advanced systemic mastocytosis (e.g., SM-AHNMD) before treating or preventing advanced systemic mastocytosis (e.g., SM-AHNMD) in the individual, wherein the method comprises administering an effective amount of an antibody (e.g., an anti-Siglec-8 antibody) or an agonist (e.g., a 6'-sulfo-sLe$^x$-containing agonist) that binds to human Siglec-8, whereby administration of the antibody or agonist results in improvement of one or more symptom of advanced systemic mastocytosis described herein (e.g., skin lesions). In some embodiments, the method further comprises a step of diagnosing an individual with advanced systemic mastocytosis (e.g., SM-AHNMD), selecting an individual with advanced systemic mastocytosis (e.g., SM- AHNMD) for treatment, and/or determining if an individual has advanced systemic mastocytosis (e.g., SM-AHNMD) before treating or preventing advanced systemic mastocytosis (e.g., SM-AHNMD) in the individual, wherein the method comprises administering an effective amount of an antibody (e.g., an anti-Siglec-8 antibody) or an agonist (e.g., a 6'-sulfo-sLe$^X$-containing agonist) that binds to human Siglec-8, whereby administration of the antibody or agonist results in improvement of one or more pathologic parameter of advanced systemic mastocytosis described herein (e.g., mast cell infiltration). In some embodiments, the method further comprises a step of diagnosing an individual with advanced systemic mastocytosis (e.g., SM-AHNMD), selecting an individual with advanced systemic mastocytosis (e.g., SM-AHNMD) for treatment, and/or determining if an individual has advanced systemic mastocytosis (e.g., SM-AHNMD) after treating or preventing advanced systemic mastocytosis (e.g., SM-AHNMD) in the individual, wherein the method comprises administering an effective amount of an antibody (e.g., an anti-Siglec-8 antibody) or an agonist (e.g., a 6'-sulfo-sLe$^X$-containing agonist) that binds to human Siglec-8. In some embodiments, the method further comprises a step of diagnosing an individual with advanced systemic mastocytosis (e.g., SM-AHNMD), selecting an individual with advanced systemic mastocytosis (e.g., SM-AHNMD) for treatment, and/or determining if an individual has advanced systemic mastocytosis (e.g., SM-AHNMD) after treating or preventing advanced systemic mastocytosis (e.g., SM-AHNMD) in the individual, wherein the method comprises administering an effective amount of an antibody (e.g., an anti-Siglec-8 antibody) or an agonist (e.g., a 6'-sulfo-sLe$^X$-containing agonist) that binds to human Siglec-8, whereby administration of the antibody or agonist results in improvement of one or more symptom of advanced systemic mastocytosis described herein (e.g., skin lesions). In some embodiments, the method further comprises a step of diagnosing an individual with advanced systemic mastocytosis (e.g., SM-AHNMD), selecting an individual with advanced systemic mastocytosis (e.g., SM-AHNMD) for treatment, and/or determining if an individual has advanced systemic mastocytosis (e.g., SM-AHNMD) after treating or preventing advanced systemic mastocytosis (e.g., SM-AHNMD) in the individual, wherein the method comprises administering an effective amount of an antibody (e.g., an anti-Siglec-8 antibody) or an agonist (e.g., a 6'-sulfo-sLe$^X$-containing agonist) that binds to human Siglec-8, whereby administration of the antibody or agonist results in improvement of one or more pathologic parameter of advanced systemic mastocytosis described herein (e.g., mast cell infiltration).

In some embodiments, provided herein is a method for treating or preventing advanced systemic mastocytosis in an individual comprising administering to the individual an effective amount of an antibody (e.g., an anti-Siglec-8 antibody) or an agonist (e.g., a 6'-sulfo-sLe$^X$-containing agonist) that binds to human Siglec-8. In some embodiments, provided herein is a method for treating or preventing aggressive systemic mastocytosis (ASM) in an individual comprising administering to the individual an effective amount of an antibody (e.g., an anti-Siglec-8 antibody) or an agonist (e.g., a 6'-sulfo-sLe$^X$-containing agonist) that binds to human Siglec-8. In some embodiments, provided herein is a method for treating or preventing mast cell leukemia (MCL) in an individual comprising administering to the individual an effective amount of an antibody (e.g., an anti-Siglec-8 antibody) or an agonist (e.g., a 6'-sulfo-sLe$^X$-containing agonist) that binds to human Siglec-8. In some embodiments, provided herein is a method for treating or preventing systemic mastocytosis with an associated hematologic non-mast-cell lineage disease (SM-AHNMD) in an individual comprising administering to the individual an effective amount of an antibody (e.g., an anti-Siglec-8 antibody) or an agonist (e.g., a 6'-sulfo-sLe$^X$-containing agonist) that binds to human Siglec-8. In some embodiments, provided herein is a method for treating or preventing SM-myelodysplastic syndrome (SM-MDS) in an individual comprising administering to the individual an effective amount of an antibody (e.g., an anti-Siglec-8 antibody) or an agonist (e.g., a 6'-sulfo-sLe$^X$-containing agonist) that binds to human Siglec-8. In some embodiments, provided herein is a method for treating or preventing SM-myeloproliferative neoplasm (SM-MPN) in an individual comprising administering to the individual an effective amount of an antibody (e.g., an anti-Siglec-8 antibody) or an agonist (e.g., a 6'-sulfo-sLe$^X$-containing agonist) that binds to human Siglec-8. In some embodiments, provided herein is a method for treating or preventing SM-chronic myelomonocytic leukemia (SM-CMML) in an individual comprising administering to the individual an effective amount of an antibody (e.g., an anti-Siglec-8 antibody) or an agonist (e.g., a 6'-sulfo-sLe$^X$-containing agonist) that binds to human Siglec-8. In some embodiments, provided herein is a method for treating or preventing SM-chronic eosinophilic leukemia (SM-CEL) in an individual comprising administering to the individual an effective amount of an antibody (e.g., an anti-Siglec-8 antibody) or an agonist (e.g., a 6'-sulfo-sLe$^X$-containing agonist) that binds to human Siglec-8. In some embodiments, provided herein is a method for treating or preventing SM-acute myeloid leukemia (SM-AML) in an individual comprising administering to the individual an effective amount of an antibody (e.g., an anti-Siglec-8 antibody) or an agonist (e.g., a 6'-sulfo-sLe$^X$-containing agonist) that binds to human Siglec-8. In some embodiments, the advanced systemic mastocytosis is associated with eosinophilia. In some embodiments, the advanced systemic mastocytosis is without eosinophilia.

In some of the embodiments herein, one or more symptom in an individual with advanced systemic mastocytosis (e.g., SM-AHNMD) is reduced or improved (e.g., a reference value) as compared to a baseline level before administration of the antibody that binds to human Siglec-8 (e.g., an anti-Siglec-8 antibody). In some of the embodiments herein, one or more symptom in an individual with advanced systemic mastocytosis (e.g., SM-AHNMD) is reduced or improved (e.g., a reference value) as compared to a baseline level before administration of the agonist that binds to human Siglec-8 (e.g., a 6'-sulfo-sLe$^X$-containing agonist). In some embodiments, the one or more symptom in the individual with advanced systemic mastocytosis (e.g., SM-AHNMD) is selected from the group consisting of: weight loss, skin lesions, enlarged spleen, enlarged liver, enlarged lymph nodes, abdominal discomfort or pain, early satiety, anemia, thrombocytopenia, ascites, bone fractures, vomiting, nausea, diarrhea, flushing, pruritus, uticaria pigmentosa, angioedema, episodic anaphylactoid attacks, and organ dysfunction. In some of the embodiments herein, the antibody is in a pharmaceutical composition comprising the antibody and a pharmaceutically acceptable carrier. In some of the embodiments herein, the agonist is in a pharmaceutical composition comprising the agonist and a pharmaceutically acceptable carrier.

In some of the embodiments herein, one or more pathological parameter, such as a diagnostic criteria of systemic mastocytosis described herein, in an individual with advanced systemic mastocytosis (e.g., SM-AHNMD) is reduced or improved (e.g., a reference value) as compared to a baseline level before administration of the antibody that binds to human Siglec-8 (e.g., an anti-Siglec-8 antibody). In some embodiments, one or more pathologic parameter in an individual with advanced systemic mastocytosis (e.g., SM-AHNMD) is selected from the group consisting of: ascites or pleural effusions, liver function abnormalities, hypoalbuminemia, symptomatic marked splenomegaly, absolute neutrophil count, anemia (transfusion-independent and transfusion-dependent), thrombocytopenia (transfusion-independent and transfusion-dependent), serum tryptase levels, mast cell infiltration, mast cell number, mast cell degranulation, and any other pathologic parameter described herein as a diagnostic criteria of systemic mastocytosis. In some embodiments herein, the individual is a human. In some of the embodiments herein, the antibody is in a pharmaceutical composition comprising the antibody and a pharmaceutically acceptable carrier. In some of the embodiments herein, the agonist is in a pharmaceutical composition comprising the agonist and a pharmaceutically acceptable carrier.

In some of the embodiments herein, the individual with advanced systemic mastocytosis (e.g., SM-AHNMD) is resistant to treatment with one or more therapeutic agent. In some embodiments, the one or more therapeutic agent is selected from the group consisting of: a cytotoxic agent; a cytokine; a growth inhibitory agent; a protein kinase inhibitor; a corticosteroid; an antibody; an mTOR inhibitor; and an anti-cancer agent. In some of the embodiments herein, the individual with advanced systemic mastocytosis (e.g., SM-AHNMD) is resistant to treatment with one or more protein kinase inhibitor. In some embodiments, the individual with advanced systemic mastocytosis (e.g., SM-AHNMD) is resistant to treatment with midostaurin, imatinib, nilotinib, dasatinib, and/or masitinib. In some of the embodiments herein, the individual with advanced systemic mastocytosis (e.g., SM-AHNMD) is resistant to treatment with interferon-α. In some of the embodiments herein, the individual with advanced systemic mastocytosis (e.g., SM-AHNMD) is resistant to treatment with rituximab and/or daclizumab. In some of the embodiments herein, the individual with advanced systemic mastocytosis (e.g., SM-AHNMD) is resistant to treatment with RAD001. In some of the embodiments herein, the individual with advanced systemic mastocytosis (e.g., SM-AHNMD) is resistant to treatment with rituximab and/or daclizumab. In some of the embodiments herein, the individual with advanced systemic mastocytosis (e.g., SM-AHNMD) is resistant to treatment with cladribine, denileukin diftitox, lenalidomide, thalidomide, and/or hydroxyurea. Such individuals can benefit from treatment with an antibody or agonist that binds to a human Siglec-8 described herein. In some embodiments, the individual with advanced systemic mastocytosis (e.g., SM-AHNMD) that is resistant to treatment with one or more therapeutic agent described herein (e.g., a protein kinase inhibitor) responds to treatment with an antibody or agonist that binds to a human Siglec-8 described herein. In some embodiments, the individual with advanced systemic mastocytosis (e.g., SM-AHNMD) that is resistant to treatment with one or more therapeutic agent described herein (e.g., a protein kinase inhibitor) responds to treatment with an antibody or agonist that binds to a human Siglec-8 described herein administered in combination with one or more therapeutic agent described herein (e.g., a protein kinase inhibitor).

Individuals with advanced systemic mastocytosis may have an activating point mutation in the phosphotransferase domain of c-Kit. The main activating mutation is the mutation of an aspartate residue at position 816 of c-Kit to a valine residue (i.e., a KIT D816V mutation). In some of the embodiments herein, the individual with advanced systemic mastocytosis (e.g., SM-AHNMD) has a mutation in a c-Kit gene. In some embodiments, the individual has a KIT D816V mutation. In some embodiments, the individual does not have a KIT D816V mutation. Methods for detection of a KIT D816V mutation are known in the art. See for example, Hermine et al., 2008, PLos One, 3:e2266. In some embodiments, an individual with a KIT D816V mutation is resistant to treatment with one or more therapeutic agent selected from the group consisting of: a cytotoxic agent; a cytokine; a growth inhibitory agent; a protein kinase inhibitor; a corticosteroid; an antibody; an mTOR inhibitor; and an anti-cancer agent. In some embodiments, the individual with a KIT D816V mutation responds to treatment with an antibody or agonist that binds to a human Siglec-8 described herein. In some embodiments, the individual with a KIT D816V mutation responds to treatment with an antibody or agonist that binds to a human Siglec-8 described herein administered in combination with one or more therapeutic agent described herein (e.g., a protein kinase inhibitor).

The terms "baseline" or "baseline value" used interchangeably herein can refer to a measurement or characterization of a symptom (e.g., mast cell infiltration, mast cell number, serum tryptase levels, weight loss, etc.) before the administration of the therapy (e.g., an anti-Siglec-8 antibody) or at the beginning of administration of the therapy. The baseline value can be compared to a reference value in order to determine the reduction or improvement of a symptom of a type of advanced systemic mastocytosis contemplated herein. The terms "reference" or "reference value" used interchangeably herein can refer to a measurement or characterization of a symptom after administration of the therapy (e.g., an anti-Siglec-8 antibody). The reference value can be measured one or more times during a dosage regimen or treatment cycle or at the completion of the dosage regimen or treatment cycle. A "reference value" can be an absolute value; a relative value; a value that has an upper and/or lower limit; a range of values; an average value; a median value; a mean value; or a value as compared to a baseline value. Similarly, a "baseline value" can be an absolute value; a relative value; a value that has an upper and/or lower limit; a range of values; an average value; a median value; a mean value; or a value as compared to a reference value. The reference value and/or baseline value can be obtained from one individual, from two different individuals or from a group of individuals (e.g., a group of two, three, four, five or more individuals). For example, an individual with advanced systemic mastocytosis (e.g., SM-AHNMD) can have a reduced level of mast cell infiltration after administration of the antibody that binds to human Siglec-8 (e.g., a reference value) as compared to the level of mast cell infiltration before or at the beginning of administration of the antibody that binds to human Siglec-8 in the individual (e.g., a baseline value). In another example, an individual with advanced systemic mastocytosis (e.g., SM-AHNMD) can have a reduced level of mast cell infiltration after administration of the antibody that binds to human Siglec-8 (e.g., a reference value) as compared to the level of mast cell infiltration before or at the beginning of administration of the antibody that binds to human Siglec-8 in a different individual (e.g., a baseline value). In yet another example, an individual with advanced systemic mastocytosis (e.g., SM-AHNMD) can have a reduced level of mast cell infiltration after administration of the antibody that binds to human Siglec-8 (e.g., a reference value) as compared to the level of mast cell infiltration before or at the beginning of administration of the antibody that binds to human Siglec-8 in a group of individuals (e.g., a baseline value). In another example, a group of individuals with advanced systemic mastocytosis (e.g., SM-AHNMD) can have a reduced level of mast cell infiltration after administration of the antibody that binds to human Siglec-8 (e.g., a reference value) as compared to the level of mast cell infiltration before or at the beginning of administration of the antibody that binds to human Siglec-8 in a group of individuals (e.g., a baseline value). In any of the embodiments herein, the baseline value can be obtained from one individual, from two different individuals or from a group of individuals (e.g., a group of two, three, four, five or more individuals) that are not treated with an antibody that binds to human Siglec-8.

In some embodiments, an individual described herein is administered an effective amount of an antibody or agonist that binds to human Siglec-8, or compositions thereof, for depletion or reduction of eosinophils (e.g., eosinophils expressing Siglec-8). In some embodiments, the anti-Siglec-8 antibody or agonist depletes or reduces at least about 20%, about 30%, about 40%, about 50%, about 60%, about 70%, about 80%, about 90% or about 100% of the eosinophils (e.g., eosinophils expressing Siglec-8) in a sample obtained from the individual as compared to a baseline level before administration of the antibody or agonist. In some embodiments, the anti-Siglec-8 antibody or agonist depletes or reduces at least about 20% of the eosinophils (e.g., eosinophils expressing Siglec-8) in a sample obtained from the individual as compared to a baseline level before administration of the antibody or agonist. In some embodiments, the depletion or reduction of eosinophils is measured by comparing the eosinophil population number in a sample (e.g., a tissue sample or a biological fluid sample) from an individual after treatment with the antibody or agonist to the eosinophil population number in a sample from an individual before treatment with the antibody or agonist. In some embodiments, the depletion or reduction of eosinophils is measured by comparing the eosinophil population number in a sample (e.g., a tissue sample or a biological fluid sample) from an individual after treatment with the antibody or agonist to the eosinophil population number in a sample from another individual without the antibody treatment or the agonist treatment or average eosinophil population number in samples from individuals without the antibody treatment or the agonist treatment. In some embodiments, the sample is a tissue sample (e.g., a skin sample, a bone marrow sample, etc.). In some embodiments, the tissue sample is a bone marrow sample, a skin sample, a spleen sample, a lymph node sample, a liver sample or a gastrointestinal tract sample. In some embodiments herein, the antibody depletes eosinophils in a tissue sample. In some embodiments, the sample is a biological fluid sample (e.g., a blood sample, urine sample, etc.). In some embodiments herein, the antibody or agonist depletes eosinophils in a biological fluid sample. In some embodiments of the methods herein, the effective amount of an antibody or agonist that binds to human Siglec-8, or compositions thereof, induces apoptosis of activated eosinophils. Eosinophils can be activated or sensitized by cytokines or hormones such as, but not limited to, IL-5, GM-CSF, IL-33, IFN-γ, TNF-α, and leptin. In some embodiments of the methods herein, the effective amount of an antibody or agonist described herein that binds to human Siglec-8, or compositions thereof, induces apoptosis of resting eosinophils. In some embodiments, the effective amount of an antibody or agonist described herein that binds to human Siglec-8, or compositions thereof, has antibody-dependent cell-mediated cytotoxicity (ADCC) activity against eosinophils. In some embodiments, the effective amount of an antibody or agonist described herein that binds to human Siglec-8, or compositions thereof, prevents or reduces eosinophil production of inflammatory mediators. Exemplary inflammatory mediators include, but are not limited to, reactive oxygen species, granule proteins (e.g., eosinophil cationic protein, major basic protein, eosinophil-derived neurotoxin, eosinophil peroxidase, etc.), lipid mediators (e.g., PAF, PGE1, PGE2, etc.), enzymes (e.g., elastase), growth factors (e.g., VEGF, PDGF, TGF-α, TGF-β, etc.), chemokines (e.g., RANTES, MCP-1, MCP-3, MCP4, eotaxin, etc.) and cytokines (e.g., IL-3, IL-5, IL-10, IL-13, IL-15, IL-33, TNF-α, etc.).

In some embodiments, an individual described herein is administered an effective amount of an antibody or agonist that binds to human Siglec-8, or compositions thereof, for depletion or reduction of mast cells (e.g., mast cells expressing Siglec-8). In some embodiments, the anti-Siglec-8 antibody or agonist depletes or reduces at least about 20%, about 30%, about 40%, about 50%, about 60%, about 70%, about 80%, about 90% or about 100% of the mast cells expressing Siglec-8 in a sample obtained from the individual as compared to a baseline level before administration of the antibody or agonist. In some embodiments, the anti-Siglec-8 antibody or agonist depletes or reduces at least about 20% of the mast cells expressing Siglec-8 in a sample obtained from the individual as compared to a baseline level before administration of the antibody or agonist. In some embodiments, the anti-Siglec-8 antibody or agonist depletes or reduces at least about 30% of the mast cells expressing Siglec-8 in a sample obtained from the individual as compared to a baseline level before administration of the antibody or agonist. In some embodiments, the anti-Siglec-8 antibody or agonist depletes or reduces at least about 40% of the mast cells expressing Siglec-8 in a sample obtained from the individual as compared to a baseline level before administration of the antibody or agonist. In some embodiments, the anti-Siglec-8 antibody or agonist depletes or reduces at least about 50% of the mast cells expressing Siglec-8 in a sample obtained from the individual as compared to a baseline level before administration of the antibody or agonist. In some embodiments, the depletion or reduction of mast cells is measured by comparing the mast cell population number in a sample (e.g., a tissue sample or a biological fluid sample) from an individual after treatment with the antibody or agonist to the mast cell population number in a sample from an individual before treatment with the antibody or agonist. In some embodiments, the depletion or reduction of mast cells is measured by comparing the mast cell population number in a sample (e.g., a tissue sample or a biological fluid sample) from an individual after treatment with the antibody or agonist to the mast cell population number in a sample from another individual without the antibody treatment or agonist treatment or average mast cell population number in samples from individuals without the antibody treatment or agonist treatment. In some embodiments, the sample is a tissue sample (e.g., a skin sample, a bone marrow sample, etc.). In some embodiments, the tissue sample is a bone marrow sample, a skin sample, a spleen sample, a lymph node sample, a liver sample or a gastrointestinal tract sample. In some embodiments, the sample is a biological fluid sample (e.g., a blood sample, a urine sample, etc.). In some embodiments, the effective amount of an antibody or agonist described herein that binds to human Siglec-8, or compositions thereof, has antibody-dependent cell-mediated cytotoxicity (ADCC) activity against mast cells. In some embodiments, depletion or reduction of mast cells prevents or reduces preformed or newly formed inflammatory mediators produced from mast cells. Exemplary inflammatory mediators include, but are not limited to, histamine, N-methyl histamine, enzymes (e.g., tryptase, chymase, cathespin G, carboxypeptidase, etc.), lipid mediators (e.g., prostaglandin D2, prostaglandin E2, leukotriene B4, leukotriene C4, platelet-activating factor, 11-beta-prostaglandin F2, etc.), chemokines (e.g., CCL2, CCL3, CCL4, CCL11 (i.e., eotaxin), CXCL1, CXCL2, CXCL3, CXCL10, etc.), and cytokines (e.g., IL-3, IL-4, IL-5, IL-15, IL-33, GM-CSF, TNF, etc.).

In some embodiments, an individual described herein is administered an effective amount of an antibody or agonist that binds to human Siglec-8, or compositions thereof, for depleting mast cells expressing Siglec-8, wherein the anti-Siglec-8 antibody kills mast cells expressing Siglec-8 by ADCC activity. In some embodiments, the anti-Siglec-8 antibody or agonist depletes at least about 20%, about 30%, about 40%, about 50%, about 60%, about 70%, about 80%, about 90% or about 100% of the mast cells expressing Siglec-8 in a sample obtained from the individual as compared to a baseline level before administration of the antibody or agonist. In some embodiments, the anti-Siglec-8 antibody or agonist depletes at least about 20% of the mast cells expressing Siglec-8 in a sample obtained from the individual as compared to a baseline level before administration of the antibody or agonist. In some embodiments, the anti-Siglec-8 antibody or agonist depletes at least about 30% of the mast cells expressing Siglec-8 in a sample obtained from the individual as compared to a baseline level before administration of the antibody or agonist. In some embodiments, the anti-Siglec-8 antibody or agonist depletes at least about 40% of the mast cells expressing Siglec-8 in a sample obtained from the individual as compared to a baseline level before administration of the antibody or agonist. In some embodiments, the anti-Siglec-8 antibody or agonist depletes at least about 50% of the mast cells expressing Siglec-8 in a sample obtained from the individual as compared to a baseline level before administration of the antibody or agonist. In some embodiments, the depletion or killing of mast cells is measured by comparing the mast cell population number in a sample (e.g., a tissue sample or a biological fluid sample) from an individual after treatment with the antibody or agonist to the mast cell population number in a sample from an individual before treatment with the antibody or agonist. In some embodiments, the depletion or killing of mast cells is measured by comparing the mast cell population number in a sample (e.g., a tissue sample or a biological fluid sample) from an individual after treatment with the antibody or agonist to the mast cell population number in a sample from another individual without the antibody treatment or agonist treatment or average mast cell population number in samples from individuals without the antibody treatment or agonist treatment. In some embodiments, the sample is a tissue sample (e.g., a skin sample, a bone marrow sample, etc.). In some embodiments, the tissue sample is a bone marrow sample, a skin sample, a spleen sample, a lymph node sample, a liver sample or a gastrointestinal tract sample. In some embodiments, the sample is a biological fluid sample (e.g., a blood sample, urine sample, etc.). In some embodiments, the anti-Siglec-8 antibody has been engineered to improve ADCC activity. In some embodiments, the anti-Siglec-8 antibody comprises at least one amino acid substitution in the Fc region that improves ADCC activity. In some embodiments, at least one or two of the heavy chains of the antibody is non-fucosylated. In some embodiments, depletion or killing of mast cells prevents or reduces preformed or newly formed inflammatory mediators produced from mast cells. Exemplary inflammatory mediators include, but are not limited to, histamine, N-methyl histamine, enzymes (e.g., tryptase, chymase, cathespin G, carboxypeptidase, etc.), lipid mediators (e.g., prostaglandin D2, prostaglandin E2, leukotriene B4, leukotriene C4, platelet-activating factor, 11-beta-prostaglandin F2, etc.), chemokines (e.g., CCL2, CCL3, CCL4, CCL11 (i.e., eotaxin), CXCL1, CXCL2, CXCL3, CXCL10, etc.), and cytokines (e.g., IL-3, IL-4, IL-5, IL-13, IL-15, IL-33, GM-CSF, TNF, etc.).

In some embodiments, an individual described herein is administered an effective amount of an antibody or agonist that binds to human Siglec-8, or compositions thereof, for the inhibition of mast cell-mediated activity. In some embodiments, the anti-Siglec-8 antibody or agonist inhibits at least about 20%, about 30%, about 40%, about 50%, about 60%, about 70%, about 80%, about 90% or about 100% of the mast cell-mediated activity in a sample obtained from the individual as compared to a baseline level before administration of the antibody or agonist. In some embodiments, the anti-Siglec-8 antibody or agonist inhibits at least about 20% of the mast cell-mediated activity in a sample obtained from the individual as compared to a baseline level before administration of the antibody or agonist. In some embodiments, the inhibition of mast cell-mediated activity is measured by comparing the mast cell-mediated activity in a sample (e.g., a tissue sample or a biological fluid sample) from an individual after treatment with the antibody or agonist to the mast cell-mediated activity in a sample from an individual before treatment with the antibody or agonist. In some embodiments, the inhibition of mast cell-mediated activity is measured by comparing the mast cell-mediated activity in a sample (e.g., a tissue sample or a biological fluid sample) from an individual after treatment with the antibody or agonist to the mast cell-mediated activity in a sample from another individual without the antibody treatment or agonist treatment or average mast cell-mediated activity in samples from individuals without the antibody treatment or agonist treatment. In some embodiments, the sample is a tissue sample (e.g., a skin sample, a bone marrow sample, etc.). In some embodiments, the tissue sample is a bone marrow sample, a skin sample, a spleen sample, a lymph node sample, a liver sample or a gastrointestinal tract sample. In some embodiments, the sample is a biological fluid sample (e.g., a blood sample, a urine sample, etc.). In some embodiments, inhibition of mast cell-mediated activity is the inhibition of mast cell degranulation. In some embodiments, inhibition of mast cell-mediated activity is the inhibition of mast cell infiltration to organs and/or bone marrow. In some embodiments, inhibition of mast cell-mediated activity is the inhibition of cytokine release. In some embodiments, inhibition of mast cell-mediated activity is the reduction in the number of mast cells in the individual. In some embodiments, inhibition of mast cell-mediated activity is the inhibition of release of preformed or newly formed inflammatory mediators from mast cells. Exemplary inflammatory mediators include, but are not limited to, histamine, N-methyl histamine, enzymes (e.g., tryptase, chymase, cathespin G, carboxypeptidase, etc.), lipid mediators (e.g., prostaglandin D2, prostaglandin E2, leukotriene B4, leukotriene C4, platelet-activating factor, 11-beta-prostaglandin F2, etc.), chemokines (e.g., CCL2, CCL3, CCL4, CCL11

(i.e., eotaxin), CXCL1, CXCL2, CXCL3, CXCL10, etc.), and cytokines (e.g., IL-3, IL-4, IL-5, IL-13, IL-15, IL-33, GM-CSF, TNF, etc.).

For the prevention or treatment of disease, the appropriate dosage of an active agent, will depend on the type of disease to be treated, as defined above, the severity and course of the disease, whether the agent is administered for preventive or therapeutic purposes, previous therapy, the individual's clinical history and response to the agent, and the discretion of the attending physician. The agent is suitably administered to the individual at one time or over a series of treatments. In some embodiments of the methods described herein, an interval between administrations of an anti-Siglec-8 antibody (e.g., an antibody that binds to human Siglec-8) or agonist described herein is about one month or longer. In some embodiments, the interval between administrations is about two months, about three months, about four months, about five months, about six months or longer. As used herein, an interval between administrations refers to the time period between one administration of the antibody or agonist and the next administration of the antibody or agonist. As used herein, an interval of about one month includes four weeks. Accordingly, in some embodiments, the interval between administrations is about four weeks, about five weeks, about six weeks, about seven weeks, about eight weeks, about nine weeks, about ten weeks, about eleven weeks, about twelve weeks, about sixteen weeks, about twenty weeks, about twenty four weeks, or longer. In some embodiments, the treatment includes multiple administrations of the antibody or agonist, wherein the interval between administrations may vary. For example, the interval between the first administration and the second administration is about one month, and the intervals between the subsequent administrations are about three months. In some embodiments, the interval between the first administration and the second administration is about one month, the interval between the second administration and the third administration is about two months, and the intervals between the subsequent administrations are about three months. In some embodiments, an anti-Siglec-8 antibody described herein (e.g., an antibody that binds to human Siglec-8) or agonist described herein is administered at a flat dose. In some embodiments, an anti-Siglec-8 antibody described herein (e.g., an antibody that binds to human Siglec-8) or agonist described herein is administered to an individual at a dosage from about 0.1 mg to about 1800 mg per dose. In some embodiments, the anti-Siglec-8 antibody (e.g., an antibody that binds to human Siglec-8) or agonist is administered to an individual at a dosage of about any of 0.1 mg, 0.5 mg, 1 mg, 5 mg, 10 mg, 20 mg, 30 mg, 40 mg, 50 mg, 60 mg, 70 mg, 80 mg, 90 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 950 mg, 1000 mg, 1100 mg, 1200 mg, 1300 mg, 1400 mg, 1500 mg, 1600 mg, 1700 mg, and 1800 mg per dose. In some embodiments, an anti-Siglec-8 antibody described herein (e.g., an antibody that binds to human Siglec-8) or agonist described herein is administered to an individual at a dosage from about 150 mg to about 450 mg per dose. In some embodiments, the anti-Siglec-8 antibody (e.g., an antibody that binds to human Siglec-8) or agonist is administered to an individual at a dosage of about any of 150 mg, 200 mg, 250 mg, 300 mg, 350 mg, 400 mg, and 450 mg per dose. In some embodiments, an anti-Siglec-8 antibody described herein (e.g., an antibody that binds to human Siglec-8) or agonist described herein is administered to an individual at a dosage from about 0.1 mg/kg to about 20 mg/kg per dose. In some embodiments, an anti-Siglec-8 antibody described herein (e.g., an antibody that binds to human Siglec-8) or agonist described herein is administered to an individual at a dosage from about 0.01 mg/kg to about 10 mg/kg per dose. In some embodiments, an anti-Siglec-8 antibody described herein (e.g., an antibody that binds to human Siglec-8) or agonist described herein is administered to an individual at a dosage from about 0.1 mg/kg to about 10 mg/kg or about 1.0 mg/kg to about 10 mg/kg. In some embodiments, an anti-Siglec-8 antibody described herein is administered to an individual at a dosage of about any of 0.1 mg/kg, 0.5 mg/kg, 1.0 mg/kg, 1.5 mg/kg, 2.0 mg/kg, 2.5 mg/kg, 3.0 mg/kg, 3.5 mg/kg, 4.0 mg/kg, 4.5 mg/kg, 5.0 mg/kg, 5.5 mg/kg, 6.0 mg/kg, 6.5 mg/kg, 7.0 mg/kg, 7.5 mg/kg, 8.0 mg/kg, 8.5 mg/kg, 9.0 mg/kg, 9.5 mg/kg, or 10.0 mg/kg. Any of the dosing frequency described above may be used. Any dosing frequency described above may be used in the methods or uses of the compositions described herein. Efficacy of treatment with an antibody described herein (e.g., an antibody that binds to human Siglec-8) or agonist described herein can be assessed using any of the methodologies or assays described herein at intervals ranging between every week and every three months. In some embodiments of the methods described herein, efficacy of treatment (e.g., reduction or improvement of one or more symptom) is assessed about every one month, about every two months, about every three months, about every four months, about every five months, about every six months or longer after administration of an antibody or agonist that binds to human Siglec-8. In some embodiments of the methods described herein, efficacy of treatment (e.g., reduction or improvement of one or more symptom) is assessed about every one week, about every two weeks, about every three weeks, about every four weeks, about every five weeks, about every six weeks, about every seven weeks, about every eight weeks, about every nine weeks, about every ten weeks, about every eleven weeks, about every twelve weeks, about every sixteen weeks, about every twenty weeks, about every twenty four weeks, or longer.

Antibodies and agonists described herein that bind to human Siglec-8 can be used either alone or in combination with other agents in the methods described herein. For instance, an antibody that binds to a human Siglec-8 may be co-administered with one or more additional therapeutic agent. Therapeutic agents contemplated herein include, but are not limited to, cytotoxic agents; cytokines such as interferon-α; growth inhibitory agents; protein kinase inhibitors such as midostaurin, imatinib, nilotinib, dasatinib, and masitinib; corticosteroids; antibodies such as rituximab and daclizumab; mTOR inhibitors such as RAD001; and anti-cancer agents such as cladribine, denileukin diftitox, lenalidomide, thalidomide, and hydroxyurea. In certain embodiments, one or more additional therapeutic agent is selected from the group consisting of: a cytotoxic agent, a cytokine (e.g., interferon-α), a growth inhibitory agent, a protein kinase inhibitor (e.g., a tyrosine kinase inhibitor such as midostaurin), a corticosteroid, an antibody (e.g., rituximab), or an anti-cancer agent (e.g., an antimetabolite such as cladribine). In some embodiments, the additional therapeutic agent is a tyrosine kinase inhibitor.

Such combination therapies noted above encompass combined administration (where two or more therapeutic agents are included in the same or separate formulations), and separate administration, in which case, administration of the antibody of the invention can occur prior to, simultaneously, and/or following, administration of the one or more additional therapeutic agent or agents. In some embodiments, administration of an anti-Siglec-8 antibody described herein and administration of one or more additional therapeutic agent occur within about one month, about two months, about three months, about four months, about five months or about six months of each other. In some embodiments, administration of an anti-Siglec-8 antibody described herein and administration of one or more additional therapeutic agent occur within about one week, about two weeks or about three weeks of each other. In some embodiments, administration of an anti-Siglec-8 antibody described herein and administration of one or more additional therapeutic agent occur within about one day, about two days, about three days, about four days, about five days, or about six days of each other.

Agonists of Siglec-8

In one aspect, the present invention provides for agonists for use in any of the methods herein. In some embodiments, an agonist is an agent that binds to Siglec-8 expressed on eosinophils and induces apoptosis of eosinophils in vitro or in vivo. In some embodiments, an agonist is an agent that binds to Siglec-8 expressed on mast cells and inhibits activation of mast cells in vitro or in vivo. In some embodiments, an agonist is an agent that binds to Siglec-8 expressed on mast cells and depletes or reduces the number of mast cells in vitro or in vivo. In some embodiments, an agonist is an agent that binds to Siglec-8 expressed on mast cells and kills mast cells expressing Siglec-8 by ADCC activity in vitro and in vivo. In some embodiments, the agonist is an agonist antibody. In some embodiments, the agonist is an agonist antibody. In some embodiments, the agonist antibody (e.g., antibody 2E2 provided herein) crosslinks Siglec-8 expressed by eosinophils and induces activation of one or more caspases (e.g., caspase-8, caspase-3, and caspase-9) in eosinophils and/or loss of mitochondrial membrane potential. See Nutku et al., *Biochem Biophys Res Commun.*, 336:918-924, 2005. Siglec-8 binds to the glycan 6'-sulfo-sialyl Lewis X (also referred to herein as 6'-sulfo-sLe$^X$) and engagement to this glycan induces apoptosis of Siglec-8 expressing cells (e.g., eosinophils). See Hudson et al., *J Pharmacol Exp Ther.*, 330(2):608-12, 2009. In some embodiments herein, an agonist of Siglec-8 is a molecule having a 6'-sulfo-sLe$^X$ attached or linked to a molecule (e.g., a polymer, an oligosaccharide, a polypeptide, a glycoprotein, etc.). In some embodiments herein, the agonist is a 6'-sulfo-sLe$^X$-containing agonist molecule (e.g., a 6'-sulfo-sLe$^X$-containing ligand, a 6'-sulfo-sLe$^X$-containing oligosaccharide, a 6'-sulfo-sLe$^X$-containing polypeptide, and a 6'-sulfo-sLe$^X$-containing glycoprotein).

Agonists may be identified from a variety of sources, for example, cells, cell-free preparations, chemical libraries, and natural product mixtures. Such agonists may be natural or modified substrates, ligands, receptors, oligonucleotides, polypeptides, or antibodies that contain the glycan 6'-sulfo-sLe$^X$ and bind to Siglec-8, or may be structural or functional mimetics thereof. Structural or functional mimetics of such natural or modified substrates, ligands, receptors, oligonucleotides, or antibodies that contain the glycan 6'-sulfo-sLe$^X$ are referred to herein as a "6'-sulfo-sLe$^X$-containing glycomimetic." See Coligan et al., *Current Protocols in Immunology* 1(2):Chapter 5, 1991. For example, a 6'-sulfo-sLe$^X$-containing glycomimetic may be a synthetic polymer-based ligand decorated with 6'-sulfo-sLe$^X$ that structurally or functionally mimics the activity of the natural ligand of Siglec-8. See Hudson et al., *J Pharmacol Exp Ther.*, 330 (2):608-12, 2009 for examples of glycomimetics contemplated herein. Other examples of potential agonists include antibodies or, in some cases, oligonucleotides or polypeptides which are closely related to the natural ligand of Siglec-8, or small molecules which bind to Siglec-8. Synthetic compounds that mimic the conformation and desirable features of a particular polysaccharide ligand (e.g., a 6'-sulfo-sLe$^X$-containing ligand) that binds to Siglec-8, and preferably avoid at least some undesirable features (such as low binding affinity, short half-life in vivo, and the like) of the original polysaccharide ligand of interest (e.g., a 6'-sulfo-sLe$^X$-containing ligand), are referred to herein as "mimetics". See U.S. Pat. No. 8,178,512 for examples of mimetics contemplated herein.

In some aspects, an agonist that binds to human Siglec-8 (e.g., 6'-sulfo-sLeX-containing agonist or an antibody) described herein induces apoptosis of eosinophils. Apoptosis of eosinophils can be assessed by methods well known in the art. See Hudson et al., *J Pharmacol Exp Ther.*, 330(2):608-12, 2009 and Nutku et al., *Biochem Biophys Res Commun.*, 336:918-924, 2005. For example, human eosinophils are isolated from peripheral blood, purified, and cultured for 24 or 72 hours in IL-5 followed by incubation with the agonist that binds to human Siglec-8 for an additional 24 hours. Cell survival is then assessed by flow cytometric analysis after labeling with annexin-V and propidium iodide. Agonist activity may also be assessed using by detecting activation of caspases (e.g., caspase-8, caspase-3, and caspase-9) in eosinophils and/or loss of mitochondrial membrane potential in eosinophils. These assays are described in Nutku et al., *Biochem Biophys Res Commun.*, 336:918-924, 2005.

In some aspects, an agonist that binds to human Siglec-8 (e.g., 6'-sulfo-sLeX-containing agonist or an antibody) described herein depletes or reduces mast cells expressing Siglec-8. In some embodiments, the anti-Siglec-8 antibody kills mast cells expressing Siglec-8 by ADCC activity. Assays for assessing ADCC activity are well known in the art and described herein. In an exemplary assay, to measure ADCC activity, effector cells and target cells are used. Examples of effector cells include natural killer (NK) cells, large granular lymphocytes (LGL), lymphokine-activated killer (LAK) cells and PBMC comprising NK and LGL, or leukocytes having Fc receptors on the cell surfaces, such as neutrophils, eosinophils and macrophages. The target cell is any cell which expresses on the cell surface antigens that antibodies to be evaluated can recognize. An example of such a target cell is a mast cell which expresses Siglec-8 on the cell surface (e.g., Ramos 2C10 target cell line). Target cells can be labeled with a reagent that enables detection of cytolysis. Examples of reagents for labeling include a radioactive substance such as sodium chromate ($Na_2^{51}CrO_4$). See, e.g., *Immunology*, 14, 181 (1968); *J. Immunol. Methods.*, 172, 227 (1994); and *J. Immunol. Methods.*, 184, 29 (1995).

Antibodies

In one aspect, the invention provides isolated antibodies that bind to a human Siglec-8 (e.g., an agonist antibody that binds to human Siglec-8). In some embodiments, an anti-Siglec-8 antibody described herein has one or more of the following characteristics: (1) binds a human Siglec-8; (2) binds to an extracellular domain of a human Siglec-8; (3) binds a human Siglec-8 with a higher affinity than mouse antibody 2E2 and/or mouse antibody 2C4; (4) binds a human Siglec-8 with a higher avidity than mouse antibody 2E2 and/or mouse antibody 2C4; (5) has a $T_m$ of about 70° C.-72° C. or higher in a thermal shift assay; (6) has a reduced degree of fucosylation or is non-fucosylated; (7) binds a human Siglec-8 expressed on eosinophils and induces apoptosis of eosinophils; (8) binds a human Siglec-8 expressed on mast cells and depletes or reduces the number of mast cells; (9) binds a human Siglec-8 expressed on mast cells and inhibits FcεRI-dependent activities of mast cells (e.g., histamine release, PGD$_2$ release, Ca$^{2+}$ flux, and/or β-hexosaminidase release, etc.); (10) has been engineered to improve ADCC activity; and (11) binds a human Siglec-8 expressed on a B cell line sensitive to ADCC activity and depletes or reduces the number of B cells.

In one aspect, the invention provides antibodies that bind to a human Siglec-8. In some embodiments, the human Siglec-8 comprises an amino acid sequence of SEQ ID NO:72. In some embodiments, the human Siglec-8 comprises an amino acid sequence of SEQ ID NO:73. In some embodiments, an antibody described herein binds to a human Siglec-8 expressed on eosinophils and induces apoptosis of eosinophils. In some embodiments, an antibody described herein binds to a human Siglec-8 expressed on mast cells and depletes or reduces the number of mast cells. In some embodiments, an antibody described herein binds to a human Siglec-8 expressed on mast cells and inhibits mast cell-mediated activity.

In one aspect, an anti-Siglec-8 antibody described herein is a monoclonal antibody. In one aspect, an anti-Siglec-8 antibody described herein is an antibody fragment (including antigen-binding fragment), e.g., a Fab, Fab'-SH, Fv, scFv, or (Fab')$_2$ fragment. In one aspect, an anti-Siglec-8 antibody described herein comprises an antibody fragment (including antigen-binding fragment), e.g., a Fab, Fab'-SH, Fv, scFv, or (Fab')$_2$ fragment. In one aspect, an anti-Siglec-8 antibody described herein is a chimeric, humanized, or human antibody. In one aspect, any of the anti-Siglec-8 antibodies described herein are purified.

In one aspect, anti-Siglec-8 antibodies that compete with murine 2E2 antibody and murine 2C4 antibody binding to Siglec-8 are provided. Anti-Siglec-8 antibodies that bind to the same epitope as murine 2E2 antibody and murine 2C4 antibody are also provided. Murine antibodies to Siglec-8, 2E2 and 2C4 antibody are described in U.S. Pat. Nos. 8,207,305; 8,197,811, 7,871,612, and 7,557,191.

In one aspect, anti-Siglec-8 antibodies that compete with any anti-Siglec-8 antibody described herein (e.g., HEKA, HEKF, 1C3, 1H10, 4F11, 2C4, 2E2) for binding to Siglec-8 are provided. Anti-Siglec-8 antibodies that bind to the same epitope as any anti-Siglec-8 antibody described herein (e.g., HEKA, HEKF, 1C3, 1H10, 4F11, 2C4, 2E2) are also provided.

In one aspect of the invention, polynucleotides encoding anti-Siglec-8 antibodies are provided. In certain embodiments, vectors comprising polynucleotides encoding anti-Siglec-8 antibodies are provided. In certain embodiments, host cells comprising such vectors are provided. In another aspect of the invention, compositions comprising anti-Siglec-8 antibodies or polynucleotides encoding anti-Siglec-8 antibodies are provided. In certain embodiments, a composition of the invention is a pharmaceutical formulation for the treatment of advanced systemic mastocytosis (e.g., SM-AHNMD), such as described herein. In certain embodiments, a composition of the invention is a pharmaceutical formulation for the prevention of advanced systemic mastocytosis (e.g., SM-AHNMD), such as described herein.

In one aspect, provided herein is an anti-Siglec-8 antibody comprising 1, 2, 3, 4, 5, or 6 of the HVR sequences of the murine antibody 2C4. In one aspect, provided herein is an anti-Siglec-8 antibody comprising 1, 2, 3, 4, 5, or 6 of the HVR sequences of the murine antibody 2E2. In some embodiments, the HVR is a Kabat CDR or a Chothia CDR.

In one aspect, provided herein is an anti-Siglec-8 antibody comprising 1, 2, 3, 4, 5, or 6 of the HVR sequences of the murine antibody 1C3. In one aspect, provided herein is an anti-Siglec-8 antibody comprising 1, 2, 3, 4, 5, or 6 of the HVR sequences of the murine antibody 4F11. In one aspect, provided herein is an anti-Siglec-8 antibody comprising 1, 2, 3, 4, 5, or 6 of the HVR sequences of the murine antibody 1H10. In some embodiments, the HVR is a Kabat CDR or a Chothia CDR.

In one aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence of SEQ ID NO:63; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:66.

In one aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence selected from SEQ ID NOs:67-70; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:66.

In one aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence of SEQ ID NO:63; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:71.

In another aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:61, (ii) HVR-H2 comprising the amino acid sequence of SEQ ID NO:62, and (iii) HVR-H3 comprising the amino acid sequence selected from SEQ ID NOs:67-70; and/or wherein the light chain variable region comprises (i) HVR-L1 comprising the amino acid sequence of SEQ ID NO:64, (ii) HVR-L2 comprising the amino acid sequence of SEQ ID NO:65, and (iii) HVR-L3 comprising the amino acid sequence of SEQ ID NO:71.

In another aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:88, (ii) HVR-H2 comprising the amino acid sequence of SEQ ID NO:91, and (iii) HVR-H3 comprising the amino acid sequence of SEQ ID NO:94; and/or a light chain variable region comprising (i) HVR-L1 comprising the amino acid sequence of SEQ ID NO:97, (ii) HVR-L2 comprising the amino acid sequence of SEQ ID NO:100, and (iii) HVR-L3 comprising the amino acid sequence of SEQ ID NO:103.

In another aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:89, (ii) HVR-H2 comprising the amino acid sequence of SEQ ID NO:92, and (iii) HVR-H3 comprising the amino acid sequence of SEQ ID NO:95; and/or a light chain variable region comprising (i) HVR-L1 comprising the amino acid sequence of SEQ ID NO:98, (ii) HVR-L2 comprising the amino acid sequence of SEQ ID NO:101, and (iii) HVR-L3 comprising the amino acid sequence of SEQ ID NO:104.

In another aspect, provided herein is an anti-Siglec-8 antibody comprising a heavy chain variable region and a light chain variable region, wherein the heavy chain variable region comprises (i) HVR-H1 comprising the amino acid sequence of SEQ ID NO:90, (ii) HVR-H2 comprising the amino acid sequence of SEQ ID NO:93, and (iii) HVR-H3 comprising the amino acid sequence of SEQ ID NO:96; and/or a light chain variable region comprising (i) HVR-L1 comprising the amino acid sequence of SEQ ID NO:99, (ii) HVR-L2 comprising the amino acid sequence of SEQ ID NO:102, and (iii) HVR-L3 comprising the amino acid sequence of SEQ ID NO:105.

An anti-Siglec-8 antibody described herein may comprise any suitable framework variable domain sequence, provided that the antibody retains the ability to bind human Siglec-8. As used herein, heavy chain framework regions are designated "HC-FR1-FR4," and light chain framework regions are designated "LC-FR1-FR4." In some embodiments, the anti-Siglec-8 antibody comprises a heavy chain variable domain framework sequence of SEQ ID NO:26, 34, 38, and 45 (HC-FR1, HC-FR2, HC-FR3, and HC-FR4, respectively). In some embodiments, the anti-Siglec-8 antibody comprises a light chain variable domain framework sequence of SEQ ID NO:48, 51, 55, and 60 (LC-FR1, LC-FR2, LC-FR3, and LC-FR4, respectively). In some embodiments, the anti-Siglec-8 antibody comprises a light chain variable domain framework sequence of SEQ ID NO:48, 51, 58, and 60 (LC-FR1, LC-FR2, LC-FR3, and LC-FR4, respectively).

In one embodiment, an anti-Siglec-8 antibody comprises a heavy chain variable domain comprising a framework sequence and hypervariable regions, wherein the framework sequence comprises the HC-FR1-HC-FR4 sequences SEQ ID NOs:26-29 (HC-FR1), SEQ ID NOs:31-36 (HC-FR2), SEQ ID NOs:38-43 (HC-FR3), and SEQ ID NOs:45 or 46 (HC-FR4), respectively; the HVR-H1 comprises the amino acid sequence of SEQ ID NO:61; the HVR-H2 comprises the amino acid sequence of SEQ ID NO:62; and the HVR-H3 comprises an amino acid sequence of SEQ ID NO:63. In one embodiment, an anti-Siglec-8 antibody comprises a heavy chain variable domain comprising a framework sequence and hypervariable regions, wherein the framework sequence comprises the HC-FR1-HC-FR4 sequences SEQ ID NOs:26-29 (HC-FR1), SEQ ID NOs:31-36 (HC-FR2), SEQ ID NOs:38-43 (HC-FR3), and SEQ ID NOs:45 or 46 (HC-FR4), respectively; the HVR-H1 comprises the amino acid sequence of SEQ ID NO:61; the HVR-H2 comprises the amino acid sequence of SEQ ID NO:62; and the HVR-H3 comprises an amino acid sequence selected from SEQ ID NOs:67-70. In one embodiment, an anti-Siglec-8 antibody comprises a light chain variable domain comprising a framework sequence and hypervariable regions, wherein the framework sequence comprises the LC-FR1-LC-FR4 sequences SEQ ID NOs:48 or 49 (LC-FR1), SEQ ID NOs:51-53 (LC-FR2), SEQ ID NOs:55-58 (LC-FR3), and SEQ ID NO:60 (LC-FR4), respectively; the HVR-L1 comprises the amino acid sequence of SEQ ID NO:64; the HVR-L2 comprises the amino acid sequence of SEQ ID NO:65; and the HVR-L3 comprises an amino acid sequence of SEQ ID NO:66. In one embodiment, an anti-Siglec-8 antibody comprises a light chain variable domain comprising a framework sequence and hypervariable regions, wherein the framework sequence comprises the LC-FR1-LC-FR4 sequences SEQ ID NOs:48 or 49 (LC-FR1), SEQ ID NOs:51-53 (LC-FR2), SEQ ID NOs:55-58 (LC-FR3), and SEQ ID NO:60 (LC-FR4), respectively; the HVR-L1 comprises the amino acid sequence of SEQ ID NO:64; the HVR-L2 comprises the amino acid sequence of SEQ ID NO:65; and the HVR-L3 comprises an amino acid sequence of SEQ ID NO:71. In one embodiment of these antibodies, the heavy chain variable domain comprises an amino acid sequence selected from SEQ ID NOs:2-10 and the light chain variable domain comprises and amino acid sequence selected from SEQ ID NOs:16-22. In one embodiment of these antibodies, the heavy chain variable domain comprises an amino acid sequence selected from SEQ ID NOs:2-10 and the light chain variable domain comprises and amino acid sequence selected from SEQ ID NOs:23 or 24. In one embodiment of these antibodies, the heavy chain variable domain comprises an amino acid sequence selected from SEQ ID NOs:11-14 and the light chain variable domain comprises and amino acid sequence selected from SEQ ID NOs:16-22. In one embodiment of these antibodies, the heavy chain variable domain comprises an amino acid sequence selected from SEQ ID NOs:11-14 and the light chain variable domain comprises and amino acid sequence selected from SEQ ID NOs:23 or 24. In one embodiment of these antibodies, the heavy chain variable domain comprises an amino acid sequence of SEQ ID NO:6 and the light chain variable domain comprises and amino acid sequence of SEQ ID NO:16. In one embodiment of these antibodies, the heavy chain variable domain comprises an amino acid sequence of SEQ ID NO:6 and the light chain variable domain comprises and amino acid sequence of SEQ ID NO:21.

In some embodiments, the heavy chain HVR sequences comprise the following:

a) HVR-H1 (IYGAH (SEQ ID NO: 61));

b) HVR-H2 (VIWAGGSTNYNSALMS (SEQ ID NO: 62)); and c) HVR-H3 (DGSSPYYYSMEY (SEQ ID NO: 63);
    DGSSPYYYGMEY (SEQ ID NO: 67);
    DGSSPYYYSMDY (SEQ ID NO: 68);
    DGSSPYYYSMEV (SEQ ID NO: 69); or
    GSSPYYYGMDV (SEQ ID NO: 70)).

In some embodiments, the heavy chain HVR sequences comprise the following:

a) HVR-H1 (SYAMS (SEQ ID NO: 88); DYYMY (SEQ ID NO: 89); or SSWMN (SEQ ID NO: 90));

b) HVR-H2 (IISSGGSYTYYSDSVKG (SEQ ID NO: 91);
    RIAPEDGDTEYAPKFQG (SEQ ID NO: 92); or
    QIYPGDDYTNYNGKFKG (SEQ ID NO: 93)); and c) HVR-H3 (HETAQAAWFAY (SEQ ID NO: 94);
    EGNYYGSSILDY (SEQ ID NO: 95); or
    LGPYGPFAD (SEQ ID NO: 96)).

In some embodiments, the heavy chain FR sequences comprise the following:

```
a) HC-FR1 (EVQLVESGGGLVQPGGSLRLSCAASGFSLT (SEQ ID NO: 26);
          EVQLVESGGGLVQPGGSLRLSCAVSGFSLT (SEQ ID NO: 27);
          QVQLQESGPGLVKPSETLSLTCTVSGGSIS (SEQ ID NO: 28); or
          QVQLQESGPGLVKPSETLSLTCTVSGFSLT (SEQ ID NO: 29));

b) HC-FR2 (WVRQAPGKGLEWVS (SEQ ID NO: 31); WVRQAPGKGLEWLG (SEQ ID NO: 32);
          WVRQAPGKGLEWLS (SEQ ID NO: 33); WVRQAPGKGLEWVG (SEQ ID NO: 34);
          WIRQPPGKGLEWIG (SEQ ID NO: 35); or WVRQPPGKGLEWLG (SEQ ID NO: 36));

c) HC-FR3 (RFTISKDNSKNTVYLQMNSLRAEDTAVYYCAR (SEQ ID NO: 38);
          RLSISKDNSKNTVYLQMNSLRAEDTAVYYCAR (SEQ ID NO: 39);
          RLTISKDNSKNTVYLQMNSLRAEDTAVYYCAR (SEQ ID NO: 40);
          RFSISKDNSKNTVYLQMNSLRAEDTAVYYCAR (SEQ ID NO: 41);
          RVTISVDTSKNQFSLKLSSVTAATAVYYCAR (SEQ ID NO: 42); or
          RLSISKDNSKNQVSLKLSSVTAATAVYYCAR (SEQ ID NO: 43));
and d) HC-FR4 (WGQGTTVTVSS (SEQ ID NO: 45); or WGQGTLVTVSS (SEQ ID NO: 46)).
```

In some embodiments, the light chain HVR sequences comprise the following:

```
a) HVR-L1    (SATSSVSYMH (SEQ ID NO: 64));

b) HVR-L2    (STSNLAS (SEQ ID NO: 65));
and c) HVR-L3    (QQRSSYPFT (SEQ ID NO: 66); or
             QQRSSYPYT (SEQ ID NO: 71)).
```

In some embodiments, the light chain HVR sequences comprise the following:

```
a) HVR-L1    (SASSSVSYMH (SEQ ID NO: 97);
             RASQDITNYLN (SEQ ID NO: 98); or
             SASSSVSYMY (SEQ ID NO: 99));

b) HVR-L2    (DTSKLAY (SEQ ID NO: 100);
             FTSRLHS (SEQ ID NO: 101); or
             DTSSLAS (SEQ ID NO: 102));
and c) HVR-L3    (QQWSSNPPT (SEQ ID NO: 103);
             QQGNTLPWT (SEQ ID NO: 104); or
             QQWNSDPYT (SEQ ID NO: 105)).
```

In some embodiments, the light chain FR sequences comprise the following:

```
a) LC-FR1 (EIVLTQSPATLSLSPGERATLSC (SEQ ID NO: 48); or
          EIILTQSPATLSLSPGERATLSC (SEQ ID NO: 49));

b) LC-FR2 (WFQQKPGQAPRLLIY (SEQ ID NO: 51); WFQQKPGQAPRLWIY (SEQ ID NO: 52);
          or WYQQKPGQAPRLLIY (SEQ ID NO: 53));

c) LC-FR3 (GIPARFSGSGSGTDFTLTISSLEPEDFAVYYC (SEQ ID NO: 55);
          GVPARFSGSGSGTDYTLTISSLEPEDFAVYYC (SEQ ID NO: 56);
          GVPARFSGSGSGTDFTLTISSLEPEDFAVYYC (SEQ ID NO: 57); or
          GIPARFSGSGSGTDYTLTISSLEPEDFAVYYC (SEQ ID NO: 58));
and d) LC-FR4 (FGPGTKLDIK (SEQ ID NO: 60)).
```

In some embodiments, provided herein is an anti-Siglec-8 antibody (e.g., a humanized anti-Siglec-8) antibody that binds to human Siglec-8, wherein the antibody comprises a heavy chain variable region and a light chain variable region, wherein the antibody comprises:
(a) heavy chain variable domain comprising:
(1) an HC-FR1 comprising the amino acid sequence selected from SEQ ID NOs:26-29;
(2) an HVR-H1 comprising the amino acid sequence of SEQ ID NO:61;
(3) an HC-FR2 comprising the amino acid sequence selected from SEQ ID NOs:31-36;
(4) an HVR-H2 comprising the amino acid sequence of SEQ ID NO:62;
(5) an HC-FR3 comprising the amino acid sequence selected from SEQ ID NOs:38-43;
(6) an HVR-H3 comprising the amino acid sequence of SEQ ID NO:63; and
(7) an HC-FR4 comprising the amino acid sequence selected from SEQ ID NOs:45-46, and/or
(b) a light chain variable domain comprising:
(1) an LC-FR1 comprising the amino acid sequence selected from SEQ ID NOs:48-49;
(2) an HVR-L1 comprising the amino acid sequence of SEQ ID NO:64;
(3) an LC-FR2 comprising the amino acid sequence selected from SEQ ID NOs:51-53;
(4) an HVR-L2 comprising the amino acid sequence of SEQ ID NO:65;
(5) an LC-FR3 comprising the amino acid sequence selected from SEQ ID NOs:55-58;
(6) an HVR-L3 comprising the amino acid sequence of SEQ ID NO:66; and
(7) an LC-FR4 comprising the amino acid sequence of SEQ ID NO:60.

In one aspect, provided herein is an anti-Siglec-8 antibody comprising a heavy chain variable domain selected from SEQ ID NOs:2-10 and/or comprising a light chain variable domain selected from SEQ ID NOs:16-22. In one aspect, provided herein is an anti-Siglec-8 antibody comprising a heavy chain variable domain selected from SEQ ID NOs:2-10 and/or comprising a light chain variable domain selected from SEQ ID NO:23 or 24. In one aspect, provided herein is an anti-Siglec-8 antibody comprising a heavy chain variable domain selected from SEQ ID NOs:11-14 and/or comprising a light chain variable domain selected from SEQ ID NOs:16-22. In one aspect, provided herein is an anti- Siglec-8 antibody comprising a heavy chain variable domain selected from SEQ ID NOs:11-14 and/or comprising a light chain variable domain selected from SEQ ID NO:23 or 24. In one aspect, provided herein is an anti-Siglec-8 antibody comprising a heavy chain variable domain of SEQ ID NO:6 and/or comprising a light chain variable domain selected from SEQ ID NO:16 or 21.

In one aspect, provided herein is an anti-Siglec-8 antibody comprising a heavy chain variable domain selected from SEQ ID NOs:106-108 and/or comprising a light chain variable domain selected from SEQ ID NOs:109-111. In one aspect, provided herein is an anti-Siglec-8 antibody comprising a heavy chain variable domain of SEQ ID NO:106 and/or comprising a light chain variable domain of SEQ ID NO:109. In one aspect, provided herein is an anti-Siglec-8 antibody comprising a heavy chain variable domain of SEQ ID NO:107 and/or comprising a light chain variable domain of SEQ ID NO:110. In one aspect, provided herein is an anti-Siglec-8 antibody comprising a heavy chain variable domain of SEQ ID NO:108 and/or comprising a light chain variable domain of SEQ ID NO:111.

In some embodiments, provided herein is an anti-Siglec-8 antibody comprising a heavy chain variable domain comprising an amino acid sequence having at least 90%, 91%, 92%, 93%, 94%, 95%, 96%, 97%, 98%, or 99% sequence identity to an amino acid sequence selected from SEQ ID NOs:2-14. In some embodiments, provided herein is an anti-Siglec-8 antibody comprising a heavy chain variable domain comprising an amino acid sequence having at least 90%, 91%, 92%, 93%, 94%, 95%, 96%, 97%, 98%, or 99% sequence identity to an amino acid sequence selected from SEQ ID NOs:106-108. In some embodiments, an amino acid sequence having at least 90%, 91%, 92%, 93%, 94%, 95%, 96%, 97%, 98%, or 99% sequence identity contains substitutions, insertions, or deletions relative to the reference sequence, but an antibody comprising that amino acid sequence retains the ability to bind to human Siglec-8. In some embodiments, the substitutions, insertions, or deletions (e.g., 1, 2, 3, 4, or 5 amino acids) occur in regions outside the HVRs (i.e., in the FRs). In some embodiments, an anti-Siglec-8 antibody comprises a heavy chain variable domain comprising an amino acid sequence of SEQ ID NO:6. In some embodiments, an anti-Siglec-8 antibody comprises a heavy chain variable domain comprising an amino acid sequence selected from SEQ ID NOs:106-108.

In some embodiments, provided herein is an anti-Siglec-8 antibody comprising a light chain variable domain comprising an amino acid sequence having at least 90%, 91%, 92%, 93%, 94%, 95%, 96%, 97%, 98%, or 99% sequence identity to an amino acid sequence selected from SEQ ID NOs:16-24. In some embodiments, provided herein is an anti-Siglec-8 antibody comprising a light chain variable domain comprising an amino acid sequence having at least 90%, 91%, 92%, 93%, 94%, 95%, 96%, 97%, 98%, or 99% sequence identity to an amino acid sequence selected from SEQ ID NOs:109-111. In some embodiments, an amino acid sequence having at least 90%, 91%, 92%, 93%, 94%, 95%, 96%, 97%, 98%, or 99% sequence identity contains substitutions, insertions, or deletions relative to the reference sequence, but an antibody comprising that amino acid sequence retains the ability to bind to human Siglec-8. In some embodiments, the substitutions, insertions, or deletions (e.g., 1, 2, 3, 4, or 5 amino acids) occur in regions outside the HVRs (i.e., in the FRs). In some embodiments, an anti-Siglec-8 antibody comprises a light chain variable domain comprising an amino acid sequence of SEQ ID NO:16 or 21. In some embodiments, an anti-Siglec-8 antibody comprises a heavy chain variable domain comprising an amino acid sequence selected from SEQ ID NOs:109-111.

In one aspect, the invention provides an anti-Siglec-8 antibody comprising (a) one, two, or three VH HVRs selected from those shown in Table 1 and/or (b) one, two, or three VL HVRs selected from those shown in Table 1.

In one aspect, the invention provides an anti-Siglec-8 antibody comprising (a) one, two, or three VH HVRs selected from those shown in Table 2 and/or (b) one, two, or three VL HVRs selected from those shown in Table 2.

In one aspect, the invention provides an anti-Siglec-8 antibody comprising (a) one, two, three or four VH FRs selected from those shown in Table 3 and/or (b) one, two, three or four VL FRs selected from those shown in Table 3.

In some embodiments, provided herein is an anti-Siglec-8 antibody comprising a heavy chain variable domain and/or a light chain variable domain of an antibody shown in Table 4, for example, HAKA antibody, HAKB antibody, HAKC antibody, etc.

TABLE 1

Amino acid sequences of HVRs of antibodies

| Antibody Chain | HVR1 | HVR2 | HVR3 |
|---|---|---|---|
| 2E2 antibody | | | |
| Heavy chain | IYGAH<br>SEQ ID NO: 61 | VIWAGGSTNYNSALMS<br>SEQ ID NO: 62 | DGSSPYYYSMEY<br>SEQ ID NO: 63 |
| Light chain | SATSSVSYMH<br>SEQ ID NO: 64 | STSNLAS<br>SEQ ID NO: 65 | QQRSSYPFT<br>SEQ ID NO: 66 |
| Humanized Heavy Chain Variants 2E2 RHA, 2E2 RHB, 2E2 RHC, 2E2 RHD, 2E2 RHE, 2E2 RHF, 2E2 RHG, 2E2 RHA2, and 2E2 RHB2 | | | |
| Heavy chain | IYGAH<br>SEQ ID NO: 61 | VIWAGGSTNYNSALMS<br>SEQ ID NO: 62 | DGSSPYYYSMEY<br>SEQ ID NO: 63 |
| Humanized Light Chain Variants 2E2 RKA, 2E2 RKB, 2E2 RKC, 2E2 RKD, 2E2 RKE, 2E2 RKF, and 2E2 RKG | | | |
| Light chain | SATSSVSYMH<br>SEQ ID NO: 64 | STSNLAS<br>SEQ ID NO: 65 | QQRSSYPFT<br>SEQ ID NO: 66 |

TABLE 1-continued

Amino acid sequences of HVRs of antibodies

| Antibody | Chain | HVR1 | HVR2 | HVR3 |
|---|---|---|---|---|

Humanized Heavy Chain Variants 2E2 RHE S-G, 2E2 RHE E-D, 2E2 RHE Y-V, and 2E2 RHE triple

| Antibody | HVR1 | HVR2 | HVR3 |
|---|---|---|---|
| 2E2 RHE S-G | IYGAH<br>SEQ ID NO: 61 | VIWAGGSTNYNSALMS<br>SEQ ID NO: 62 | DGSSPYYYGMEY<br>SEQ ID NO: 67 |
| 2E2 RHE E-D | IYGAH<br>SEQ ID NO: 61 | VIWAGGSTNYNSALMS<br>SEQ ID NO: 62 | DGSSPYYYSMDY<br>SEQ ID NO: 68 |
| 2E2 RHE Y-V | IYGAH<br>SEQ ID NO: 61 | VIWAGGSTNYNSALMS<br>SEQ ID NO: 62 | DGSSPYYYSMEV<br>SEQ ID NO: 69 |
| 2E2 RH3 triple | IYGAH<br>SEQ ID NO: 61 | VIWAGGSTNYNSALMS<br>SEQ ID NO: 62 | DGSSPYYYGMDV<br>SEQ ID NO: 70 |

Humanized Light Chain Variants 2E2 RKA F-Y and 2E2 RKF F-Y

| Antibody | HVR1 | HVR2 | HVR3 |
|---|---|---|---|
| 2E2 RKA F-Y | SATSSVSYMH<br>SEQ ID NO: 64 | STSNLAS<br>SEQ ID NO: 65 | QQRSSYPYT<br>SEQ ID NO: 71 |
| 2E2 RKF F-Y | SATSSVSYMH<br>SEQ ID NO: 64 | STSNLAS<br>SEQ ID NO: 65 | QQRSSYPYT<br>SEQ ID NO: 71 |

TABLE 2

Amino acid sequences of HVRs from murine 1C3, 1H10, and 4F11 antibodies

| Antibody | Chain | HVR1 | HVR2 | HVR3 |
|---|---|---|---|---|
| 1C3 | Heavy Chain | SYAMS<br>SEQ ID NO: 88 | IISSGGSYTYYSDSVKG<br>SEQ ID NO: 91 | HETAQAAWFAY<br>SEQ ID NO: 94 |
| 1H10 | Heavy Chain | DYYMY<br>SEQ ID NO: 89 | RIAPEDGDTEYAPKFQG<br>SEQ ID NO: 92 | EGNYYGSSILDY<br>SEQ ID NO: 95 |
| 4F11 | Heavy Chain | SSWMN<br>SEQ ID NO: 90 | QIYPGDDYTNYNGKFKG<br>SEQ ID NO: 93 | LGPYGPFAD<br>SEQ ID NO: 96 |
| 1C3 | Light Chain | SASSSVSYMH<br>SEQ ID NO: 97 | DTSKLAY<br>SEQ ID NO: 100 | QQWSSNPPT<br>SEQ ID NO: 103 |
| 1H10 | Light Chain | RASQDITNYLN<br>SEQ ID NO: 98 | FTSRLHS<br>SEQ ID NO: 101 | QQGNTLPWT<br>SEQ ID NO: 104 |
| 4F11 | Light Chain | SASSSVSYMY<br>SEQ ID NO: 99 | DTSSLAS<br>SEQ ID NO: 102 | QQWNSDPYT<br>SEQ ID NO: 105 |

TABLE 3

Amino acid sequences of FRs of antibodies

| Heavy Chain | FR1 | FR2 | FR3 | FR4 |
|---|---|---|---|---|
| 2E2 | QVQLKESGPGLVAPSQS<br>LSITCTVSGFSLT<br>(SEQ ID NO: 25) | WVRQPPGKGLEWLG<br>(SEQ ID NO: 30) | RLSISKDNSKSQVFLKI<br>NSLQTDDTALYYCAR<br>(SEQ ID NO: 37) | WGQGTSVTVSS<br>(SEQ ID NO: 44) |
| 2E2 RHA | EVQLVESGGGLVQPGGS<br>LRLSCAASGFSLT<br>(SEQ ID NO: 26) | WVRQAPGKGLEWVS<br>(SEQ ID NO: 31) | RFTISKDNSKNTVYLQM<br>NSLRAEDTAVYYCAR<br>(SEQ ID NO: 38) | WGQGTTVTVSS<br>(SEQ ID NO: 45) |
| 2E2 RHB | EVQLVESGGGLVQPGGS<br>LRLSCAVSGFSLT<br>(SEQ ID NO: 27) | WVRQAPGKGLEWLG<br>(SEQ ID NO: 32) | RLSISKDNSKNTVYLQM<br>NSLRAEDTAVYYCAR<br>(SEQ ID NO: 39) | WGQGTTVTVSS<br>(SEQ ID NO: 45) |
| 2E2 RHC | EVQLVESGGGLVQPGGS<br>LRLSCAVSGFSLT<br>(SEQ ID NO: 27) | WVRQAPGKGLEWVS<br>(SEQ ID NO: 31) | RFTISKDNSKNTVYLQM<br>NSLRAEDTAVYYCAR<br>(SEQ ID NO: 38) | WGQGTTVTVSS<br>(SEQ ID NO: 45) |
| 2E2 RHD | EVQLVESGGGLVQPGGS<br>LRLSCAASGFSLT<br>(SEQ ID NO: 26) | WVRQAPGKGLEWLS<br>(SEQ ID NO: 33) | RFTISKDNSKNTVYLQM<br>NSLRAEDTAVYYCAR<br>(SEQ ID NO: 38) | WGQGTTVTVSS<br>(SEQ ID NO: 45) |
| 2E2 RHE | EVQLVESGGGLVQPGGS<br>LRLSCAASGFSLT<br>(SEQ ID NO: 26) | WVRQAPGKGLEWVG<br>(SEQ ID NO: 34) | RFTISKDNSKNTVYLQM<br>NSLRAEDTAVYYCAR<br>(SEQ ID NO: 38) | WGQGTTVTVSS<br>(SEQ ID NO: 45) |
| 2E2 RHF | EVQLVESGGGLVQPGGS<br>LRLSCAASGFSLT<br>(SEQ ID NO: 26) | WVRQAPGKGLEWVS<br>(SEQ ID NO: 31) | RLTISKDNSKNTVYLQM<br>NSLRAEDTAVYYCAR<br>(SEQ ID NO: 40) | WGQGTTVTVSS<br>(SEQ ID NO: 45) |

TABLE 3-continued

Amino acid sequences of FRs of antibodies

| | FR1 | FR2 | FR3 | FR4 |
|---|---|---|---|---|
| 2E2 RHG | EVQLVESGGGLVQPGGS LRLSCAASGFSLT (SEQ ID NO: 26) | WVRQAPGKGLEWVS (SEQ ID NO: 31) | RFSISKDNSKNTVYLQM NSLRAEDTAVYYCAR (SEQ ID NO: 41) | WGQGTTVTVSS (SEQ ID NO: 45) |
| 2E2 RHA2 | QVQLQESGPGLVKPSET LSLTCTVSGGSIS (SEQ ID NO: 28) | WIRQPPGKGLEWIG (SEQ ID NO: 35) | RVTISVDTSKNQFSLKL SSVTAADTAVYYCAR (SEQ ID NO: 42) | WGQGTLVTVSS (SEQ ID NO: 46) |
| 2E2 RHB2 | QVQLQESGPGLVKPSET LSLTCTVSGFSLT (SEQ ID NO: 29) | WVRQPPGKGLEWLG (SEQ ID NO: 36) | RLSISKDNSKNQVSLKL SSVTAADTAVYYCAR (SEQ ID NO: 43) | WGQGTLVTVSS (SEQ ID NO: 46) |
| 2E2 RHE S-G | EVQLVESGGGLVQPGGS LRLSCAASGFSLT (SEQ ID NO: 26) | WVRQAPGKGLEWVG (SEQ ID NO: 34) | RFTISKDNSKNTVYLQM NSLRAEDTAVYYCAR (SEQ ID NO: 38) | WGQGTTVTVSS (SEQ ID NO: 45) |
| 2E2 RHE E-D | EVQLVESGGGLVQPGGS LRLSCAASGFSLT (SEQ ID NO: 26) | WVRQAPGKGLEWVG (SEQ ID NO: 34) | RFTISKDNSKNTVYLQM NSLRAEDTAVYYCAR (SEQ ID NO: 38) | WGQGTTVTVSS (SEQ ID NO: 45) |
| 2E2 RHE Y-V | EVQLVESGGGLVQPGGS LRLSCAASGFSLT (SEQ ID NO: 26) | WVRQAPGKGLEWVG (SEQ ID NO: 34) | RFTISKDNSKNTVYLQM NSLRAEDTAVYYCAR (SEQ ID NO: 38) | WGQGTTVTVSS (SEQ ID NO: 45) |
| 2E2 RHE triple | EVQLVESGGGLVQPGGS LRLSCAASGFSLT (SEQ ID NO: 26) | WVRQAPGKGLEWVG (SEQ ID NO: 34) | RFTISKDNSKNTVYLQM NSLRAEDTAVYYCAR (SEQ ID NO: 38) | WGQGTTVTVSS (SEQ ID NO: 45) |
| Light Chain | FR1 | FR2 | FR3 | FR4 |
| 2E2 | QILTQSPAIMSASPGEK VSITC (SEQ ID NO: 47) | WFQQKPGTSPKLWIY (SEQ ID NO: 50) | GVPVRFSGSGSGTSYSL TISRMEAEDAATYYC (SEQ ID NO: 54) | FGSGTKLEIK (SEQ ID NO: 59) |
| RKA | EIVLTQSPATLSLSPGE RATLSC (SEQ ID NO: 48) | WFQQKPGQAPRLLIY (SEQ ID NO: 51) | GIPARFSGSGSGTDFTL TISSLEPEDFAVYYC (SEQ ID NO: 55) | FGPGTKLDIK (SEQ ID NO: 60) |
| RKB | EIILTQSPATLSLSPGE RATLSC (SEQ ID NO: 49) | WFQQKPGQAPRLWIY (SEQ ID NO: 52) | GVPARFSGSGSGTDYTL TISSLEPEDFAVYYC (SEQ ID NO: 56) | FGPGTKLDIK (SEQ ID NO: 60) |
| RKC | EIILTQSPATLSLSPGE RATLSC (SEQ ID NO: 49) | WFQQKPGQAPRLLIY (SEQ ID NO: 51) | GIPARFSGSGSGTDFTL TISSLEPEDFAVYYC (SEQ ID NO: 55) | FGPGTKLDIK (SEQ ID NO: 60) |
| RKD | EIVLTQSPATLSLSPGE RATLSC (SEQ ID NO: 48) | WFQQKPGQAPRLWIY (SEQ ID NO: 52) | GIPARFSGSGSGTDFTL TISSLEPEDFAVYYC (SEQ ID NO: 55) | FGPGTKLDIK (SEQ ID NO: 60) |
| RKE | EIVLTQSPATLSLSPGE RATLSC (SEQ ID NO: 48) | WFQQKPGQAPRLLIY (SEQ ID NO: 51) | GVPARFSGSGSGTDFTL TISSLEPEDFAVYYC (SEQ ID NO: 57) | FGPGTKLDIK (SEQ ID NO: 60) |
| RKF | EIVLTQSPATLSLSPGE RATLSC (SEQ ID NO: 48) | WFQQKPGQAPRLLIY (SEQ ID NO: 51) | GIPARFSGSGSGTDYTL TISSLEPEDFAVYYC (SEQ ID NO: 58) | FGPGTKLDIK (SEQ ID NO: 60) |
| RKG | EIVLTQSPATLSLSPGE RATLSC (SEQ ID NO: 48) | WYQQKPGQAPRLLIY (SEQ ID NO: 53) | GIPARFSGSGSGTDFTL TISSLEPEDFAVYYC (SEQ ID NO: 55) | FGPGTKLDIK (SEQ ID NO: 60) |
| RKA F-Y | EIVLTQSPATLSLSPGE RATLSC (SEQ ID NO: 48) | WFQQKPGQAPRLLIY (SEQ ID NO: 51) | GIPARFSGSGSGTDFTL TISSLEPEDFAVYYC (SEQ ID NO: 55) | FGPGTKLDIK (SEQ ID NO: 60) |
| RKF F-Y | EIVLTQSPATLSLSPGE RATLSC (SEQ ID NO: 48) | WFQQKPGQAPRLLIY (SEQ ID NO: 51) | GIPARFSGSGSGTDFTL TISSLEPEDFAVYYC (SEQ ID NO: 55) | FGPGTKLDIK (SEQ ID NO: 60) |

TABLE 4

Amino acid sequences of variable regions of antibodies

| Antibody Name | Variable Heavy Chain | Variable Light Chain |
|---|---|---|
| ch2C4 | ch2C4 VH | ch2C4 VK |
| ch2E2 | ch2E2 VH (SEQ ID NO: 1) | ch2E2 VK (SEQ ID NO: 15) |
| cVHKA | ch2E2 VH (SEQ ID NO: 1) | 2E2 RKA (SEQ ID NO: 16) |
| cVHKB | ch2E2 VH (SEQ ID NO: 1) | 2E2 RKB (SEQ ID NO: 17) |
| HAcVK | 2E2 RHA (SEQ ID NO: 2) | ch2E2 VK (SEQ ID NO: 15) |
| HBcVK | 2E2 RHB (SEQ ID NO: 3) | ch2E2 VK (SEQ ID NO: 15) |
| HAKA | 2E2 RHA (SEQ ID NO: 2) | 2E2 RKA (SEQ ID NO: 16) |
| HAKB | 2E2 RHA (SEQ ID NO: 2) | 2E2 RKB (SEQ ID NO: 17) |
| HAKC | 2E2 RHA (SEQ ID NO: 2) | 2E2 RKC (SEQ ID NO: 18) |
| HAKD | 2E2 RHA (SEQ ID NO: 2) | 2E2 RKD (SEQ ID NO: 19) |
| HAKE | 2E2 RHA (SEQ ID NO: 2) | 2E2 RKE (SEQ ID NO: 20) |
| HAKF | 2E2 RHA (SEQ ID NO: 2) | 2E2 RKF (SEQ ID NO: 21) |
| HAKG | 2E2 RHA (SEQ ID NO: 2) | 2E2 RKG (SEQ ID NO: 22) |
| HBKA | 2E2 RHB (SEQ ID NO: 3) | 2E2 RKA (SEQ ID NO: 16) |

TABLE 4-continued

Amino acid sequences of variable regions of antibodies

| Antibody Name | Variable Heavy Chain | Variable Light Chain |
|---|---|---|
| HBKB | 2E2 RHB (SEQ ID NO: 3) | 2E2 RKB (SEQ ID NO: 17) |
| HBKC | 2E2 RHB (SEQ ID NO: 3) | 2E2 RKC (SEQ ID NO: 18) |
| HBKD | 2E2 RHB (SEQ ID NO: 3) | 2E2 RKD (SEQ ID NO: 19) |
| HBKE | 2E2 RHB (SEQ ID NO: 3) | 2E2 RKE (SEQ ID NO: 20) |
| HBKF | 2E2 RHB (SEQ ID NO: 3) | 2E2 RKF (SEQ ID NO: 21) |
| HBKG | 2E2 RHB (SEQ ID NO: 3) | 2E2 RKG (SEQ ID NO: 22) |
| HCKA | 2E2 RHC (SEQ ID NO: 4) | 2E2 RKA (SEQ ID NO: 16) |
| HCKB | 2E2 RHC (SEQ ID NO: 4) | 2E2 RKB (SEQ ID NO: 17) |
| HCKC | 2E2 RHC (SEQ ID NO: 4) | 2E2 RKC (SEQ ID NO: 18) |
| HCKD | 2E2 RHC (SEQ ID NO: 4) | 2E2 RKD (SEQ ID NO: 19) |
| HCKE | 2E2 RHC (SEQ ID NO: 4) | 2E2 RKE (SEQ ID NO: 20) |
| HCKF | 2E2 RHC (SEQ ID NO: 4) | 2E2 RKF (SEQ ID NO: 21) |
| HCKG | 2E2 RHC (SEQ ID NO: 4) | 2E2 RKG (SEQ ID NO: 22) |
| HDKA | 2E2 RHD (SEQ ID NO: 5) | 2E2 RKA (SEQ ID NO: 16) |
| HDKB | 2E2 RHD (SEQ ID NO: 5) | 2E2 RKB (SEQ ID NO: 17) |
| HDKC | 2E2 RHD (SEQ ID NO: 5) | 2E2 RKC (SEQ ID NO: 18) |
| HDKD | 2E2 RHD (SEQ ID NO: 5) | 2E2 RKD (SEQ ID NO: 19) |
| HDKE | 2E2 RHD (SEQ ID NO: 5) | 2E2 RKE (SEQ ID NO: 20) |
| HDKF | 2E2 RHD (SEQ ID NO: 5) | 2E2 RKF (SEQ ID NO: 21) |
| HDKG | 2E2 RHD (SEQ ID NO: 5) | 2E2 RKG (SEQ ID NO: 22) |
| HEKA | 2E2 RHE (SEQ ID NO: 6) | 2E2 RKA (SEQ ID NO: 16) |
| HEKB | 2E2 RHE (SEQ ID NO: 6) | 2E2 RKB (SEQ ID NO: 17) |
| HEKC | 2E2 RHE (SEQ ID NO: 6) | 2E2 RKC (SEQ ID NO: 18) |
| HEKD | 2E2 RHE (SEQ ID NO: 6) | 2E2 RKD (SEQ ID NO: 19) |
| HEKE | 2E2 RHE (SEQ ID NO: 6) | 2E2 RKE (SEQ ID NO: 20) |
| HEKF | 2E2 RHE (SEQ ID NO: 6) | 2E2 RKF (SEQ ID NO: 21) |
| HEKG | 2E2 RHE (SEQ ID NO: 6) | 2E2 RKG (SEQ ID NO: 22) |
| HFKA | 2E2 RHF (SEQ ID NO: 7) | 2E2 RKA (SEQ ID NO: 16) |
| HFKB | 2E2 RHF (SEQ ID NO: 7) | 2E2 RKB (SEQ ID NO: 17) |
| HFKC | 2E2 RHF (SEQ ID NO: 7) | 2E2 RKC (SEQ ID NO: 18) |
| HFKD | 2E2 RHF (SEQ ID NO: 7) | 2E2 RKD (SEQ ID NO: 19) |
| HFKE | 2E2 RHF (SEQ ID NO: 7) | 2E2 RKE (SEQ ID NO: 20) |
| HFKF | 2E2 RHF (SEQ ID NO: 7) | 2E2 RKF (SEQ ID NO: 21) |
| HFKG | 2E2 RHF (SEQ ID NO: 7) | 2E2 RKG (SEQ ID NO: 22) |
| HGKA | 2E2 RHG (SEQ ID NO: 8) | 2E2 RKA (SEQ ID NO: 16) |
| HGKB | 2E2 RHG (SEQ ID NO: 8) | 2E2 RKB (SEQ ID NO: 17) |
| HGKC | 2E2 RHG (SEQ ID NO: 8) | 2E2 RKC (SEQ ID NO: 18) |
| HGKD | 2E2 RHG (SEQ ID NO: 8) | 2E2 RKD (SEQ ID NO: 19) |
| HGKE | 2E2 RHG (SEQ ID NO: 8) | 2E2 RKE (SEQ ID NO: 20) |
| HGKF | 2E2 RHG (SEQ ID NO: 8) | 2E2 RKF (SEQ ID NO: 21) |
| HGHG | 2E2 RHG (SEQ ID NO: 8) | 2E2 RKG (SEQ ID NO: 22) |
| HA2KA | 2E2 RHA2 (SEQ ID NO: 9) | 2E2 RKA (SEQ ID NO: 16) |
| HA2KB | 2E2 RHA2 (SEQ ID NO: 9) | 2E2 RKB (SEQ ID NO: 17) |
| HB2KA | 2E2 RHB2 (SEQ ID NO: 10) | 2E2 RKA (SEQ ID NO: 16) |
| HB2KB | 2E2 RHB2 (SEQ ID NO: 10) | 2E2 RKB (SEQ ID NO: 17) |
| HA2KF | 2E2 RHA2 (SEQ ID NO: 9) | 2E2 RKF (SEQ ID NO: 21) |
| HB2KF | 2E2 RHB2 (SEQ ID NO: 10) | 2E2 RKF (SEQ ID NO: 21) |
| HA2KC | 2E2 RHA2 (SEQ ID NO: 9) | 2E2 RKC (SEQ ID NO: 18) |
| HA2KD | 2E2 RHA2 (SEQ ID NO: 9) | 2E2 RKD (SEQ ID NO: 19) |
| HA2KE | 2E2 RHA2 (SEQ ID NO: 9) | 2E2 RKE (SEQ ID NO: 20) |
| HA2KF | 2E2 RHA2 (SEQ ID NO: 9) | 2E2 RKF (SEQ ID NO: 21) |
| HA2KG | 2E2 RHA2 (SEQ ID NO: 9) | 2E2 RKG (SEQ ID NO: 22) |
| HB2KC | 2E2 RHB2 (SEQ ID NO: 10) | 2E2 RKC (SEQ ID NO: 18) |
| HB2KD | 2E2 RHB2 (SEQ ID NO: 10) | 2E2 RKD (SEQ ID NO: 19) |
| HB2KE | 2E2 RHB2 (SEQ ID NO: 10) | 2E2 RKE (SEQ ID NO: 20) |
| HA2KFmut | 2E2 RHA2 (SEQ ID NO: 9) | 2E2 RKF F-Y mut (SEQ ID NO: 24) |
| HB2KFmut | 2E2 RHB2 (SEQ ID NO: 10) | 2E2 RKF F-Y mut (SEQ ID NO: 24) |
| HEKAmut | 2E2 RHE (SEQ ID NO: 6) | 2E2 RKA F-Y mut (SEQ ID NO: 23) |
| HEKFmut | 2E2 RHE (SEQ ID NO: 6) | 2E2 RKF F-Y mut (SEQ ID NO: 24) |
| HAKFmut | 2E2 RHA (SEQ ID NO: 2) | 2E2 RKF F-Y mut (SEQ ID NO: 24) |
| HBKFmut | 2E2 RHB (SEQ ID NO: 3) | 2E2 RKF F-Y mut (SEQ ID NO: 24) |
| HCKFmut | 2E2 RHC (SEQ ID NO: 4) | 2E2 RKF F-Y mut (SEQ ID NO: 24) |
| HDKFmut | 2E2 RHD (SEQ ID NO: 5) | 2E2 RKF F-Y mut (SEQ ID NO: 24) |
| HFKFmut | 2E2 RHF (SEQ ID NO: 7) | 2E2 RKF F-Y mut (SEQ ID NO: 24) |
| HGKFmut | 2E2 RHG (SEQ ID NO: 8) | 2E2 RKF F-Y mut (SEQ ID NO: 24) |
| RHE Y-VKA | 2E2 RHE Y-V (SEQ ID NO: 13) | 2E2 RKA (SEQ ID NO: 16) |
| RHE Y-VKB | 2E2 RHE Y-V (SEQ ID NO: 13) | 2E2 RKB (SEQ ID NO: 17) |
| RHE Y-VKC | 2E2 RHE Y-V (SEQ ID NO: 13) | 2E2 RKC (SEQ ID NO: 18) |
| RHE Y-VKD | 2E2 RHE Y-V (SEQ ID NO: 13) | 2E2 RKD (SEQ ID NO: 19) |
| RHE Y-VKE | 2E2 RHE Y-V (SEQ ID NO: 13) | 2E2 RKE (SEQ ID NO: 20) |
| RHE Y-VKF | 2E2 RHE Y-V (SEQ ID NO: 13) | 2E2 RKF (SEQ ID NO: 21) |
| RHE Y-VKG | 2E2 RHE Y-V (SEQ ID NO: 13) | 2E2 RKG (SEQ ID NO: 22) |
| RHE E-DKA | 2E2 RHE E-D (SEQ ID NO: 12) | 2E2 RKA (SEQ ID NO: 16) |
| RHE E-DKB | 2E2 RHE E-D (SEQ ID NO: 12) | 2E2 RKB (SEQ ID NO: 17) |
| RHE E-DKC | 2E2 RHE E-D (SEQ ID NO: 12) | 2E2 RKC (SEQ ID NO: 18) |
| RHE E-DKD | 2E2 RHE E-D (SEQ ID NO: 12) | 2E2 RKD (SEQ ID NO: 19) |

TABLE 4-continued

Amino acid sequences of variable regions of antibodies

| Antibody Name | Variable Heavy Chain | Variable Light Chain |
| --- | --- | --- |
| RHE E-DKE | 2E2 RHE E-D (SEQ ID NO: 12) | 2E2 RKE (SEQ ID NO: 20) |
| RHE E-DKF | 2E2 RHE E-D (SEQ ID NO: 12) | 2E2 RKF (SEQ ID NO: 21) |
| RHE E-DKG | 2E2 RHE E-D (SEQ ID NO: 12) | 2E2 RKG (SEQ ID NO: 22) |
| RHE E-DKFmut | 2E2 RHE E-D (SEQ ID NO: 12) | 2E2 RKF F-Y mut (SEQ ID NO: 24) |
| RHE S-GKA | 2E2 RHE S-G (SEQ ID NO: 11) | 2E2 RKA (SEQ ID NO: 16) |
| RHE S-GKB | 2E2 RHE S-G (SEQ ID NO: 11) | 2E2 RKB (SEQ ID NO: 17) |
| RHE S-GKC | 2E2 RHE S-G (SEQ ID NO: 11) | 2E2 RKC (SEQ ID NO: 18) |
| RHE S-GKD | 2E2 RHE S-G (SEQ ID NO: 11) | 2E2 RKD (SEQ ID NO: 19) |
| RHE S-GKE | 2E2 RHE S-G (SEQ ID NO: 11) | 2E2 RKE (SEQ ID NO: 20) |
| RHE S-GKF | 2E2 RHE S-G (SEQ ID NO: 11) | 2E2 RKF (SEQ ID NO: 21) |
| RHE S-GKG | 2E2 RHE S-G (SEQ ID NO: 11) | 2E2 RKG (SEQ ID NO: 22) |
| RHE Triple-KA | 2E2 RHE triple (SEQ ID NO: 14) | 2E2 RKA (SEQ ID NO: 16) |
| RHE Triple-KB | 2E2 RHE triple (SEQ ID NO: 14) | 2E2 RKB (SEQ ID NO: 17) |
| RHE Triple-KC | 2E2 RHE triple (SEQ ID NO: 14) | 2E2 RKC (SEQ ID NO: 18) |
| RHE Triple-KD | 2E2 RHE triple (SEQ ID NO: 14) | 2E2 RKD (SEQ ID NO: 19) |
| RHE Triple-KE | 2E2 RHE triple (SEQ ID NO: 14) | 2E2 RKE (SEQ ID NO: 20) |
| RHE Triple-KF | 2E2 RHE triple (SEQ ID NO: 14) | 2E2 RKF (SEQ ID NO: 21) |
| RHE Triple-KG | 2E2 RHE triple (SEQ ID NO: 14) | 2E2 RKG (SEQ ID NO: 22) |
| RHE Triple-KFmut | 2E2 RHE triple (SEQ ID NO: 14) | 2E2 RKF F-Y mut (SEQ ID NO: 24) |
| RHE Y-VKFmut | 2E2 RHE Y-V (SEQ ID NO: 13) | 2E2 RKF F-Y mut (SEQ ID NO: 24) |
| RHE E-DKFmut | 2E2 RHE E-D (SEQ ID NO: 12) | 2E2 RKF F-Y mut (SEQ ID NO: 24) |

There are five classes of immunoglobulins: IgA, IgD, IgE, IgG and IgM, having heavy chains designated α, δ, ε, γ and μ, respectively. The γ and α classes are further divided into subclasses e.g., humans express the following subclasses: IgG1, IgG2, IgG3, IgG4, IgA1 and IgA2. IgG1 antibodies can exist in multiple polymorphic variants termed allotypes (reviewed in Jefferis and Lefranc 2009. mAbs Vol 1 Issue 4 1-7) any of which are suitable for use in some of the embodiments herein. Common allotypic variants in human populations are those designated by the letters a,f,n,z or combinations thereof. In any of the embodiments herein, the antibody may comprise a heavy chain Fc region comprising a human IgG Fc region. In further embodiments, the human IgG Fc region comprises a human IgG1 or IgG4. In some embodiments, the human IgG4 comprises the amino acid substitution S228P, wherein the amino acid residues are numbered according to the EU index as in Kabat. In some embodiments, the human IgG1 comprises the amino acid sequence of SEQ ID NO:78. In some embodiments, the human IgG4 comprises the amino acid sequence of SEQ ID NO:79.

In some embodiments, provided herein is an anti-Siglec-8 antibody comprising a heavy chain comprising the amino acid sequence of SEQ ID NO:75; and/or a light chain comprising the amino acid sequence selected from SEQ ID NOs:76 or 77. In some embodiments, the antibody may comprise a heavy chain comprising the amino acid sequence of SEQ ID NO:87; and/or a light chain comprising the amino acid sequence of SEQ ID NO:76. In some embodiments, the anti-Siglec-8 antibody induces apoptosis of activated eosinophils. In some embodiments, the anti-Siglec-8 antibody induces apoptosis of resting eosinophils. In some embodiments, the anti-Siglec-8 antibody depletes activated eosinophils and inhibits mast cell activation. In some embodiments, the anti-Siglec-8 antibody depletes or reduces mast cells and inhibits mast cell activation. In some embodiments, the anti-Siglec-8 antibody depleted or reduces the number of mast cells. In some embodiments, the anti-Siglec-8 antibody kills mast cells by ADCC activity. In some embodiments herein, the antibody depletes or reduces mast cells expressing Siglec-8 in a tissue (e.g., bone marrow). In some embodiments herein, the antibody depletes or reduces mast cells expressing Siglec-8 in a biological fluid (e.g., blood).

1. Antibody Affinity

In some aspects, an anti-Siglec-8 antibody described herein binds to human Siglec-8 with about the same or higher affinity and/or higher avidity as compared to mouse antibody 2E2 and/or mouse antibody 2C4. In certain embodiments, an anti-Siglec-8 antibody provided herein has a dissociation constant (Kd) of ≤1 µM, ≤150 nM, ≤100 nM, ≤50 nM, ≤10 nM, ≤1 nM, ≤0.1 nM, ≤0.01 nM, or ≤0.001 nM (e.g. 10-8 M or less, e.g. from 10-8 M to 10-13 M, e.g., from 10-9 M to 10-13 M). In some embodiments, an anti-Siglec-8 antibody described herein binds to human Siglec-8 at about 1.5-fold, about 2-fold, about 3-fold, about 4-fold, about 5-fold, about 6-fold, about 7-fold, about 8-fold, about 9-fold or about 10-fold higher affinity than mouse antibody 2E2 and/or mouse antibody 2C4. In some embodiments herein, the anti-Siglec-8 antibody comprises a heavy chain variable region comprising the amino acid sequence of SEQ ID NO:6; and/or a light chain variable region comprising the amino acid sequence selected from SEQ ID NOs:16 or 21.

In one embodiment, the binding affinity of the anti-Siglec-8 antibody can be determined by a surface plasmon resonance assay. For example, the Kd or Kd value can be measured by using a BIAcore™-2000 or a BIAcore™-3000 (BIAcore, Inc., Piscataway, N.J.) at 25° C. with immobilized antigen CM5 chips at ~10 response units (RU). Briefly, carboxymethylated dextran biosensor chips (CM5, BIAcore® Inc.) are activated with N-ethyl-N'-(3-dimethylaminopropyl)-carbodiimide hydrochloride (EDC) and N-hydroxysuccinimide (NHS) according to the supplier's instructions. Capture antibodies (e.g., anti-human-Fc) are diluted with 10 mM sodium acetate, pH 4.8, before injection at a flow rate of 30 µl/minute and further immobilized with an anti-Siglec-8 antibody. For kinetics measurements, two-fold serial dilutions of dimeric Siglec-8 are injected in PBS with 0.05% Tween 20 (PBST) at 25° C. at a flow rate of approximately 25 µl/min. Association rates (kon) and dissociation rates (koff) are calculated using a simple one-to-one Langmuir binding model (BIAcore® Evaluation Software version 3.2) by simultaneously fitting the association and dissociation sensorgrams. The equilibrium dissociation constant (Kd) is calculated as the ratio koff/kon. See, e.g., Chen, Y., et al., (1999) J. Mol. Biol. 293:865-881.

In another embodiment, biolayer interferometry may be used to determine the affinity of anti-Siglec-8 antibodies against Siglec-8. In an exemplary assay, Siglec-8-Fc tagged protein is immobilized onto anti-human capture sensors, and incubated with increasing concentrations of mouse, chimeric, or humanized anti-Siglec-8 Fab fragments to obtain affinity measurements using an instrument such as, for example, the Octet Red 384 System (ForteBio).

The binding affinity of the anti-Siglec-8 antibody can, for example, also be determined by the Scatchard analysis described in Munson et al., Anal. Biochem., 107:220 (1980) using standard techniques well known in the relevant art. See also Scatchard, G., Ann. N.Y. Acad. Sci. 51:660 (1947).

2. Antibody Avidity

In one embodiment, the binding avidity of the anti-Siglec-8 antibody can be determined by a surface plasmon resonance assay. For example, the Kd or Kd value can be measured by using a BIAcore T100. Capture antibodies (e.g., goat-anti-human-Fc and goat-anti-mouse-Fc) are immobilized on a CM5 chip. Flow-cells can be immobilized with anti-human or with anti-mouse antibodies. The assay is conducted at a certain temperature and flow rate, for example, at 25° C. at a flow rate of 30 µl/min. Dimeric Siglec-8 is diluted in assay buffer at various concentrations, for example, at a concentration ranging from 15 nM to 1.88 pM. Antibodies are captured and high performance injections are conducted, followed by dissociations. Flow cells are regenerated with a buffer, for example, 50 mM glycine pH 1.5. Results are blanked with an empty reference cell and multiple assay buffer injections, and analyzed with 1:1 global fit parameters.

3. Competition Assays

Competition-assays can be used to determine whether two antibodies bind the same epitope by recognizing identical or sterically overlapping epitopes or one antibody competitively inhibits binding of another antibody to the antigen. These assays are known in the art. Typically, antigen or antigen expressing cells is immobilized on a multi-well plate and the ability of unlabeled antibodies to block the binding of labeled antibodies is measured. Common labels for such competition assays are radioactive labels or enzyme labels. In some embodiments, an anti-Siglec-8 antibody described herein competes with a 2E2 antibody described herein, for binding to the epitope present on the cell surface of a cell (e.g., an eosinophil or a mast cell). In some embodiments, an anti-Siglec-8 antibody described herein competes with an antibody comprising a heavy chain variable domain comprising the amino acid sequence of SEQ ID NO:1, and a light chain variable region comprising the amino acid sequence of SEQ ID NO:15, for binding to the epitope present on the cell surface of a cell (e.g., an eosinophil or a mast cell). In some embodiments, an anti-Siglec-8 antibody described herein competes with a 2C4 antibody described herein, for binding to the epitope present on the cell surface of a cell (e.g., an eosinophil or a mast cell). In some embodiments, an anti-Siglec-8 antibody described herein competes with an antibody comprising a heavy chain variable domain comprising the amino acid sequence of SEQ ID NO:2 (as found in U.S. Pat. No. 8,207,305), and a light chain variable region comprising the amino acid sequence of SEQ ID NO:4 (as found in U.S. Pat. No. 8,207,305), for binding to the epitope present on the cell surface of a cell (e.g., an eosinophil or a mast cell).

4. Thermal Stability

In some aspects, an anti-Siglec-8 described herein has a melting temperature (Tm) of at least about 70° C., at least about 71° C., or at least about 72° C. in a thermal shift assay. In an exemplary thermal shift assay, samples comprising a humanized anti-Siglec-8 antibody are incubated with a fluorescent dye (Sypro Orange) for 71 cycles with 1° C. increase per cycle in a qPCR thermal cycler to determine the Tm. In some embodiments herein, the anti-Siglec-8 antibody has a similar or higher Tm as compared to mouse 2E2 antibody and/or mouse 2C4 antibody. In some embodiments herein, the anti-Siglec-8 antibody comprises a heavy chain variable region comprising the amino acid sequence of SEQ ID NO:6; and/or a light chain variable region comprising the amino acid sequence selected from SEQ ID NOs:16 or 21. In some embodiments, the anti-Siglec-8 antibody has the same or higher Tm as compared to a chimeric 2C4 antibody. In some embodiments, the anti-Siglec-8 antibody has the same or higher Tm as compared to an antibody having a heavy chain comprising the amino acid sequence of SEQ ID NO:84 and a light chain comprising the amino acid sequence of SEQ ID NO:85.

5. Biological Activity Assays

In some aspects, an anti-Siglec-8 antibody described herein induces apoptosis of eosinophils. In some other aspects, an anti-Siglec-8 antibody described herein depletes mast cells. Assays for assessing apoptosis of cells are well known in the art, for example staining with Annexin V and the TUNNEL assay. In an exemplary cell apoptosis assay, fresh buffy coat from a blood sample is resuspended in media and plated in a 96-well U-bottom plate. A series of serial 5-fold dilutions of anti-Siglec-8 antibody is added to each well and the plate is incubated at 37° C. at 5% $CO_2$ for greater than four hours. The cells are fixed with paraformaldehyde diluted in PBS and stained with conjugated antibodies specific for eosinophils for detection using a microscope. The eosinophil population in the total peripheral blood leukocytes is evaluated when the buffy coat is incubated in the presence of the anti-Siglec-8 antibody as compared to when the buffy coat is not incubated in the presence of the anti-Siglec-8 antibody. In another exemplary assay, eosinophils purified from a blood sample (e.g., Miltenyi Eosinophil Isolation Kit) are resuspended in media and cultured in the presence or absence of IL-5 overnight. The cultured eosinophils are subsequently harvested by centrifugation, resuspended in media, and plated in a 96-well U-bottom plate. A series of serial 5-fold dilutions of anti-Siglec-8 antibody is added to each well and the plate is incubated at 37° C. at 5% $CO_2$ for greater than four hours. The cells are fixed and stained with Annexin-V using standard techniques well known in the art the number of eosinophils is detected using a microscope. The eosinophil population in the sample is evaluated when the purified cells are incubated in the presence of the anti-Siglec-8 antibody as compared to when the purified cells are not incubated in the presence of the anti-Siglec-8 antibody.

In some aspects, an anti-Siglec-8 antibody described herein induces ADCC activity. In some other aspects, an anti-Siglec-8 antibody described herein kills mast cells expressing Siglec-8 by ADCC activity. In some embodiments, a composition comprises non-fucosylated (i.e., afucosylated) anti-Siglec-8 antibodies. In some embodiments, a composition comprising non-fucosylated anti-Siglec-8 antibodies described herein enhances ADCC activity as compared to a composition comprising partially fucosylated anti-Siglec-8 antibodies. Assays for assessing ADCC activity are well known in the art and described herein. In an exemplary assay, to measure ADCC activity, effector cells and target cells are used. Examples of effector cells include natural killer (NK) cells, large granular lymphocytes (LGL), lymphokine-activated killer (LAK) cells and PBMC comprising NK and LGL, or leukocytes having Fc receptors on the cell surfaces, such as neutrophils, eosinophils and macrophages. Effector cells can be isolated from any source including individuals with a disease of interest (e.g., advanced systemic mastocytosis). The target cell is any cell which expresses on the cell surface antigens that antibodies to be evaluated can recognize. An example of such a target cell is an eosinophil which expresses Siglec-8 on the cell surface. Another example of such a target cell is a mast cell which expresses Siglec-8 on the cell surface (e.g., a mast cell from individual with advanced systemic mastocytosis). Another example of such a target cell is a cell line (e.g., Ramos cell line) which expresses Siglec-8 on the cell surface (e.g., Ramos 2C10)). Target cells can be labeled with a reagent that enables detection of cytolysis. Examples of reagents for labeling include a radio-active substance such as sodium chromate ($Na_2{}^{51}CrO_4$). See, e.g., *Immunology*, 14, 181 (1968); *J. Immunol. Methods.*, 172, 227 (1994); and *J. Immunol. Methods.*, 184, 29 (1995).

In another exemplary assay to assess ADCC and apoptotic activity of anti-Siglec-8 antibodies on mast cells, human mast cells are isolated from human tissues (e.g., bone marrow) or biological fluids (e.g., blood) according to published protocols (Guhl et al., *Biosci. Biotechnol. Biochem.*, 2011, 75:382-384; Kulka et al., *In Current Protocols in Immunology*, 2001, (John Wiley & Sons, Inc.)) or differentiated from human hematopoietic stem cells, for example as described by Yokoi et al., *J Allergy Clin Immunol.*, 2008, 121:499-505. Purified mast cells are resuspended in Complete RPMI medium in a sterile 96-well U-bottom plate and incubated in the presence or absence of anti-Siglec-8 antibodies for 30 minutes at concentrations ranging between 0.0001 ng/ml and 10 μg/ml. Samples are incubated for a further 4 to 48 hours with and without purified natural killer (NK) cells or fresh PBL to induce ADCC. Cell-killing by apoptosis or ADCC is analyzed by flow cytometry using fluorescent conjugated antibodies to detect mast cells (CD117 and FcεR1) and Annexin-V and 7AAD to discriminate live and dead or dying cells. Annexin-V and 7AAD staining are performed according to manufacturer's instructions.

ADCC activity induced by anti-Siglec-8 antibodies described herein can be assayed using a method described herein, including the methods described in Example 1.

In some aspects, an anti-Siglec-8 antibody described herein inhibits mast cell-mediated activities. Mast cell tryptase has been used as a biomarker for total mast cell number and activation. For example, total and active tryptase as well as histamine, N-methyl histamine, and 11-beta-prostaglandin F2 can be measured in blood or urine to assess the reduction in mast cells. See, e.g., U.S. Patent Application Publication No. US 20110293631 for an exemplary mast cell activity assay.

Antibody Preparation

The antibody described herein (e.g., an antibody that binds to human Siglec-8) is prepared using techniques available in the art for generating antibodies, exemplary methods of which are described in more detail in the following sections.

1. Antibody Fragments

The present invention encompasses antibody fragments. Antibody fragments may be generated by traditional means, such as enzymatic digestion, or by recombinant techniques. In certain circumstances there are advantages of using antibody fragments, rather than whole antibodies. For a review of certain antibody fragments, see Hudson et al. (2003) Nat. Med. 9:129-134.

Various techniques have been developed for the production of antibody fragments. Traditionally, these fragments were derived via proteolytic digestion of intact antibodies (see, e.g., Morimoto et al., Journal of Biochemical and Biophysical Methods 24:107-117 (1992); and Brennan et al., Science, 229:81 (1985)). However, these fragments can now be produced directly by recombinant host cells. Fab, Fv and ScFv antibody fragments can all be expressed in and secreted from *E. coli*, thus allowing the facile production of large amounts of these fragments. Antibody fragments can be isolated from the antibody phage libraries discussed above. Alternatively, Fab'-SH fragments can be directly recovered from *E. coli* and chemically coupled to form F(ab')$_2$ fragments (Carter et al., Bio/Technology 10: 163-167 (1992)). According to another approach, F(ab')$_2$ fragments can be isolated directly from recombinant host cell culture. Fab and F(ab')$_2$ fragment with increased in vivo half-life comprising salvage receptor binding epitope residues are described in U.S. Pat. No. 5,869,046. Other techniques for the production of antibody fragments will be apparent to the skilled practitioner. In certain embodiments, an antibody is a single chain Fv fragment (scFv). See WO 93/16185; U.S. Pat. Nos. 5,571,894; and 5,587,458. Fv and scFv are the only species with intact combining sites that are devoid of constant regions; thus, they may be suitable for reduced nonspecific binding during in vivo use. scFv fusion proteins may be constructed to yield fusion of an effector protein at either the amino or the carboxy terminus of an scFv. See Antibody Engineering, ed. Borrebaeck, supra. The antibody fragment may also be a "linear antibody", e.g., as described in U.S. Pat. No. 5,641,870, for example. Such linear antibodies may be monospecific or bispecific.

2. Humanized Antibodies

The invention encompasses humanized antibodies. Various methods for humanizing non-human antibodies are known in the art. For example, a humanized antibody can have one or more amino acid residues introduced into it from a source which is non-human. These non-human amino acid residues are often referred to as "import" residues, which are typically taken from an "import" variable domain. Humanization can be essentially performed following the method of Winter (Jones et al. (1986) Nature 321:522-525; Riechmann et al. (1988) Nature 332:323-327; Verhoeyen et al. (1988) Science 239:1534-1536), by substituting hypervariable region sequences for the corresponding sequences of a human antibody. Accordingly, such "humanized" antibodies are chimeric antibodies (U.S. Pat. No. 4,816,567) wherein substantially less than an intact human variable domain has been substituted by the corresponding sequence from a non-human species. In practice, humanized antibodies are typically human antibodies in which some hypervariable region residues and possibly some FR residues are substituted by residues from analogous sites in rodent antibodies.

The choice of human variable domains, both light and heavy, to be used in making the humanized antibodies can be important to reduce antigenicity. According to the so-called "best-fit" method, the sequence of the variable domain of a rodent (e.g., mouse) antibody is screened against the entire library of known human variable-domain sequences. The human sequence which is closest to that of the rodent is then accepted as the human framework for the humanized antibody (Sims et al. (1993) *J. Immunol.* 151: 2296; Chothia et al. (1987) J. Mol. Biol. 196:901. Another method uses a particular framework derived from the consensus sequence of all human antibodies of a particular subgroup of light or heavy chains. The same framework may be used for several different humanized antibodies (Carter et al. (1992) Proc. Natl. Acad. Sci. USA, 89:4285; Presta et al. (1993) J. Immunol., 151:2623.

It is further generally desirable that antibodies be humanized with retention of high affinity for the antigen and other favorable biological properties. To achieve this goal, according to one method, humanized antibodies are prepared by a process of analysis of the parental sequences and various conceptual humanized products using three-dimensional models of the parental and humanized sequences. Three-dimensional immunoglobulin models are commonly available and are familiar to those, skilled in the art. Computer programs are available which illustrate and display probable three-dimensional conformational structures of selected candidate immunoglobulin sequences. Inspection of these displays permits analysis of the likely role of the residues in the functioning of the candidate immunoglobulin sequence, i.e., the analysis of residues that influence the ability of the candidate immunoglobulin to bind its antigen. In this way, FR residues can be selected and combined from the recipient and import sequences so that the desired antibody characteristic, such as increased affinity for the target antigen(s), is achieved. In general, the hypervariable region residues are directly and most substantially involved in influencing antigen binding.

3. Human Antibodies

Human anti-Siglec-8 antibodies of the invention can be constructed by combining Fv clone variable domain sequence(s) selected from human-derived phage display libraries with known human constant domain sequences(s). Alternatively, human monoclonal anti-Siglec-8 antibodies of the invention can be made by the hybridoma method. Human myeloma and mouse-human heteromyeloma cell lines for the production of human monoclonal antibodies have been described, for example, by Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).

It is possible to produce transgenic animals (e.g., mice) that are capable, upon immunization, of producing a full repertoire of human antibodies in the absence of endogenous immunoglobulin production. For example, it has been described that the homozygous deletion of the antibody heavy-chain joining region (JH) gene in chimeric and germ-line mutant mice results in complete inhibition of endogenous antibody production. Transfer of the human germ-line immunoglobulin gene array in such germ-line mutant mice will result in the production of human antibodies upon antigen challenge. See, e.g., Jakobovits et al., Proc. Natl. Acad. Sci. USA, 90: 2551 (1993); Jakobovits et al., Nature, 362: 255 (1993); Bruggermann et al., Year in Immunol., 7: 33 (1993).

Gene shuffling can also be used to derive human antibodies from non-human (e.g., rodent) antibodies, where the human antibody has similar affinities and specificities to the starting non-human antibody. According to this method, which is also called "epitope imprinting", either the heavy or light chain variable region of a non-human antibody fragment obtained by phage display techniques as described herein is replaced with a repertoire of human V domain genes, creating a population of non-human chain/human chain scFv or Fab chimeras. Selection with antigen results in isolation of a non-human chain/human chain chimeric scFv or Fab wherein the human chain restores the antigen binding site destroyed upon removal of the corresponding non-human chain in the primary phage display clone, i.e., the epitope governs the choice of the human chain partner. When the process is repeated in order to replace the remaining non-human chain, a human antibody is obtained (see PCT WO 93/06213 published Apr. 1, 1993). Unlike traditional humanization of non-human antibodies by CDR grafting, this technique provides completely human antibodies, which have no FR or CDR residues of non-human origin.

4. Bispecific Antibodies

Bispecific antibodies are monoclonal antibodies that have binding specificities for at least two different antigens. In certain embodiments, bispecific antibodies are human or humanized antibodies. In certain embodiments, one of the binding specificities is for Siglec-8 and the other is for any other antigen. In certain embodiments, bispecific antibodies may bind to two different epitopes of Siglec-8. Bispecific antibodies may also be used to localize cytotoxic agents to cells which express Siglec-8. Bispecific antibodies can be prepared as full length antibodies or antibody fragments (e.g. F(ab')$_2$ bispecific antibodies).

Methods for making bispecific antibodies are known in the art. See Milstein and Cuello, Nature, 305: 537 (1983), WO 93/08829 published May 13, 1993, and Traunecker et al., EMBO J., 10: 3655 (1991). For further details of generating bispecific antibodies see, for example, Suresh et al., Methods in Enzymology, 121:210 (1986). Bispecific antibodies include cross-linked or "heteroconjugate" antibodies. For example, one of the antibodies in the heteroconjugate can be coupled to avidin, the other to biotin. Heteroconjugate antibodies may be made using any convenient cross-linking method. Suitable cross-linking agents are well known in the art, and are disclosed in U.S. Pat. No. 4,676,980, along with a number of cross-linking techniques.

5. Single-Domain Antibodies

In some embodiments, an antibody of the invention is a single-domain antibody. A single-domain antibody is a single polypeptide chain comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1). In one embodiment, a single-domain antibody consists of all or a portion of the heavy chain variable domain of an antibody.

6. Antibody Variants

In some embodiments, amino acid sequence modification(s) of the antibodies described herein are contemplated. For example, it may be desirable to improve the binding affinity and/or other biological properties of the antibody. Amino acid sequence variants of the antibody may be prepared by introducing appropriate changes into the nucleotide sequence encoding the antibody, or by peptide synthesis. Such modifications include, for example, deletions from, and/or insertions into and/or substitutions of, residues within the amino acid sequences of the antibody. Any combination of deletion, insertion, and substitution can be made to arrive at the final construct, provided that the final construct possesses the desired characteristics. The amino acid alterations may be introduced in the subject antibody amino acid sequence at the time that sequence is made.

A useful method for identification of certain residues or regions of the antibody that are preferred locations for mutagenesis is called "alanine scanning mutagenesis" as described by Cunningham and Wells (1989) Science, 244: 1081-1085. Here, a residue or group of target residues are identified (e.g., charged residues such as arg, asp, his, lys, and glu) and replaced by a neutral or negatively charged amino acid (e.g., alanine or polyalanine) to affect the interaction of the amino acids with antigen. Those amino acid locations demonstrating functional sensitivity to the substitutions then are refined by introducing further or other variants at, or for, the sites of substitution. Thus, while the site for introducing an amino acid sequence variation is predetermined, the nature of the mutation per se need not be predetermined. For example, to analyze the performance of a mutation at a given site, ala scanning or random mutagenesis is conducted at the target codon or region and the expressed immunoglobulins are screened for the desired activity.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme or a polypeptide which increases the serum half-life of the antibody.

In some embodiments, monoclonal antibodies have a C-terminal cleavage at the heavy chain and/or light chain. For example, 1, 2, 3, 4, or 5 amino acid residues are cleaved at the C-terminus of heavy chain and/or light chain. In some embodiments, the C-terminal cleavage removes a C-terminal lysine from the heavy chain. In some embodiments, monoclonal antibodies have an N-terminal cleavage at the heavy chain and/or light chain. For example, 1, 2, 3, 4, or 5 amino acid residues are cleaved at the N-terminus of heavy chain and/or light chain. In some embodiments, truncated forms of monoclonal antibodies can be made by recombinant techniques.

In certain embodiments, an antibody of the invention is altered to increase or decrease the extent to which the antibody is glycosylated. Glycosylation of polypeptides is typically either N-linked or O-linked. N-linked refers to the attachment of a carbohydrate moiety to the side chain of an asparagine residue. The tripeptide sequences asparagine-X-serine and asparagine-X-threonine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-aceylgalactosamine, galactose, or xylose to a hydroxyamino acid, most commonly serine or threonine, although 5-hydroxyproline or 5-hydroxylysine may also be used.

Addition or deletion of glycosylation sites to the antibody is conveniently accomplished by altering the amino acid sequence such that one or more of the above-described tripeptide sequences (for N-linked glycosylation sites) is created or removed. The alteration may also be made by the addition, deletion, or substitution of one or more serine or threonine residues to the sequence of the original antibody (for O-linked glycosylation sites).

Where the antibody comprises an Fc region, the carbohydrate attached thereto may be altered. For example, antibodies with a mature carbohydrate structure that lacks fucose attached to an Fc region of the antibody are described in US Pat Appl No US 2003/0157108 (Presta, L.). See also US 2004/0093621 (Kyowa Hakko Kogyo Co., Ltd). Antibodies with a bisecting N-acetylglucosamine (GlcNAc) in the carbohydrate attached to an Fc region of the antibody are referenced in WO 2003/011878, Jean-Mairet et al. and U.S. Pat. No. 6,602,684, Umana et al. Antibodies with at least one galactose residue in the oligosaccharide attached to an Fc region of the antibody are reported in WO 1997/30087, Patel et al. See, also, WO 1998/58964 (Raju, S.) and WO 1999/22764 (Raju, S.) concerning antibodies with altered carbohydrate attached to the Fc region thereof. See also US 2005/0123546 (Umana et al.) on antigen-binding molecules with modified glycosylation.

In certain embodiments, a glycosylation variant comprises an Fc region, wherein a carbohydrate structure attached to the Fc region lacks fucose. Such variants have improved ADCC function. Optionally, the Fc region further comprises one or more amino acid substitutions therein which further improve ADCC, for example, substitutions at positions 298, 333, and/or 334 of the Fc region (Eu numbering of residues). Examples of publications related to "defucosylated" or "fuco se-deficient" antibodies include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; Okazaki et al. J. Mol. Biol. 336:1239-1249 (2004); Yamane-Ohnuki et al. Biotech. Bioeng. 87: 614 (2004). Examples of cell lines producing defucosylated antibodies include Lec13 CHO cells deficient in protein fucosylation (Ripka et al. Arch. Biochem. Biophys. 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (Yamane-Ohnuki et al. Biotech. Bioeng. 87: 614 (2004)), and cells overexpressing β1,4-N-acetylglycosminyltransferase III (GnT-III) and Golgi μ-mannosidase II (ManII).

Antibodies are contemplated herein that have reduced fucose relative to the amount of fucose on the same antibody produced in a wild-type CHO cell. For example, the antibody has a lower amount of fucose than it would otherwise have if produced by native CHO cells (e.g., a CHO cell that produce a native glycosylation pattern, such as, a CHO cell containing a native FUT8 gene). In certain embodiments, an anti-Siglec-8 antibody provided herein is one wherein less than about 50%, 40%, 30%, 20%, 10%, 5% or 1% of the N-linked glycans thereon comprise fucose. In certain embodiments, an anti-Siglec-8 antibody provided herein is one wherein none of the N-linked glycans thereon comprise fucose, i.e., wherein the antibody is completely without fucose, or has no fucose or is non-fucosylated or is afucosylated. The amount of fucose can be determined by calculating the average amount of fucose within the sugar chain at Asn297, relative to the sum of all glycostructures attached to Asn297 (e.g., complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. In some embodiments, at least one or two of the heavy chains of the antibody is non-fucosylated.

In one embodiment, the antibody is altered to improve its serum half-life. To increase the serum half-life of the antibody, one may incorporate a salvage receptor binding epitope into the antibody (especially an antibody fragment) as described in U.S. Pat. No. 5,739,277, for example. As used herein, the term "salvage receptor binding epitope" refers to an epitope of the Fc region of an IgG molecule (e.g., IgG1, IgG2, IgG3, or IgG4) that is responsible for increasing the in vivo serum half-life of the IgG molecule (US 2003/0190311, U.S. Pat. Nos. 6,821,505; 6,165,745; 5,624,821; 5,648,260; 6,165,745; 5,834,597).

Another type of variant is an amino acid substitution variant. These variants have at least one amino acid residue in the antibody molecule replaced by a different residue. Sites of interest for substitutional mutagenesis include the hypervariable regions, but FR alterations are also contemplated. Conservative substitutions are shown in Table 5 under the heading of "preferred substitutions." If such substitutions result in a desirable change in biological activity, then more substantial changes, denominated "exemplary substitutions" in Table 5, or as further described below in reference to amino acid classes, may be introduced and the products screened.

TABLE 5

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or c) the bulk of the side chain. Amino acids may be grouped according to similarities in the properties of their side chains (in A. L. Lehninger, in Biochemistry, second ed., pp. 73-75, Worth Publishers, New York (1975)):
  (1) non-polar: Ala (A), Val (V), Leu (L), Ile (I), Pro (P), Phe (F), Trp (W), Met (M)
  (2) uncharged polar: Gly (G), Ser (S), Thr (T), Cys (C), Tyr (Y), Asn (N), Gln (Q)
  (3) acidic: Asp (D), Glu (E)
  (4) basic: Lys (K), Arg (R), His (H)

Alternatively, naturally occurring residues may be divided into groups based on common side-chain properties:
  (1) hydrophobic: Norleucine, Met, Ala, Val, Leu, Ile;
  (2) neutral hydrophilic: Cys, Ser, Thr, Asn, Gln;
  (3) acidic: Asp, Glu;
  (4) basic: His, Lys, Arg;
  (5) residues that influence chain orientation: Gly, Pro;
  (6) aromatic: Trp, Tyr, Phe.

Non-conservative substitutions will entail exchanging a member of one of these classes for another class. Such substituted residues also may be introduced into the conservative substitution sites or, into the remaining (non-conserved) sites.

One type of substitutional variant involves substituting one or more hypervariable region residues of a parent antibody (e.g., a humanized or human antibody). Generally, the resulting variant(s) selected for further development will have modified (e.g., improved) biological properties relative to the parent antibody from which they are generated. A convenient way for generating such substitutional variants involves affinity maturation using phage display. Briefly, several hypervariable region sites (e.g., 6-7 sites) are mutated to generate all possible amino acid substitutions at each site. The antibodies thus generated are displayed from filamentous phage particles as fusions to at least part of a phage coat protein (e.g., the gene III product of M13) packaged within each particle. The phage-displayed variants are then screened for their biological activity (e.g., binding affinity). In order to identify candidate hypervariable region sites for modification, scanning mutagenesis (e.g., alanine scanning) can be performed to identify hypervariable region residues contributing significantly to antigen binding. Alternatively, or additionally, it may be beneficial to analyze a crystal structure of the antigen-antibody complex to identify contact points between the antibody and antigen. Such contact residues and neighboring residues are candidates for substitution according to techniques known in the art, including those elaborated herein. Once such variants are generated, the panel of variants is subjected to screening using techniques known in the art, including those described herein, and antibodies with superior properties in one or more relevant assays may be selected for further development.

Nucleic acid molecules encoding amino acid sequence variants of the antibody are prepared by a variety of methods known in the art. These methods include, but are not limited to, isolation from a natural source (in the case of naturally occurring amino acid sequence variants) or preparation by oligonucleotide-mediated (or site-directed) mutagenesis, PCR mutagenesis, and cassette mutagenesis of an earlier prepared variant or a non-variant version of the antibody.

It may be desirable to introduce one or more amino acid modifications in an Fc region of antibodies of the invention, thereby generating an Fc region variant. The Fc region variant may comprise a human Fc region sequence (e.g., a human IgG1, IgG2, IgG3 or IgG4 Fc region) comprising an amino acid modification (e.g., a substitution) at one or more amino acid positions including that of a hinge cysteine. In some embodiments, the Fc region variant comprises a human IgG4 Fc region. In a further embodiment, the human IgG4 Fc region comprises the amino acid substitution S228P, wherein the amino acid residues are numbered according to the EU index as in Kabat.

In accordance with this description and the teachings of the art, it is contemplated that in some embodiments, an antibody of the invention may comprise one or more alterations as compared to the wild type counterpart antibody, e.g. in the Fc region. These antibodies would nonetheless retain substantially the same characteristics required for therapeutic utility as compared to their wild type counterpart. For example, it is thought that certain alterations can be made in the Fc region that would result in altered (i.e., either improved or diminished) C1q binding and/or Complement Dependent Cytotoxicity (CDC), e.g., as described in WO99/51642. See also Duncan & Winter Nature 322:738-40

(1988); U.S. Pat. Nos. 5,648,260; 5,624,821; and WO94/29351 concerning other examples of Fc region variants. WO00/42072 (Presta) and WO 2004/056312 (Lowman) describe antibody variants with improved or diminished binding to FcRs. The content of these patent publications are specifically incorporated herein by reference. See, also, Shields et al. J. Biol. Chem. 9(2): 6591-6604 (2001). Antibodies with increased half-lives and improved binding to the neonatal Fc receptor (FcRn), which is responsible for the transfer of maternal IgGs to the fetus (Guyer et al., J. Immunol. 117:587 (1976) and Kim et al., J. Immunol. 24:249 (1994)), are described in US2005/0014934A1 (Hinton et al.). These antibodies comprise an Fc region with one or more substitutions therein which improve binding of the Fc region to FcRn. Polypeptide variants with altered Fc region amino acid sequences and increased or decreased C1q binding capability are described in U.S. Pat. No. 6,194,551B1, WO99/51642. The contents of those patent publications are specifically incorporated herein by reference. See, also, Idusogie et al. *J. Immunol.* 164: 4178-4184 (2000).

7. Vectors, Host Cells, and Recombinant Methods

For recombinant production of an antibody of the invention, the nucleic acid encoding it is isolated and inserted into a replicable vector for further cloning (amplification of the DNA) or for expression. DNA encoding the antibody is readily isolated and sequenced using conventional procedures (e.g., by using oligonucleotide probes that are capable of binding specifically to genes encoding the heavy and light chains of the antibody). Many vectors are available. The choice of vector depends in part on the host cell to be used. Generally, host cells are of either prokaryotic or eukaryotic (generally mammalian) origin. It will be appreciated that constant regions of any isotype can be used for this purpose, including IgG, IgM, IgA, IgD, and IgE constant regions, and that such constant regions can be obtained from any human or animal species.

Generating Antibodies Using Prokaryotic Host Cells:

a) Vector Construction

Polynucleotide sequences encoding polypeptide components of the antibody of the invention can be obtained using standard recombinant techniques. Desired polynucleotide sequences may be isolated and sequenced from antibody producing cells such as hybridoma cells. Alternatively, polynucleotides can be synthesized using nucleotide synthesizer or PCR techniques. Once obtained, sequences encoding the polypeptides are inserted into a recombinant vector capable of replicating and expressing heterologous polynucleotides in prokaryotic hosts. Many vectors that are available and known in the art can be used for the purpose of the present invention. Selection of an appropriate vector will depend mainly on the size of the nucleic acids to be inserted into the vector and the particular host cell to be transformed with the vector. Each vector contains various components, depending on its function (amplification or expression of heterologous polynucleotide, or both) and its compatibility with the particular host cell in which it resides. The vector components generally include, but are not limited to: an origin of replication, a selection marker gene, a promoter, a ribosome binding site (RBS), a signal sequence, the heterologous nucleic acid insert and a transcription termination sequence.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is typically transformed using pBR322, a plasmid derived from an *E. coli* species. pBR322 contains genes-encoding ampicillin (Amp) and tetracycline (Tet) resistance and thus provides easy means for identifying transformed cells. pBR322, its derivatives, or other microbial plasmids or bacteriophage may also contain, or be modified to contain, promoters which can be used by the microbial organism for expression of endogenous proteins. Examples of pBR322 derivatives used for expression of particular antibodies are described in detail in Carter et al., U.S. Pat. No. 5,648,237.

In addition, phage vectors containing replicon and control sequences that are compatible with the host microorganism can be used as transforming vectors in connection with these hosts. For example, bacteriophage such as λGEM.TM.-11 may be utilized in making a recombinant vector which can be used to transform susceptible host cells such as *E. coli* LE392.

The expression vector of the invention may comprise two or more promoter-cistron pairs, encoding each of the polypeptide components. A promoter is an untranslated regulatory sequence located upstream (5') to a cistron that modulates its expression. Prokaryotic promoters typically fall into two classes, inducible and constitutive. Inducible promoter is a promoter that initiates increased levels of transcription of the cistron under its control in response to changes in the culture condition, e.g. the presence or absence of a nutrient or a change in temperature.

A large number of promoters recognized by a variety of potential host cells are well known. The selected promoter can be operably linked to cistron DNA encoding the light or heavy chain by removing the promoter from the source DNA via restriction enzyme digestion and inserting the isolated promoter sequence into the vector of the invention. Both the native promoter sequence and many heterologous promoters may be used to direct amplification and/or expression of the target genes. In some embodiments, heterologous promoters are utilized, as they generally permit greater transcription and higher yields of expressed target gene as compared to the native target polypeptide promoter.

Promoters suitable for use with prokaryotic hosts include the PhoA promoter, the β-galactamase and lactose promoter systems, a tryptophan (trp) promoter system and hybrid promoters such as the tac or the trc promoter. However, other promoters that are functional in bacteria (such as other known bacterial or phage promoters) are suitable as well. Their nucleotide sequences have been published, thereby enabling a skilled worker operably to ligate them to cistrons encoding the target light and heavy chains (Siebenlist et al. (1980) Cell 20: 269) using linkers or adaptors to supply any required restriction sites.

In one aspect of the invention, each cistron within the recombinant vector comprises a secretion signal sequence component that directs translocation of the expressed polypeptides across a membrane. In general, the signal sequence may be a component of the vector, or it may be a part of the target polypeptide DNA that is inserted into the vector. The signal sequence selected for the purpose of this invention should be one that is recognized and processed (i.e. cleaved by a signal peptidase) by the host cell. For prokaryotic host cells that do not recognize and process the signal sequences native to the heterologous polypeptides, the signal sequence is substituted by a prokaryotic signal sequence selected, for example, from the group consisting of the alkaline phosphatase, penicillinase, lpp, or heat-stable enterotoxin II (STII) leaders, LamB, PhoE, PelB, OmpA and MBP. In one embodiment of the invention, the signal sequences used in both cistrons of the expression system are STII signal sequences or variants thereof.

In another aspect, the production of the immunoglobulins according to the invention can occur in the cytoplasm of the host cell, and therefore does not require the presence of secretion signal sequences within each cistron. In that regard, immunoglobulin light and heavy chains are expressed, folded and assembled to form functional immunoglobulins within the cytoplasm. Certain host strains (e.g., the E. coli trxB-strains) provide cytoplasm conditions that are favorable for disulfide bond formation, thereby permitting proper folding and assembly of expressed protein subunits. Proba and Pluckthun Gene, 159:203 (1995).

Antibodies of the invention can also be produced by using an expression system in which the quantitative ratio of expressed polypeptide components can be modulated in order to maximize the yield of secreted and properly assembled antibodies of the invention. Such modulation is accomplished at least in part by simultaneously modulating translational strengths for the polypeptide components.

One technique for modulating translational strength is disclosed in Simmons et al., U.S. Pat. No. 5,840,523. It utilizes variants of the translational initiation region (TIR) within a cistron. For a given TIR, a series of amino acid or nucleic acid sequence variants can be created with a range of translational strengths, thereby providing a convenient means by which to adjust this factor for the desired expression level of the specific chain. TIR variants can be generated by conventional mutagenesis techniques that result in codon changes which can alter the amino acid sequence. In certain embodiments, changes in the nucleotide sequence are silent. Alterations in the TIR can include, for example, alterations in the number or spacing of Shine-Dalgarno sequences, along with alterations in the signal sequence. One method for generating mutant signal sequences is the generation of a "codon bank" at the beginning of a coding sequence that does not change the amino acid sequence of the signal sequence (i.e., the changes are silent). This can be accomplished by changing the third nucleotide position of each codon; additionally, some amino acids, such as leucine, serine, and arginine, have multiple first and second positions that can add complexity in making the bank. This method of mutagenesis is described in detail in Yansura et al. (1992) METHODS: A Companion to Methods in Enzymol. 4:151-158.

In one embodiment, a set of vectors is generated with a range of TIR strengths for each cistron therein. This limited set provides a comparison of expression levels of each chain as well as the yield of the desired antibody products under various TIR strength combinations. TIR strengths can be determined by quantifying the expression level of a reporter gene as described in detail in Simmons et al. U.S. Pat. No. 5,840,523. Based on the translational strength comparison, the desired individual TIRs are selected to be combined in the expression vector constructs of the invention.

Prokaryotic host cells suitable for expressing antibodies of the invention include Archaebacteria and Eubacteria, such as Gram-negative or Gram-positive organisms. Examples of useful bacteria include Escherichia (e.g., E. coli), Bacilli (e.g., B. subtilis), Enterobacteria, Pseudomonas species (e.g., P. aeruginosa), Salmonella typhimurium, Serratia marcescans, Klebsiella, Proteus, Shigella, Rhizobia, Vitreoscilla, or Paracoccus. In one embodiment, gram-negative cells are used. In one embodiment, E. coli cells are used as hosts for the invention. Examples of E. coli strains include strain W3110 (Bachmann, Cellular and Molecular Biology, vol. 2 (Washington, D.C.: American Society for Microbiology, 1987), pp. 1190-1219; ATCC Deposit No. 27,325) and derivatives thereof, including strain 33D3 having genotype W3110 ΔfhuA (ΔtonA) ptr3 lac Iq lacL8 ΔompTΔ(nmpc-fepE) degP41 kanR (U.S. Pat. No. 5,639,635). Other strains and derivatives thereof, such as E. coli 294 (ATCC 31,446), E. coli B, E. coliλ⁻, 1776 (ATCC 31,537) and E. coli RV308(ATCC 31,608) are also suitable. These examples are illustrative rather than limiting. Methods for constructing derivatives of any of the above-mentioned bacteria having defined genotypes are known in the art and described in, for example, Bass et al., Proteins, 8:309-314 (1990). It is generally necessary to select the appropriate bacteria taking into consideration replicability of the replicon in the cells of a bacterium. For example, E. coli, Serratia, or Salmonella species can be suitably used as the host when well known plasmids such as pBR322, pBR325, pACYC177, or pKN410 are used to supply the replicon. Typically the host cell should secrete minimal amounts of proteolytic enzymes, and additional protease inhibitors may desirably be incorporated in the cell culture.

b) Antibody Production

Host cells are transformed with the above-described expression vectors and cultured in conventional nutrient media modified as appropriate for inducing promoters, selecting transformants, or amplifying the genes encoding the desired sequences.

Transformation means introducing DNA into the prokaryotic host so that the DNA is replicable, either as an extrachromosomal element or by chromosomal integrant. Depending on the host cell used, transformation is done using standard techniques appropriate to such cells. The calcium treatment employing calcium chloride is generally used for bacterial cells that contain substantial cell-wall barriers. Another method for transformation employs polyethylene glycol/DMSO. Yet another technique used is electroporation.

Prokaryotic cells used to produce the polypeptides of the invention are grown in media known in the art and suitable for culture of the selected host cells. Examples of suitable media include luria broth (LB) plus necessary nutrient supplements. In some embodiments, the media also contains a selection agent, chosen based on the construction of the expression vector, to selectively permit growth of prokaryotic cells containing the expression vector. For example, ampicillin is added to media for growth of cells expressing ampicillin resistant gene.

Any necessary supplements besides carbon, nitrogen, and inorganic phosphate sources may also be included at appropriate concentrations introduced alone or as a mixture with another supplement or medium such as a complex nitrogen source. Optionally the culture medium may contain one or more reducing agents selected from the group consisting of glutathione, cysteine, cystamine, thioglycollate, dithioerythritol and dithiothreitol.

The prokaryotic host cells are cultured at suitable temperatures. In certain embodiments, for E. coli growth, growth temperatures range from about 20° C. to about 39° C.; from about 25° C. to about 37° C.; or about 30° C. The pH of the medium may be any pH ranging from about 5 to about 9, depending mainly on the host organism. In certain embodiments, for E. coli, the pH is from about 6.8 to about 7.4, or about 7.0.

If an inducible promoter is used in the expression vector of the invention, protein expression is induced under conditions suitable for the activation of the promoter. In one aspect of the invention, PhoA promoters are used for controlling transcription of the polypeptides. Accordingly, the transformed host cells are cultured in a phosphate-limiting medium for induction. In certain embodiments, the phosphate-limiting medium is the C.R.A.P. medium (see, e.g., Simmons et al., J. Immunol. Methods (2002), 263:133-147). A variety of other inducers may be used, according to the vector construct employed, as is known in the art.

In one embodiment, the expressed polypeptides of the present invention are secreted into and recovered from the periplasm of the host cells. Protein recovery typically involves disrupting the microorganism, generally by such means as osmotic shock, sonication or lysis. Once cells are disrupted, cell debris or whole cells may be removed by centrifugation or filtration. The proteins may be further purified, for example, by affinity resin chromatography. Alternatively, proteins can be transported into the culture media and isolated therein. Cells may be removed from the culture and the culture supernatant being filtered and concentrated for further purification of the proteins produced. The expressed polypeptides can be further isolated and identified using commonly known methods such as polyacrylamide gel electrophoresis (PAGE) and Western blot assay.

In one aspect of the invention, antibody production is conducted in large quantity by a fermentation process. Various large-scale fed-batch fermentation procedures are available for production of recombinant proteins. Large-scale fermentations have at least 1000 liters of capacity, and in certain embodiments, about 1,000 to 100,000 liters of capacity. These fermentors use agitator impellers to distribute oxygen and nutrients, especially glucose. Small scale fermentation refers generally to fermentation in a fermentor that is no more than approximately 100 liters in volumetric capacity, and can range from about 1 liter to about 100 liters.

In a fermentation process, induction of protein expression is typically initiated after the cells have been grown under suitable conditions to a desired density, e.g., an OD550 of about 180-220, at which stage the cells are in the early stationary phase. A variety of inducers may be used, according to the vector construct employed, as is known in the art and described above. Cells may be grown for shorter periods prior to induction. Cells are usually induced for about 12-50 hours, although longer or shorter induction time may be used.

To improve the production yield and quality of the polypeptides of the invention, various fermentation conditions can be modified. For example, to improve the proper assembly and folding of the secreted antibody polypeptides, additional vectors overexpressing chaperone proteins, such as Dsb proteins (DsbA, DsbB, DsbC, DsbD and or DsbG) or FkpA (a peptidylprolyl cis,trans-isomerase with chaperone activity) can be used to co-transform the host prokaryotic cells. The chaperone proteins have been demonstrated to facilitate the proper folding and solubility of heterologous proteins produced in bacterial host cells. Chen et al. (1999) J. Biol. Chem. 274:19601-19605; Georgiou et al., U.S. Pat. No. 6,083,715; Georgiou et al., U.S. Pat. No. 6,027,888; Bothmann and Pluckthun (2000) J. Biol. Chem. 275:17100-17105; Ramm and Pluckthun (2000) J. Biol. Chem. 275: 17106-17113; Arie et al. (2001) Mol. Microbiol. 39:199-210.

To minimize proteolysis of expressed heterologous proteins (especially those that are proteolytically sensitive), certain host strains deficient for proteolytic enzymes can be used for the present invention. For example, host cell strains may be modified to effect genetic mutation(s) in the genes encoding known bacterial proteases such as Protease III, OmpT, DegP, Tsp, Protease I, Protease Mi, Protease V, Protease VI and combinations thereof. Some E. coli protease-deficient strains are available and described in, for example, Joly et al. (1998), supra; Georgiou et al., U.S. Pat. No. 5,264,365; Georgiou et al., U.S. Pat. No. 5,508,192; Hara et al., Microbial Drug Resistance, 2:63-72 (1996).

In one embodiment, E. coli strains deficient for proteolytic enzymes and transformed with plasmids overexpressing one or more chaperone proteins are used as host cells in the expression system of the invention.

c) Antibody Purification

In one embodiment, the antibody protein produced herein is further purified to obtain preparations that are substantially homogeneous for further assays and uses. Standard protein purification methods known in the art can be employed. The following procedures are exemplary of suitable purification procedures: fractionation on immunoaffinity or ion-exchange columns, ethanol precipitation, reverse phase HPLC, chromatography on silica or on a cation-exchange resin such as DEAE, chromatofocusing, SDS-PAGE, ammonium sulfate precipitation, and gel filtration using, for example, Sephadex G-75.

In one aspect, Protein A immobilized on a solid phase is used for immunoaffinity purification of the antibody products of the invention. Protein A is a 41 kD cell wall protein from *Staphylococcus aureas* which binds with a high affinity to the Fc region of antibodies. Lindmark et al (1983) J. Immunol. Meth. 62:1-13. The solid phase to which Protein A is immobilized can be a column comprising a glass or silica surface, or a controlled pore glass column or a silicic acid column. In some applications, the column is coated with a reagent, such as glycerol, to possibly prevent non-specific adherence of contaminants.

As the first step of purification, a preparation derived from the cell culture as described above can be applied onto a Protein A immobilized solid phase to allow specific binding of the antibody of interest to Protein A. The solid phase would then be washed to remove contaminants non-specifically bound to the solid phase. Finally the antibody of interest is recovered from the solid phase by elution.

Generating Antibodies Using Eukaryotic Host Cells:

A vector for use in a eukaryotic host cell generally includes one or more of the following non-limiting components: a signal sequence, an origin of replication, one or more marker genes, an enhancer element, a promoter, and a transcription termination sequence.

a) Signal Sequence Component

A vector for use in a eukaryotic host cell may also contain a signal sequence or other polypeptide having a specific cleavage site at the N-terminus of the mature protein or polypeptide of interest. The heterologous signal sequence selected may be one that is recognized and processed (i.e., cleaved by a signal peptidase) by the host cell. In mammalian cell expression, mammalian signal sequences as well as viral secretory leaders, for example, the herpes simplex gD signal, are available. The DNA for such a precursor region is ligated in reading frame to DNA encoding the antibody.

b) Origin of Replication

Generally, an origin of replication component is not needed for mammalian expression vectors. For example, the SV40 origin may typically be used only because it contains the early promoter.

c) Selection Gene Component

Expression and cloning vectors may contain a selection gene, also termed a selectable marker. Typical selection genes encode proteins that (a) confer resistance to antibiotics or other toxins, e.g., ampicillin, neomycin, methotrexate, or tetracycline, (b) complement auxotrophic deficiencies, where relevant, or (c) supply critical nutrients not available from complex media.

One example of a selection scheme utilizes a drug to arrest growth of a host cell. Those cells that are successfully transformed with a heterologous gene produce a protein conferring drug resistance and thus survive the selection regimen. Examples of such dominant selection use the drugs neomycin, mycophenolic acid and hygromycin.

Another example of suitable selectable markers for mammalian cells are those that enable the identification of cells competent to take up the antibody nucleic acid, such as DHFR, thymidine kinase, metallothionein-I and -II, primate metallothionein genes, adenosine deaminase, ornithine decarboxylase, etc.

For example, in some embodiments, cells transformed with the DHFR selection gene are first identified by culturing all of the transformants in a culture medium that contains methotrexate (Mtx), a competitive antagonist of DHFR. In some embodiments, an appropriate host cell when wild-type DHFR is employed is the Chinese hamster ovary (CHO) cell line deficient in DHFR activity (e.g., ATCC CRL-9096).

Alternatively, host cells (particularly wild-type hosts that contain endogenous DHFR) transformed or co-transformed with DNA sequences encoding an antibody, wild-type DHFR protein, and another selectable marker such as aminoglycoside 3'-phosphotransferase (APH) can be selected by cell growth in medium containing a selection agent for the selectable marker such as an aminoglycosidic antibiotic, e.g., kanamycin, neomycin, or G418. See U.S. Pat. No. 4,965,199. Host cells may include NS0, CHOK1, CHOK1SV or derivatives, including cell lines deficient in glutamine synthetase (GS). Methods for the use of GS as a selectable marker for mammalian cells are described in U.S. Pat. Nos. 5,122,464 and 5,891,693.

d) Promoter Component

Expression and cloning vectors usually contain a promoter that is recognized by the host organism and is operably linked to nucleic acid encoding a polypeptide of interest (e.g., an antibody). Promoter sequences are known for eukaryotes. For example, virtually all eukaryotic genes have an AT-rich region located approximately 25 to 30 bases upstream from the site where transcription is initiated. Another sequence found 70 to 80 bases upstream from the start of transcription of many genes is a CNCAAT region where N may be any nucleotide. At the 3' end of most eukaryotic genes is an AATAAA sequence that may be the signal for addition of the poly A tail to the 3' end of the coding sequence. In certain embodiments, any or all of these sequences may be suitably inserted into eukaryotic expression vectors.

Transcription from vectors in mammalian host cells is controlled, for example, by promoters obtained from the genomes of viruses such as polyoma virus, fowlpox virus, adenovirus (such as Adenovirus 2), bovine papilloma virus, avian sarcoma virus, cytomegalovirus, a retrovirus, hepatitis-B virus and Simian Virus 40 (SV40), from heterologous mammalian promoters, e.g., the actin promoter or an immunoglobulin promoter, from heat-shock promoters, provided such promoters are compatible with the host cell systems.

The early and late promoters of the SV40 virus are conveniently obtained as an SV40 restriction fragment that also contains the SV40 viral origin of replication. The immediate early promoter of the human cytomegalovirus is conveniently obtained as a HindIII E restriction fragment. A system for expressing DNA in mammalian hosts using the bovine papilloma virus as a vector is disclosed in U.S. Pat. No. 4,419,446. A modification of this system is described in U.S. Pat. No. 4,601,978. See also Reyes et al., Nature 297:598-601 (1982), describing expression of human β-interferon cDNA in mouse cells under the control of a thymidine kinase promoter from herpes simplex virus. Alternatively, the Rous Sarcoma Virus long terminal repeat can be used as the promoter.

e) Enhancer Element Component

Transcription of DNA encoding an antibody of this invention by higher eukaryotes is often increased by inserting an enhancer sequence into the vector. Many enhancer sequences are now known from mammalian genes (globin, elastase, albumin, α-fetoprotein, and insulin). Typically, however, one will use an enhancer from a eukaryotic cell virus. Examples include the SV40 enhancer on the late side of the replication origin (bp 100-270), the human cytomegalovirus early promoter enhancer, the mouse cytomegalovirus early promoter enhancer, the polyoma enhancer on the late side of the replication origin, and adenovirus enhancers. See also Yaniv, Nature 297:17-18 (1982) describing enhancer elements for activation of eukaryotic promoters. The enhancer may be spliced into the vector at a position 5' or 3' to the antibody polypeptide-encoding sequence, but is generally located at a site 5' from the promoter.

f) Transcription Termination Component

Expression vectors used in eukaryotic host cells may also contain sequences necessary for the termination of transcription and for stabilizing the mRNA. Such sequences are commonly available from the 5' and, occasionally 3', untranslated regions of eukaryotic or viral DNAs or cDNAs. These regions contain nucleotide segments transcribed as polyadenylated fragments in the untranslated portion of the mRNA encoding an antibody. One useful transcription termination component is the bovine growth hormone polyadenylation region. See WO94/11026 and the expression vector disclosed therein.

g) Selection and Transformation of Host Cells

Suitable host cells for cloning or expressing the DNA in the vectors herein include higher eukaryote cells described herein, including vertebrate host cells. Propagation of vertebrate cells in culture (tissue culture) has become a routine procedure. Examples of useful mammalian host cell lines are monkey kidney CV1 line transformed by SV40 (COS-7, ATCC CRL 1651); human embryonic kidney line (293 or 293 cells subcloned for growth in suspension culture, Graham et al., J. Gen Virol. 36:59 (1977)); baby hamster kidney cells (BHK, ATCC CCL 10); Chinese hamster ovary cells/-DHFR (CHO, Urlaub et al., Proc. Natl. Acad. Sci. USA 77:4216 (1980)); mouse sertoli cells (TM4, Mather, Biol. Reprod. 23:243-251 (1980)); monkey kidney cells (CV1 ATCC CCL 70); African green monkey kidney cells (VERO-76, ATCC CRL-1587); human cervical carcinoma cells (HELA, ATCC CCL 2); canine kidney cells (MDCK, ATCC CCL 34); buffalo rat liver cells (BRL 3A, ATCC CRL 1442); human lung cells (W138, ATCC CCL 75); human liver cells (Hep G2, HB 8065); mouse mammary tumor (MMT 060562, ATCC CCL51); TRI cells (Mather et al., Annals N.Y. Acad. Sci. 383:44-68 (1982)); MRC 5 cells; FS4 cells; CHOK1 cells, CHOK1SV cells or derivatives and a human hepatoma line (Hep G2).

Host cells are transformed with the above-described-expression or cloning vectors for antibody production and cultured in conventional nutrient media modified as appropriate for inducing promoters, selecting transformants, or amplifying the genes encoding the desired sequences.

h) Culturing the Host Cells

The host cells used to produce an antibody of this invention may be cultured in a variety of media. Commercially available media such as Ham's F10 (Sigma), Minimal Essential Medium ((MEM), Sigma), RPMI-1640 (Sigma), and Dulbecco's Modified Eagle's Medium ((DMEM), Sigma) are suitable for culturing the host cells. In addition, any of the media described in Ham et al., Meth. Enz. 58:44 (1979), Barnes et al., Anal. Biochem. 102:255 (1980), U.S. Pat. Nos. 4,767,704; 4,657,866; 4,927,762; 4,560,655; or 5,122,469; WO 90/03430; WO 87/00195; or U.S. Pat. Re. 30,985 may be used as culture media for the host cells. Any of these media may be supplemented as necessary with hormones and/or other growth factors (such as insulin, transferrin, or epidermal growth factor), salts (such as sodium chloride, calcium, magnesium, and phosphate), buffers (such as HEPES), nucleotides (such as adenosine and thymidine), antibiotics (such as GENTAMYCIN™ drug), trace elements (defined as inorganic compounds usually present at final concentrations in the micromolar range), and glucose or an equivalent energy source. Any other supplements may also be included at appropriate concentrations that would be known to those skilled in the art. The culture conditions, such as temperature, pH, and the like, are those previously used with the host cell selected for expression, and will be apparent to the ordinarily skilled artisan.

i) Purification of Antibody

When using recombinant techniques, the antibody can be produced intracellularly, or directly secreted into the medium. If the antibody is produced intracellularly, as a first step, the particulate debris, either host cells or lysed fragments, may be removed, for example, by centrifugation or ultrafiltration. Where the antibody is secreted into the medium, supernatants from such expression systems may be first concentrated using a commercially available protein concentration filter, for example, an Amicon or Millipore Pellicon ultrafiltration unit. A protease inhibitor such as PMSF may be included in any of the foregoing steps to inhibit proteolysis, and antibiotics may be included to prevent the growth of adventitious contaminants.

The antibody composition prepared from the cells can be purified using, for example, hydroxylapatite chromatography, gel electrophoresis, dialysis, and affinity chromatography, with affinity chromatography being a convenient technique. The suitability of protein A as an affinity ligand depends on the species and isotype of any immunoglobulin Fc domain that is present in the antibody. Protein A can be used to purify antibodies that are based on human γ1, γ2, or γ4 heavy chains (Lindmark et al., J. Immunol. Methods 62:1-13 (1983)). Protein G is recommended for all mouse isotypes and for human γ3 (Guss et al., EMBO J. 5:15671575 (1986)). The matrix to which the affinity ligand is attached may be agarose, but other matrices are available. Mechanically stable matrices such as controlled pore glass or poly(styrenedivinyl)benzene allow for faster flow rates and shorter processing times than can be achieved with agarose. Where the antibody comprises a CH3 domain, the Bakerbond ABX™ resin (J. T. Baker, Phillipsburg, N.J.) is useful for purification. Other techniques for protein purification such as fractionation on an ion-exchange column, ethanol precipitation, Reverse Phase HPLC, chromatography on silica, chromatography on heparin SEPHAROSE™ chromatography on an anion or cation exchange resin (such as a polyaspartic acid column), chromatofocusing, SDS-PAGE, and ammonium sulfate precipitation are also available depending on the antibody to be recovered.

Following any preliminary purification step(s), the mixture comprising the antibody of interest and contaminants may be subjected to further purification, for example, by low pH hydrophobic interaction chromatography using an elution buffer at a pH between about 2.5-4.5, performed at low salt concentrations (e.g., from about 0-0.25M salt).

In general, various methodologies for preparing antibodies for use in research, testing, and clinical use are well-established in the art, consistent with the above-described methodologies and/or as deemed appropriate by one skilled in the art for a particular antibody of interest.

Production of Non-Fucosylated Antibodies

Provided herein are methods for preparing antibodies with a reduced degree of fucosylation. For example, methods contemplated herein include, but are not limited to, use of cell lines deficient in protein fucosylation (e.g., Lec13 CHO cells, alpha-1,6-fucosyltransferase gene knockout CHO cells, cells overexpressing β1,4-N-acetylglycosminyltransferase III and further overexpressing Golgi μ-mannosidase II, etc.), and addition of a fucose analog(s) in a cell culture medium used for the production of the antibodies. See Ripka et al. Arch. Biochem. Biophys. 249:533-545 (1986); US Pat Appl No US 2003/0157108 A1, Presta, L; WO 2004/056312 A1; Yamane-Ohnuki et al. Biotech. Bioeng. 87: 614 (2004); and U.S. Pat. No. 8,574,907. Additional techniques for reducing the fucose content of antibodies include Glymaxx technology described in U.S. Patent Application Publication No. 2012/0214975. Additional techniques for reducing the fucose content of antibodies also include the addition of one or more glycosidase inhibitors in a cell culture medium used for the production of the antibodies. Glycosidase inhibitors include α-glucosidase I, α-glucosidase II, and α-mannosidase I. In some embodiments, the glycosidase inhibitor is an inhibitor of α-mannosidase I (e.g., kifunensine).

As used herein, "core fucosylation" refers to addition of fucose ("fucosylation") to N-acetylglucosamine ("GlcNAc") at the reducing terminal of an N-linked glycan. Also provided are antibodies produced by such methods and compositions thereof.

In some embodiments, fucosylation of complex N-glycoside-linked sugar chains bound to the Fc region (or domain) is reduced. As used herein, a "complex N-glycoside-linked sugar chain" is typically bound to asparagine 297 (according to the number of Kabat), although a complex N-glycoside linked sugar chain can also be linked to other asparagine residues. A "complex N-glycoside-linked sugar chain" excludes a high mannose type of sugar chain, in which only mannose is incorporated at the non-reducing terminal of the core structure, but includes 1) a complex type, in which the non-reducing terminal side of the core structure has one or more branches of galactose-N-acetylglucosamine (also referred to as "gal-GlcNAc") and the non-reducing terminal side of Gal-GlcNAc optionally has a sialic acid, bisecting N-acetylglucosamine or the like; or 2) a hybrid type, in which the non-reducing terminal side of the core structure has both branches of the high mannose N-glycoside-linked sugar chain and complex N-glycoside-linked sugar chain.

In some embodiments, the "complex N-glycoside-linked sugar chain" includes a complex type in which the non-reducing terminal side of the core structure has zero, one or more branches of galactose-N-acetylglucosamine (also referred to as "gal-GlcNAc") and the non-reducing terminal side of Gal-GlcNAc optionally further has a structure such as a sialic acid, bisecting N-acetylglucosamine or the like.

According to the present methods, typically only a minor amount of fucose is incorporated into the complex N-glycoside-linked sugar chain(s). For example, in various embodiments, less than about 60%, less than about 50%, less than about 40%, less than about 30%, less than about 20%, less than about 15%, less than about 10%, less than about 5%, or less than about 1% of the antibody has core fucosylation by fucose in a composition. In some embodiments, substantially none (i.e., less than about 0.5%) of the antibody has core fucosylation by fucose in a composition. In some embodiments, more than about 40%, more than about 50%, more than about 60%, more than about 70%, more than about 80%, more than about 90%, more than about 91%, more than about 92%, more than about 93%, more than about 94%, more than about 95%, more than about 96%, more than about 97%, more than about 98%, or more than about 99% of the antibody is nonfucosylated in a composition.

In some embodiments, provided herein is an antibody wherein substantially none (i.e., less than about 0.5%) of the N-glycoside-linked carbohydrate chains contain a fucose residue. In some embodiments, provided herein is an antibody wherein at least one or two of the heavy chains of the antibody is non-fucosylated.

As described above, a variety of mammalian host-expression vector systems can be utilized to express an antibody. In some embodiments, the culture media is not supplemented with fucose. In some embodiments, an effective amount of a fucose analog is added to the culture media. In this context, an "effective amount" refers to an amount of the analog that is sufficient to decrease fucose incorporation into a complex N-glycoside-linked sugar chain of an antibody by at least about 10%, at least about 20%, at least about 30%, at least about 40% or at least about 50%. In some embodiments, antibodies produced by the instant methods comprise at least about 10%, at least about 20%, at least about 30%, at least about 40% or at least about 50% non-core fucosylated protein (e.g., lacking core fucosylation), as compared with antibodies produced from the host cells cultured in the absence of a fucose analog.

The content (e.g., the ratio) of sugar chains in which fucose is not bound to N-acetylglucosamine in the reducing end of the sugar chain versus sugar chains in which fucose is bound to N-acetylglucosamine in the reducing end of the sugar chain can be determined, for example, as described in the Examples. Other methods include hydrazinolysis or enzyme digestion (see, e.g., Biochemical Experimentation Methods 23: Method for Studying Glycoprotein Sugar Chain (Japan Scientific Societies Press), edited by Reiko Takahashi (1989)), fluorescence labeling or radioisotope labeling of the released sugar chain and then separating the labeled sugar chain by chromatography. Also, the compositions of the released sugar chains can be determined by analyzing the chains by the HPAEC-PAD method (see, e.g., J. Liq Chromatogr. 6:1557 (1983)). (See generally U.S. Patent Application Publication No. 2004/0110282.).

B. Compositions of the Invention

In some aspects, also provided herein are compositions (e.g., pharmaceutical compositions) comprising any of the anti-Siglec-8 antibodies described herein (e.g., an antibody that binds to Siglec-8) or agonists described herein. In some aspects, provided herein is a composition comprising an anti-Siglec-8 antibody described herein, wherein the antibody comprises a Fc region and N-glycoside-linked carbohydrate chains linked to the Fc region, wherein less than about 50% of the N-glycoside-linked carbohydrate chains contain a fucose residue. In some embodiments, the antibody comprises a Fc region and N-glycoside-linked carbohydrate chains linked to the Fc region, wherein less than about 45%, about 40%, about 35%, about 30%, about 25%, about 20%, or about 15% of the N-glycoside-linked carbohydrate chains contain a fucose residue. In some aspects, provided herein is a composition comprising an anti-Siglec-8 antibody described herein, wherein the antibody comprises a Fc region and N-glycoside-linked carbohydrate chains linked to the Fc region, wherein substantially none of the N-glycoside-linked carbohydrate chains contain a fucose residue.

Therapeutic formulations are prepared for storage by mixing the active ingredient having the desired degree of purity with optional pharmaceutically acceptable carriers, excipients or stabilizers (Remington: The Science and Practice of Pharmacy, 20th Ed., Lippincott Williams & Wiklins, Pub., Gennaro Ed., Philadelphia, Pa. 2000). Acceptable carriers, excipients, or stabilizers are nontoxic to recipients at the dosages and concentrations employed, and include buffers, antioxidants including ascorbic acid, methionine, Vitamin E, sodium metabisulfite; preservatives, isotonicifiers, stabilizers, metal complexes (e.g., Zn-protein complexes); chelating agents such as EDTA and/or non-ionic surfactants.

Buffers can be used to control the pH in a range which optimizes the therapeutic effectiveness, especially if stability is pH dependent. Buffers can be present at concentrations ranging from about 50 mM to about 250 mM. Suitable buffering agents for use with the present invention include both organic and inorganic acids and salts thereof. For example, citrate, phosphate, succinate, tartrate, fumarate, gluconate, oxalate, lactate, acetate. Additionally, buffers may be comprised of histidine and trimethylamine salts such as Tris.

Preservatives can be added to prevent microbial growth, and are typically present in a range from about 0.2%-1.0% (w/v). Suitable preservatives for use with the present invention include octadecyldimethylbenzyl ammonium chloride; hexamethonium chloride; benzalkonium halides (e.g., chloride, bromide, iodide), benzethonium chloride; thimerosal, phenol, butyl or benzyl alcohol; alkyl parabens such as methyl or propyl paraben; catechol; resorcinol; cyclohexanol, 3-pentanol, and m-cresol.

Tonicity agents, sometimes known as "stabilizers" can be present to adjust or maintain the tonicity of liquid in a composition. When used with large, charged biomolecules such as proteins and antibodies, they are often termed "stabilizers" because they can interact with the charged groups of the amino acid side chains, thereby lessening the potential for inter and intra-molecular interactions. Tonicity agents can be present in any amount between about 0.1% to about 25% by weight or between about 1 to about 5% by weight, taking into account the relative amounts of the other ingredients. In some embodiments, tonicity agents include polyhydric sugar alcohols, trihydric or higher sugar alcohols, such as glycerin, erythritol, arabitol, xylitol, sorbitol and mannitol.

Additional excipients include agents which can serve as one or more of the following: (1) bulking agents, (2) solubility enhancers, (3) stabilizers and (4) and agents preventing denaturation or adherence to the container wall. Such excipients include: polyhydric sugar alcohols (enumerated above); amino acids such as alanine, glycine, glutamine, asparagine, histidine, arginine, lysine, ornithine, leucine, 2-phenylalanine, glutamic acid, threonine, etc.; organic sugars or sugar alcohols such as sucrose, lactose, lactitol, trehalose, stachyose, mannose, sorbose, xylose, ribose, ribitol, myoinisitose, myoinisitol, galactose, galactitol, glycerol, cyclitols (e.g., inositol), polyethylene glycol; sulfur containing reducing agents, such as urea, glutathione, thioctic acid, sodium thioglycolate, thioglycerol, α-monothioglycerol and sodium thio sulfate; low molecular weight proteins such as human serum albumin, bovine serum albumin, gelatin or other immunoglobulins; hydrophilic polymers such as polyvinylpyrrolidone; monosaccharides (e.g., xylose, mannose, fructose, glucose; disaccharides (e.g., lactose, maltose, sucrose); trisaccharides such as raffinose; and polysaccharides such as dextrin or dextran.

Non-ionic surfactants or detergents (also known as "wetting agents") can be present to help solubilize the therapeutic agent as well as to protect the therapeutic protein against agitation-induced aggregation, which also permits the formulation to be exposed to shear surface stress without causing denaturation of the active therapeutic protein or antibody. Non-ionic surfactants are present in a range of about 0.05 mg/ml to about 1.0 mg/ml or about 0.07 mg/ml to about 0.2 mg/ml. In some embodiments, non-ionic surfactants are present in a range of about 0.001% to about 0.1% w/v or about 0.01% to about 0.1% w/v or about 0.01% to about 0.025% w/v.

Suitable non-ionic surfactants include polysorbates (20, 40, 60, 65, 80, etc.), polyoxamers (184, 188, etc.), PLURONIC® polyols, TRITON®, polyoxyethylene sorbitan monoethers (TWEEN®-20, TWEEN®-80, etc.), lauromacrogol 400, polyoxyl 40 stearate, polyoxyethylene hydrogenated castor oil 10, 50 and 60, glycerol monostearate, sucrose fatty acid ester, methyl celluose and carboxymethyl cellulose. Anionic detergents that can be used include sodium lauryl sulfate, dioctyle sodium sulfosuccinate and dioctyl sodium sulfonate. Cationic detergents include benzalkonium chloride or benzethonium chloride.

In order for the formulations to be used for in vivo administration, they must be sterile. The formulation may be rendered sterile by filtration through sterile filtration membranes. The therapeutic compositions herein generally are placed into a container having a sterile access port, for example, an intravenous solution bag or vial having a stopper pierceable by a hypodermic injection needle.

The route of administration is in accordance with known and accepted methods, such as by single or multiple bolus or infusion over a long period of time in a suitable manner, e.g., injection or infusion by subcutaneous, intravenous, intraperitoneal, intramuscular, intraarterial, intralesional or intraarticular routes, topical administration, inhalation or by sustained release or extended-release means.

The formulation herein may also contain more than one active compound as necessary for the particular indication being treated, preferably those with complementary activities that do not adversely affect each other. Alternatively, or in addition, the composition may comprise one or more of a cytotoxic agent, a cytokine (e.g., interferon-α), a growth inhibitory agent, a protein kinase inhibitor (e.g., a tyrosine kinase inhibitor such as midostaurin), a corticosteroid, an antibody (e.g., rituximab), or an anti-cancer agent (e.g., an antimetabolite such as cladribine). Such active compounds are suitably present in combination in amounts that are effective for the purpose intended.

III. Articles of Manufacture or Kits

In another aspect, an article of manufacture or kit is provided which comprises an anti-Siglec-8 antibody described herein (e.g., an antibody that binds human Siglec-8) or an agonist described herein. The article of manufacture or kit may further comprise instructions for use of the antibody or agonist in the methods of the invention. Thus, in certain embodiments, the article of manufacture or kit comprises instructions for the use of an anti-Siglec-8 antibody or agonist that binds to human Siglec-8 in methods for treating or preventing advanced systemic mastocytosis in an individual comprising administering to the individual an effective amount of an anti-Siglec-8 antibody or agonist that binds to human Siglec-8. In certain embodiments, the article of manufacture comprises a medicament comprising an antibody or agonist that binds to human Siglec-8 and a package insert comprising instructions for administration of the medicament in an individual in need thereof to treat or prevent advanced systemic mastocytosis. In some embodiments, the advanced systemic mastocytosis is selected from the group consisting of: aggressive systemic mastocytosis (ASM), mast cell leukemia (MCL), and systemic mastocytosis with an associated hematologic non-mast-cell lineage disorder (SM-AHNMD). In some embodiments, SM-AHNMD is selected from the group consisting of: SM-myelodysplastic syndrome (SM-MDS), SM-myeloproliferative neoplasm (SM-MPN), SM-chronic myelomonocytic leukemia (SM-CMML), SM-chronic eosinophilic leukemia (SM-CEL), and SM-acute myeloid leukemia (SM-AML). In some embodiments, the advanced systemic mastocytosis is associated with eosinophilia. In some embodiments, the advanced systemic mastocytosis is not adequately controlled by cladribine, interferon-α, a corticosteroid, a tyrosine kinase inhibitor or a combination thereof. In some embodiments, the individual has a mutation in KIT. In some embodiments, the individual has a KIT D816V mutation. In some embodiments, the package insert further indicates that the treatment is effective in depleting at least about 20% of the mast cells expressing Siglec-8 in a sample obtained from the individual as compared to a baseline level before administration of the medicament comprising the antibody or agonist. In some embodiments, the sample is a tissue sample or a biological fluid. In some embodiments, the biological fluid sample is blood or urine. In some embodiments, the tissue sample is skin or bone marrow. In some embodiments, the package insert further indicates that the treatment is effective in reducing one or more symptom in the individual with advanced systemic mastocytosis as compared to a baseline level before administration of the medicament. In some embodiments, the individual is diagnosed with advanced systemic mastocytosis before administration of the medicament comprising the antibody or agonist. In certain embodiments, the individual is a human.

The article of manufacture or kit may further comprise a container. Suitable containers include, for example, bottles, vials (e.g., dual chamber vials), syringes (such as single or dual chamber syringes) and test tubes. The container may be formed from a variety of materials such as glass or plastic. The container holds the formulation.

The article of manufacture or kit may further comprise a label or a package insert, which is on or associated with the container, may indicate directions for reconstitution and/or use of the formulation. The label or package insert may further indicate that the formulation is useful or intended for subcutaneous, intravenous, or other modes of administration for treating or preventing advanced systemic mastocytosis in an individual. The container holding the formulation may be a single-use vial or a multi-use vial, which allows for repeat administrations of the reconstituted formulation. The article of manufacture or kit may further comprise a second container comprising a suitable diluent. The article of manufacture or kit may further include other materials desirable from a commercial, therapeutic, and user standpoint, including other buffers, diluents, filters, needles, syringes, and package inserts with instructions for use.

In a specific embodiment, the present invention provides kits for a single dose-administration unit. Such kits comprise a container of an aqueous formulation of therapeutic antibody, including both single or multi-chambered pre-filled syringes. Exemplary pre-filled syringes are available from Vetter GmbH, Ravensburg, Germany.

In another embodiment, provided herein is an article of manufacture or kit comprising the formulations described herein for administration in an auto-injector device. An auto-injector can be described as an injection device that upon activation, will deliver its contents without additional necessary action from the patient or administrator. They are particularly suited for self-medication of therapeutic formulations when the delivery rate must be constant and the time of delivery is greater than a few moments.

In another aspect, an article of manufacture or kit is provided which comprises an anti-Siglec-8 antibody described herein (e.g., an antibody that binds human Siglec-8) or an agonist described herein. The article of manufacture or kit may further comprise instructions for use of the antibody or agonist in the methods of the invention. Thus, in certain embodiments, the article of manufacture or kit comprises instructions for the use of an anti-Siglec-8 antibody or agonist that binds to human Siglec-8 in methods for treating or preventing advanced systemic mastocytosis in an individual comprising administering to the individual an effective amount of an anti-Siglec-8 antibody or agonist that binds to human Siglec-8. In certain embodiments, the article of manufacture or kit comprises a medicament comprising an antibody or agonist that binds to human Siglec-8 and a package insert comprising instructions for administration of the medicament in an individual in need thereof to treat or prevent advanced systemic mastocytosis.

The present invention also provides an article of manufacture or kit which comprises an anti-Siglec-8 antibody described herein (e.g., an antibody that binds human Siglec-8) or an agonist described herein in combination with one or more additional medicament (e.g., a second medicament) for treating or preventing advanced systemic mastocytosis in an individual. The article of manufacture or kit may further comprise instructions for use of the antibody or agonist in combination with one or more additional medicament in the methods of the invention. For example, the article of manufacture or kit herein optionally further comprises a container comprising a second medicament, wherein the anti-Siglec-8 antibody or agonist is a first medicament, and which article or kit further comprises instructions on the label or package insert for treating the individual with the second medicament, in an effective amount. Thus in certain embodiments, the article of manufacture or kit comprises instructions for the use of an anti-Siglec-8 antibody or agonist that binds to human Siglec-8 in combination with one or more additional medicament in methods for treating or preventing advanced systemic mastocytosis in an individual. In certain embodiments, the article of manufacture or kit comprises a medicament comprising an antibody or agonist that binds to human Siglec-8 (e.g., a first medicament), one or more additional medicament and a package insert comprising instructions for administration of the first medicament in combination with the one or more additional medicament (e.g., a second medicament). In some embodiments, the one or more additional medicament is a cytotoxic agent, a cytokine (e.g., interferon-α), a growth inhibitory agent, a protein kinase inhibitor (e.g., a tyrosine kinase inhibitor such as midostaurin), a corticosteroid, an antibody (e.g., rituximab), or an anti-cancer agent (e.g., an antimetabolite such as cladribine).

It is understood that the aspects and embodiments described herein are for illustrative purposes only and that various modifications or changes in light thereof will be suggested to persons skilled in the art and are to be included within the spirit and purview of this application and scope of the appended claims.

The invention will be more fully understood by reference to the following examples. They should not, however, be construed as limiting the scope of the invention. It is understood that the examples and embodiments described herein are for illustrative purposes only and that various modifications or changes in light thereof will be suggested to persons skilled in the art and are to be included within the spirit and purview of this application and scope of the appended claims.

EXAMPLES

Example 1: In Vitro Activity of Anti-Siglec-8 Antibodies on Cells from Systemic Mastocytosis Patients The activity of anti-Siglec-8 antibodies in blood and bone marrow samples from individuals with systemic mastocytosis (SM) was investigated.

Materials and Methods
Antibodies

The anti-Siglec-8 antibodies used in this study included a humanized antibody with an IgG4 isotype (referred to herein as "Antibody 1"), a humanized antibody engineered to have non-fucosylated IgG1κ constant regions for the purpose of enhancing antibody-dependent cell-mediated cytotoxicity (ADCC) activity (referred to herein as "Antibody 2"), and a murine antibody with an IgG1κ isotype (referred to herein as "murine 1H10 antibody") that was conjugated to Alexa Fluor® 647 (Table 6). Antibodies used for the in vitro characterization of human cells can be found at Table 7.

TABLE 6

| Anti-Siglec-8 Antibodies | | | | | | |
|---|---|---|---|---|---|---|
| Target | Format | Clone | Target Species | Host Species | Isotype | Concentration (mg/mL) |
| Siglec-8 | Alexa Fluor® 647 | 1H10 | Human | Mouse | IgG1κ | 1.7 |
| Siglec-8 | Alexa Fluor® 647 | 1H10 | Human | Mouse | IgG1κ | 1.8 |

TABLE 6-continued

Anti-Siglec-8 Antibodies

| Target | Format | Clone | Target Species | Host Species | Isotype | Concentration (mg/mL) |
|---|---|---|---|---|---|---|
| Siglec-8 | Unlabeled | Antibody 1 | Human | Humanized | IgG4 | 14.8 |
| Siglec-8 | Unlabeled | Antibody 2 | Human | Humanized | IgG1 aFuc | 15.7 |

Abbreviations:
aFuc = non-Fuc;
Fuc = fucosylated;
Ig = immunoglobulin;
NA = not applicable;
Siglec = sialic acid-binding immunoglobulin-like lectin.

TABLE 7

Antibodies and Reagents for the Characterization of Human Cells In Vitro

| Target | Format | Clone | Target Species | Host Species | Isotype | Vendor | Catalog Number |
|---|---|---|---|---|---|---|---|
| Isotype | Purified | NA | NA | Human | IgG4 | Eureka | ET904 |
| Isotype | Purified | NA | NA | Human | IgG1 | Eureka | ET901 |
| CD117 | APC | A3C6E2 | Human | Mouse | IgG1 | Miltenyi | 130-091-733 |
| CD16 | FITC | 3G8 | Human | Mouse | IgG1 | BD | 555406 |
| CD16 | PE | 3G8 | Human | Mouse | IgG1 | BD | 556619 |
| CD16 | PerCP-Cy5.5 | 3G8 | Human | Mouse | IgG1 | BD | 560717 |
| CD16 | Alexa Fluor ® 647 | 3G8 | Human | Mouse | IgG1 | BD | 557710 |
| CD193 (CCR3) | PE | 5E8 | Human | Mouse | IgG2b | BD | 558165 |
| CD193 (CCR3) | Alexa Fluor ® 647 | 5E8 | Human | Mouse | IgG2b | BD | 558208 |
| CD20 | FITC | 2H7 | Human | Mouse | IgG2b | BD | 560503 |
| CD25 | PerCP-Cy5.5 | M-A251 | Human | Mouse | IgG1 | BD | 560503 |
| CD3 | FITC | HIT3a | Human | Mouse | IgG2b | BD | 555339 |
| CD32 | FITC | FLI8.26 (2003) | Human | Mouse | IgG2b | BD | 555448 |
| CD38 | PerCP-Cy5.5 | HIT2 | Human | Mouse | IgG1 | BD | 561106 |
| CD45 | PerCP-Cy5.5 | 2D1 | Human | Mouse | IgG1 | BD | 340953 |
| CD56 | PE | B159 | Human | Mouse | IgG1 | BD | 555516 |
| CD64 | PE | 10.1 | Human | Mouse | IgG1 | BD | 558592 |
| CD69 | FITC | FN50 | Human | Mouse | IgG1κ | BD | 555530 |
| CD69 | APC | FN50 | Human | Mouse | IgG1κ | BD | 555533 |
| CD69 | PE | FN50 | Human | Mouse | IgG1κ | BD | 555531 |
| CD88 (C5aR) | PE | D53-1473 | Human | Mouse | IgG1 | BD | 550494 |
| CD95 | Purified | EOS9.1 | Human | Mouse | IgM | BD | 550042 |
| CDw125 (IL-5Ra) | PE | A14 | Human | Mouse | IgG1 | BD | 555902 |
| cPARP | Alexa Fluor ® 647 | F21-852 | Human | Mouse | IgG1 | BD | 558710 |
| EPX | Purified | Ascites | Human | Mouse | IgG1 | Millipore | MAB1087 |
| FCeR1a | FITC | AER-37 CRA1 | Human | Mouse | IgG2b | Miltenyi | 130-095-978 |
| hIgE | Biotin | G7-26 | Human | Mouse | IgG2a | BD | 555858 |
| CD117 | PerCP-Cy5.5 | YB5.B8 | Human | Mouse | IgG1 | BD | 562094 |
| 7-AAD | 7-AAD | N/A | N/A | N/A | N/A | BD | 559925 |

Abbreviations:
APC = allophycocyanin;
BD = Becton, Dickinson and Company;
CCR = C-C chemokine receptor;
FITC = fluorescein isothiocyanate;
hIg = human Ig;
NA = not applicable;
PE = phycoerythrin.

Isolation of Peripheral Blood Leukocytes and Natural Killer Cells

Fresh human blood (anti-coagulated with sodium heparin) was obtained from patients with systemic mastocytosis. Blood was processed through two rounds of red blood cell (RBC) lysis in 1×RBC lysis buffer (eBioscience, 00-4300-54) according to manufacturer instructions. The peripheral blood leukocyte (PBL) cell pellet was washed twice with 50 mL phosphate-buffered saline (PBS), centrifuged, suspended in 10 mL in RPMI-1640 containing 10% fetal calf serum, and passed through a 40 μm nylon filter. The leukocytes were counted. A Natural Killer (NK) Cell Isolation kit (Miltenyi Biotech, #130-092-657) was used to further isolate NK cells from peripheral blood cells of systemic mastocytosis patients. The enriched population was counted and suspended in RPMI-1640 containing 10% fetal calf serum. Isolation of Cells from Systemic Mastocytosis Patient Bone Marrow Aspirates and CD117+ Enrichment of Mast Cells Fresh human bone marrow aspirates (anti-coagulated with sodium heparin) were obtained from patients with systemic mastocytosis. Bone marrow aspirates was processed through one round of red blood cell (RBC) lysis in 1×RBC lysis buffer (eBioscience, 00-4300-54) according to manufacturer instructions. The cell pellet was washed twice with 50 mL phosphate-buffered saline (PBS), centrifuged, suspended in 10 mL in RPMI-1640 containing 10% fetal calf serum (FCS) and passed through a 40 µm nylon filter. The cells were counted. In samples where mast cell enrichment was performed, the purified cells were instead suspended in 5 mL in PBS containing 100 ng/ml rhSCF (R&D Systems, 255-SC). The cells were counted and CD117+ high mast cells were enriched by positive selection with a CD117 Microbead Kit (Miltenyi Biotech, #130-091-332) according to manufacturer's instructions. The enriched population was counted and suspended in RPMI-1640 containing 10% fetal calf serum (FCS) containing 100 ng/ml rhSCF.

Generation of a Siglec-8-Expressing Ramos Cell Line

Ramos, a human B-cell cell line sensitive to ADCC and complement-dependent cytotoxicity (CDC) activity, was transfected with full-length Siglec-8 to generate a stably transfected cell line expressing Siglec-8. A clone (2C10) with uniform, stable expression of Siglec-8 was identified (referred to herein as "Ramos 2C10 target cells"). Ramos 2C10 target cells expressed approximately 51,000 Siglec-8 molecules per cell.

Non-Fucosylated Anti-Siglec-8 Antibody Induced ADCC Depletion Assay Against Siglec-8+ Target Cells Using PBL from Systemic Mastocytosis Patients PBLs isolated from patient blood were seeded in a 96-well plate (Falcon, 353077) at $5 \times 10^5$ cells per well in 100 µL medium containing 10% FCS. Siglec-8 transfected Ramos cells (Ramos 2C10 target cells) expressing Siglec-8 at levels similar to mast cells were added at $5 \times 10^4$ cells per well (Effector:Target cell ratio of 10:1). Non-fuscosylated humanized anti-Siglec-8 antibody (Antibody 2) or human IgG1 isotype control antibody was diluted in media and added to cells in a 10-fold dilution series, from 10 µg/mL to 1 pg/mL. The cells were incubated for 48 hours at 37° C. in 5% $CO_2$. The plate was centrifuged at 300 g for 2 minutes and the supernatant was removed. Cells were stained for flow cytometric analysis at 4° C. for 20 minutes with an antibody that binds to CD20, a marker for Ramos cells, and the viability dye 7-Aminoactinomycin D (7-AAD) in fluorescence-activated cell sorting (FACS) buffer (See Table 7). The plates were then centrifuged at 300 g for 2 minutes and the supernatants were removed. The cells were suspended in 1% paraformaldehyde in PBS and analyzed by flow cytometry on a FACS Calibur instrument (Becton, Dickinson and Company). Ramos 2C10 target cell depletion was measured by the loss of $CD20^+$, $SSC/FSC^{hi}$ Ramos 2C10 target cells in the presence of non-fuscosylated humanized anti-Siglec-8 antibody (Antibody 2) compared with human IgG1 isotype control.

Results

Bone marrow or blood samples from 7 patients with systemic mastocytosis were included in the analysis (SSM, n=1; ASM, n=1; and SM-AHNMD, n=5 with subtypes of SM-CMML, n=3; SM-MDS, n=1; SM-CEL, n=1). The demographic and clinical features of each systemic mastocytosis patient were taken at the time of obtaining bone marrow and blood samples (Table 8). All patients in the systemic mastocytosis study population were Caucasian. Six patients were KIT D816V positive. At the time of sample collection, treatments included midostaurin (n=2); cladribine (n=1); corticosteroids (n=1); and three patients were not receiving any biologic or cytoreductive therapy.

TABLE 8

Systemic Mastocytosis Patient Characteristics at Time of Sampling

| Patient | Age | Gender | Diagnosis | Serum Tryptase | MCs % BM | Medications | Mutations |
|---|---|---|---|---|---|---|---|
| JG01 | 79 | M | SM-AHNMD-CMML | 96 | 60-70% | None | KIT D816V+ |
| JG02 | 78 | M | SM-AHNMD-MDS | 20 | 5% | Steroids Rituxan | KIT D816V+ |
| JG03 | 71 | F | SM-AHNMD-CMML | 96 | 20% | Midostaurin | KIT D816V+ |
| JG04 | 77 | F | ASM | 174 | 50% | Midostaurin | KIT-D816V+ |
| JG05 | 63 | F | SSM | 575 | 40% | None | KIT D816V+ |
| JG06 | 78 | F | SM-AHNMD-CMML | 122 | 80% | None | KIT D816V+ |
| JG07 | 70 | M | SM-AHNMD-CMML | 109 | 20-30% | Cladribine | KIT D816V+ |

Abbreviations:
MC = Mast cells;
BM = Bone Marrow Aspirates;
PB = Peripheral Blood;
SM = Systemic Mastocytosis;
ASM = Aggressive SM;
SSM = Smoldering SM;
SM-AHNMD = SM-Associated clonal hematologic non-mast cell lineage disease;
CMML = chronic myelomonocytic leukemia;
MDS = myelodysplastic syndrome.

Figure 2:
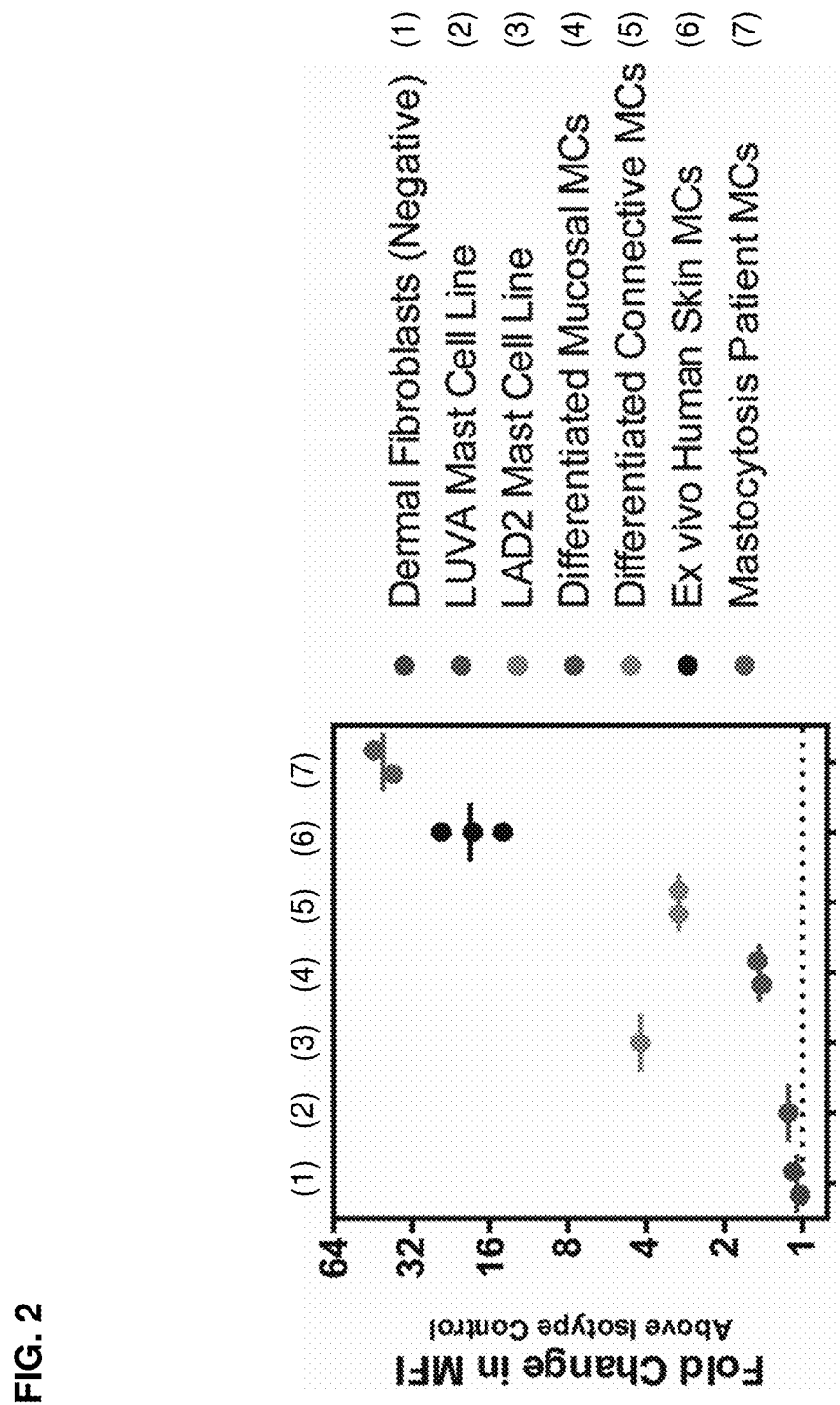
FIG. 2 is a graph showing Siglec-8 expression on mast cells isolated from bone marrow of systemic mastocytosis patients. The level of Siglec-8 on human mast cells (MCs) was determined by flow cytometry using an antibody specific for Siglec-8 (R&D Systems, Clone: 837535) and expressed as the change in mean fluorescence intensity (MFI) compared with the MFI obtained with an isotype control antibody. Primary human MCs were isolated from human skin samples or bone marrow aspirates of mastocytosis patients (JG01, JG02). Differentiated MCs were generated from $CD34^+$ hematopoietic stem cells by in vitro culture for more than 6 weeks in presence of cytokines SCF, IL-3, IL-4, IL-6, and IL-9

Anti-coagulated bone marrow aspirate from each systemic mastocytosis patients (JG01-JG05) was cleared of RBC by lysis and the remaining leukocytes were labeled with a cocktail of antibodies directed against CD117, FcεR1α/IgER, CD45, and Siglec-8 (R&D Systems, Clone: 837535) or CD117, FcεR1α/IgER, and CD25. The samples were evaluated by flow cytometry and Siglec-8 expression on the surface of mast cells was determined. Mast cells in bone marrow were characterized by the presence of CD117 receptor (CD117$^+$) and Fc fragment of IgE, high affinity I, receptor alpha polypeptide FcεR1α (IgER$^+$). Percentage of CD117+IgER+ mast cells was obtained for each patient and these mast cells were gated for analysis of Siglec-8 expression (FIG. 1A-E, left panel for each patient). The expression of Siglec-8 (FIG. 1A-E, middle panel for each patient) and CD25 (FIG. 1A-E, right panel for each patient) was evaluated compared with matched isotype control antibodies on mast cells (CD117$^+$IgER$^+$). All bone marrow samples showed detectable CD117+ mast cells. High level of Siglec-8 expression was confirmed on the surface of all viable mast cells (CD117$^+$IgER$^+$) (FIG. 1A-E, middle panel for each patient). The expression level of Siglec-8 on mast cells from bone marrow of systemic mastocytosis patients was comparable to or higher than the expression level of Siglec-8 on mast cells isolated from primary human skin (FIG. 2). The expression level of Siglec-8 on mast cell immortal cell lines or mast cells differentiated in vitro was substantially lower than the expression level of Siglec-8 on primary mast cells isolated directly from human (FIG. 2). No difference in Siglec-8 expression was observed between patients receiving different therapies or no therapy.

The ability of NK cells from systemic mastocytosis patients to engage non-fucosylated humanized anti-Siglec-8 antibody was evaluated. PBL from patients with systemic mastocytosis (JG03, JG04, JG05, and JG06) or bone marrow aspirates from a patient with systemic mastocytosis (JG01) were incubated with fluorochrome-labeled non-fucosylated humanized anti-Siglec-8 antibody or isotype-matched antibody at 1 µg/mL and fluorochrome-labeled antibodies against CD16 and CD56. The cells were then evaluated by FACS. Percentage of NK cells (CD16+CD56+SSClow) in bone marrow or PBL was obtained from each patient tested and these NK cells were gated for analysis of non-fucosylated humanized anti-Siglec-8 antibody or isotype-matched antibody binding to NK cells. Percentage of NK cells (CD16+CD56+SSClow) in bone marrow of patient JG01 was 1.3%. The percentage of NK cells (CD16+CD56+SSClow) in PBL of patients JG03, JG04, JG05, and JG06 was 1.7%, 1.4%, 4.3% and 6.0%, respectively. NK cells from systemic mastocytosis patients were engaged by non-fucosylated humanized anti-Siglec-8 antibody (FIG. 3A-E).

ADCC activity has been reported to be defective in some cancer patients. See Marcondes et al. PNAS, 2008, 105: 2865-2870; Kiladjian et al., Leukemia, 2006, 20:463-470; Pahl et al., Immunobiology, 2015, doi: 10.1016/j.imbio.2015.07.012; and Cheng et al., Cell. Mol. Immunol., 2013, 10:230-252, 2013. It is unclear if systemic mastocytosis patients have intact ADCC function. To evaluate the ability of non-fucosylated humanized anti-Siglec-8 antibody (Antibody 2) to induce ADCC in systemic mastocytosis patients, an assay was developed using a Siglec-8 transfected target cell line, Ramos 2C10 target cell line. The Ramos 2C10 target cell line was generated from Ramos cells, a human B-cell line sensitive to ADCC activity. Using peripheral blood leukocytes as effector cells, 1 µg/mL of non-fuscosylated humanized anti-Siglec-8 antibody (Antibody 2) showed potent depletion of the Ramos 2C10 target cell line when incubated in PBL preparation from systemic mastocytosis patients which is consistent with ADCC-mediated killing. ADCC was observed in all five samples tested (FIG. 4A). Titration of increasing amounts of non-fuscosylated humanized anti-Siglec-8 antibody (Antibody 2) was performed on samples from two patients. Potent ADCC activity was observed in samples from patient JG03 and patient JG04, with an EC50 for target depletion of 49 ng/mL (FIG. 4B) and 65 ng/mL (FIG. 4C) of anti-Siglec-8 antibody, respectively.

The ADCC activity of non-fucosylated humanized anti-Siglec-8 antibody on mast cells was evaluated. Mast cells from bone marrow aspirate of patient JG01 and patient JG07 were enriched utilizing CD117 targeting magnetic beads. Enriched mast cells were treated with either isotype-matched (isotype) or non-fucosylated humanized anti-Siglec-8 antibody (Antibody 2) at a concentration of 1 µg/mL in the presence of purified NK effector cells. Significant anti-Siglec-8-mediated ADCC activity on mast cells was observed using non-autologous NK cells, 69% average reduction (FIG. 5A), or autologous NK cells, 76% average reduction (FIG. 5B), indicating that non-fucosylated humanized anti-Siglec-8 antibody has the potential to reduce mast cell burden in these patients.

---

SEQUENCES

Amino acid sequence of mouse 2E2 heavy chain variable domain
QVQLKESGPGLVAPSQSLSITCTVSGFSLTIYGAHWVRQPPGKGLEWLGVIWAGGSTNYNSALMSRLSISKDNSKSQVFLKINSLQTDDTA
LYYCARDGSSPYYYSMEYWGQGTSVTVSS (SEQ ID NO: 1)

Amino acid sequence of 2E2 RHA heavy chain variable domain
EVQLVESGGGLVQPGGSLRLSCAASGFSLTIYGAHWVRQAPGKGLEWVSVIWAGGSTNYNSALMSRFTISKDNSKNTVYLQMNSLRAEDTA
VYYCARDGSSPYYYSMEYWGQGTTVTVSS (SEQ ID NO: 2)

Amino acid sequence of 2E2 RHB heavy chain variable domain
EVQLVESGGGLVQPGGSLRLSCAVSGFSLTIYGAHWVRQAPGKGLEWLGVIWAGGSTNYNSALMSRLSISKDNSKNTVYLQMNSLRAEDTA
VYYCARDGSSPYYYSMEYWGQGTTVTVSS (SEQ ID NO: 3)

Amino acid sequence of 2E2 RHC heavy chain variable domain
EVQLVESGGGLVQPGGSLRLSCAVSGFSLTIYGAHWVRQAPGKGLEWVSVIWAGGSTNYNSALMSRFTISKDNSKNTVYLQMNSLRAEDTA
VYYCARDGSSPYYYSMEYWGQGTTVTVSS (SEQ ID NO: 4)

Amino acid sequence of 2E2 RHD heavy chain variable domain
EVQLVESGGGLVQPGGSLRLSCAASGFSLTIYGAHWVRQAPGKGLEWLSVIWAGGSTNYNSALMSRFTISKDNSKNTVYLQMNSLRAEDTA
VYYCARDGSSPYYYSMEYWGQGTTVTVSS (SEQ ID NO: 5)

-continued

SEQUENCES

Amino acid sequence of 2E2 RHE heavy chain variable domain
EVQLVESGGGLVQPGGSLRLSCAASGFSLTIYGAHWVRQAPGKGLEWVGVIWAGGSTNYNSALMSRFTISKDNSKNTVYLQMNSLRAEDTA
VYYCARDGSSPYYYSMEYWGQGTTVTVSS (SEQ ID NO: 6)

Amino acid sequence of 2E2 RHF heavy chain variable domain
EVQLVESGGGLVQPGGSLRLSCAASGFSLTIYGAHWVRQAPGKGLEWVSVIWAGGSTNYNSALMSRLTISKDNSKNTVYLQMNSLRAEDTA
VYYCARDGSSPYYYSMEYWGQGTTVTVSS (SEQ ID NO: 7)

Amino acid sequence of 2E2 RHG heavy chain variable domain
EVQLVESGGGLVQPGGSLRLSCAASGFSLTIYGAHWVRQAPGKGLEWVSVIWAGGSTNYNSALMSRFSISKDNSKNTVYLQMNSLRAEDTA
VYYCARDGSSPYYYSMEYWGQGTTVTVSS (SEQ ID NO: 8)

Amino acid sequence of 2E2 RHA2 heavy chain variable domain
QVQLQESGPGLVKPSETLSLTCTVSGGSISIYGAHWIRQPPGKGLEWIGVIWAGGSTNYNSALMSRVTISVDTSKNQFSLKLSSVTAADTA
VYYCARDGSSPYYYSMEYWGQGTLVTVSS (SEQ ID NO: 9)

Amino acid sequence of 2E2 RHB2 heavy chain variable domain
QVQLQESGPGLVKPSETLSLTCTVSGFSLTIYGAHWVRQPPGKGLEWLGVIWAGGSTNYNSALMSRLSISKDNSKNQVSLKLSSVTAADTA
VYYCARDGSSPYYYSMEYWGQGTLVTVSS (SEQ ID NO: 10)

Amino acid sequence of 2E2 RHE S-G mutant heavy chain variable domain
EVQLVESGGGLVQPGGSLRLSCAASGFSLTIYGAHWVRQAPGKGLEWVGVIWAGGSTNYNSALMSRFTISKDNSKNTVYLQMNSLRAEDTA
VYYCARDGSSPYYYGMEYWGQGTTVTVSS (SEQ ID NO: 11)

Amino acid sequence of 2E2 RHE E-D heavy chain variable domain
EVQLVESGGGLVQPGGSLRLSCAASGFSLTIYGAHWVRQAPGKGLEWVGVIWAGGSTNYNSALMSRFTISKDNSKNTVYLQMNSLRAEDTA
VYYCARDGSSPYYYSMDYWGQGTTVTVSS (SEQ ID NO: 12)

Amino acid sequence of 2E2 RHE Y-V heavy chain variable domain
EVQLVESGGGLVQPGGSLRLSCAASGFSLTIYGAHWVRQAPGKGLEWVGVIWAGGSTNYNSALMSRFTISKDNSKNTVYLQMNSLRAEDTA
VYYCARDGSSPYYYSMEVWGQGTTVTVSS (SEQ ID NO: 13)

Amino acid sequence of 2E2 RHE triple mutant heavy chain variable domain
EVQLVESGGGLVQPGGSLRLSCAASGFSLTIYGAHWVRQAPGKGLEWVGVIWAGGSTNYNSALMSRFTISKDNSKNTVYLQMNSLRAEDTA
VYYCARDGSSPYYYGMDVWGQGTTVTVSS (SEQ ID NO: 14)

Amino acid sequence of mouse 2E2 light chain variable domain
QIILTQSPAIMSASPGEKVSITCSATSSVSYMHWFQQKPGTSPKLWIYSTSNLASGVPVRFSGSGSGTSYSLTISRMEAEDAATYYCQQRS
SYPFTFGSGTKLEIK (SEQ ID NO: 15)

Amino acid sequence of 2E2 RKA light chain variable domain
EIVLTQSPATLSLSPGERATLSCSATSSVSYMHWFQQKPGQAPRLLIYSTSNLASGIPARFSGSGSGTDFTLTISSLEPEDFAVYYCQQRS
SYPFTFGPGTKLDIK (SEQ ID NO: 16)

Amino acid sequence of 2E2 RKB light chain variable domain
EIILTQSPATLSLSPGERATLSCSATSSVSYMHWFQQKPGQAPRLWIYSTSNLASGVPARFSGSGSGTDYTLTISSLEPEDFAVYYCQQRS
SYPFTFGPGTKLDIK (SEQ ID NO: 17)

Amino acid sequence of 2E2 RKC light chain variable domain
EIILTQSPATLSLSPGERATLSCSATSSVSYMHWFQQKPGQAPRLLIYSTSNLASGIPARFSGSGSGTDFTLTISSLEPEDFAVYYCQQRS
SYPFTFGPGTKLDIK (SEQ ID NO: 18)

Amino acid sequence of 2E2 RKD light chain variable domain
EIVLTQSPATLSLSPGERATLSCSATSSVSYMHWFQQKPGQAPRLWIYSTSNLASGIPARFSGSGSGTDFTLTISSLEPEDFAVYYCQQRS
SYPFTFGPGTKLDIK (SEQ ID NO: 19)

Amino acid sequence of 2E2 RKE light chain variable domain
EIVLTQSPATLSLSPGERATLSCSATSSVSYMHWFQQKPGQAPRLLIYSTSNLASGVPARFSGSGSGTDFTLTISSLEPEDFAVYYCQQRS
SYPFTFGPGTKLDIK (SEQ ID NO: 20)

Amino acid sequence of 2E2 RKF light chain variable domain
EIVLTQSPATLSLSPGERATLSCSATSSVSYMHWFQQKPGQAPRLLIYSTSNLASGIPARFSGSGSGTDYTLTISSLEPEDFAVYYCQQRS
SYPFTFGPGTKLDIK (SEQ ID NO: 21)

Amino acid sequence of 2E2 RKG light chain variable domain
EIVLTQSPATLSLSPGERATLSCSATSSVSYMHWYQQKPGQAPRLLIYSTSNLASGIPARFSGSGSGTDFTLTISSLEPEDFAVYYCQQRS
SYPFTFGPGTKLDIK (SEQ ID NO: 22)

Amino acid sequence of 2E2 RKA F-Y mutant light chain variable domain
EIVLTQSPATLSLSPGERATLSCSATSSVSYMHWFQQKPGQAPRLLIYSTSNLASGIPARFSGSGSGTDFTLTISSLEPEDFAVYYCQQRS
SYPYTFGPGTKLDIK (SEQ ID NO: 23)

Amino acid sequence of 2E2 RKF F-Y mutant light chain variable domain
EIVLTQSPATLSLSPGERATLSCSATSSVSYMHWFQQKPGQAPRLLIYSTSNLASGIPARFSGSGSGTDYTLTISSLEPEDFAVYYCQQRS
SYPYTFGPGTKLDIK (SEQ ID NO: 24)

-continued

SEQUENCES

Amino acid sequence of HEKA heavy chain and HEKF heavy chain
EVQLVESGGGLVQPGGSLRLSCAASGFSLTIYGAHWVRQAPGKGLEWVGVIWAGGSTNYNSALMSRFTISKDNSKNTVYLQMNSLRAEDTA
VYYCARDGSSPYYYSMEYWGQGTTVTVSSASTKGPSVFPLAPSSKSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCPPCPAPELLGGPSVFLFPPKPKDTLMISRTPEVTCVVVDVSHED
PEVKFNWYVDGVEVHNAKTKPREEQYNSTYRVVSVLTVLHQDWLNGKEYKCKVSNKALPAPIEKTISKAKGQPREPQVYTLPPSREEMTKN
QVSLTCLVKGFYPSDIAVEWESNGQPENNYKTTPPVLDSDGSFFLYSKLTVDKSRWQQGNVFSCSVMHEALHNHYTQKSLSLSPG
(SEQ ID NO: 75)

Amino acid sequence of HEKA light chain
EIVLTQSPATLSLSPGERATLSCSATSSVSYMHWFQQKPGQAPRLLIYSTSNLASGIPARFSGSGSGTDFTLTISSLEPEDFAVYYCQQRS
SYPFTFGPGTKLDIKRTVAAPSVFIFPPSDEQLKSGTASVVCLLNNFYPREAKVQWKVDNALQSGNSQESVTEQDSKDSTYSLSSTLTLSK
ADYEKHKVYACEVTHQGLSSPVTKSFNRGEC (SEQ ID NO: 76)

Amino acid sequence of HEKF light chain
EIVLTQSPATLSLSPGERATLSCSATSSVSYMHWFQQKPGQAPRLLIYSTSNLASGIPARFSGSGSGTDYTLTISSLEPEDFAVYYCQQRS
SYPFTFGPGTKLDIKRTVAAPSVFIFPPSDEQLKSGTASVVCLLNNFYPREAKVQWKVDNALQSGNSQESVTEQDSKDSTYSLSSTLTLSK
ADYEKHKVYACEVTHQGLSSPVTKSFNRGEC (SEQ ID NO: 77)

Amino acid sequence of IgG1 heavy chain constant region
ASTKGPSVFPLAPSSKSTSGGTAALGCLVKDYFPEPVTVSWNSGALTSGVHTFPAVLQSSGLYSLSSVVTVPSSSLGTQTYICNVNHKPSN
TKVDKRVEPKSCDKTHTCPPCPAPELLGGPSVFLFPPKPKDTLMISRTPEVTCVVVDVSHEDPEVKFNWYVDGVEVHNAKTKPREEQYNST
YRVVSVLTVLHQDWLNGKEYKCKVSNKALPAPIEKTISKAKGQPREPQVYTLPPSREEMTKNQVSLTCLVKGFYPSDIAVEWESNGQPENN
YKTTPPVLDSDGSFFLYSKLTVDKSRWQQGNVFSCSVMHEALHNHYTQKSLSLSPG (SEQ ID NO: 78)

Amino acid sequence of IgG4 heavy chain constant region
ASTKGPSVFPLAPCSRSTSESTAALGCLVKDYFPEPVTVSWNSGALTSGVHTFPAVLQSSGLYSLSSVVTVPSSSLGTKTYTCNVDHKPSN
TKVDKRVESKYGPPCPPCPAPEFLGGPSVFLFPPKPKDTLMISRTPEVTCVVVDVSQEDPEVQFNWYVDGVEVHNAKTKPREEQFNSTYRV
VSVLTVLHQDWLNGKEYKCKVSNKGLPSSIEKTISKAKGQPREPQVYTLPPSQEEMTKNQVSLTCLVKGFYPSDIAVEWESNGQPENNYKT
TPPVLDSDGSFFLYSRLTVDKSRWQEGNVFSCSVMHEALHNHYTQKSLSLSLG (SEQ ID NO: 79)

Amino acid sequence of Ig kappa light chain constant region
RTVAAPSVFIFPPSDEQLKSGTASVVCLLNNFYPREAKVQWKVDNALQSGNSQESVTEQDSKDSTYSLSSTLTLSKADYEKHKVYACEVTH
QGLSSPVTKSFNRGEC (SEQ ID NO: 80)

Amino acid sequence of murine 2C4 and 2E2 IgG1 heavy chain
QVQLKRASGPGLVAPSQSLSITCTVSGFSLTIYGAHWVRQPPGKGLEWLGVIWAGGSTNYNSALMSRLSISKDNSKSQVFLKINSLQTDDT
ALYYCARDGSSPYYYSMEYWGQGTSVTVSSAKTTPPSVYPLAPGSAAQTNSMVTLGCLVKGYFPEPVTVTWNSGSLSSGVHTFPAVLESDL
YTLSSSVTVPSSPRPSETVTCNVAHPASSTKVDKKIVPRDCGCKPCICTVPEVSSVFIFPPKPKDVLTITLTPKVTCVVVDISKDDPEVQF
SWFVDDVEVHTAQTQPREEQFNSTFRSVSELPIMHQDWLNGKEFKCRVNSAAFPAPIEKTISKTKGRPKAPQVYTIPPPKEQMAKDKVSLT
CMITDFFPEDITVEWQWNGQPAENYKNTQPIMNTNGSYFVYSKLNVQKSNWEAGNTFTCSVLHEGLHNHHTEKSLSHSPG
(SEQ ID NO: 81)

Amino acid sequence of murine 2C4 kappa light chain
EIILTQSPAIMSASPGEKVSITCSATSSVSYMHWFQQKPGTSPKLWIYSTSNLASGVPVRFSGSGSGTSYSLTISRMEAEDAATYYCQQRS
SYPFTFGSGTKLEIKADAAPTVSIFPPSSEQLTSGGASVVCFLNNFYPKDINVKWKIDGSERQNGVLNSWTDQDSKDSTYSMSSTLTLTKD
EYERHNSYTCEATHKTSTSPIVKSFNRNEC (SEQ ID NO: 82)

Amino acid sequence of murine 2E2 kappa light chain
QIILTQSPAIMSASPGEKVSITCSATSSVSYMHWFQQKPGTSPKLWIYSTSNLASGVPVRFSGSGSGTSYSLTISRMEAEDAATYYCQQRS
SYPFTFGSGTKLEIKADAAPTVSIFPPSSEQLTSGGASVVCFLNNFYPKDINVKWKIDGSERQNGVLNSWTDQDSKDSTYSMSSTLTLTKD
EYERHNSYTCEATHKTSTSPIVKSFNRNEC (SEQ ID NO: 83)

Amino acid sequence of chimeric 2C4 and 2E2 IgG1 heavy chain
QVQLKRASGPGLVAPSQSLSITCTVSGFSLTIYGAHWVRQPPGKGLEWLGVIWAGGSTNYNSALMSRLSISKDNSKSQVFLKINSLQTDDT
ALYYCARDGSSPYYYSMEYWGQGTSVTVSSASTKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKRVEPKSCDKTHTCPPCPAPELLGGPSVFLFPPKPKDTLMISRTPEVTCVVVDVSHE
DPEVKFNWYVDGVEVHNAKTKPREEQYNSTYRVVSVLTVLHQDWLNGKEYKCKVSNKALPAPIEKTISKAKGQPREPQVYTLPPSREEMTK
NQVSLTCLVKGFYPSDIAVEWESNGQPENNYKTTPPVLDSDGSFFLYSKLTVDKSRWQQGNVFSCSVMHEALHNHYTQKSLSLSPG
(SEQ ID NO: 84)

Amino acid sequence of chimeric 2C4 kappa light chain
EIILTQSPAIMSASPGEKVSITCSATSSVSYMHWFQQKPGTSPKLWIYSTSNLASGVPVRFSGSGSGTSYSLTISRMEAEDAATYYCQQRS
SYPFTFGSGTKLEIKRTVAAPSVFIFPPSDEQLKSGTASVVCLLNNFYPREAKVQWKVDNALQSGNSQESVTEQDSKDSTYSLSSTLTLSK
ADYEKHKVYACEVTHQGLSSPVTKSFNRGEC (SEQ ID NO: 85)

Amino acid sequence of chimeric 2E2 kappa light chain
QIILTQSPAIMSASPGEKVSITCSATSSVSYMHWFQQKPGTSPKLWIYSTSNLASGVPVRFSGSGSGTSYSLTISRMEAEDAATYYCQQRS
SYPFTFGSGTKLEIKRTVAAPSVFIFPPSDEQLKSGTASVVCLLNNFYPREAKVQWKVDNALQSGNSQESVTEQDSKDSTYSLSSTLTLSK
ADYEKHKVYACEVTHQGLSSPVTKSFNRGEC (SEQ ID NO: 86)

Amino acid sequence of HEKA IgG4 heavy chain (IgG4 contains a S228P mutation)
EVQLVESGGGLVQPGGSLRLSCAASGFSLTIYGAHWVRQAPGKGLEWVGVIWAGGSTNYNSALMSRFTISKDNSKNTVYLQMNSLRAEDTA
VYYCARDGSSPYYYSMEYWGQGTTVTVSSASTKGPSVFPLAPCSRSTSESTAALGCLVKDYFPEPVTVSWNSGALTSGVHTFPAVLQSSGL

| SEQUENCES |
|---|
| YSLSSVVTVPSSSLGTKTYTCNVDHKPSNTKVDKRVESKYGPPCPPCPAPEFLGGPSVFLFPPKPKDTLMISRTPEVTCVVVDVSQEDPEV<br>QFNWYVDGVEVHNAKTKPREEQFNSTYRVVSVLTVLHQDWLNGKEYKCKVSNKGLPSSIEKTISKAKGQPREPQVYTLPPSQEEMTKNQVS<br>LTCLVKGFYPSDIAVEWESNGQPENNYKTTPPVLDSDGSFFLYSRLTVDKSRWQEGNVFSCSVMHEALHNHYTQKSLSLSLG<br>(SEQ ID NO: 87)<br><br>Amino acid sequence of mouse 1C3 heavy chain variable domain (underlined residues comprise<br>CDRs H1 and H2 according to Chothia numbering)<br>EVQVVESGGDLVKSGGSLKLSCAAS<u>GFPFSSY</u>AMSWVRQTPDKRLEWVAII<u>SSGGSY</u>TYYSDSVKGRFTISRDNAKNTLYLQMSSLKSEDT<br>AMYYCARHETAQAAWFAYWGQGTLVTVSA (SEQ ID NO: 106)<br><br>Amino acid sequence of mouse 1H10 heavy chain variable domain (underlined residues comprise<br>CDRs H1 and H2 according to Chothia numbering)<br>EVQLQQSGAELVRPGASVKLSCTAS<u>GFNIKDY</u>YMYWVKQRPEQGLEWIGRI<u>APEDGD</u>TEYAPKFQGKATVTADTSSNTAYLHLSSLTSEDT<br>AVYYCTTEGNYYGSSILDYWGQGTTLTVSS (SEQ ID NO: 107)<br><br>Amino acid sequence of mouse 4F11 heavy chain variable domain (underlined residues comprise<br>CDRs H1 and H2 according to Chothia numbering)<br>QVQLQQSGAELVKPGASVKISCKAS<u>GYAFRSS</u>WMNWVKQRPGKGLEWIGQI<u>YPGDDY</u>TNYNGKFKGKVTLTADRSSTAYMQLSSLTSEDS<br>AVYFCARLGPYGPFADWGQGTLVTVSA (SEQ ID NO: 108)<br><br>Amino acid sequence of mouse 1C3 light chain variable domain<br>QIVLTQSPAIMSASPGEKVTMTCSASSSVSYMHWYQQKSGTSPKRWIYDTSKLAYGVPARFSGSGSGTSYSLTISSMEAEDAATYYCQQWS<br>SNPPTFGGGTKLEIK (SEQ ID NO: 109)<br><br>Amino acid sequence of mouse 1H10 light chain variable domain<br>DIQMTQTTSSLSASLGDRVTISCRASQDITNYLNWYQQKPDGTVKLLIYFTSRLHSGVPSRFSGSGSGTDYSLTISNLEQEDIATYFCQQG<br>NTLPWTFGGGTKLEIK (SEQ ID NO: 110)<br><br>Amino acid sequence of mouse 4F11 light chain variable domain<br>QIVLTQSPAIVSASPGEKVTMTCSASSSVSYMYWYQQRPGSSPRLLIYDTSSLASGVPVRFSGSGSGTSYSLTISRIESEDAANYYCQQWN<br>SDPYTFGGGTKLEIK (SEQ ID NO: 111) |

What is claimed is:

1. A method for treating indolent systemic mastocytosis (ISM) in an individual comprising administering to the individual an effective amount of an antibody that binds to human Siglec-8, wherein the antibody comprises a heavy chain variable region and a light chain variable region, wherein the heavy chain variable region comprises the amino acid sequence of SEQ ID NO:6, and the light chain variable region comprises the amino acid sequence of SEQ ID NO:16, wherein the individual is a human.

2. The method of claim 1, wherein the antibody comprises a human IgG1 or human IgG4 heavy chain Fc region.

3. The method of claim 1, wherein the antibody comprises a heavy chain comprising the amino acid sequence of SEQ ID NO:75 and a light chain comprising the amino acid sequence of SEQ ID NO:76.

4. The method of claim 2, wherein the antibody has been engineered to improve antibody-dependent cell-mediated cytotoxicity (ADCC) activity.

5. The method of claim 4, wherein the antibody comprises at least one amino acid substitution in the Fc region that improves ADCC activity.

6. The method of claim 2, wherein one or two of the heavy chains of the antibody is non-fucosylated.

7. The method of claim 1, wherein the antibody is in a pharmaceutical composition comprising the antibody and a pharmaceutically acceptable carrier.

8. The method of claim 1, wherein one or more symptom in the individual with ISM is reduced as compared to a baseline level before administration of the antibody.

9. The method of claim 8, wherein the one or more symptom is selected from the group consisting of skin lesions, abdominal pain, diarrhea, flushing, and pruritus.

10. The method of claim 3, wherein one or two of the heavy chains of the antibody is non-fucosylated.

* * * * *

SEQUENCE LISTING

```
<160> NUMBER OF SEQ ID NOS: 111

<210> SEQ ID NO 1
<211> LENGTH: 120
<212> TYPE: PRT
<213> ORGANISM: Artificial Sequence
<220> FEATURE:
<223> OTHER INFORMATION: Synthetic Construct

<400> SEQUENCE: 1

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr Ile Tyr
            20                  25                  30

Gly Ala His Trp Val Arg Gln Pro Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Ser Gln Val Phe Leu
65                  70                  75                  80

Lys Ile Asn Ser Leu Gln Thr Asp Asp Thr Ala Leu Tyr Tyr Cys Ala
                85                  90                  95

Arg Asp Gly Ser Ser Pro Tyr Tyr Tyr Ser Met Glu Tyr Trp Gly Gln
                100                 105                 110

Gly Thr Ser Val Thr Val Ser Ser
            115                 120

<210> SEQ ID NO 2
<211> LENGTH: 120
<212> TYPE: PRT
```

<213> ORGANISM: Artificial Sequence
<220> FEATURE:
<223> OTHER INFORMATION: Synthetic Construct

<400> SEQUENCE: 2

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Ser Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
        115                 120

<210> SEQ ID NO 3
<211> LENGTH: 120
<212> TYPE: PRT
<213> ORGANISM: Artificial Sequence
<220> FEATURE:
<223> OTHER INFORMATION: Synthetic Construct

<400> SEQUENCE: 3

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Ile Tyr
            20                  25                  30

Gly Ala His Trp Val Arg Gln Ala Pro Gly Lys Gly Leu Glu Trp Leu
        35                  40                  45

Gly Val Ile Trp Ala Gly Gly Ser Thr Asn Tyr Asn Ser Ala Leu Met
    50                  55                  60

Ser Arg Leu Ser Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
        115                 120

<210> SEQ ID NO 4
<211> LENGTH: 120
<212> TYPE: PRT
<213> ORGANISM: Artificial Sequence
<220> FEATURE:
<223> OTHER INFORMATION: Synthetic Construct

<400> SEQUENCE: 4

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr Ile Tyr
            20                  25                  30

Gly Ala His Trp Val Arg Gln Ala Pro Gly Lys Gly Leu Glu Trp Val
            35                  40                  45

Ser Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
            115                 120

<210> SEQ ID NO 5
<211> LENGTH: 120
<212> TYPE: PRT
<213> ORGANISM: Artificial Sequence
<220> FEATURE:
<223> OTHER INFORMATION: Synthetic Construct

<400> SEQUENCE: 5

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Leu
            35                  40                  45

Ser Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
            115                 120

<210> SEQ ID NO 6
<211> LENGTH: 120
<212> TYPE: PRT
<213> ORGANISM: Artificial Sequence
<220> FEATURE:
<223> OTHER INFORMATION: Synthetic Construct

<400> SEQUENCE: 6

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
            35                  40                  45

Gly Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala 85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
        115                 120

<210> SEQ ID NO 7
<211> LENGTH: 120
<212> TYPE: PRT
<213> ORGANISM: Artificial Sequence
<220> FEATURE:
<223> OTHER INFORMATION: Synthetic Construct

<400> SEQUENCE: 7

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Ser Val Ile Trp Ala Gly Gly Ser Thr Asn Tyr Asn Ser Ala Leu Met
    50                  55                  60

Ser Arg Leu Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
        115                 120

<210> SEQ ID NO 8
<211> LENGTH: 120
<212> TYPE: PRT
<213> ORGANISM: Artificial Sequence
<220> FEATURE:
<223> OTHER INFORMATION: Synthetic Construct

<400> SEQUENCE: 8

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Ser Val Ile Trp Ala Gly Gly Ser Thr Asn Tyr Asn Ser Ala Leu Met
    50                  55                  60

Ser Arg Phe Ser Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser
        115                 120

<210> SEQ ID NO 9
<211> LENGTH: 120

<212> TYPE: PRT
<213> ORGANISM: Artificial Sequence
<220> FEATURE:
<223> OTHER INFORMATION: Synthetic Construct

<400> SEQUENCE: 9

Gln Val Gln Leu Gln Glu Ser Gly Pro Gly Leu Val Lys Pro Ser Glu
1               5                   10                  15

Thr Leu Ser Leu Thr Cys Thr Val Ser Gly Ser Ile Ser Ile Tyr
            20                  25                  30

Gly Ala His Trp Ile Arg Gln Pro Pro Gly Lys Gly Leu Glu Trp Ile
            35                  40                  45

Gly Val Ile Trp Ala Gly Gly Ser Thr Asn Tyr Asn Ser Ala Leu Met
        50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Leu Val Thr Val Ser Ser
        115                 120

<210> SEQ ID NO 10
<211> LENGTH: 120
<212> TYPE: PRT
<213> ORGANISM: Artificial Sequence
<220> FEATURE:
<223> OTHER INFORMATION: Synthetic Construct

<400> SEQUENCE: 10

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr Ile Tyr
            20                  25                  30

Gly Ala His Trp Val Arg Gln Pro Pro Gly Lys Gly Leu Glu Trp Leu
            35                  40                  45

Gly Val Ile Trp Ala Gly Gly Ser Thr Asn Tyr Asn Ser Ala Leu Met
        50                  55                  60

Ser Arg Leu Ser Ile Ser Lys Asp Asn Ser Lys Asn Gln Val Ser Leu
65                  70                  75                  80

Lys Leu Ser Ser Val Thr Ala Ala Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Leu Val Thr Val Ser Ser
        115                 120

<210> SEQ ID NO 11
<211> LENGTH: 120
<212> TYPE: PRT
<213> ORGANISM: Artificial Sequence
<220> FEATURE:
<223> OTHER INFORMATION: Synthetic Construct

<400> SEQUENCE: 11

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr

```
            20                  25                  30
Gly Ala His Trp Val Arg Gln Ala Pro Gly Lys Gly Leu Glu Trp Val
            35                  40                  45

Gly Val Ile Trp Ala Gly Gly Ser Thr Asn Tyr Asn Ser Ala Leu Met
        50                  55                  60

Ser Arg Phe Thr Ile Ser Lys Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Gly Met Glu Tyr Trp Gly Gln
                100                 105                 110

Gly Thr Thr Val Thr Val Ser Ser
            115                 120

<210> SEQ ID NO 12
<211> LENGTH: 120
<212> TYPE: PRT
<213> ORGANISM: Artificial Sequence
<220> FEATURE:
<223> OTHER INFORMATION: Synthetic Construct

<400> SEQUENCE: 12

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
            35                  40                  45

Gly Val Ile Trp Ala Gly Gly Ser Thr Asn Tyr Asn Ser Ala Leu Met
        50                  55                  60

Ser Arg Phe Thr Ile Ser Lys Asp Asn Ser Lys Asn Thr Val Tyr Leu
 65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Asp Tyr Trp Gly Gln
                100                 105                 110

Gly Thr Thr Val Thr Val Ser Ser
            115                 120

<210> SEQ ID NO 13
<211> LENGTH: 120
<212> TYPE: PRT
<213> ORGANISM: Artificial Sequence
<220> FEATURE:
<223> OTHER INFORMATION: Synthetic Construct

<400> SEQUENCE: 13

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
            35                  40                  45

Gly Val Ile Trp Ala Gly Gly Ser Thr Asn Tyr Asn Ser Ala Leu Met
        50                  55                  60

Ser Arg Phe Thr Ile Ser Lys Asp Asn Ser Lys Asn Thr Val Tyr Leu
 65                  70                  75                  80
```

```
Gln Met Asn Ser Leu Arg Ala Glu Asp Thr Ala Val Tyr Tyr Cys Ala
                85                  90                  95

Arg Asp Gly Ser Ser Pro Tyr Tyr Ser Met Glu Val Trp Gly Gln
            100                 105                 110

Gly Thr Thr Val Thr Val Ser Ser
        115                 120

<210> SEQ ID NO 14
<211> LENGTH: 120
<212> TYPE: PRT
<213> ORGANISM: Artificial Sequence
<220> FEATURE:
<223> OTHER INFORMATION: Synthetic Construct

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Gly Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Gly Met Asp Val Trp Gly Gln
            100                 105                 110

Gly Thr Thr Val Thr Val Ser Ser
        115                 120

<210> SEQ ID NO 15
<211> LENGTH: 106
<212> TYPE: PRT
<213> ORGANISM: Artificial Sequence
<220> FEATURE:
<223> OTHER INFORMATION: Synthetic Construct

<400> SEQUENCE: 15

Gln Ile Ile Leu Thr Gln Ser Pro Ala Ile Met Ser Ala Ser Pro Gly
1               5                   10                  15

Glu Lys Val Ser Ile Thr Cys Ser Ala Thr Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys
            100                 105

<210> SEQ ID NO 16
<211> LENGTH: 106
<212> TYPE: PRT
<213> ORGANISM: Artificial Sequence
```

```
<220> FEATURE:
<223> OTHER INFORMATION: Synthetic Construct

<400> SEQUENCE: 16

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65              70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 17
<211> LENGTH: 106
<212> TYPE: PRT
<213> ORGANISM: Artificial Sequence
<220> FEATURE:
<223> OTHER INFORMATION: Synthetic Construct

<400> SEQUENCE: 17

Glu Ile Ile Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Trp Ile Tyr
        35                  40                  45

Ser Thr Ser Asn Leu Ala Ser Gly Val Pro Ala Arg Phe Ser Gly Ser
    50                  55                  60

Gly Ser Gly Thr Asp Tyr Thr Leu Thr Ile Ser Ser Leu Glu Pro Glu
65              70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 18
<211> LENGTH: 106
<212> TYPE: PRT
<213> ORGANISM: Artificial Sequence
<220> FEATURE:
<223> OTHER INFORMATION: Synthetic Construct

<400> SEQUENCE: 18

Glu Ile Ile Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60
```

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 19
<211> LENGTH: 106
<212> TYPE: PRT
<213> ORGANISM: Artificial Sequence
<220> FEATURE:
<223> OTHER INFORMATION: Synthetic Construct

<400> SEQUENCE: 19

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
                20                  25                  30

His Trp Phe Gln Gln Lys Pro Gly Gln Ala Pro Arg Leu Trp Ile Tyr
            35                  40                  45

Ser Thr Ser Asn Leu Ala Ser Gly Ile Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 20
<211> LENGTH: 106
<212> TYPE: PRT
<213> ORGANISM: Artificial Sequence
<220> FEATURE:
<223> OTHER INFORMATION: Synthetic Construct

<400> SEQUENCE: 20

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
                20                  25                  30

His Trp Phe Gln Gln Lys Pro Gly Gln Ala Pro Arg Leu Leu Ile Tyr
            35                  40                  45

Ser Thr Ser Asn Leu Ala Ser Gly Val Pro Ala Arg Phe Ser Gly Ser
        50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 21
<211> LENGTH: 106
<212> TYPE: PRT
<213> ORGANISM: Artificial Sequence
<220> FEATURE:
<223> OTHER INFORMATION: Synthetic Construct

<400> SEQUENCE: 21

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 22
<211> LENGTH: 106
<212> TYPE: PRT
<213> ORGANISM: Artificial Sequence
<220> FEATURE:
<223> OTHER INFORMATION: Synthetic Construct

<400> SEQUENCE: 22

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Tyr Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys
            100                 105

<210> SEQ ID NO 23
<211> LENGTH: 106
<212> TYPE: PRT
<213> ORGANISM: Artificial Sequence
<220> FEATURE:
<223> OTHER INFORMATION: Synthetic Construct

<400> SEQUENCE: 23

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

```
Asp Phe Ala Val Tyr Tyr Cys Gln Gln Arg Ser Ser Tyr Pro Tyr Thr
                85                  90                  95

Phe Gly Pro Gly Thr Lys Leu Asp Ile Lys
            100                 105

<210> SEQ ID NO 24
<211> LENGTH: 106
<212> TYPE: PRT
<213> ORGANISM: Artificial Sequence
<220> FEATURE:
<223> OTHER INFORMATION: Synthetic Construct

<400> SEQUENCE: 24

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
                20                  25                  30

His Trp Phe Gln Gln Lys Pro Gly Gln Ala Pro Arg Leu Leu Ile Tyr
            35                  40                  45

Ser Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Arg Ser Ser Tyr Pro Tyr Thr
                85                  90                  95

Phe Gly Pro Gly Thr Lys Leu Asp Ile Lys
            100                 105

<210> SEQ ID NO 25
<211> LENGTH: 30
<212> TYPE: PRT
<213> ORGANISM: Artificial Sequence
<220> FEATURE:
<223> OTHER INFORMATION: Synthetic Construct

<400> SEQUENCE: 25

Gln Val Gln Leu Lys Glu Ser Gly Pro Gly Leu Val Ala Pro Ser Gln
1               5                   10                  15

Ser Leu Ser Ile Thr Cys Thr Val Ser Gly Phe Ser Leu Thr
                20                  25                  30

<210> SEQ ID NO 26
<211> LENGTH: 30
<212> TYPE: PRT
<213> ORGANISM: Artificial Sequence
<220> FEATURE:
<223> OTHER INFORMATION: Synthetic Construct

<400> SEQUENCE: 26

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr
                20                  25                  30

<210> SEQ ID NO 27
<211> LENGTH: 30
<212> TYPE: PRT
<213> ORGANISM: Artificial Sequence
<220> FEATURE:
<223> OTHER INFORMATION: Synthetic Construct

<400> SEQUENCE: 27
```

Glu Val Gln Leu Val Glu Ser Gly Gly Gly Leu Val Gln Pro Gly Gly
1               5                   10                  15

Ser Leu Arg Leu Ser Cys Ala Val Ser Gly Phe Ser Leu Thr
            20                  25                  30

<210> SEQ ID NO 28
<211> LENGTH: 30
<212> TYPE: PRT
<213> ORGANISM: Artificial Sequence
<220> FEATURE:
<223> OTHER INFORMATION: Synthetic Construct

<400> SEQUENCE: 28

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Ile Ser
            20                  25                  30

<210> SEQ ID NO 29
<211> LENGTH: 30
<212> TYPE: PRT
<213> ORGANISM: Artificial Sequence
<220> FEATURE:
<223> OTHER INFORMATION: Synthetic Construct

<400> SEQUENCE: 29

Gln Val Gln Leu Gln Glu Ser Gly Pro Gly Leu Val Lys Pro Ser Glu
1               5                   10                  15

Thr Leu Ser Leu Thr Cys Thr Val Ser Gly Phe Ser Leu Thr
            20                  25                  30

<210> SEQ ID NO 30
<211> LENGTH: 14
<212> TYPE: PRT
<213> ORGANISM: Artificial Sequence
<220> FEATURE:
<223> OTHER INFORMATION: Synthetic Construct

<400> SEQUENCE: 30

Trp Val Arg Gln Pro Pro Gly Lys Gly Leu Glu Trp Leu Gly
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Synthetic Construct

<400> SEQUENCE: 31

Trp Val Arg Gln Ala Pro Gly Lys Gly Leu Glu Trp Val Ser
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Synthetic Construct

<400> SEQUENCE: 32

Trp Val Arg Gln Ala Pro Gly Lys Gly Leu Glu Trp Leu Gly
1               5                   10

<210> SEQ ID NO 33

```
<211> LENGTH: 14
<212> TYPE: PRT
<213> ORGANISM: Artificial Sequence
<220> FEATURE:
<223> OTHER INFORMATION: Synthetic Construct

<400> SEQUENCE: 33

Trp Val Arg Gln Ala Pro Gly Lys Gly Leu Glu Trp Leu Ser
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic Construct

<400> SEQUENCE: 34

Trp Val Arg Gln Ala Pro Gly Lys Gly Leu Glu Trp Val Gly
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Synthetic Construct

<400> SEQUENCE: 35

Trp Ile Arg Gln Pro Pro Gly Lys Gly Leu Glu Trp Ile Gly
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic Construct

<400> SEQUENCE: 36

Trp Val Arg Gln Pro Pro Gly Lys Gly Leu Glu Trp Leu Gly
1               5                   10

<210> SEQ ID NO 37
<211> LENGTH: 32
<212> TYPE: PRT
<213> ORGANISM: Artificial Sequence
<220> FEATURE:
<223> OTHER INFORMATION: Synthetic Construct

<400> SEQUENCE: 37

Arg Leu Ser Ile Ser Lys Asp Asn Ser Lys Ser Gln Val Phe Leu Lys
1               5                   10                  15

Ile Asn Ser Leu Gln Thr Asp Asp Thr Ala Leu Tyr Tyr Cys Ala Arg
            20                  25                  30

<210> SEQ ID NO 38
<211> LENGTH: 32
<212> TYPE: PRT
<213> ORGANISM: Artificial Sequence
<220> FEATURE:
<223> OTHER INFORMATION: Synthetic Construct

<400> SEQUENCE: 38

Arg Phe Thr Ile Ser Lys Asp Asn Ser Lys Asn Thr Val Tyr Leu Gln
1               5                   10                  15
```

Met Asn Ser Leu Arg Ala Glu Asp Thr Ala Val Tyr Tyr Cys Ala Arg
            20                  25                  30

<210> SEQ ID NO 39
<211> LENGTH: 32
<212> TYPE: PRT
<213> ORGANISM: Artificial Sequence
<220> FEATURE:
<223> OTHER INFORMATION: Synthetic Construct

<400> SEQUENCE: 39

Arg Leu Ser Ile Ser Lys Asp Asn Ser Lys Asn Thr Val Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 40
<211> LENGTH: 32
<212> TYPE: PRT
<213> ORGANISM: Artificial Sequence
<220> FEATURE:
<223> OTHER INFORMATION: Synthetic Construct

<400> SEQUENCE: 40

Arg Leu Thr Ile Ser Lys Asp Asn Ser Lys Asn Thr Val Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 41
<211> LENGTH: 32
<212> TYPE: PRT
<213> ORGANISM: Artificial Sequence
<220> FEATURE:
<223> OTHER INFORMATION: Synthetic Construct

<400> SEQUENCE: 41

Arg Phe Ser Ile Ser Lys Asp Asn Ser Lys Asn Thr Val Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 42
<211> LENGTH: 32
<212> TYPE: PRT
<213> ORGANISM: Artificial Sequence
<220> FEATURE:
<223> OTHER INFORMATION: Synthetic Construct

<400> SEQUENCE: 42

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 43
<211> LENGTH: 32
<212> TYPE: PRT
<213> ORGANISM: Artificial Sequence
<220> FEATURE:
<223> OTHER INFORMATION: Synthetic Construct

<400> SEQUENCE: 43

Arg Leu Ser Ile Ser Lys Asp Asn Ser Lys Asn Gln Val Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 44
<211> LENGTH: 11
<212> TYPE: PRT
<213> ORGANISM: Artificial Sequence
<220> FEATURE:
<223> OTHER INFORMATION: Synthetic Construct

<400> SEQUENCE: 44

Trp Gly Gln Gly Thr Ser Val Thr Val Ser Ser
1               5                   10

<210> SEQ ID NO 45
<211> LENGTH: 11
<212> TYPE: PRT
<213> ORGANISM: Artificial Sequence
<220> FEATURE:
<223> OTHER INFORMATION: Synthetic Construct

<400> SEQUENCE: 45

Trp Gly Gln Gly Thr Thr Val Thr Val Ser Ser
1               5                   10

<210> SEQ ID NO 46
<211> LENGTH: 11
<212> TYPE: PRT
<213> ORGANISM: Artificial Sequence
<220> FEATURE:
<223> OTHER INFORMATION: Synthetic Construct

<400> SEQUENCE: 46

Trp Gly Gln Gly Thr Leu Val Thr Val Ser Ser
1               5                   10

<210> SEQ ID NO 47
<211> LENGTH: 23
<212> TYPE: PRT
<213> ORGANISM: Artificial Sequence
<220> FEATURE:
<223> OTHER INFORMATION: Synthetic Construct

<400> SEQUENCE: 47

Gln Ile Ile Leu Thr Gln Ser Pro Ala Ile Met Ser Ala Ser Pro Gly
1               5                   10                  15

Glu Lys Val Ser Ile Thr Cys
            20

<210> SEQ ID NO 48
<211> LENGTH: 23
<212> TYPE: PRT
<213> ORGANISM: Artificial Sequence
<220> FEATURE:
<223> OTHER INFORMATION: Synthetic Construct

<400> SEQUENCE: 48

Glu Ile Val Leu Thr Gln Ser Pro Ala Thr Leu Ser Leu Ser Pro Gly
1               5                   10                  15

Glu Arg Ala Thr Leu Ser Cys
            20

<210> SEQ ID NO 49
<211> LENGTH: 23
<212> TYPE: PRT

```
<213> ORGANISM: Artificial Sequence
<220> FEATURE:
<223> OTHER INFORMATION: Synthetic Construct

<400> SEQUENCE: 49

Glu Ile Ile Leu Thr Gln Ser Pro Ala Thr Leu Ser Leu Ser Pro Gly
1               5                   10                  15

Glu Arg Ala Thr Leu Ser Cys
            20

<210> SEQ ID NO 50
<211> LENGTH: 15
<212> TYPE: PRT
<213> ORGANISM: Artificial Sequence
<220> FEATURE:
<223> OTHER INFORMATION: Synthetic Construct

<400> SEQUENCE: 50

Trp Phe Gln Gln Lys Pro Gly Thr Ser Pro Lys Leu Trp Ile Tyr
1               5                   10                  15

<210> SEQ ID NO 51
<211> LENGTH: 15
<212> TYPE: PRT
<213> ORGANISM: Artificial Sequence
<220> FEATURE:
<223> OTHER INFORMATION: Synthetic Construct

<400> SEQUENCE: 51

Trp Phe Gln Gln Lys Pro Gly Gln Ala Pro Arg Leu Leu Ile Tyr
1               5                   10                  15

<210> SEQ ID NO 52
<211> LENGTH: 15
<212> TYPE: PRT
<213> ORGANISM: Artificial Sequence
<220> FEATURE:
<223> OTHER INFORMATION: Synthetic Construct

<400> SEQUENCE: 52

Trp Phe Gln Gln Lys Pro Gly Gln Ala Pro Arg Leu Trp Ile Tyr
1               5                   10                  15

<210> SEQ ID NO 53
<211> LENGTH: 15
<212> TYPE: PRT
<213> ORGANISM: Artificial Sequence
<220> FEATURE:
<223> OTHER INFORMATION: Synthetic Construct

<400> SEQUENCE: 53

Trp Tyr Gln Gln Lys Pro Gly Gln Ala Pro Arg Leu Leu Ile Tyr
1               5                   10                  15

<210> SEQ ID NO 54
<211> LENGTH: 32
<212> TYPE: PRT
<213> ORGANISM: Artificial Sequence
<220> FEATURE:
<223> OTHER INFORMATION: Synthetic Construct

<400> SEQUENCE: 54

Gly Val Pro Val Arg Phe Ser Gly Ser Gly Ser Gly Thr Ser Tyr Ser
1               5                   10                  15

Leu Thr Ile Ser Arg Met Glu Ala Glu Asp Ala Ala Thr Tyr Tyr Cys
            20                  25                  30
```

```
<210> SEQ ID NO 55
<211> LENGTH: 32
<212> TYPE: PRT
<213> ORGANISM: Artificial Sequence
<220> FEATURE:
<223> OTHER INFORMATION: Synthetic Construct

<400> SEQUENCE: 55

Gly Ile Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 56
<211> LENGTH: 32
<212> TYPE: PRT
<213> ORGANISM: Artificial Sequence
<220> FEATURE:
<223> OTHER INFORMATION: Synthetic Construct

<400> SEQUENCE: 56

Gly Val Pro Ala Arg Phe Ser Gly Ser Gly Ser Gly Thr Asp Tyr Thr
1               5                   10                  15

Leu Thr Ile Ser Ser Leu Glu Pro Glu Asp Phe Ala Val Tyr Tyr Cys
            20                  25                  30

<210> SEQ ID NO 57
<211> LENGTH: 32
<212> TYPE: PRT
<213> ORGANISM: Artificial Sequence
<220> FEATURE:
<223> OTHER INFORMATION: Synthetic Construct

<400> SEQUENCE: 57

Gly Val Pro Ala Arg Phe Ser Gly Ser Gly Ser Gly Thr Asp Phe Thr
1               5                   10                  15

Leu Thr Ile Ser Ser Leu Glu Pro Glu Asp Phe Ala Val Tyr Tyr Cys
            20                  25                  30

<210> SEQ ID NO 58
<211> LENGTH: 32
<212> TYPE: PRT
<213> ORGANISM: Artificial Sequence
<220> FEATURE:
<223> OTHER INFORMATION: Synthetic Construct

<400> SEQUENCE: 58

Gly Ile Pro Ala Arg Phe Ser Gly Ser Gly Ser Gly Thr Asp Tyr Thr
1               5                   10                  15

Leu Thr Ile Ser Ser Leu Glu Pro Glu Asp Phe Ala Val Tyr Tyr Cys
            20                  25                  30

<210> SEQ ID NO 59
<211> LENGTH: 10
<212> TYPE: PRT
<213> ORGANISM: Artificial Sequence
<220> FEATURE:
<223> OTHER INFORMATION: Synthetic Construct

<400> SEQUENCE: 59

Phe Gly Ser Gly Thr Lys Leu Glu Ile Lys
1               5                   10
```

```
<210> SEQ ID NO 60
<211> LENGTH: 10
<212> TYPE: PRT
<213> ORGANISM: Artificial Sequence
<220> FEATURE:
<223> OTHER INFORMATION: Synthetic Construct

<400> SEQUENCE: 60

Phe Gly Pro Gly Thr Lys Leu Asp Ile Lys
1               5                   10

<210> SEQ ID NO 61
<211> LENGTH: 5
<212> TYPE: PRT
<213> ORGANISM: Artificial Sequence
<220> FEATURE:
<223> OTHER INFORMATION: Synthetic Construct

<400> SEQUENCE: 61

Ile Tyr Gly Ala His
1               5

<210> SEQ ID NO 62
<211> LENGTH: 16
<212> TYPE: PRT
<213> ORGANISM: Artificial Sequence
<220> FEATURE:
<223> OTHER INFORMATION: Synthetic Construct

<400> SEQUENCE: 62

Val Ile Trp Ala Gly Gly Ser Thr Asn Tyr Asn Ser Ala Leu Met Ser
1               5                   10                  15

<210> SEQ ID NO 63
<211> LENGTH: 12
<212> TYPE: PRT
<213> ORGANISM: Artificial Sequence
<220> FEATURE:
<223> OTHER INFORMATION: Synthetic Construct

<400> SEQUENCE: 63

Asp Gly Ser Ser Pro Tyr Tyr Tyr Ser Met Glu Tyr
1               5                   10

<210> SEQ ID NO 64
<211> LENGTH: 10
<212> TYPE: PRT
<213> ORGANISM: Artificial Sequence
<220> FEATURE:
<223> OTHER INFORMATION: Synthetic Construct

<400> SEQUENCE: 64

Ser Ala Thr Ser Ser Val Ser Tyr Met His
1               5                   10

<210> SEQ ID NO 65
<211> LENGTH: 7
<212> TYPE: PRT
<213> ORGANISM: Artificial Sequence
<220> FEATURE:
<223> OTHER INFORMATION: Synthetic Construct

<400> SEQUENCE: 65

Ser Thr Ser Asn Leu Ala Ser
1               5

<210> SEQ ID NO 66
```

```
<211> LENGTH: 9
<212> TYPE: PRT
<213> ORGANISM: Artificial Sequence
<220> FEATURE:
<223> OTHER INFORMATION: Synthetic Construct

<400> SEQUENCE: 66

Gln Gln Arg Ser Ser Tyr Pro Phe Thr
1               5

<210> SEQ ID NO 67
<211> LENGTH: 12
<212> TYPE: PRT
<213> ORGANISM: Artificial Sequence
<220> FEATURE:
<223> OTHER INFORMATION: Synthetic Construct

<400> SEQUENCE: 67

Asp Gly Ser Ser Pro Tyr Tyr Tyr Gly Met Glu Tyr
1               5                   10

<210> SEQ ID NO 68
<211> LENGTH: 12
<212> TYPE: PRT
<213> ORGANISM: Artificial Sequence
<220> FEATURE:
<223> OTHER INFORMATION: Synthetic Construct

<400> SEQUENCE: 68

Asp Gly Ser Ser Pro Tyr Tyr Tyr Ser Met Asp Tyr
1               5                   10

<210> SEQ ID NO 69
<211> LENGTH: 12
<212> TYPE: PRT
<213> ORGANISM: Artificial Sequence
<220> FEATURE:
<223> OTHER INFORMATION: Synthetic Construct

<400> SEQUENCE: 69

Asp Gly Ser Ser Pro Tyr Tyr Tyr Ser Met Glu Val
1               5                   10

<210> SEQ ID NO 70
<211> LENGTH: 12
<212> TYPE: PRT
<213> ORGANISM: Artificial Sequence
<220> FEATURE:
<223> OTHER INFORMATION: Synthetic Construct

<400> SEQUENCE: 70

Asp Gly Ser Ser Pro Tyr Tyr Tyr Gly Met Asp Val
1               5                   10

<210> SEQ ID NO 71
<211> LENGTH: 9
<212> TYPE: PRT
<213> ORGANISM: Artificial Sequence
<220> FEATURE:
<223> OTHER INFORMATION: Synthetic Construct

<400> SEQUENCE: 71

Gln Gln Arg Ser Ser Tyr Pro Tyr Thr
1               5

<210> SEQ ID NO 72
<211> LENGTH: 474
```

```
<212> TYPE: PRT
<213> ORGANISM: Homo sapiens

<400> SEQUENCE: 72

Gly Tyr Leu Leu Gln Val Gln Glu Leu Val Thr Val Gln Glu Gly Leu
1               5                   10                  15

Cys Val His Val Pro Cys Ser Phe Ser Tyr Pro Gln Asp Gly Trp Thr
            20                  25                  30

Asp Ser Asp Pro Val His Gly Tyr Trp Phe Arg Ala Gly Asp Arg Pro
        35                  40                  45

Tyr Gln Asp Ala Pro Val Ala Thr Asn Asn Pro Asp Arg Glu Val Gln
    50                  55                  60

Ala Glu Thr Gln Gly Arg Phe Gln Leu Leu Gly Asp Ile Trp Ser Asn
65                  70                  75                  80

Asp Cys Ser Leu Ser Ile Arg Asp Ala Arg Lys Arg Asp Lys Gly Ser
                85                  90                  95

Tyr Phe Phe Arg Leu Glu Arg Gly Ser Met Lys Trp Ser Tyr Lys Ser
            100                 105                 110

Gln Leu Asn Tyr Lys Thr Lys Gln Leu Ser Val Phe Val Thr Ala Leu
        115                 120                 125

Thr His Arg Pro Asp Ile Leu Ile Leu Gly Thr Leu Glu Ser Gly His
    130                 135                 140

Ser Arg Asn Leu Thr Cys Ser Val Pro Trp Ala Cys Lys Gln Gly Thr
145                 150                 155                 160

Pro Pro Met Ile Ser Trp Ile Gly Ala Ser Val Ser Ser Pro Gly Pro
                165                 170                 175

Thr Thr Ala Arg Ser Ser Val Leu Thr Leu Thr Pro Lys Pro Gln Asp
            180                 185                 190

His Gly Thr Ser Leu Thr Cys Gln Val Thr Leu Pro Gly Thr Gly Val
        195                 200                 205

Thr Thr Thr Ser Thr Val Arg Leu Asp Val Ser Tyr Pro Pro Trp Asn
    210                 215                 220

Leu Thr Met Thr Val Phe Gln Gly Asp Ala Thr Ala Ser Thr Ala Leu
225                 230                 235                 240

Gly Asn Gly Ser Ser Leu Ser Val Leu Glu Gly Gln Ser Leu Arg Leu
                245                 250                 255

Val Cys Ala Val Asn Ser Asn Pro Pro Ala Arg Leu Ser Trp Thr Arg
            260                 265                 270

Gly Ser Leu Thr Leu Cys Pro Ser Arg Ser Ser Asn Pro Gly Leu Leu
        275                 280                 285

Glu Leu Pro Arg Val His Val Arg Asp Glu Gly Glu Phe Thr Cys Arg
    290                 295                 300

Ala Gln Asn Ala Gln Gly Ser Gln His Ile Ser Leu Ser Leu Ser Leu
305                 310                 315                 320

Gln Asn Glu Gly Thr Gly Thr Ser Arg Pro Val Ser Gln Val Thr Leu
                325                 330                 335

Ala Ala Val Gly Gly Ala Gly Ala Thr Ala Leu Ala Phe Leu Ser Phe
            340                 345                 350

Cys Ile Ile Phe Ile Ile Val Arg Ser Cys Arg Lys Lys Ser Ala Arg
        355                 360                 365

Pro Ala Ala Gly Val Gly Asp Thr Gly Met Glu Asp Ala Lys Ala Ile
    370                 375                 380

Arg Gly Ser Ala Ser Gln Gly Pro Leu Thr Glu Ser Trp Lys Asp Gly
385                 390                 395                 400
```

Asn Pro Leu Lys Lys Pro Pro Ala Val Ala Pro Ser Ser Gly Glu
            405             410             415

Glu Gly Glu Leu His Tyr Ala Thr Leu Ser Phe His Lys Val Lys Pro
        420                 425                 430

Gln Asp Pro Gln Gly Gln Glu Ala Thr Asp Ser Glu Tyr Ser Glu Ile
        435                 440                 445

Lys Ile His Lys Arg Glu Thr Ala Glu Thr Gln Ala Cys Leu Arg Asn
    450                 455                 460

His Asn Pro Ser Ser Lys Glu Val Arg Gly
465             470

<210> SEQ ID NO 73
<211> LENGTH: 474
<212> TYPE: PRT
<213> ORGANISM: Homo sapiens

<400> SEQUENCE: 73

Gly Tyr Leu Leu Gln Val Gln Glu Leu Val Thr Val Gln Glu Gly Leu
1               5                   10                  15

Cys Val His Val Pro Cys Ser Phe Ser Tyr Pro Gln Asp Gly Trp Thr
            20                  25                  30

Asp Ser Asp Pro Val His Gly Tyr Trp Phe Arg Ala Gly Asp Arg Pro
        35                  40                  45

Tyr Gln Asp Ala Pro Val Ala Thr Asn Asn Pro Asp Arg Glu Val Gln
    50                  55                  60

Ala Glu Thr Gln Gly Arg Phe Gln Leu Leu Gly Asp Ile Trp Ser Asn
65                  70                  75                  80

Asp Cys Ser Leu Ser Ile Arg Asp Ala Arg Lys Arg Asp Lys Gly Ser
                85                  90                  95

Tyr Phe Phe Arg Leu Glu Arg Gly Ser Met Lys Trp Ser Tyr Lys Ser
            100                 105                 110

Gln Leu Asn Tyr Lys Thr Lys Gln Leu Ser Val Phe Val Thr Ala Leu
        115                 120                 125

Thr His Arg Pro Asp Ile Leu Ile Leu Gly Thr Leu Glu Ser Gly His
    130                 135                 140

Pro Arg Asn Leu Thr Cys Ser Val Pro Trp Ala Cys Lys Gln Gly Thr
145                 150                 155                 160

Pro Pro Met Ile Ser Trp Ile Gly Ala Ser Val Ser Ser Pro Gly Pro
                165                 170                 175

Thr Thr Ala Arg Ser Ser Val Leu Thr Leu Thr Pro Lys Pro Gln Asp
            180                 185                 190

His Gly Thr Ser Leu Thr Cys Gln Val Thr Leu Pro Gly Thr Gly Val
        195                 200                 205

Thr Thr Thr Ser Thr Val Arg Leu Asp Val Ser Tyr Pro Pro Trp Asn
    210                 215                 220

Leu Thr Met Thr Val Phe Gln Gly Asp Ala Thr Ala Ser Thr Ala Leu
225                 230                 235                 240

Gly Asn Gly Ser Ser Leu Ser Val Leu Glu Gly Gln Ser Leu Arg Leu
                245                 250                 255

Val Cys Ala Val Asn Ser Asn Pro Pro Ala Arg Leu Ser Trp Thr Arg
            260                 265                 270

Gly Ser Leu Thr Leu Cys Pro Ser Arg Ser Ser Asn Pro Gly Leu Leu
        275                 280                 285

Glu Leu Pro Arg Val His Val Arg Asp Glu Gly Glu Phe Thr Cys Arg

```
            290                 295                 300
Ala Gln Asn Ala Gln Gly Ser Gln His Ile Ser Leu Ser Leu Ser Leu
305                 310                 315                 320

Gln Asn Glu Gly Thr Gly Thr Ser Arg Pro Val Ser Gln Val Thr Leu
                325                 330                 335

Ala Ala Val Gly Gly Ala Gly Ala Thr Ala Leu Ala Phe Leu Ser Phe
                340                 345                 350

Cys Ile Ile Phe Ile Ile Val Arg Ser Cys Arg Lys Lys Ser Ala Arg
                355                 360                 365

Pro Ala Ala Gly Val Gly Asp Thr Gly Met Glu Asp Ala Lys Ala Ile
370                 375                 380

Arg Gly Ser Ala Ser Gln Gly Pro Leu Thr Glu Ser Trp Lys Asp Gly
385                 390                 395                 400

Asn Pro Leu Lys Lys Pro Pro Ala Val Ala Pro Ser Ser Gly Glu
                405                 410                 415

Glu Gly Glu Leu His Tyr Ala Thr Leu Ser Phe His Lys Val Lys Pro
                420                 425                 430

Gln Asp Pro Gln Gly Gln Glu Ala Thr Asp Ser Glu Tyr Ser Glu Ile
                435                 440                 445

Lys Ile His Lys Arg Glu Thr Ala Glu Thr Gln Ala Cys Leu Arg Asn
                450                 455                 460

His Asn Pro Ser Ser Lys Glu Val Arg Gly
465                 470

<210> SEQ ID NO 74
<211> LENGTH: 573
<212> TYPE: PRT
<213> ORGANISM: Artificial Sequence
<220> FEATURE:
<223> OTHER INFORMATION: Synthetic Construct

<400> SEQUENCE: 74

Gly Tyr Leu Leu Gln Val Gln Glu Leu Val Thr Val Gln Glu Gly Leu
1               5                   10                  15

Cys Val His Val Pro Cys Ser Phe Ser Tyr Pro Gln Asp Gly Trp Thr
                20                  25                  30

Asp Ser Asp Pro Val His Gly Tyr Trp Phe Arg Ala Gly Asp Arg Pro
                35                  40                  45

Tyr Gln Asp Ala Pro Val Ala Thr Asn Asn Pro Asp Arg Glu Val Gln
                50                  55                  60

Ala Glu Thr Gln Gly Arg Phe Gln Leu Leu Gly Asp Ile Trp Ser Asn
65                  70                  75                  80

Asp Cys Ser Leu Ser Ile Arg Asp Ala Arg Lys Arg Asp Lys Gly Ser
                85                  90                  95

Tyr Phe Phe Arg Leu Glu Arg Gly Ser Met Lys Trp Ser Tyr Lys Ser
                100                 105                 110

Gln Leu Asn Tyr Lys Thr Lys Gln Leu Ser Val Phe Val Thr Ala Leu
                115                 120                 125

Thr His Arg Pro Asp Ile Leu Ile Leu Gly Thr Leu Glu Ser Gly His
                130                 135                 140

Ser Arg Asn Leu Thr Cys Ser Val Pro Trp Ala Cys Lys Gln Gly Thr
145                 150                 155                 160

Pro Pro Met Ile Ser Trp Ile Gly Ala Ser Val Ser Ser Pro Gly Pro
                165                 170                 175

Thr Thr Ala Arg Ser Ser Val Leu Thr Leu Thr Pro Lys Pro Gln Asp
```

```
            180                 185                 190
His Gly Thr Ser Leu Thr Cys Gln Val Thr Leu Pro Gly Thr Gly Val
            195                 200                 205
Thr Thr Thr Ser Thr Val Arg Leu Asp Val Ser Tyr Pro Pro Trp Asn
        210                 215                 220
Leu Thr Met Thr Val Phe Gln Gly Asp Ala Thr Ala Ser Thr Ala Leu
225                 230                 235                 240
Gly Asn Gly Ser Ser Leu Ser Val Leu Glu Gly Gln Ser Leu Arg Leu
                245                 250                 255
Val Cys Ala Val Asn Ser Asn Pro Pro Ala Arg Leu Ser Trp Thr Arg
            260                 265                 270
Gly Ser Leu Thr Leu Cys Pro Ser Arg Ser Ser Asn Pro Gly Leu Leu
            275                 280                 285
Glu Leu Pro Arg Val His Val Arg Asp Glu Gly Glu Phe Thr Cys Arg
        290                 295                 300
Ala Gln Asn Ala Gln Gly Ser Gln His Ile Ser Leu Ser Leu Ser Leu
305                 310                 315                 320
Gln Asn Glu Gly Thr Gly Thr Ser Arg Pro Val Ser Gln Val Thr Leu
                325                 330                 335
Ala Ala Val Gly Gly Ile Glu Gly Arg Ser Asp Lys Thr His Thr Cys
            340                 345                 350
Pro Pro Cys Pro Ala Pro Glu Leu Leu Gly Gly Pro Ser Val Phe Leu
            355                 360                 365
Phe Pro Pro Lys Pro Lys Asp Thr Leu Met Ile Ser Arg Thr Pro Glu
        370                 375                 380
Val Thr Cys Val Val Val Asp Val Ser His Glu Asp Pro Glu Val Lys
385                 390                 395                 400
Phe Asn Trp Tyr Val Asp Gly Val Glu Val His Asn Ala Lys Thr Lys
                405                 410                 415
Pro Arg Glu Glu Gln Tyr Asn Ser Thr Tyr Arg Val Val Ser Val Leu
            420                 425                 430
Thr Val Leu His Gln Asp Trp Leu Asn Gly Lys Glu Tyr Lys Cys Lys
            435                 440                 445
Val Ser Asn Lys Ala Leu Pro Ala Pro Ile Glu Lys Thr Ile Ser Lys
        450                 455                 460
Ala Lys Gly Gln Pro Arg Glu Pro Gln Val Tyr Thr Leu Pro Pro Ser
465                 470                 475                 480
Arg Glu Glu Met Thr Lys Asn Gln Val Ser Leu Thr Cys Leu Val Lys
                485                 490                 495
Gly Phe Tyr Pro Ser Asp Ile Ala Val Glu Trp Glu Ser Asn Gly Gln
            500                 505                 510
Pro Glu Asn Asn Tyr Lys Thr Thr Pro Pro Val Leu Asp Ser Asp Gly
            515                 520                 525
Ser Phe Phe Leu Tyr Ser Lys Leu Thr Val Asp Lys Ser Arg Trp Gln
        530                 535                 540
Gln Gly Asn Val Phe Ser Cys Ser Val Met His Glu Ala Leu His Asn
545                 550                 555                 560
His Tyr Thr Gln Lys Ser Leu Ser Leu Ser Pro Gly Lys
                565                 570

<210> SEQ ID NO 75
<211> LENGTH: 449
<212> TYPE: PRT
<213> ORGANISM: Artificial Sequence
```

<220> FEATURE:
<223> OTHER INFORMATION: Synthetic Construct

<400> SEQUENCE: 75

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Gly Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Arg Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400
```

Leu Asp Ser Asp Gly Ser Phe Phe Leu Tyr Ser Lys Leu Thr Val Asp
            405                 410                 415

Lys Ser Arg Trp Gln Gln Gly Asn Val Phe Ser Cys Ser Val Met His
        420                 425                 430

Glu Ala Leu His Asn His Tyr Thr Gln Lys Ser Leu Ser Leu Ser Pro
        435                 440                 445

Gly

<210> SEQ ID NO 76
<211> LENGTH: 213
<212> TYPE: PRT
<213> ORGANISM: Artificial Sequence
<220> FEATURE:
<223> OTHER INFORMATION: Synthetic Construct

<400> SEQUENCE: 76

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
        35                  40                  45

Ser Thr Ser Asn Leu Ala Ser Gly Ile Pro Ala Arg Phe Ser Gly Ser
    50                  55                  60

Gly Ser Gly Thr Asp Phe Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 77
<211> LENGTH: 213
<212> TYPE: PRT
<213> ORGANISM: Artificial Sequence
<220> FEATURE:
<223> OTHER INFORMATION: Synthetic Construct

<400> SEQUENCE: 77

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Lys Pro Gly Gln Ala Pro Arg Leu Leu Ile Tyr
            35                  40                  45

Ser Thr Ser Asn Leu Ala Ser Gly Ile Pro Ala Arg Phe Ser Gly Ser
    50                  55                  60

Gly Ser Gly Thr Asp Tyr Thr Leu Thr Ile Ser Ser Leu Glu Pro Glu
65                  70                  75                  80

Asp Phe Ala Val Tyr Tyr Cys Gln Gln Arg Ser Ser Tyr Pro Phe Thr
                85                  90                  95

Phe Gly Pro Gly Thr Lys Leu Asp Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 78
<211> LENGTH: 329
<212> TYPE: PRT
<213> ORGANISM: Homo sapiens

<400> SEQUENCE: 78

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Arg Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu

```
            180                 185                 190
His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 79
<211> LENGTH: 326
<212> TYPE: PRT
<213> ORGANISM: Homo sapiens

<400> SEQUENCE: 79

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220
```

```
Glu Pro Gln Val Tyr Thr Leu Pro Pro Ser Gln Glu Met Thr Lys
225                 230                 235                 240

Asn Gln Val Ser Leu Thr Cys Leu Val Lys Gly Phe Tyr Pro Ser Asp
            245                 250                 255

Ile Ala Val Glu Trp Glu Ser Asn Gly Gln Pro Glu Asn Asn Tyr Lys
        260                 265                 270

Thr Thr Pro Pro Val Leu Asp Ser Asp Gly Ser Phe Phe Leu Tyr Ser
    275                 280                 285

Arg Leu Thr Val Asp Lys Ser Arg Trp Gln Gln Gly Asn Val Phe Ser
290                 295                 300

Cys Ser Val Met His Glu Ala Leu His Asn His Tyr Thr Gln Lys Ser
305                 310                 315                 320

Leu Ser Leu Ser Leu Gly
                325

<210> SEQ ID NO 80
<211> LENGTH: 107
<212> TYPE: PRT
<213> ORGANISM: Homo sapiens

<400> SEQUENCE: 80

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 81
<211> LENGTH: 444
<212> TYPE: PRT
<213> ORGANISM: Mus musculus

<400> SEQUENCE: 81

Gln Val Gln Leu Lys Arg Ala Ser Gly Pro Gly Leu Val Ala Pro Ser
1               5                   10                  15

Gln Ser Leu Ser Ile Thr Cys Thr Val Ser Gly Phe Ser Leu Thr Ile
            20                  25                  30

Tyr Gly Ala His Trp Val Arg Gln Pro Pro Gly Lys Gly Leu Glu Trp
        35                  40                  45

Leu Gly Val Ile Trp Ala Gly Gly Ser Thr Asn Tyr Asn Ser Ala Leu
    50                  55                  60

Met Ser Arg Leu Ser Ile Ser Lys Asp Asn Ser Lys Ser Gln Val Phe
65                  70                  75                  80

Leu Lys Ile Asn Ser Leu Gln Thr Asp Asp Thr Ala Leu Tyr Tyr Cys
                85                  90                  95

Ala Arg Asp Gly Ser Ser Pro Tyr Tyr Tyr Ser Met Glu Tyr Trp Gly
            100                 105                 110
```

Gln Gly Thr Ser Val Thr Val Ser Ser Ala Lys Thr Thr Pro Pro Ser
            115                 120                 125

Val Tyr Pro Leu Ala Pro Gly Ser Ala Ala Gln Thr Asn Ser Met Val
        130                 135                 140

Thr Leu Gly Cys Leu Val Lys Gly Tyr Phe Pro Glu Pro Val Thr Val
145                 150                 155                 160

Thr Trp Asn Ser Gly Ser Leu Ser Ser Gly Val His Thr Phe Pro Ala
                165                 170                 175

Val Leu Glu Ser Asp Leu Tyr Thr Leu Ser Ser Ser Val Thr Val Pro
            180                 185                 190

Ser Ser Pro Arg Pro Ser Glu Thr Val Thr Cys Asn Val Ala His Pro
        195                 200                 205

Ala Ser Ser Thr Lys Val Asp Lys Lys Ile Val Pro Arg Asp Cys Gly
210                 215                 220

Cys Lys Pro Cys Ile Cys Thr Val Pro Glu Val Ser Ser Val Phe Ile
225                 230                 235                 240

Phe Pro Pro Lys Pro Lys Asp Val Leu Thr Ile Thr Leu Thr Pro Lys
                245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
        275                 280                 285

Pro Arg Glu Glu Gln Phe Asn Ser Thr Phe Arg Ser Val Ser Glu Leu
290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
                325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
        355                 360                 365

Asp Phe Phe Pro Glu Asp Ile Thr Val Glu Trp Gln Trp Asn Gly Gln
370                 375                 380

Pro Ala Glu Asn Tyr Lys Asn Thr Gln Pro Ile Met Asn Thr Asn Gly
385                 390                 395                 400

Ser Tyr Phe Val Tyr Ser Lys Leu Asn Val Gln Lys Ser Asn Trp Glu
                405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly
        435                 440

<210> SEQ ID NO 82
<211> LENGTH: 212
<212> TYPE: PRT
<213> ORGANISM: Mus musculus

<400> SEQUENCE: 82

Glu Ile Ile Leu Thr Gln Ser Pro Ala Ile Met Ser Ala Ser Pro Gly
1               5                   10                  15

Glu Lys Val Ser Ile Thr Cys Ser Ala Thr Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Val Arg Phe Ser Gly Ser
 50                  55                  60

Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Arg Ser Ser Tyr Pro Phe Thr
                 85                  90                  95

Phe Gly Ser Gly Thr Lys Leu Glu Ile Lys Ala Asp Ala Ala Pro Thr
                100                 105                 110

Val Ser Ile Phe Pro Pro Ser Ser Glu Gln Leu Thr Ser Gly Gly Ala
                115                 120                 125

Ser Val Val Cys Phe Leu Asn Asn Phe Tyr Pro Lys Asp Ile Asn Val
                130                 135                 140

Lys Trp Lys Ile Asp Gly Ser Glu Arg Gln Asn Gly Val Leu Asn Ser
145                 150                 155                 160

Trp Thr Asp Gln Asp Ser Lys Asp Ser Thr Tyr Ser Met Ser Ser Thr
                165                 170                 175

Leu Thr Leu Thr Lys Asp Glu Tyr Glu Arg His Asn Ser Tyr Thr Cys
                180                 185                 190

Glu Ala Thr His Lys Thr Ser Thr Ser Pro Ile Val Lys Ser Phe Asn
                195                 200                 205

Arg Asn Glu Cys
    210

<210> SEQ ID NO 83
<211> LENGTH: 212
<212> TYPE: PRT
<213> ORGANISM: Mus musculus

<400> SEQUENCE: 83

Gln Ile Ile Leu Thr Gln Ser Pro Ala Ile Met Ser Ala Ser Pro Gly
1               5                   10                  15

Glu Lys Val Ser Ile Thr Cys Ser Ala Thr Ser Ser Val Ser Tyr Met
                20                  25                  30

His Trp Phe Gln Gln Lys Pro Gly Thr Ser Pro Lys Leu Trp Ile Tyr
            35                  40                  45

Ser Thr Ser Asn Leu Ala Ser Gly Val Pro Val Arg Phe Ser Gly Ser
 50                  55                  60

Gly Ser Gly Thr Ser Tyr Ser Leu Thr Ile Ser Arg Met Glu Ala Glu
 65                  70                  75                  80

Asp Ala Ala Thr Tyr Tyr Cys Gln Gln Arg Ser Ser Tyr Pro Phe Thr
                 85                  90                  95

Phe Gly Ser Gly Thr Lys Leu Glu Ile Lys Ala Asp Ala Ala Pro Thr
                100                 105                 110

Val Ser Ile Phe Pro Pro Ser Ser Glu Gln Leu Thr Ser Gly Gly Ala
                115                 120                 125

Ser Val Val Cys Phe Leu Asn Asn Phe Tyr Pro Lys Asp Ile Asn Val
                130                 135                 140

Lys Trp Lys Ile Asp Gly Ser Glu Arg Gln Asn Gly Val Leu Asn Ser
145                 150                 155                 160

Trp Thr Asp Gln Asp Ser Lys Asp Ser Thr Tyr Ser Met Ser Ser Thr
                165                 170                 175

Leu Thr Leu Thr Lys Asp Glu Tyr Glu Arg His Asn Ser Tyr Thr Cys
                180                 185                 190

Glu Ala Thr His Lys Thr Ser Thr Ser Pro Ile Val Lys Ser Phe Asn

-continued

```
            195                 200                 205

Arg Asn Glu Cys
    210

<210> SEQ ID NO 84
<211> LENGTH: 450
<212> TYPE: PRT
<213> ORGANISM: Artificial Sequence
<220> FEATURE:
<223> OTHER INFORMATION: Synthetic Construct

<400> SEQUENCE: 84

Gln Val Gln Leu Lys Arg Ala Ser Gly Pro Gly Leu Val Ala Pro Ser
1               5                   10                  15

Gln Ser Leu Ser Ile Thr Cys Thr Val Ser Gly Phe Ser Leu Thr Ile
            20                  25                  30

Tyr Gly Ala His Trp Val Arg Gln Pro Pro Gly Lys Gly Leu Glu Trp
        35                  40                  45

Leu Gly Val Ile Trp Ala Gly Gly Ser Thr Asn Tyr Asn Ser Ala Leu
    50                  55                  60

Met Ser Arg Leu Ser Ile Ser Lys Asp Asn Ser Lys Ser Gln Val Phe
65                  70                  75                  80

Leu Lys Ile Asn Ser Leu Gln Thr Asp Asp Thr Ala Leu Tyr Tyr Cys
                85                  90                  95

Ala Arg Asp Gly Ser Ser Pro Tyr Tyr Tyr Ser Met Glu Tyr Trp Gly
            100                 105                 110

Gln Gly Thr Ser Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Arg Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270

Glu Asp Pro Glu Val Lys Phe Asn Trp Tyr Val Asp Gly Val Glu Val
        275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
```

```
            340                 345                 350
Tyr Thr Leu Pro Pro Ser Arg Glu Glu Met Thr Lys Asn Gln Val Ser
            355                 360                 365
Leu Thr Cys Leu Val Lys Gly Phe Tyr Pro Ser Asp Ile Ala Val Glu
            370                 375                 380
Trp Glu Ser Asn Gly Gln Pro Glu Asn Asn Tyr Lys Thr Thr Pro Pro
385                 390                 395                 400
Val Leu Asp Ser Asp Gly Ser Phe Phe Leu Tyr Ser Lys Leu Thr Val
                    405                 410                 415
Asp Lys Ser Arg Trp Gln Gln Gly Asn Val Phe Ser Cys Ser Val Met
                    420                 425                 430
His Glu Ala Leu His Asn His Tyr Thr Gln Lys Ser Leu Ser Leu Ser
            435                 440                 445
Pro Gly
    450

<210> SEQ ID NO 85
<211> LENGTH: 213
<212> TYPE: PRT
<213> ORGANISM: Artificial Sequence
<220> FEATURE:
<223> OTHER INFORMATION: Synthetic Construct

<400> SEQUENCE: 85

Glu Ile Ile Leu Thr Gln Ser Pro Ala Ile Met Ser Ala Ser Pro Gly
1               5                   10                  15
Glu Lys Val Ser Ile Thr Cys Ser Ala Thr Ser Ser Val Ser Tyr Met
            20                  25                  30
His Trp Phe Gln Gln Lys Pro Gly Thr Ser Pro Lys Leu Trp Ile Tyr
        35                  40                  45
Ser Thr Ser Asn Leu Ala Ser Gly Val Pro Val Arg Phe Ser Gly Ser
    50                  55                  60
Gly Ser Gly Thr Ser Tyr Ser Leu Thr Ile Ser Arg Met Glu Ala Glu
65                  70                  75                  80
Asp Ala Ala Thr Tyr Tyr Cys Gln Gln Arg Ser Ser Tyr Pro Phe Thr
                85                  90                  95
Phe Gly Ser Gly Thr Lys Leu Glu Ile Lys Arg Thr Val Ala Ala Pro
            100                 105                 110
Ser Val Phe Ile Phe Pro Pro Ser Asp Glu Gln Leu Lys Ser Gly Thr
        115                 120                 125
Ala Ser Val Val Cys Leu Leu Asn Asn Phe Tyr Pro Arg Glu Ala Lys
    130                 135                 140
Val Gln Trp Lys Val Asp Asn Ala Leu Gln Ser Gly Asn Ser Gln Glu
145                 150                 155                 160
Ser Val Thr Glu Gln Asp Ser Lys Asp Ser Thr Tyr Ser Leu Ser Ser
                165                 170                 175
Thr Leu Thr Leu Ser Lys Ala Asp Tyr Glu Lys His Lys Val Tyr Ala
            180                 185                 190
Cys Glu Val Thr His Gln Gly Leu Ser Ser Pro Val Thr Lys Ser Phe
        195                 200                 205
Asn Arg Gly Glu Cys
    210

<210> SEQ ID NO 86
<211> LENGTH: 213
<212> TYPE: PRT
```

<213> ORGANISM: Artificial Sequence
<220> FEATURE:
<223> OTHER INFORMATION: Synthetic Construct

<400> SEQUENCE: 86

```
Gln Ile Ile Leu Thr Gln Ser Pro Ala Ile Met Ser Ala Ser Pro Gly
1               5                   10                  15

Glu Lys Val Ser Ile Thr Cys Ser Ala Thr Ser Ser Val Ser Tyr Met
            20                  25                  30

His Trp Phe Gln Gln Lys Pro Gly Thr Ser Pro Lys Leu Trp Ile Tyr
        35                  40                  45

Ser Thr Ser Asn Leu Ala Ser Gly Val Pro Val Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Ser Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210
```

<210> SEQ ID NO 87
<211> LENGTH: 446
<212> TYPE: PRT
<213> ORGANISM: Artificial Sequence
<220> FEATURE:
<223> OTHER INFORMATION: Synthetic Construct

<400> SEQUENCE: 87

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Leu Thr Ile Tyr
            20                  25                  30

Gly Ala His Trp Val Arg Gln Ala Pro Gly Lys Gly Leu Glu Trp Val
        35                  40                  45

Gly Val Ile Trp Ala Gly Gly Ser Thr Asn Tyr Asn Ser Ala Leu Met
    50                  55                  60

Ser Arg Phe Thr Ile Ser Lys Asp Asn Ser Lys Asn Thr Val Tyr Leu
65                  70                  75                  80

Gln Met Asn Ser Leu Arg Ala Glu Asp Thr Ala Val Tyr Tyr Cys Ala
                85                  90                  95

Arg Asp Gly Ser Ser Pro Tyr Tyr Tyr Ser Met Glu Tyr Trp Gly Gln
            100                 105                 110
```

```
Gly Thr Thr Val Thr Val Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly
            435                 440                 445

<210> SEQ ID NO 88
<211> LENGTH: 5
<212> TYPE: PRT
<213> ORGANISM: Mus musculus

<400> SEQUENCE: 88

Ser Tyr Ala Met Ser
1               5

<210> SEQ ID NO 89
<211> LENGTH: 5
<212> TYPE: PRT
<213> ORGANISM: Mus musculus
```

```
<400> SEQUENCE: 89

Asp Tyr Tyr Met Tyr
1               5

<210> SEQ ID NO 90
<211> LENGTH: 5
<212> TYPE: PRT
<213> ORGANISM: Mus musculus

<400> SEQUENCE: 90

Ser Ser Trp Met Asn
1               5

<210> SEQ ID NO 91
<211> LENGTH: 17
<212> TYPE: PRT
<213> ORGANISM: Mus musculus

<400> SEQUENCE: 91

Ile Ile Ser Ser Gly Gly Ser Tyr Thr Tyr Tyr Ser Asp Ser Val Lys
1               5                  10                  15

Gly

<210> SEQ ID NO 92
<211> LENGTH: 17
<212> TYPE: PRT
<213> ORGANISM: Mus musculus

<400> SEQUENCE: 92

Arg Ile Ala Pro Glu Asp Gly Asp Thr Glu Tyr Ala Pro Lys Phe Gln
1               5                  10                  15

Gly

<210> SEQ ID NO 93
<211> LENGTH: 17
<212> TYPE: PRT
<213> ORGANISM: Mus musculus

<400> SEQUENCE: 93

Gln Ile Tyr Pro Gly Asp Asp Tyr Thr Asn Tyr Asn Gly Lys Phe Lys
1               5                  10                  15

Gly

<210> SEQ ID NO 94
<211> LENGTH: 11
<212> TYPE: PRT
<213> ORGANISM: Mus musculus

<400> SEQUENCE: 94

His Glu Thr Ala Gln Ala Ala Trp Phe Ala Tyr
1               5                  10

<210> SEQ ID NO 95
<211> LENGTH: 12
<212> TYPE: PRT
<213> ORGANISM: Mus musculus

<400> SEQUENCE: 95

Glu Gly Asn Tyr Tyr Gly Ser Ser Ile Leu Asp Tyr
1               5                  10
```

```
<210> SEQ ID NO 96
<211> LENGTH: 9
<212> TYPE: PRT
<213> ORGANISM: Mus musculus

<400> SEQUENCE: 96

Leu Gly Pro Tyr Gly Pro Phe Ala Asp
1               5

<210> SEQ ID NO 97
<211> LENGTH: 10
<212> TYPE: PRT
<213> ORGANISM: Mus musculus

<400> SEQUENCE: 97

Ser Ala Ser Ser Ser Val Ser Tyr Met His
1               5                   10

<210> SEQ ID NO 98
<211> LENGTH: 11
<212> TYPE: PRT
<213> ORGANISM: Mus musculus

<400> SEQUENCE: 98

Arg Ala Ser Gln Asp Ile Thr Asn Tyr Leu Asn
1               5                   10

<210> SEQ ID NO 99
<211> LENGTH: 10
<212> TYPE: PRT
<213> ORGANISM: Mus musculus

<400> SEQUENCE: 99

Ser Ala Ser Ser Ser Val Ser Tyr Met Tyr
1               5                   10

<210> SEQ ID NO 100
<211> LENGTH: 7
<212> TYPE: PRT
<213> ORGANISM: Mus musculus

<400> SEQUENCE: 100

Asp Thr Ser Lys Leu Ala Tyr
1               5

<210> SEQ ID NO 101
<211> LENGTH: 7
<212> TYPE: PRT
<213> ORGANISM: Mus musculus

<400> SEQUENCE: 101

Phe Thr Ser Arg Leu His Ser
1               5

<210> SEQ ID NO 102
<211> LENGTH: 7
<212> TYPE: PRT
<213> ORGANISM: Mus musculus

<400> SEQUENCE: 102

Asp Thr Ser Ser Leu Ala Ser
1               5

<210> SEQ ID NO 103
<211> LENGTH: 9
```

```
<212> TYPE: PRT
<213> ORGANISM: Mus musculus

<400> SEQUENCE: 103

Gln Gln Trp Ser Ser Asn Pro Pro Thr
1               5

<210> SEQ ID NO 104
<211> LENGTH: 9
<212> TYPE: PRT
<213> ORGANISM: Mus musculus

<400> SEQUENCE: 104

Gln Gln Gly Asn Thr Leu Pro Trp Thr
1               5

<210> SEQ ID NO 105
<211> LENGTH: 9
<212> TYPE: PRT
<213> ORGANISM: Mus musculus

<400> SEQUENCE: 105

Gln Gln Trp Asn Ser Asp Pro Tyr Thr
1               5

<210> SEQ ID NO 106
<211> LENGTH: 120
<212> TYPE: PRT
<213> ORGANISM: Mus musculus

<400> SEQUENCE: 106

Glu Val Gln Val Val Glu Ser Gly Gly Asp Leu Val Lys Ser Gly Gly
1               5                   10                  15

Ser Leu Lys Leu Ser Cys Ala Ala Ser Gly Phe Pro Phe Ser Ser Tyr
            20                  25                  30

Ala Met Ser Trp Val Arg Gln Thr Pro Asp Lys Arg Leu Glu Trp Val
        35                  40                  45

Ala Ile Ile Ser Ser Gly Gly Ser Tyr Thr Tyr Tyr Ser Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Lys Ser Glu Asp Thr Ala Met Tyr Tyr Cys
                85                  90                  95

Ala Arg His Glu Thr Ala Gln Ala Ala Trp Phe Ala Tyr Trp Gly Gln
            100                 105                 110

Gly Thr Leu Val Thr Val Ser Ala
        115                 120

<210> SEQ ID NO 107
<211> LENGTH: 121
<212> TYPE: PRT
<213> ORGANISM: Mus musculus

<400> SEQUENCE: 107

Glu Val Gln Leu Gln Gln Ser Gly Ala Glu Leu Val Arg Pro Gly Ala
1               5                   10                  15

Ser Val Lys Leu Ser Cys Thr Ala Ser Gly Phe Asn Ile Lys Asp Tyr
            20                  25                  30

Tyr Met Tyr Trp Val Lys Gln Arg Pro Glu Gln Gly Leu Glu Trp Ile
        35                  40                  45
```

Gly Arg Ile Ala Pro Glu Asp Gly Asp Thr Glu Tyr Ala Pro Lys Phe
        50                  55                  60

Gln Gly Lys Ala Thr Val Thr Ala Asp Thr Ser Ser Asn Thr Ala Tyr
 65                  70                  75                  80

Leu His Leu Ser Ser Leu Thr Ser Glu Asp Thr Ala Val Tyr Tyr Cys
                 85                  90                  95

Thr Thr Glu Gly Asn Tyr Tyr Gly Ser Ser Ile Leu Asp Tyr Trp Gly
            100                 105                 110

Gln Gly Thr Thr Leu Thr Val Ser Ser
            115                 120

<210> SEQ ID NO 108
<211> LENGTH: 118
<212> TYPE: PRT
<213> ORGANISM: Mus musculus

<400> SEQUENCE: 108

Gln Val Gln Leu Gln Gln Ser Gly Ala Glu Leu Val Lys Pro Gly Ala
 1               5                  10                  15

Ser Val Lys Ile Ser Cys Lys Ala Ser Gly Tyr Ala Phe Arg Ser Ser
                 20                  25                  30

Trp Met Asn Trp Val Lys Gln Arg Pro Gly Lys Gly Leu Glu Trp Ile
             35                  40                  45

Gly Gln Ile Tyr Pro Gly Asp Asp Tyr Thr Asn Tyr Asn Gly Lys Phe
        50                  55                  60

Lys Gly Lys Val Thr Leu Thr Ala Asp Arg Ser Ser Thr Ala Tyr
 65                  70                  75                  80

Met Gln Leu Ser Ser Leu Thr Ser Glu Asp Ser Ala Val Tyr Phe Cys
                 85                  90                  95

Ala Arg Leu Gly Pro Tyr Gly Pro Phe Ala Asp Trp Gly Gln Gly Thr
            100                 105                 110

Leu Val Thr Val Ser Ala
            115

<210> SEQ ID NO 109
<211> LENGTH: 106
<212> TYPE: PRT
<213> ORGANISM: Mus musculus

<400> SEQUENCE: 109

Gln Ile Val Leu Thr Gln Ser Pro Ala Ile Met Ser Ala Ser Pro Gly
 1               5                  10                  15

Glu Lys Val Thr Met Thr Cys Ser Ala Ser Ser Ser Val Ser Tyr Met
                 20                  25                  30

His Trp Tyr Gln Gln Lys Ser Gly Thr Ser Pro Lys Arg Trp Ile Tyr
             35                  40                  45

Asp Thr Ser Lys Leu Ala Tyr Gly Val Pro Ala Arg Phe Ser Gly Ser
        50                  55                  60

Gly Ser Gly Thr Ser Tyr Ser Leu Thr Ile Ser Ser Met Glu Ala Glu
 65                  70                  75                  80

Asp Ala Ala Thr Tyr Tyr Cys Gln Gln Trp Ser Ser Asn Pro Pro Thr
                 85                  90                  95

Phe Gly Gly Gly Thr Lys Leu Glu Ile Lys
            100                 105

<210> SEQ ID NO 110
<211> LENGTH: 107

```
<212> TYPE: PRT
<213> ORGANISM: Mus musculus

<400> SEQUENCE: 110

Asp Ile Gln Met Thr Gln Thr Thr Ser Ser Leu Ser Ala Ser Leu Gly
1               5                   10                  15

Asp Arg Val Thr Ile Ser Cys Arg Ala Ser Gln Asp Ile Thr Asn Tyr
                20                  25                  30

Leu Asn Trp Tyr Gln Gln Lys Pro Asp Gly Thr Val Lys Leu Leu Ile
            35                  40                  45

Tyr Phe Thr Ser Arg Leu His Ser Gly Val Pro Ser Arg Phe Ser Gly
        50                  55                  60

Ser Gly Ser Gly Thr Asp Tyr Ser Leu Thr Ile Ser Asn Leu Glu Gln
65                  70                  75                  80

Glu Asp Ile Ala Thr Tyr Phe Cys Gln Gln Gly Asn Thr Leu Pro Trp
                85                  90                  95

Thr Phe Gly Gly Gly Thr Lys Leu Glu Ile Lys
                100                 105

<210> SEQ ID NO 111
<211> LENGTH: 106
<212> TYPE: PRT
<213> ORGANISM: Mus musculus

<400> SEQUENCE: 111

Gln Ile Val Leu Thr Gln Ser Pro Ala Ile Val Ser Ala Ser Pro Gly
1               5                   10                  15

Glu Lys Val Thr Met Thr Cys Ser Ala Ser Ser Ser Val Ser Tyr Met
                20                  25                  30

Tyr Trp Tyr Gln Gln Arg Pro Gly Ser Ser Pro Arg Leu Leu Ile Tyr
            35                  40                  45

Asp Thr Ser Ser Leu Ala Ser Gly Val Pro Val Arg Phe Ser Gly Ser
        50                  55                  60

Gly Ser Gly Thr Ser Tyr Ser Leu Thr Ile Ser Arg Ile Glu Ser Glu
65                  70                  75                  80

Asp Ala Ala Asn Tyr Tyr Cys Gln Gln Trp Asn Ser Asp Pro Tyr Thr
                85                  90                  95

Phe Gly Gly Gly Thr Lys Leu Glu Ile Lys
                100                 105
```